United States Patent
Perez Bay et al.

(10) Patent No.: US 12,037,411 B2
(45) Date of Patent: Jul. 16, 2024

(54) ANTIBODIES, AND BISPECIFIC ANTIGEN-BINDING MOLECULES THAT BIND HER2 AND/OR APLP2, CONJUGATES, AND USES THEREOF

(71) Applicant: Regeneron Pharmaceuticals, Inc., Tarrytown, NY (US)

(72) Inventors: Andres Perez Bay, Cos Cob, CT (US); Julian Andreev, Sleepy Hollow, NY (US); Terra Potocky, Dobbs Ferry, NY (US); Xunbao Duan, Brewster, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 764 days.

(21) Appl. No.: 17/051,987

(22) PCT Filed: Apr. 29, 2019

(86) PCT No.: PCT/US2019/029640
§ 371 (c)(1),
(2) Date: Oct. 30, 2020

(87) PCT Pub. No.: WO2019/212965
PCT Pub. Date: Nov. 7, 2019

(65) Prior Publication Data
US 2021/0246224 A1    Aug. 12, 2021

Related U.S. Application Data

(60) Provisional application No. 62/825,144, filed on Mar. 28, 2019, provisional application No. 62/728,622, filed on Sep. 7, 2018, provisional application No. 62/664,924, filed on Apr. 30, 2018.

(51) Int. Cl.
| | |
|---|---|
| *C07K 16/32* | (2006.01) |
| *A61K 39/00* | (2006.01) |
| *A61K 47/68* | (2017.01) |
| *A61P 35/00* | (2006.01) |

(52) U.S. Cl.
CPC .......... *C07K 16/32* (2013.01); *A61K 47/6849* (2017.08); *A61K 47/6879* (2017.08); *A61P 35/00* (2018.01); *A61K 2039/505* (2013.01)

(58) Field of Classification Search
CPC .............. C07K 16/32; C07K 2317/515; C07K 2317/30; C07K 2317/31; C07K 2317/77; C07K 2317/92; C07K 2317/94; C07K 16/28; C07K 16/18; C07K 2317/565; A61K 47/6849; A61K 47/6879; A61K 2039/505; A61K 47/6855; A61P 35/00
See application file for complete search history.

(56) References Cited

U.S. PATENT DOCUMENTS

| | | |
|---|---|---|
| 4,444,878 A | 4/1984 | Paulus |
| 4,975,278 A | 12/1990 | Senter et al. |
| 5,030,717 A | 7/1991 | Tramontano et al. |
| 5,126,258 A | 6/1992 | Lerner et al. |
| 5,156,965 A | 10/1992 | Schochetman et al. |
| 5,208,020 A | 5/1993 | Chari et al. |
| 5,229,272 A | 7/1993 | Paul et al. |
| 5,436,153 A | 7/1995 | Sprecher et al. |
| 5,441,931 A | 8/1995 | Sprecher et al. |
| 5,500,362 A | 3/1996 | Robinson et al. |
| 5,585,108 A | 12/1996 | Ruddy et al. |

(Continued)

FOREIGN PATENT DOCUMENTS

| | | |
|---|---|---|
| WO | 1999/036437 A1 | 7/1999 |
| WO | 2001/036005 A2 | 5/2001 |

(Continued)

OTHER PUBLICATIONS

Almagro et. al., Front. Immunol. 2018; 8:1751 (Year: 2018).*
Rudikoff et al., Proc. Nat'l Acad. Sci. USA, 79:1979-83 (1982) (Year: 1982).*
Brown et al., J. Immunol., 156(9):3285-91 (1996) (Year: 1996).*
Chiu et al., Antibodies, 8(55):1-80. (2019) (Year: 2019).*
Angal et al. (1993) "A single amino acid substitution abolishes the heterogeneity of chimeric mouse/human (IgG4) antibody," Molecular Immunology 30(1):105-108 Abstract Only.

(Continued)

*Primary Examiner* — Jessica H Roark
*Assistant Examiner* — Francesca Edgingtongiordan
(74) *Attorney, Agent, or Firm* — FisherBroyles, LLP; Rita S. Wu; Kajal Chowdhury

(57) ABSTRACT

The protein known as human epidermal growth factor 2 (HER2) is expressed in breast cancer cells and its expression is correlated with aggressive tumor growth. The present invention provides novel full-length human (IgG) antibodies that bind to human HER2 (monospecific antibodies) or to APLP2 (monospecific antibodies). The present invention also provides novel bispecific antibodies (bsAbs) that bind to both HER2 and APLP2 and mediate internalization and degradation of HER2 via the APLP2 complex in the presence of HER2-expressing tumors. Described are bispecific antigen-binding molecules and ADCs comprising a first antigen-binding domain that specifically binds human APLP2, and a second antigen-binding domain that specifically binds human HER2. The described bispecific ADCs are capable of inhibiting the growth of certain tumors expressing HER2 and may be useful for the treatment of breast cancer and disorders in which targeting a therapeutic agent to HER2-expressing tumor cell is desirable and/or therapeutically beneficial. For example, the bispecific antibodies of the invention are useful for the treatment of breast cancers, including breast cancers having a IHC2+ classification. The present invention also includes anti-HER2 antibody drug conjugates which inhibit tumor growth in vivo.

28 Claims, 16 Drawing Sheets
Specification includes a Sequence Listing.

(56) References Cited

U.S. PATENT DOCUMENTS

| | | | |
|---|---|---|---|
| 5,601,819 A | 2/1997 | Wong et al. |
| 5,602,021 A | 2/1997 | Davis et al. |
| 5,677,146 A | 10/1997 | Sprecher et al. |
| 5,714,586 A | 2/1998 | Kunstmann et al. |
| 5,731,168 A | 3/1998 | Carter et al. |
| 5,821,337 A | 10/1998 | Carter et al. |
| 5,851,527 A | 12/1998 | Hansen |
| 5,858,728 A | 1/1999 | Gram et al. |
| 5,935,854 A | 8/1999 | Sprecher et al. |
| 6,235,714 B1 | 5/2001 | Paul et al. |
| 6,306,393 B1 | 10/2001 | Goldenberg et al. |
| 6,372,205 B1 | 4/2002 | Duncan et al. |
| 6,387,674 B1 | 5/2002 | Trasciatti et al. |
| 6,479,265 B1 | 11/2002 | Napper et al. |
| 6,703,488 B1 | 3/2004 | Burton et al. |
| 6,855,804 B2 | 2/2005 | Paul et al. |
| 7,041,298 B2 | 5/2006 | Deshaies et al. |
| 7,087,411 B2 | 8/2006 | Daly et al. |
| 7,105,348 B2 | 9/2006 | Murphy et al. |
| 7,223,556 B1 | 5/2007 | Zhou et al. |
| 7,235,641 B2 | 6/2007 | Kufer et al. |
| 7,335,504 B2 | 2/2008 | Haupts et al. |
| 7,371,539 B2 | 5/2008 | Church et al. |
| 7,560,424 B2 | 7/2009 | LeBowitz et al. |
| 7,592,429 B2 | 9/2009 | Paszty et al. |
| 7,750,116 B1 | 7/2010 | Doronina et al. |
| 7,754,681 B2 | 7/2010 | Feng |
| 7,771,997 B2 | 8/2010 | Chen et al. |
| 7,914,787 B2 | 3/2011 | Goldenberg et al. |
| 8,058,399 B2 | 11/2011 | Jung |
| 8,257,745 B2 | 9/2012 | Ketelson et al. |
| 8,586,713 B2 | 11/2013 | Davis et al. |
| 8,815,226 B2 | 8/2014 | Yurkovetskiy et al. |
| 9,359,437 B2 | 6/2016 | Davis et al. |
| 9,950,076 B2 | 4/2018 | Nittoli et al. |
| 2006/0099205 A1 | 5/2006 | Adams et al. |
| 2007/0041978 A1 | 2/2007 | Hatiori et al. |
| 2007/0258987 A1 | 8/2007 | Francisco et al. |
| 2007/0280945 A1 | 12/2007 | Stevens et al. |
| 2008/0305497 A1 | 12/2008 | Kosmeder et al. |
| 2009/0142354 A1 | 6/2009 | Papadopoulos et al. |
| 2010/0081796 A1 | 4/2010 | Brinkmann et al. |
| 2010/0129314 A1 | 5/2010 | Singh et al. |
| 2010/0233173 A1 | 9/2010 | Wu et al. |
| 2010/0330034 A1 | 12/2010 | Bigler et al. |
| 2010/0331527 A1 | 12/2010 | Davis et al. |
| 2011/0027286 A1 | 2/2011 | Thurston et al. |
| 2011/0195454 A1 | 8/2011 | McWhirter et al. |
| 2013/0101546 A1 | 4/2013 | Yurkovetskiy et al. |
| 2013/0243775 A1 | 9/2013 | Papadopoulos et al. |
| 2014/0243504 A1 | 8/2014 | Davis et al. |
| 2015/0056221 A1 | 2/2015 | Papadopoulos et al. |
| 2016/0375147 A1 | 12/2016 | Nittoli et al. |
| 2017/0007715 A1 | 1/2017 | Andreev et al. |
| 2017/0209591 A1 | 7/2017 | Nittoli et al. |
| 2019/0309061 A1 | 10/2019 | Papadopoulos et al. |

FOREIGN PATENT DOCUMENTS

| | | | |
|---|---|---|---|
| WO | 2005/089808 A2 | 9/2005 | |
| WO | 2006/072166 A1 | 7/2006 | |
| WO | 2008/011711 A1 | 1/2008 | |
| WO | 2008/014404 A2 | 1/2008 | |
| WO | 2008/019290 A2 | 2/2008 | |
| WO | 2008/122039 A2 | 10/2008 | |
| WO | 2008/150485 A2 | 12/2008 | |
| WO | 2009/094561 A1 | 7/2009 | |
| WO | 2010/010324 A1 | 1/2010 | |
| WO | 2010/115552 A1 | 10/2010 | |
| WO | 2010/119119 A1 | 10/2010 | |
| WO | 2011/018611 A1 | 2/2011 | |
| WO | 2011/130598 A1 | 10/2011 | |
| WO | 2011/147986 A1 | 12/2011 | |
| WO | 2012/005982 A2 | 1/2012 | |
| WO | 2012/143379 A1 | 10/2012 | |
| WO | 2012/143523 A1 | 10/2012 | |
| WO | 2012/143524 A1 | 10/2012 | |
| WO | 2012/166559 A1 | 12/2012 | |
| WO | 2013/053872 A1 | 4/2013 | |
| WO | 2013/053873 A1 | 4/2013 | |
| WO | 2013/055990 A1 | 4/2013 | |
| WO | 2013/055993 A1 | 4/2013 | |
| WO | 2013/068874 A1 | 5/2013 | |
| WO | 2013/085925 A1 | 6/2013 | |
| WO | 2013/138400 A1 | 9/2013 | |
| WO | 2013/166604 A1 | 11/2013 | |
| WO | 2014/065661 A1 | 5/2014 | |
| WO | 2014/145090 A1 | 9/2014 | |
| WO | 2014/182970 A1 | 11/2014 | |
| WO | 2015/031396 A1 | 3/2015 | |
| WO | 2016/065319 A1 | 4/2016 | |
| WO | 2016/085820 A1 | 6/2016 | |
| WO | 2016/160615 A1 | 10/2016 | |
| WO | 2017/007796 A1 | 1/2017 | |
| WO | 2017/134197 A1 | 8/2017 | |
| WO | WO-2017190079 A1 * | 11/2017 | ......... C07K 16/1203 |

OTHER PUBLICATIONS

Audran et al., "Internalization of human macrophage surface antigens induced by monoclonal antibodies," Journal of Immunological Methods, 1995, 188:147-154.

Demetrick, et al. "ME491 Melanoma-Associated Glycoprotein Family: Antigenic Identity of ME491, NKI/C-3, Neuroglandular Antigen (NGA), and CD63 Proteins," Journal Natl. Cancer Inst., 1992; 84(6):422-429.

Ferrara et al., "Recombinant renewable polyclonal antibodies," mAbs, 2015, 7(1):32-41.

Huston et al, "Protein engineering of antibody binding sites: Recovery of specific activity in an anti-digoxin single-chain Fv analogue produced in *Escherichia coli*," PNAS, 1988, 85:16:5879-5883.

Lee et al., "Novel strategy for a bispecific antibody: induction of dual target internalization and degradation," Oncogene, 2016, 35(34):4437-4446.

Robinson e al., "Optimizing the stability of single-chain proteins by linker length and composition mutagenesis," PNAS, 1998, 95(11):5929-5934.

Trastuzumab https://www.accessdata.fda.gov/drugsatfda_docs/label/1998/trasgen092598lb.pdf (Sep. 1998).

Dako A0485 https://www.agilent.com/cs/library/packageinsert/public/103814005.PDF (2013).

Statement of Relatedness under MPEP 2001.06 with Respect to U.S. Appl. No. 17/051,987 dated Aug. 17, 2022.

Agarwal et al., "A Pictet-Spengler ligation for protein chemical modification," Proc. Natl. Acad. Sci., USA, 2013, 110:46-51.

Ahmad et al., "ScFv Antibody: Principles and Clinical Application," Clinical and Developmental Immunology, vol. 2012, article ID 980250, 15 pages.

Al-Lazikani et al., "Standard Conformations for the Canonical Structures of Immunoglobulins," J. Mol. Biol., 1997, 273:927-948.

Altschul et al., "Basic Local Alignment Search Tool," J. Mol. Biol., 1990, 215:403-410.

Altschul et al., "Gapped BLAST and PSI-BLAST: a new generation of protein database search programs," Nucleic Acids Res., 1997, 25(17):3389-3402.

Andreev et al., "Abstract A131: Rapid constitutive internalization and degradation of prolactin receptor (PRLR) is associated with potent cell killing by PRLR antibody drug conjugates (ADC)," Molecular targets and Cancer Therapeutics, 14(12):supp. 2, Abstract No. A131 (Dec. 2015).

Andreev et al., "Bispecific Antibodies and Antibody-Drug Conjugates (ADCs) Bridging HER2 and Prolactin Receptor Improve Efficacy of HER2 ADCs," Mol. Cancer Ther., Apr. 2017, 16(4):681-693.

Arribas and Cutler, "Weibel-Palade Body Membrane Proteins Exhibit Differential Trafficking After Exocytosis in Endothelial Cells," Traffic, 2000, 1:783-793.

(56) References Cited

OTHER PUBLICATIONS

Azad et al., "A fully human CXCR4 antibody demonstrates diagnostic utility and therapeutic efficacy in solid tumor xenografts," Oncotarget, 2016, 7(11):12344-12358.
Bareford and Swaan, "Endocytic mechanisms for targeted drug delivery," Advanced Drug Delivery Reviews, 2007, 59(8):748-758.
Benedict et al., "Determination of the binding affinity of an anti-CD34 single-chain antibody using a novel, flow cytometry based assay," J Immunol Methods., 1997, 201(2):223-231.
Berditchevski et al., "Generation of Monoclonal Antibodies to Integrin-associated Proteins," Journal of Biological Chemistry, Nov. 1997, 272(46):29174-29180.
Bode et al., "Antibody-Directed Fibrinolysis: An Antibody Specific for Both Fibrin and Tissue Plasminogen Activator," Journal of Biological Chemistry, Jan. 1989, 264(2):944-948.
Boersma et al., "DARPins and other repeat protein scaffolds: advances in engineering and applications," Curr. Opin. Biotechnol., 2011, 22:849-885.
Bonardi et al., "Delivery of Saporin to Human B-Cell Lymphoma Using Bispecific Antibody: Targeting via CD22 but not CD19, CD37, or Immunoglobulin Results in Efficient Killing," Cancer Research, Jul. 1993, 53(13):3015-3021.
Bostrom et al., "Variants of the Antibody Herceptin That Interact with HER2 and VEGF at the Antigen Binding Site," Science, 2009, 323(5921):1610-1614.
Brissinck et al., (1993) "Bispecific Antibodies in Lymphoma," Intern. Rev. Immunol., 10(2-3):187-194.
Carrico et al., "Introducing genetically encoded aldehydes into proteins," Nat. Chem. Biol., 2007, 3:321-322.
Clynes et al., "Fc receptors are required in passive and active immunity to melanoma," Proc. Natl. Acad. Sci. (USA), 1998, 95:652-656.
De Goeij et al., "Efficient Payload Delivery by a Bispecific Antibody-Drug Conjugate Targeting HER2 and CD63," Mol. Cancer Ther., 2016, 15(11):2688-2697.
Devay et al., "Characterization of proprotein convertase subtilisin/kexin type 9 (PCSK9) trafficking reveals a novel lysosomal targeting mechanism via amyloid precursor-like protein 2 (APLP2)," J. Biol. Chem., Apr. 2, 2013, 288(15):10805-10818, doi: 10.1074/jbc.M113.453373. Epub Feb. 19, 2013.
Devay et al., "Common Proprotein Convertase Subtilisin/Kexin Type 9 (PCSK9) Epitopes Mediate Multiple Routes for Internalization and Function," PLOS ONE, Apr. 23, 2015, 10(4):e0125127, 20 pages.
Devay et al., "Improved Lysosomal Trafficking Can Modulate the Potency of Antibody Drug Conjugates," Bioconjugate Chem., 2017, 28(4):1102-1114, DOI: 10.1021/acs.bioconjchem.7b00013.
Dipadova et al., "A Broadly Cross-Protective Monoclonal Antibody Binding to *Escherichia coli* and *Salmonella* Lipopolysaccharides," Infection and Immunity, Sep. 1993, 61(9):3863-3872.
Doronina et al., "Development of potent monoclonal antibody auristatin conjugates for cancer therapy," Nature Biotechnology, 2003, 21(7):778-784 and p. 941 Corrigendum.
Ducry and Stump, "Antibody-Drug Conjugates: Linking Cytotoxic Payloads to Monoclonal Antibodies," Bioconjugate Chem., 2010, 21:5-13.
Ehring, "Hydrogen Exchange/Electrospray Ionization Mass Spectrometry Studies of Structural Features of Proteins and Protein/Protein Interactions," Analytical Biochemistry, 1999, 267(2):252-259.
Eigenbrot et al., "Structural basis for high-affinity HER2 receptor binding by an engineered protein," PNAS, 2010, 107(34):15039-15044.
Engen and Smith, "The Basics of Ion Chromatography," Anal. Chem., 2001, 73:256A-265A.
Fu et al., "Insights into HER2 signaling from step-by-step optimization of anti-HER2 antibodies," mAbs, 2014, 6(4):978-990.
Geuijen et al. "Affinity ranking of antibodies using flow cytometry: Application in antibody phage display-based target discovery," J Immunol Methods, 2005, 302(1-2):68-77.

Ghosh et al., "An Endocytosed TGN38 Chimeric Protein is Delivered to the TGN after Trafficking Through the Endocytic Recycling Compartment in CHO Cells," J. Cell Biol., Aug. 1998, 142(4):923-936.
Gomery et al., "Antibody WN1 222-5 mimics Toll-like receptor 4 binding in the recognition of LPS," Proc. Natl. Acad. Sci USA, 2012, 109(51):20877-20882.
Gonnet et al., "Exhaustive Matching of the Entire Protein Sequence Database," Science, 1992, 256: 1443-1445.
Gordon et al., "Clinical Activity of Pertuzumab (rhuMAb 2C4), a HER Dimerization Inhibitor, in Advanced Ovarian Cancer: Potential Predictive Relationship With Tumor HER2 Activation Status," J Clin Oncol, 2006, 24(26):4324-4332.
Hamblett et al., "Effects of Drug Loading on the Antitumor Activity of a Monoclonal Antibody Drug Conjugate," Clin Cancer Res, Oct. 15, 2004, 10(20):7063-7070.
Hevir et al., "Expression of estrogen and progesterone receptors and estrogen metabolizing enzymes in different breast cancer cell lines," Chemico-Biological Interactions, 2011, 191:206-216, doi:10.1016/j.cbi.2010.12.013.
Hofer et al., "An engineered selenocysteine defines a unique class of antibody derivatives," Proc. Natl. Acad. Sci., USA, 2008, 105:12451-12456.
Hollander et al., "Selection of Reaction Additives Used in the Preparation of Monomeric Antibody-Calicheamicin Conjugates," Bioconjugate Chem., 2008, 19:358-361.
Holliger et al., ""Diabodies": Small bivalent and bispecific antibody fragments," PNAS, 1993, 90:6444-6448.
Horwitz et al., "Variant T47D human breast cancer cells with high progesterone-receptor levels despite estrogen and antiestrogen resistance," Cell. Mar. 1982 28(3):633-642.
Jackson et al., "The nuclear splicing factor RNA binding motif 5 promotes caspase activation in human neuronal cells, and increases after traumatic brain injury in mice," Journal of Cerebral Blood Flow and Metabolism: Official Journal of the International Society of Cerebral Blood Flow and Metabolism, 2015, 35(4):655-666.
Jarantow et al., "Impact of Cell-surface Antigen Expression on Target Engagement and Function of an Epidermal Growth Factor Receptor x c-MET Bispecific Antibody," J Biol Chem., Oct. 9, 2015, 290(41):24689-24704, doi: 10.1074/jbc.M115.651653.
Jeger et al., "Site-Specific and Stoichiometric Modification of Antibodies by Bacterial Transglutaminase," Angew Chemie, Inter. Ed., 2010, 49:9995-9997.
Junghans et al., "Anti-Tac-H, a Humanized Antibody to the Interleukin 2 Receptor with New Features for Immunotherapy in Malignant and Immune Disorders," Cancer Res. 1990, 50:1495-1502.
Kabat et al., (1991) "Tabulation and Analysis of Amino Acid and Nucleic Acid Sequences of Precursors, V-Regions, C-Regions, J-Chain, T-Cell Receptors for Antigen, T-Cell Surface Antigens, beta2-Microglobulins, Major Histocompatibility Antigens, Thy-1, Complement, C-Reactive Protein, Thymopoietin, Integrins, Post-gamma Globulin, alpha2-Macroglobulins, and Other Related Proteins", Sequences of Proteins of Immunological Interest, Fifth Edition; NIH Publication No. 91-3242, National Institutes of Health, Bethesda, Md. (37 pages).
Klein et al., "Progress in overcoming the chain association issue in bispecific heterodimeric IgG antibodies," mAbs, 2012, 4:6 653-663 (12 pages).
Kontermann, "Dual targeting strategies with bispecific antibodies," mAbs, 2012, 4(2):182-197.
Kraft et al., "Anti-CD63 antibodies suppress IgE-dependent allergic reactions in vitro and in vivo," JEM, 2005, 201(3):385-396.
Kufer et al., "A revival of bispecific antibodies," Trends Biotechnol., 2004, 22(5):238-244.
Lambert and Chari, "Ado-trastuzumab Emtansine (T-DM1): An Antibody-Drug Conjugate (ADC) for HER2-Positive Breast Cancer," Journal of Medicinal Chemistry, (Aug. 28, 2014), 57(16):6949-6964.
Langer, "New Methods of Drug Delivery," Science, 1990, 249:1527-1533.
Lee et al., "Impaired Retrograde Membrane Traffic Through Endosomes in a Mutant CHO Cell Defective in Phosphalidyl Serine Synthesis," Genes to Cells, 2012, 17:728-736.

(56) References Cited

OTHER PUBLICATIONS

Li et al., "Cell Type and Culture Condition-Dependent Alternative Splicing in Human Breast Cancer Cells Revealed by Splicing-Sensitive Microarrays," Cancer Res., Feb. 15, 2006, 66(4):1990-1999.
Li et al., "Dkk1 Stabilizes Wnt Co-Receptor LRP6: Implication for Wnt Ligand-Induced LRP6 Down-Regulation," PLoS One Jun. 2010, 5(6):e11014.
Lieu et al., "The Golgin GCC88 is Required for Efficient Retrograde Transport of Cargo from the Early Endosomes to the Trans-Golgi Network," Mol. Biol. Cell, Dec. 2007, 18:4979-4991.
Lloyd et al., "Modelling the human immune response: performance of a $10^{11}$ human antibody repertoire against a broad panel of therapeutically relevant antigens," Protein Engineering, Design & Selection, 2009, 22(3):159-168.
Martin et al., "Modeling antibody hypervariable loops: A combined algorithm," Proc. Natl. Acad. Sci. USA, 1989, 86:9268-9272.
Matsuda et al. "BRI3 inhibits amyloid precursor protein processing in a mechanistically distinct manner from its homologue dementia gene BRI2," Journal of Biological Chemistry, 2009, 284(23):15815-15825.
Mazor et al., "Enhanced tumor-targeting selectivity by modulating bispecific antibody binding affinity and format valence," Scientific Reports, Jan. 9, 2017, 7:40098.
McDonagh et al., "Antitumor Activity of a Novel Bispecific Antibody That Targets the ErbB2/ErbB3 Oncogenic Unit and Inhibits Heregulin-Induced Activation of ErbB3", Molecular Cancer Therapeutics, Mar. 2012, 11(3):582-593, XP002684950, ISSN: 1535-7163, DOI:10.1158/1535-7163.MCT-11-0820.
Moody et al., "Receptor Crosslinking: A General Method to Trigger Internalization and Lysosomal Targeting of Therapeutic Receptor:Ligand Complexes," Molecular Therapy, 2015, 23(12):1888-1898.
Mordenti et al., "Interspecies Scaling of Clearance and Volume of Distribution Data for Five Therapeutic Proteins," Pharmaceutical Research, 1991, 8:1351-1359.
Muller-Loennies, et al., "Identification of a Cross-reactive Epitope Widely Present in Lipopolysaccharide from Enterobacteria and Recognized by the Cross-protective Monoclonal Antibody WN1 222-5," J. Biol. Chern., 2003, 278(28):25618-25627.
Pandey et al., "Amyloid precursor-like protein 2 (APLP2) affects the actin cytoskeleton and increases pancreatic cancer growth and metastasis," Oncotarget. Feb. 10, 2015, 6(4):2064-2075.
Pandey et al., "Amyloid precursor protein and amyloid precursor-like protein 2 in cancer," Oncotarget. Apr. 12, 2016, 7(15):19430-19444, doi:10.18632/oncotarget.7103.
Paschkowsky et al., "Alternative Processing of the Amyloid Precursor Protein Family by Rhomboid Protease RHBDL4," Journal of Biological Chemistry, 2016, 291(42):21903-21912.
Pearson, "Using the FASTA Program to Search Protein and DNA Sequence Databases," Chapter 26, Methods Mol. Biol., 1994, 26:307-331.
Phillips et al., "Dual Targeting of HER2-Positive Cancer with Trastuzumab Emtansine and Pertuzumab: Critical Role for Neuregulin Blockade in Antitumor Response to Combination Therapy," Clinical Cancer Research, 2014, 20(2):456-468.
Poljak, "Production and structure of diabodies," Structure, 1994, 2:1121-1123.
Powell et al., "Compendium of Excipients for Parenteral Formulations" PDA J. Pharm. Sci. Technol., 1998, 52:238-311.
Rabuka et al., "Site-specific chemical protein conjugation using genetically encoded aldehyde tags," Nat. Protocols, 2012, 7(6):1052-1067.
Reineke, "Antibody Epitope Mapping Using Arrays of Synthetic Peptides," Methods Mol. Biol., Chapter 26, 2004, 248:443-463.
Rhoden et al., "A Modeling and Experimental Investigation of the Effects of Antigen Density, Binding Affinity, and Antigen Expression Ratio on Bispecific Antibody Binding to Cell Surface Targets," J Biol Chem. 291, May 2016, 291(21):11337-11347, doi:10.1074/jbc.M116.714287.

Ridgway et al., "'Knobs-into-holes' engineering of antibody CH3 domains for heavy chain heterodimerization," Protein Eng., 1996, 9(7):617-621.
Říhová "Receptor-mediated targeted drug or toxin delivery," Advanced Drug Delivery Reviews, 1998, 29:273-289.
Robinson et al., "Targeting ErbB2 and ErbB3 with a bispecific single-chain Fv enhances targeting selectivity and induces a therapeutic effect in vitro", British Journal of Cancer, vol. 99, No. 9, Oct. 28, 2008 (Oct. 28, 2008), pp. 1415-1425, XP009115294, ISSN: 0007-0920, DOI: 10.1038/SJ.BJC. 6604700.
Ryan et al., "Polyclonal Antibody Production Against Chito-Oligosaccharides," Food & Agriculture Immunol., 2001, 13:127-130.
Sapra et al., "Monoclonal antibody-based therapies in cancer: Advances and challenges," Pharmacol. & Therapeutics, 2013, 138:452-469.
Schanzer, J.M. et al. (Jul. 2014). "A Novel Glycoengineered Bispecific Antibody Format for Targeted Inhibition of Epidermal Growth Factor Receptor (EGFR) and Insulin-like Growth Factor Receptor Type I (IGF-1R) Demonstrating Unique Molecular Properties," J. Biol. Chem. 289(27):18693-706.
Schiweck et al., "Sequence analysis and bacterial production of the anti-c-*myc* antibody 9E10: the $V_H$ domain has an extended CDR-H3 and exhibits unusual solubility," FEBS Lett., 1997, 414(1):33-38.
Schumacher et al., "Current Status: Site-Specific Antibody Drug Conjugates," J. Clin. Immunol., 2016, 36(Suppl 1):S100-S107.
Scotti et al., "Additive effects of a prolactin receptor antagonist, G129R, and herceptin on inhibition of HER2-overexpressing breast cancer cells," Breast Cancer Research and Treatment, 2008, 111:241-250.
Sefton, "Implantable Pumps," CRC Crit. Rev. Biomed. Eng., 1987, 14(3):201-240.
Senter, "Activation of Prodrugs by Antibody-Enzyme Conjugates: A New Approach to Cancer Therapy," FASEB J., 1990, 4:188-193.
Shahied et al., "Bispecific Minibodies Targeting HER2/neu and CD16 Exhibit Improved Tumor Lysis When Placed in a Divalent Tumor Antigen Binding Format," J. Biol. Chem., Dec. 2004, 279(52):53907-53914.
Shaunak et al., "Site-specific PEGylation of native disulfide bonds in therapeutic proteins," Nat. Chem. Biol., 2006, 2(6):312-313.
Shields et al., "Lack of Fucose on Human IgG1 N-Linked Oligosaccharide Improves Binding to Human Fc RIII and Antibody-dependent Cellular Toxicity," Journal of Biological Chemistry, 2002, 277(30):26733-26740.
Shimamoto et al., "Peptibodies: A flexible alternative format to antibodies," mAbs, 2012, 4(5):586-591.
Tavare et al., "An effective immuno-PET imaging method to monitor CD8-dependent responses to immunotherapy," Cancer Res., 2016, 76(1):73-82.
Taylor et al., "A transgenic mouse that expresses a diversity of human sequence heavy and light chain immunoglobulins," Nucl. Acids Res., 1992, 20(23):6287-6295.
Hochleitner, "Characterization of a discontinuous epitope of the human immunodeficiency virus (HIV) core protein p24 by epitope excision and differential chemical modification followed by mass spectrometric peptide mapping analysis," Protein Science, 2000, 9:487-496.
Tuli et al., "Mechanism for amyloid precursor-like protein 2 enhancement of major histocompatibility complex class I molecule degradation," J Biol Chem. 2009, 284(49):34296-34307, doi: 10.1074/jbc.M109.039727. Epub Oct. 6, 2009.
Tutt et al., "Trispecific F(ab')₃ Derivatives That Use Cooperative Signaling Via the TCR/CD3 Complex and CD2 to Activate and Redirect Resting Cytotoxic T Cells," J. Immunol., 1991, 147(1):60-69.
Vincent and Zurini, "Current strategies in antibody engineering: Fc engineering and pH-dependent antigen binding, bispecific antibodies and antibody drug conjugates," Biotechnol. J., 2012, 7:1444-1450.
Ward et al., "Binding activities of a repertoire of single immunoglobulin variable domains secreted from *Escherichia coli*," Nature, 1989, 341:544-546.

(56) References Cited

OTHER PUBLICATIONS

Wu et al., "Receptor-mediated in Vitro Gene Transformation by Soluble DNA Carrier System," J. Biol. Chem., 1987, 262(10):4429-4432.
R&D Systems: "Monoclonal—Anti-human APLP-2 Antibody—Catalog No. MAB4945," R&D Systems Online Catalogue, Aug. 29, 2019, retrieved from internet, https://resources.rndsystems.com/pdfs/datasheets/mab4945.pdf.
Atlas Antibodies: "Anti-APLP2 Product Datasheet—Product No. HPA039319," Atlas Antibodies Online Catalogue, Aug. 29, 2019, retrieved from internet, https://atlasantibodies.com/api/print_datasheet/HPA039319.pdf.
Abcam: "Anti-APLP2 antibody ab128603," abcam Online Catalogue, Aug. 29, 2019, retrieved from internet, https://www.abcam.com/aplp2-antibody-ab128603.pdf.
Invitation to Pay Additional Fees with Respect to PCT/US2019/029640 Mailed Jul. 12, 2019.
International Search Report and Written Opinion with Respect to PCT/US2019/029640 Mailed Sep. 11, 2019.
Statement of Relatedness under MPEP 2001.06 with Respect to U.S. Appl. No. 17/051,987 dated Oct. 13, 2021.
Jager et al., "High level transient production of recombinant antibodies and antibody fusion proteins in HEK293 cells," BMC Biotechnol., 13:52, (2013).
Spiess et al., "Alternative molecular formats and therapeutic applications for bispecific antibodies," Mol. Immunol., 67(2 Pt A):95-106, (2015).
Statement of Relatedness under MPEP 2001.06 with Respect to U.S. Appl. No. 17/051,987 dated Feb. 1, 2024.

\* cited by examiner

Isotype Control DM1

HER2 Control DM1

25018 DM1

HER2 Control

25018 DM1

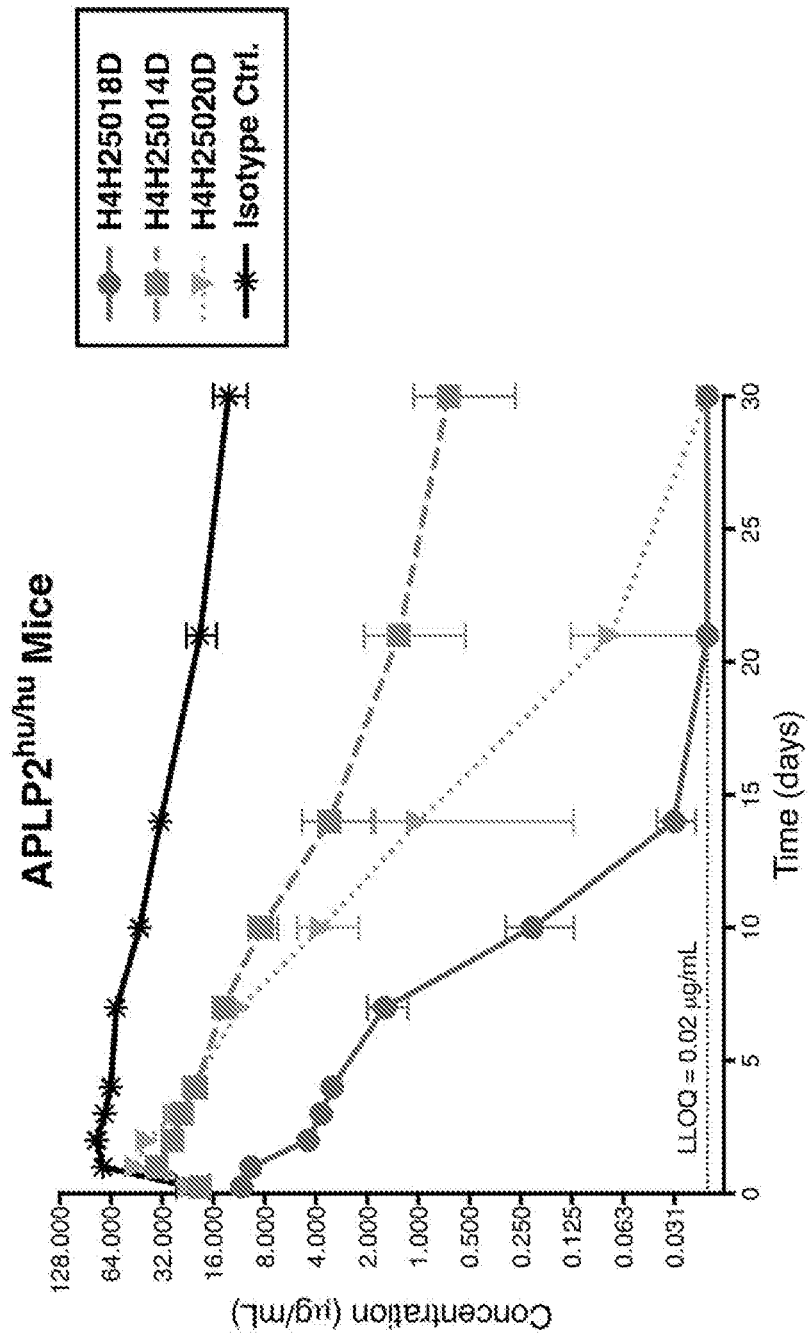

ANTIBODIES, AND BISPECIFIC ANTIGEN-BINDING MOLECULES THAT BIND HER2 AND/OR APLP2, CONJUGATES, AND USES THEREOF

This application is a U.S. National Phase Application filed under 35 U.S.C. § 371 of PCT Application No. PCT/US2019/029640, filed Apr. 29, 2019, which claims priority to U.S. Provisional Application Ser. No. 62/825,144, filed Mar. 28, 2019, U.S. Provisional Patent Application Ser. No. 62/728,622, filed Sep. 7, 2018, and U.S. Provisional Patent Application Ser. No. 62/664,924, filed Apr. 30, 2018, each of which application is incorporated by reference in its entirety.

FIELD OF THE INVENTION

The present invention relates to antibodies, and antigen-binding fragments thereof, which are specific for human epidermal growth factor receptor 2 (HER2), and methods of use thereof. The present invention also relates to bispecific antigen-binding molecules that bind HER2 and amyloid precursor-like protein 2 (APLP2), and methods of use thereof. The present invention further relates to antibody-drug conjugates comprising an anti-HER2 antibody, or anti-HER2/anti-APLP2 bispecific antibody, or fragment thereof and a therapeutic agent (e.g., a cytotoxic drug).

BACKGROUND

Human epidermal growth factor receptor 2 (HER2) is a tyrosine kinase receptor growth-promoting protein found on the surface of some cancer cells and is associated with aggressive disease. About one in five breast cancers overexpress HER2. To be considered HER2-positive, tumor cells are usually tested by one of two methods: immunohistochemistry (IHC) or fluorescent in situ hybridization (FISH). IHC test results are reported as: 0, IHC1+, IHC2+ or IHC3+. A finding of IHC3+ is considered HER2-positive. A finding of IHC2+ is borderline and typically is confirmed by a positive FISH test.

HER2 is a clinically validated antibody-drug conjugate (ADC) target in breast cancer. To achieve maximal anti-tumor effect, the ADC must bind specifically to HER2 and internalize into the cell, where ADC processing results in release of the toxin into the cytosol. While a high degree of tumor specificity and surface expression levels are known to be essential features of a good ADC target, the trafficking properties of ADC targets have not been thoroughly explored.

For example, a HER2 targeting antibody conjugated to the potent toxin maytansine "DM1" (Trastuzumab-emtansine, or T-DM1) is approved for the treatment of metastatic breast cancer. However, inefficient lysosomal trafficking of HER2 limits T-DM1 efficacy to those patients that express very high levels of HER2 (IHC 3+, or FISH amplification ratio>2). Significant efforts are being directed towards generation of HER2-ADCs that efficiently induce regression of tumors expressing intermediate HER2 levels (IHC2+). These efforts rely on the use of more potent toxins and/or on enhancing HER2 internalization.

APLP2 is a single pass transmembrane protein (Uniprot Q06481) with tyrosine-based internalization signals. Multiple APLP2 isoforms have been reported (Li, C., et al. *Cancer Res.* 2006 Feb. 15; 66(4):1990-9; Pandey, P., et al. *Oncotarget.* 2016 Apr. 12; 7(15):19430-44. doi: 10.18632/oncotarget.7103). APLP2 is ubiquitously expressed in normal tissues and reported to be overexpressed in certain cancers (Pandey, P., et al. *Oncotarget.* 2015 Feb. 10; 6(4): 2064-75.). Consistent with its subcellular localization in intracellular vesicles, APLP2 is efficiently internalized from the plasma membrane and targeted for rapid lysosomal degradation. A suggested biological function of APLP2 is to promote lysosomal targeting and degradation of PCSK9 and MHC class I (DeVray, R. M., et al. *J Biol Chem.* 2013 Apr. 12; 288(15):10805-18. doi: 10.1074/jbc.M113.453373. Epub 2013 Feb. 19.; Tuli, A., et al. *J Biol Chem.* 2009 Dec. 4; 284(49):34296-307. doi: 10.1074/jbc.M109.039727. Epub 2009 Oct. 6).

Antigen-binding molecules that enhance HER2 internalization and/or trafficking to lysosomes would provide useful therapies where specific targeting and killing of HER2-expressing cells is desired.

BRIEF SUMMARY OF THE INVENTION

In a first aspect, the present invention provides bispecific antibodies and antigen-binding fragments thereof that bind human HER2 and human APLP2. The bispecific antibodies according to this aspect of the invention are useful, inter alia, for targeting cells, e.g., breast cancer cells, expressing HER2 and APLP2, stimulating internalization of the bispecific antibodies, e.g., under circumstances where degradation and lysosomal trafficking of HER2 or the antibodies is beneficial or desirable. For example, the bispecific antibodies can direct bispecific anti-HER2×APLP2 antibody drug conjugates (ADCs) into the lysosomes of specific HER2-expressing cells, such as breast tumor cells, for release of the drug conjugate and targeted cytotoxicity. The present invention also provides antibodies and antigen-binding fragments thereof that bind to human HER2. The antibodies according to this aspect of the invention are useful, inter alia, for targeting cells expressing HER2. The present invention also provides antibodies and antigen-binding fragments thereof that bind to human APLP2. The antibodies according to this aspect of the invention are useful, inter alia, for targeting cells expressing APLP2 and a target antigen, such as HER2, for rapid internalization of the binding molecule into the cell by APLP2.

Exemplary anti-HER2 antibodies of the present invention are listed in Table 1. Table 1 sets forth the amino acid and nucleic acid sequence identifiers of the heavy chain variable regions (HCVRs) and light chain variable regions (LCVRs), as well as heavy chain complementarity determining regions (HCDR1, HCDR2 and HCDR3), and light chain complementarity determining regions (LCDR1, LCDR2 and LCDR3) of the exemplary anti-HER2 antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-HER2 antibodies listed in Table 1. In certain embodiments, the HCVR/LCVR amino acid sequence pair is selected from the group consisting of SEQ ID NOs: 2/10 (e.g., H4H135050P2) and 18/10 (e.g., H4H13055P2).

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-HER2 antibodies listed in Table 1. In certain embodiments, the HCDR3/LCDR3 amino acid sequence pair is selected from the group consisting of SEQ ID NOs: 2/10 (e.g., H4H135050P2) and 18/10 (e.g., H4H13055P2).

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-HER2 antibodies listed in Table 1. In certain embodiments, the HCDR1-HCDR2-HCDR3-LCDR1-LCDR2-LCDR3 amino acid sequences set is selected from the group consisting of SEQ ID NOs: 4-6-8-12-14-16 (e.g., H4H13050P2) and 20-22-24-12-14-16 (e.g., H4H13055P2).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-HER2 antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/10 (e.g., H4H135050P2) and 18/10 (e.g., H4H13055P2). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-HER2 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 1, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 1, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 1, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 1, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 1, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 1, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 1, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 1, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-HER2 antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-HER2 antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 1, or a substantially similar sequence thereof having at least 90%, at least 95%, at least 98% or at least 99% sequence identity thereto, and a polynucleotide sequence selected from any of the LCVR nucleic acid sequences listed in Table 1, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-HER2 antibody listed in Table 1.

The present invention also provides recombinant expression vectors capable of expressing a polypeptide comprising a heavy or light chain variable region of an anti-HER2 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments and recovering the antibodies and antibody fragments so produced.

The present invention includes anti-HER2 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shields et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds HER2 and a pharmaceutically acceptable carrier. In a related aspect, the invention features a composition which is a combination of an anti-HER2 antibody and a second therapeutic agent. In one embodiment, the second therapeutic agent is any agent that is advantageously combined with an anti-HER2 antibody. Additional combination therapies and co-formulations involving the anti-HER2 antibodies of the present invention are disclosed elsewhere herein.

In another aspect, the invention provides therapeutic methods for targeting/killing tumor cells expressing HER2 using an anti-HER2 antibody of the invention, wherein the therapeutic methods comprise administering a therapeutically effective amount of a pharmaceutical composition comprising an anti-HER2 antibody of the invention to a subject in need thereof. In some cases, the anti-HER2 antibodies (or antigen-binding fragments thereof) can be used for treating breast cancer, or may be modified to be more cytotoxic by methods, including but not limited to, modified Fc domains to increase ADCC (see e.g. Shield et al. (2002) JBC 277:26733), radioimmunotherapy, antibody-drug conjugates, or other methods for increasing the efficiency of tumor ablation.

The present invention also includes the use of an anti-HER2 antibody of the invention in the manufacture of a medicament for the treatment of a disease or disorder (e.g., cancer) related to or caused by HER2-expressing cells. In one aspect, the invention relates to a compound comprising an anti-HER2 antibody or antigen-binding fragment, or a bispecific anti-HER2×APLP2 antibody, as disclosed herein, for use in medicine. In one aspect, the invention relates to a compound comprising an antibody-drug conjugate (ADC) as disclosed herein, for use in medicine.

In yet another aspect, the invention provides monospecific anti-HER2 antibodies for diagnostic applications, such as, e.g., imaging reagents.

In yet another aspect, the invention provides therapeutic methods for enhancing HER2 internalization into and/or degradation by a lysosome using an anti-APLP2 antibody or antigen-binding portion of an antibody of the invention, wherein the therapeutic methods comprise administering a therapeutically effective amount of a pharmaceutical composition comprising an antibody.

In another aspect, the present invention provides an antibody or antigen-binding fragment thereof that binds HER2 with a $K_D$ of less than 10 nM as measured by surface plasmon resonance, or equivalent assay. In another aspect, the present invention provides an antibody or antigen-binding fragment thereof that binds HER2-expressing cells with an $EC_{50}$ of less than 50 nM as measured by FACS analysis, or equivalent assay. In another aspect, the present invention provides an antibody or antigen-binding fragment thereof that binds and is internalized into lysosomes of a HER2-expressing cells. In some embodiments, the HER2-expressing cells have an IHC2+classification.

The invention further provides an antibody or antigen-binding fragment that competes for binding to human HER2 with a reference antibody comprising an HCVR/LCVR amino acid sequence pair as set forth in Table 1. In another aspect, the invention provides an antibody or antigen-binding fragment that competes for binding to human HER2 with a reference antibody comprising an HCVR/LCVR amino acid sequence pair selected from the group consisting of SEQ ID NOs: 2/10 (e.g., H4H135050P2) and 18/10 (e.g., H4H13055P2).

The invention furthermore provides an antibody or antigen-binding fragment, wherein the antibody or antigen-binding fragment thereof binds to the same epitope on human HER2 as a reference antibody comprising an HCVR/LCVR amino acid sequence pair as set forth in Table 1. In another aspect, the antibody or antigen-binding fragment binds to the same epitope on human HER2 as a reference antibody comprising an HCVR/LCVR amino acid sequence pair selected from the group consisting of SEQ ID NOs: 2/10 (e.g., H4H135050P2) and 18/10 (e.g., H4H13055P2).

The invention further provides an isolated antibody or antigen-binding fragment thereof that binds human HER2, wherein the antibody or antigen-binding fragment comprises: the complementarity determining regions (CDRs) of a heavy chain variable region (HCVR) having an amino acid sequence as set forth in Table 1; and the CDRs of a light chain variable region (LCVR) having an amino acid sequence as set forth in Table 1. In another aspect, the isolated antibody or antigen-binding fragment comprises the heavy and light chain CDRs of a HCVR/LCVR amino acid sequence pair selected from the group consisting of SEQ ID NOs: 2/10 (e.g., H4H135050P2) and 18/10 (e.g., H4H13055P2). In yet another aspect, the isolated antibody or antigen-binding fragment comprises HCDR1-HCDR2-HCDR3-LCDR1-LCDR2-LCDR3 domains, respectively, selected from the group consisting SEQ ID NOs: 4-6-8-12-14-16 (e.g., H4H13050P2) and 20-22-24-12-14-16 (e.g., H4H13055P2). In another aspect, the invention provides an isolated antibody or antigen-binding fragment thereof that binds human HER2, wherein the antibody or antigen-binding fragment comprises: (a) a heavy chain variable region (HCVR) having an amino acid sequence selected from the group consisting of SEQ ID NOs: 4, 6, 8, 20, 22, 24; and (b) a light chain variable region (LCVR) having an amino acid sequence selected from the group consisting of SEQ ID NOs: 12, 14, 16. In a further aspect, the isolated antibody or antigen-binding fragment comprises a HCVR/LCVR amino acid sequence pair selected from the group consisting of SEQ ID NOs: 2/10 (e.g., H4H135050P2) and 18/10 (e.g., H4H13055P2).

According to another aspect, the present invention provides antibody-drug conjugates comprising an anti-HER2 antibody or antigen-binding fragment thereof and a therapeutic agent (e.g., a cytotoxic agent). In some embodiments, the antibody or antigen-binding fragment and the cytotoxic agent are covalently attached via a linker, as discussed herein. In various embodiments, the anti-HER2 antibody or antigen-binding fragment can be any of the anti-HER2 antibodies or fragments described herein.

In another aspect, the present invention provides antibodies and antigen-binding fragments thereof that bind to human amyloid precursor-like protein 2 (APLP2), which antibodies and antigen-binding fragments have a low affinity to APLP2. The antibodies according to this aspect of the invention are useful, inter alia, for specifically directing the internalization and/or degradation of another target, e.g., HER2, when the target and APLP2 are expressed by the same cell, e.g., a tumor cell. However, due to their low affinity, such anti-APLP2 antibodies remain inactive by themselves, e.g., are unable to bind absent association with a targeting arm, e.g., as a bispecific antibody, absent expression by the cell of both the target bound by the targeting arm and APLP2. As such, an aspect of the invention provides bispecific antigen-binding molecules effective for avidity-driven pairing of a tumor-associated antigen and APLP2 on tumor cells. As such, this aspect of the invention also provides bispecific antibodies and antigen-binding fragments thereof that bind human APLP2 and a human target, e.g., HER2. The bispecific antibodies according to this aspect of the invention are useful, inter alia, for targeting cells, e.g., breast cancer cells, expressing APLP2 and HER2, stimulating internalization of the bispecific antibodies, e.g., under circumstances where degradation and/or lysosomal trafficking of APLP2 or the antibodies is beneficial or desirable. For example, the bispecific antibodies can direct bispecific anti-HER2×APLP2 antibody drug conjugates (ADCs) into the lysosomes of specific HER2-expressing cells, such as breast tumor cells, for release of the drug conjugate and targeted cytotoxicity.

Exemplary anti-APLP2 antibodies of the present invention are listed in Table 2. Table 2 sets forth the amino acid and nucleic acid sequence identifiers of the heavy chain variable regions (HCVRs) and light chain variable regions (LCVRs), as well as heavy chain complementarity determining regions (HCDR1, HCDR2 and HCDR3), and light chain complementarity determining regions (LCDR1, LCDR2 and LCDR3) of the exemplary anti-APLP2 antibodies.

The present invention provides antibodies, or antigen-binding fragments thereof, comprising an HCVR comprising an amino acid sequence selected from any of the HCVR amino acid sequences listed in Table 2, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 2, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 2 paired with any of the LCVR amino acid sequences listed in Table 2. According to certain embodiments, the present invention provides antibodies, or antigen-binding fragments thereof, comprising an HCVR/LCVR amino acid sequence pair contained within any of the exemplary anti-APLP2 antibodies listed in Table 2. In certain embodiments, the HCVR/LCVR amino acid sequence pair is selected from the group consisting of SEQ ID NOs: 26/10 (e.g., H4×H21362P2), 34/10 (e.g., H4×H21387P2), and 42/10 (e.g., H4×H21371P2).

The present invention also provides antibodies, or antigen-binding fragments thereof, comprising a heavy chain CDR1 (HCDR1) comprising an amino acid sequence selected from any of the HCDR1 amino acid sequences listed in Table 2 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 2 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 2 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 2 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 2 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 2 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 2 paired with any of the LCDR3 amino acid sequences listed in Table 2. According to certain embodiments, the present invention provides antibodies, or antigen-binding fragments thereof, comprising an HCDR3/LCDR3 amino acid sequence pair contained within any of the exemplary anti-APLP2 antibodies listed in Table 2. In certain embodiments, the HCDR3/LCDR3 amino acid sequence pair is selected from the group consisting of SEQ ID NOs: 26/10 (e.g., H4xH21362P2), 34/10 (e.g., H4xH21387P2), and 42/10 (e.g., H4xH21371P2).

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-APLP2 antibodies listed in Table 2. In certain embodiments, the HCDR1-HCDR2-HCDR3-LCDR1-LCDR2-LCDR3 amino acid sequences set is selected from the group consisting of SEQ ID NOs: 28-30-32-12-14-16 (e.g., H4xH21362P2), 36-38-40-12-14-16 (e.g., H4xH21387P2) and 44-46-48-12-14-16 (e.g., H4xH21371P2).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-APLP2 antibodies listed in Table 2. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 26/10 (e.g., H4xH21362P2), 34/10 (e.g., H4xH21387P2), and 42/10 (e.g., H4xH21371P2). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-APLP2 antibodies or portions thereof. For example, the present invention provides nucleic acid molecules encoding any of the HCVR amino acid sequences listed in Table 2; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 2; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 2; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 2; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 2; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 2; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 2; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 2; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-APLP2 antibodies listed in Table 2.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-APLP2 antibodies listed in Table 2.

The present invention also provides nucleic acid molecules encoding both an HCVR and an LCVR, wherein the HCVR comprises an amino acid sequence of any of the HCVR amino acid sequences listed in Table 2, and wherein the LCVR comprises an amino acid sequence of any of the LCVR amino acid sequences listed in Table 2. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-APLP2 antibody listed in Table 2.

The present invention also provides recombinant expression vectors capable of expressing a polypeptide comprising a heavy or light chain variable region of an anti-APLP2 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 2. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present invention includes anti-APLP2 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds APLP2 and a pharmaceutically acceptable carrier. In a related aspect, the invention features a composition which is a combination of an anti-APLP2 antibody and a second therapeutic agent. In one embodiment, the second therapeutic agent is any agent that is advantageously combined with an anti-APLP2 antibody. Additional combination therapies and co-formulations involving the anti-APLP2 antibodies of the present invention are disclosed elsewhere herein.

In another aspect, the invention provides therapeutic methods for targeting/killing tumor cells expressing APLP2 using an anti-APLP2 antibody of the invention, wherein the therapeutic methods comprise administering a therapeutically effective amount of a pharmaceutical composition comprising an anti-APLP2 antibody of the invention to a subject in need thereof. In some cases, the anti-APLP2 antibodies (or antigen-binding fragments thereof) can be used for treating breast cancer, or may be modified to be more cytotoxic by methods, including but not limited to, modified Fc domains to increase ADCC (see e.g. Shield et al. (2002) JBC 277:26733), radioimmunotherapy, antibody-drug conjugates, or other methods for increasing the efficiency of tumor ablation.

The present invention also includes the use of an anti-APLP2 antibody of the invention in the manufacture of a medicament for the treatment of a disease or disorder (e.g., cancer) related to or caused by APLP2-expressing cells. In one aspect, the invention relates to a compound comprising an anti-APLP2 antibody or antigen-binding fragment, or a bispecific anti-APLP2×APLP2 antibody, as disclosed herein, for use in medicine. In one aspect, the invention relates to a compound comprising an antibody-drug conjugate (ADC) as disclosed herein, for use in medicine.

In yet another aspect, the invention provides monospecific anti-APLP2 antibodies for diagnostic applications, such as, e.g., imaging reagents.

In yet another aspect, the invention provides therapeutic methods for enhancing APLP2 internalization into and/or degradation by a lysosome using an anti-APLP2 antibody or antigen-binding portion of an antibody of the invention, wherein the therapeutic methods comprise administering a therapeutically effective amount of a pharmaceutical composition comprising an antibody.

In another aspect, the present invention provides an antibody or antigen-binding fragment thereof that binds APLP2-expressing cells with a $K_D$ of greater than 100 nM as measured by surface plasmon resonance, or equivalent assay. In another aspect, the present invention provides an antibody or antigen-binding fragment thereof that binds APLP2-expressing cells with an EC50 of greater than 100 nM as measured by FACS analysis. In another aspect, the present invention provides an antibody or antigen-binding fragment thereof that binds and is internalized into lysosomes of APLP2-expressing cells in the event that the antibody also binds to HER2 expressed on the same cell.

The invention further provides an antibody or antigen-binding fragment that competes for binding to human APLP2 with a reference antibody comprising an HCVR/LCVR amino acid sequence pair as set forth in Table 2. In another aspect, the invention provides an antibody or antigen-binding fragment that competes for binding to human APLP2 with a reference antibody comprising an HCVR/LCVR amino acid sequence pair selected from the group consisting of SEQ ID NOs: 26/10 (e.g., H4×H21362P2), 34/10 (e.g., H4×H21387P2), and 42/10 (e.g., H4×H21371P2)

The invention furthermore provides an antibody or antigen-binding fragment, wherein the antibody or antigen-binding fragment thereof binds to the same epitope on human APLP2 as a reference antibody comprising an HCVR/LCVR amino acid sequence pair as set forth in Table 2. In another aspect, the antibody or antigen-binding fragment binds to the same epitope on human APLP2 as a reference antibody comprising an HCVR/LCVR amino acid sequence pair selected from the group consisting of SEQ ID NOs: 26/10 (e.g., H4×H21362P2), 34/10 (e.g., H4×H21387P2), and 42/10 (e.g., H4×H21371P2)

The invention further provides an isolated antibody or antigen-binding fragment thereof that binds human APLP2, wherein the antibody or antigen-binding fragment comprises: the complementarity determining regions (CDRs) of a heavy chain variable region (HCVR) having an amino acid sequence as set forth in Table 2; and the CDRs of a light chain variable region (LCVR) having an amino acid sequence as set forth in Table 2. In another aspect, the isolated antibody or antigen-binding fragment comprises the heavy and light chain CDRs of a HCVR/LCVR amino acid sequence pair selected from the group consisting of SEQ ID NOs: 26/10 (e.g., H4×H21362P2), 34/10 (e.g., H4×H21387P2), and 42/10 (e.g., H4×H21371P2). In yet another aspect, the isolated antibody or antigen-binding fragment comprises HCDR1-HCDR2-HCDR3-LCDR1-LCDR2-LCDR3 domains, respectively, selected from the group consisting SEQ ID NOs: 28-30-32-12-14-16 (e.g., H4×H21362P2), 36-38-40-12-14-16 (H4×H21387P2) and 44-46-48-12-14-16 (e.g., H4×H21371P2). In another aspect, the invention provides an isolated antibody or antigen-binding fragment thereof that binds human APLP2, wherein the antibody or antigen-binding fragment comprises: (a) a heavy chain variable region (HCVR) having an amino acid sequence selected from the group consisting of SEQ ID NOs: 28, 30, 32, 36, 38, 40, 44, 46, and 48; and (b) a light chain variable region (LCVR) having an amino acid sequence selected from the group consisting of SEQ ID NOs: 12, 14, 16. In a further aspect, the isolated antibody or antigen-binding fragment comprises a HCVR/LCVR amino acid sequence pair selected from the group consisting of SEQ ID NOs: 26/10 (e.g., H4×H21362P2), 34/10 (e.g., H4×H21387P2), and 42/10 (e.g., H4×H21371P2).

According to another aspect, the present invention provides antibody-drug conjugates comprising an anti-APLP2 antibody or antigen-binding fragment thereof and a therapeutic agent (e.g., a cytotoxic agent). In some embodiments, the antibody or antigen-binding fragment and the cytotoxic agent are covalently attached via a linker, as discussed herein. In various embodiments, the anti-APLP2 antibody or antigen-binding fragment can be any of the anti-APLP2 antibodies or fragments described herein.

According to another aspect, the present invention provides bispecific antigen-binding molecules (e.g., antibodies) that bind HER2 and APLP2. Such bispecific antigen-binding molecules are also referred to herein as "anti-HER2×APLP2 binding proteins," "anti-HER2/anti-APLP2 bispecific molecules," "anti-APLP2/anti-HER2 bispecific molecules," or "HER2×APLP2 bsAbs." The anti-HER2 portion of the anti-HER2/anti-APLP2 bispecific molecule is useful for targeting cells (e.g., tumor cells) that express HER2 (e.g., breast tumors), and the anti-APLP2 portion of the bispecific molecule is useful for internalization and/or degradation of the bound HER2 molecule, which may result in the release of the drug conjugate where applicable. The simultaneous binding of HER2 and APLP2 on a tumor cell, e.g., a breast cancer cell, facilitates internalization of the anti-HER2×APLP2 binding molecule, and when conjugated to a drug, the drug which may mediate cytotoxicity of the targeted tumor cell by drug. The anti-HER2/anti-APLP2 bispecific molecules of the invention are therefore useful, inter alia, for treating diseases and disorders related to or caused by HER2-expressing tumors (e.g., breast cancers).

The bispecific antigen-binding molecules according to this aspect of the present invention comprise a first antigen-binding domain that specifically binds human APLP2, and a second antigen-binding domain that specifically binds HER2. The present invention includes anti-HER2/anti-APLP2 bispecific molecules (e.g., bispecific antibodies, bispecific binding molecules, and the like) wherein each antigen-binding domain comprises a heavy chain variable region (HCVR) paired with a light chain variable region (LCVR). In certain exemplary embodiments of the invention, the anti-APLP2 antigen-binding domain and the anti-HER2 antigen binding domain each comprise different, distinct HCVRs paired with a common LCVR. For example, as illustrated in Example 2 herein, bispecific antibodies were constructed comprising a first antigen-binding domain that specifically binds APLP2, wherein the first antigen-binding domain comprises an HCVR derived from an anti-APLP2 antibody paired with an LCVR derived from an anti-HER2 antibody (e.g., the same LCVR that is included in the anti-HER2 antigen-binding domain); and a second antigen-binding domain that specifically binds HER2, wherein the second antigen-binding domain comprises an HCVR/LCVR derived from an anti-HER2 antibody. In other words, in the exemplary molecules disclosed herein, the pairing of an HCVR from an anti-APLP2 antibody with an LCVR from an anti-HER2 antibody creates an antigen-binding domain that specifically binds APLP2 (but does not bind HER2). In such embodiments, the first and second antigen-binding domains comprise distinct anti-APLP2 and anti-HER2 HCVRs but share a common LCVR. The amino acid sequence of this LCVR is shown, e.g., in SEQ ID NO:10, and the amino acid sequences of the corresponding CDRs (i.e., LCDR1-LCDR2-LCDR3) are shown in SEQ ID NOs: 12-14-16, respectively. Genetically modified mice can be used to produce fully human bispecific antigen-binding molecules comprising two different heavy chains that associate with an identical light chain that comprises a variable domain derived from one of two different human light chain variable region gene segments. Alternatively, variable heavy chains may be paired with one common light chain and produced through recombinant expression in host cells. As such, the antibodies of the invention can comprise immunoglobulin heavy chains associated with a single rearranged light chain. In some embodiments, the light chain comprises a variable domain derived from a human Vκ1-39 gene segment or a Vκ3-20 gene segment. In other embodiments, the light chain comprises a variable domain derived from a human Vκ1-39 gene segment rearranged with a human Jκ5 or a human Jκ1 gene segment.

The present invention provides anti-APLP2/anti-HER2 bispecific molecules, wherein the first antigen-binding domain that specifically binds APLP2 comprises any of the HCVR amino acid sequences, any of the LCVR amino acid sequences, any of the HCVR/LCVR amino acid sequence pairs, any of the heavy chain CDR1-CDR2-CDR3 amino acid sequences, or any of the light chain CDR1-CDR2-CDR3 amino acid sequences as set forth in Table 2.

In addition, the present invention provides anti-APLP2/anti-HER2 bispecific molecules, wherein the first antigen-binding domain that specifically binds APLP2 comprises any of the HCVR amino acid sequences as set forth in Tables 2 and 3 herein. The first antigen-binding domain that specifically binds APLP2 may also comprise any of the LCVR amino acid sequences as set forth in Table 2 herein. According to certain embodiments, the first antigen-binding domain that specifically binds APLP2 comprises any of the HCVR/LCVR amino acid sequence pairs as set forth in Table 2 herein. The present invention also provides anti-APLP2/anti-HER2 bispecific molecules, wherein the first antigen-binding domain that specifically binds APLP2 comprises any of the heavy chain CDR1-CDR2-CDR3 amino acid sequences as set forth in Table 2 herein, and/or any of the light chain CDR1-CDR2-CDR3 amino acid sequences as set forth in Table 1 herein.

According to certain embodiments, the present invention provides anti-APLP2/anti-HER2 bispecific molecules, wherein the first antigen-binding domain that specifically binds APLP2 comprises a heavy chain variable region (HCVR) having an amino acid sequence as set forth in Table 2 herein or a substantially similar sequence thereof having at least 90%, at least 95%, at least 98% or at least 99% sequence identity.

The present invention also provides anti-APLP2/anti-HER2 bispecific molecules, wherein the first antigen-binding domain that specifically binds APLP2 comprises a light chain variable region (LCVR) having an amino acid sequence as set forth in Tables 1, 2, and 3 herein, or a substantially similar sequence thereof having at least 90%, at least 95%, at least 98% or at least 99% sequence identity.

The present invention also provides anti-APLP2/anti-HER2 bispecific molecules, wherein the first antigen-binding domain that specifically binds APLP2 comprises a HCVR and LCVR (HCVR/LCVR) amino acid sequence pair as set forth in Tables 1, 2 and 3 herein.

The present invention also provides anti-APLP2/anti-HER2 bispecific molecules, wherein the first antigen-binding domain that specifically binds APLP2 comprises a heavy chain CDR3 (HCDR3) domain having an amino acid sequence as set forth in Table 2 herein, or a substantially similar sequence thereto having at least 90%, at least 95%, at least 98% or at least 99% sequence identity; and a light chain CDR3 (LCDR3) domain having an amino acid sequence as set forth in Tables 1, 2, and 3 herein, or a substantially similar sequence thereof having at least 90%, at least 95%, at least 98% or at least 99% sequence identity.

In certain embodiments, the first antigen-binding domain that specifically binds APLP2 comprises a HCDR3/LCDR3 amino acid sequence pair as set forth in Tables 2 and 3 herein.

The present invention also provides anti-APLP2/anti-HER2 bispecific antigen-binding molecules, wherein the first antigen-binding domain that specifically binds APLP2 comprises a heavy chain CDR1 (HCDR1) domain having an amino acid as set forth in Tables 2 and 3 herein, or a substantially similar sequence thereof having at least 90%, at least 95%, at least 98% or at least 99% sequence identity; a heavy chain CDR2 (HCDR2) domain having an amino acid as set forth in 2 and 3, or a substantially similar sequence thereof having at least 90%, at least 95%, at least 98% or at least 99% sequence identity; a heavy chain CDR3 (HCDR3) domain having an amino acid as set forth in 2 and 3, or a substantially similar sequence thereof having at least 90%, at least 95%, at least 98% or at least 99% sequence identity; a light chain CDR1 (LCDR1) domain having an amino acid sequence as set forth in Tables 1, 2, and 3 herein, or a substantially similar sequence thereof having at least 90%, at least 95%, at least 98% or at least 99% sequence identity; a light chain CDR2 (LCDR2) domain having an amino acid sequence as set forth in Tables 1, 2, and 3 herein, or a substantially similar sequence thereof having at least 90%, at least 95%, at least 98% or at least 99% sequence identity, and a light chain CDR3 (LCDR3) domain having an amino acid sequence as set forth in Tables 1, 2, and 3, or a substantially similar sequence thereof having at least 90%, at least 95%, at least 98% or at least 99% sequence identity.

Certain non-limiting, exemplary anti-APLP2/anti-HER2 bispecific antigen-binding molecules of the invention include a first antigen-binding domain that specifically binds APLP2 comprising HCDR1-HCDR2-HCDR3-LCDR1-LCDR2-LCDR3 domains, respectively, having the amino acid sequences as set forth in Tables 2 and 3 herein.

The present invention further provides a bispecific antigen-binding molecule, wherein the first antigen-binding domain that specifically binds human APLP2 comprises heavy chain complementarity determining regions (HCDR1, HCDR2 and HCDR3) from a heavy chain variable region (HCVR) comprising an amino acid sequence as set forth in Tables 2 and 3 and light chain complementarity determining regions (LCDR1, LCDR2 and LCDR3) from a common light chain variable region (LCVR) comprising an amino acid sequence as set forth in Table 1, Table 2, and/or Table 3.

In another aspect, the invention provides a bispecific antigen-binding molecule wherein the first antigen-binding domain that specifically binds human APLP2 comprises heavy chain complementarity determining regions (HCDR1, HCDR2 and HCDR3) from a heavy chain variable region (HCVR) selected from the group consisting of SEQ ID NOs: 26, 34, and 42, and light chain complementarity determining regions (LCDR1, LCDR2 and LCDR3) from a light chain variable region (LCVR) comprising an amino acid sequence selected from the group consisting of SEQ ID NO: 10.

The invention further provides a bispecific antigen-binding molecule, wherein the first antigen-binding domain that specifically binds human APLP2 comprises three heavy chain complementarity determining regions (A1-HCDR1, A1-HCDR2 and A1-HCDR3) and three light chain complementarity determining regions (A1-LCDR1, A1-LCDR2 and A1-LCDR3), wherein A1-HCDR1 comprises an amino acid sequence selected from the group consisting of SEQ ID NOs: 28, 36, and 44; A1-HCDR2 comprises an amino acid sequence selected from the group consisting of SEQ ID NOs: 30, 38, and 46; A1-HCDR3 comprises an amino acid sequence selected from the group consisting of SEQ ID NOs: 32, 40, and 48; A1-LCDR1 comprises an amino acid sequence of SEQ ID NO: 12; A1-LCDR2 comprises an amino acid sequence of SEQ ID NO: 14; and A1-LCDR3 comprises an amino acid sequence of SEQ ID NO: 16.

In a further aspect, the invention provides a bispecific antigen-binding molecule, wherein the first antigen-binding domain that specifically binds human APLP2 comprises the heavy and light chain CDRs of a HCVR/LCVR amino acid sequence pair selected from the group consisting of: SEQ ID NOs: 26/10, 34/10, and 42/10.

In another aspect, the invention provides a bispecific antigen-binding molecule, wherein the first antigen-binding domain that specifically binds human APLP2 comprises three heavy chain complementarity determining regions (A1-HCDR1, A1-HCDR2 and A1-HCDR3) and three light chain complementarity determining regions (A1-LCDR1, A1-LCDR2 and A1-LCDR3), and wherein the second antigen-binding domain that specifically binds human HER2 comprises three heavy chain complementarity determining regions (A2-HCDR1, A2-HCDR2 and A2-HCDR3) and three light chain complementarity determining regions (A2-LCDR1, A2-LCDR2 and A2-LCDR3); wherein A1-HCDR1 comprises an amino acid sequence selected from the group consisting of SEQ ID NOs: 28, 36, and 44; A1-HCDR2 comprises an amino acid sequence selected from the group consisting of SEQ ID NOs: 30, 38, and 46; A1-HCDR3 comprises an amino acid sequence selected from the group consisting of SEQ ID NOs: 32, 40, and 48; A1-LCDR1 comprises an amino acid sequence of SEQ ID NO: 12; A1-LCDR2 comprises an amino acid sequence of SEQ ID NO: 14; and A1-LCDR3 comprises an amino acid sequence of SEQ ID NO: 16; and wherein A2-HCDR1 comprises an amino acid sequence selected from the group consisting of SEQ ID NOs: 4 and 20; A2-HCDR2 comprises an amino acid sequence selected from the group consisting of SEQ ID NOs: 6 and 22; A2-HCDR3 comprises an amino acid sequence selected from the group consisting of SEQ ID NOs: 8 and 24; A2-LCDR1 comprises an amino acid sequence of SEQ ID NO:12; A2-LCDR2 comprises an amino acid sequence of SEQ ID NO: 14; and A2-LCDR3 comprises an amino acid sequence of SEQ ID NO: 16.

In more embodiments, exemplary anti-APLP2/anti-HER2 bispecific antigen-binding molecules of the invention include a bispecific antigen-binding molecule wherein the first antigen-binding domain that specifically binds human APLP2 comprises a HCVR comprising HCDR1-HCDR2-HCDR3 having the amino acid sequences selected from the group consisting of SEQ ID NOs: 28-30-32, 36-38-40, and 44-46-48.

The present invention also provides anti-APLP2/anti-HER2 bispecific molecules, wherein the second antigen-binding domain that specifically binds HER2 comprises a heavy chain variable region (HCVR) having the amino acid sequence selected from the group consisting of SEQ ID NOs: 2 and 18, or a substantially similar sequence thereof having at least 90%, at least 95%, at least 98% or at least 99% sequence identity.

The present invention also provides anti-APLP2/anti-HER2 bispecific molecules, wherein the second antigen-binding domain that specifically binds HER2 comprises a light chain variable region (LCVR) having the amino acid sequence selected from the group consisting of SEQ ID NOs: 10, or a substantially similar sequence thereof having at least 90%, at least 95%, at least 98% or at least 99% sequence identity.

The present invention also provides anti-APLP2/anti-HER2 bispecific molecules, wherein the second antigen-binding domain that specifically binds HER2 comprises a HCVR and LCVR (HCVR/LCVR) amino acid sequence pair selected from the group consisting of SEQ ID NO: 2/10 and 18/10.

The present invention also provides anti-APLP2/anti-HER2 bispecific molecules, wherein the second antigen-binding domain that specifically binds HER2 comprises a heavy chain CDR3 (HCDR3) domain having an amino acid sequence of SEQ ID NO:20 or a substantially similar sequence thereto having at least 90%, at least 95%, at least 98% or at least 99% sequence identity; and a light chain CDR3 (LCDR3) domain having an amino acid sequence of SEQ ID NO: 12, or a substantially similar sequence thereof having at least 90%, at least 95%, at least 98% or at least 99% sequence identity.

In certain embodiments, the second antigen-binding domain that specifically binds HER2 comprises a HCDR3/LCDR3 amino acid sequence pair selected from the group consisting of SEQ ID NOs:18/10.

The present invention also provides anti-APLP2/anti-HER2 bispecific antigen-binding molecules, wherein the second antigen-binding domain that specifically binds HER2 comprises a heavy chain CDR1 (HCDR1) domain having an amino acid sequence selected from the group consisting of SEQ ID NOs:4 and 20, or a substantially similar sequence thereof having at least 90%, at least 95%, at least 98% or at least 99% sequence identity; a heavy chain CDR2 (HCDR2) domain having an amino acid sequence selected from the group consisting of SEQ ID NOs:6 and 22, or a substantially similar sequence thereof having at least 90%, at least 95%, at least 98% or at least 99% sequence identity; a heavy chain CDR3 (HCDR3) domain having an amino acid sequence selected from the group consisting of SEQ ID NOs:8 and 24, or a substantially similar sequence thereof having at least 90%, at least 95%, at least 98% or at least 99% sequence identity; a light chain CDR1 (LCDR1) domain having an amino acid sequence of SEQ ID NO:12, or a substantially similar sequence thereof having at least 90%, at least 95%, at least 98% or at least 99% sequence identity; and a light chain CDR2 (LCDR2) domain having an amino acid sequence of SEQ ID NOs:14, or a substantially similar sequence thereof having at least 90%, at least 95%, at least 98% or at least 99% sequence identity; and a light chain CDR3 (LCDR3) domain having an amino acid sequence of SEQ ID NOs:16, or a substantially similar sequence thereof having at least 90%, at least 95%, at least 98% or at least 99% sequence identity.

Certain non-limiting, exemplary anti-APLP2/anti-HER2 bispecific antigen-binding molecules of the invention include a second antigen-binding domain that specifically binds HER2 comprising HCDR1-HCDR2-HCDR3-LCDR1-LCDR2-LCDR3 domains, respectively, having the amino acid sequences selected from the group consisting of: SEQ ID NOs: 20-22-24-12-14-16.

In a related embodiment, the invention includes anti-APLP2/anti-HER2 bispecific antigen-binding molecules wherein the second antigen-binding domain that specifically binds HER2 comprises the heavy and light chain CDR domains contained within heavy and light chain variable region (HCVR/LCVR) sequences selected from the group consisting of SEQ ID NOs: 18/10.

In another aspect, the invention provides a bispecific antigen-binding molecule comprising a first antigen-binding domain that binds human APLP2 and a second antigen-binding domain that binds human HER2, wherein the second antigen-binding domain is derived from the antibody or antigen-binding fragment of any one of the anti-HER2 antibodies of the invention. In a further aspect, the invention provides a bispecific antigen-binding molecule comprising a first antigen-binding domain that specifically binds human APLP2, and a second antigen-binding domain that specifically binds human HER2.

The invention further provides a bispecific antigen-binding molecule which binds human cells expressing human APLP2 and/or cynomolgus monkey cells expressing cynomolgus APLP2. In another aspect, the bispecific antigen-binding molecule binds human cells expressing human HER2 and/or cynomolgus monkey cells expressing cynomolgus HER2.

In another aspect the invention provides a bispecific antigen-binding molecule which inhibits tumor growth in immunocompromised mice bearing human breast cancer xenografts.

In certain embodiments, anti-APLP2 antibodies of the invention, antigen-binding fragments and bispecific antibodies thereof were made by replacing amino acid residues of a parental in a stepwise manner based on differences between the germline sequence and the parental antibody sequence. As such, anti-APLP2 antibodies may be modified by replacing amino acid residues in CDRs to provide even lower affinity binding to APLP2.

In some embodiments, the invention provides a bispecific antigen-binding molecule, wherein the second antigen-binding domain competes for binding to human HER2 with a reference antigen-binding protein comprising three heavy chain complementarity determining regions (A2-HCDR1, A2-HCDR2 and A2-HCDR3) and three light chain complementarity determining regions (A2-LCDR1, A2-LCDR2 and A2-LCDR3), wherein A2-HCDR1 comprises an amino acid sequence selected from the group consisting of SEQ ID NOs: 20; A2-HCDR2 comprises an amino acid sequence of SEQ ID NO: 22; A2-HCDR3 comprises an amino acid sequence of SEQ ID NO: 24; A2-LCDR1 comprises an amino acid sequence of SEQ ID NO: 12; A2-LCDR2 comprises an amino acid sequence of SEQ ID NO: 14; and A2-LCDR3 comprises an amino acid sequence of SEQ ID NO:16. In some embodiments, the invention provides a bispecific antigen-binding molecule, wherein the second antigen-binding domain competes for binding to human HER2 with a reference antigen-binding protein comprising a heavy chain variable region (HCVR) comprising an amino acid sequence of SEQ ID NO: 18, and a light chain variable region (LCVR) comprising an amino acid sequence of SEQ ID NO:10.

In some embodiments, the invention provides a bispecific antigen-binding molecule, wherein the first antigen-binding domain competes for binding to human APLP2 with a reference antigen-binding protein comprising three heavy chain complementarity determining regions (A1-HCDR1, A1-HCDR2 and A1-HCDR3) and three light chain complementarity determining regions (A1-LCDR1, A1-LCDR2 and A1-LCDR3), wherein A1-HCDR1 comprises an amino acid sequence selected from the group consisting of SEQ ID NOs: 28, 36, and 44; A1-HCDR2 comprises an amino acid sequence selected from the group consisting of SEQ ID NOs: 30, 38, and 46; A1-HCDR3 comprises an amino acid sequence selected from the group consisting of SEQ ID NOs: 32, 40 and 48; A1-LCDR1 comprises an amino acid sequence of SEQ ID NO: 12; A1-LCDR2 comprises an amino acid sequence of SEQ ID NO:14; and A1-LCDR3 comprises an amino acid sequence of SEQ ID NO:16. In some embodiments, the invention provides a bispecific antigen-binding molecule, wherein the first antigen-binding domain competes for binding to human APLP2 with a reference antigen-binding protein comprising a heavy chain variable region (HCVR) comprising an amino acid sequence selected from the group consisting of SEQ ID NOs: 26, 34, and 42, and a light chain variable region (LCVR) comprising an amino acid sequence of SEQ ID NO:10.

In some embodiments, the invention provides a bispecific antigen-binding molecule, wherein the first antigen-binding domain competes for binding to human APLP2 with a reference antigen-binding protein comprising a heavy chain variable region (HCVR) comprising an amino acid sequence selected from the group consisting of SEQ ID NOs: 26, 34, and 42, and a light chain variable region (LCVR) comprising an amino acid sequence of SEQ ID NO:10; and wherein the second antigen-binding domain competes for binding to human HER2 with a reference antigen-binding protein comprising a heavy chain variable region (HCVR) comprising an amino acid sequence selected from the group consisting of SEQ ID NO:2 and 18, and a light chain variable region (LCVR) comprising an amino acid sequence of SEQ ID NO: 10.

In one aspect, the invention provides a pharmaceutical composition comprising an anti-HER2 antigen-binding molecule or anti-HER2/anti-APLP2 bispecific antigen-binding molecule and a pharmaceutically acceptable carrier or diluent. The invention further provides a method for treating a cancer in a subject, the method comprising administering to the subject the pharmaceutical composition comprising an anti-HER2 antigen-binding molecule or anti-HER2/anti-APLP2 bispecific antigen-binding molecule and a pharmaceutically acceptable carrier or diluent. In some embodiments, the cancer is selected from the group consisting of prostate cancer, bladder cancer, cervical cancer, lung cancer, colon cancer, kidney cancer, breast cancer, pancreatic cancer, stomach cancer, uterine cancer, and ovarian cancer. In some cases, the cancer is breast cancer. In some cases, the breast cancer is an IHC2+breast cancer.

In another aspect, the present invention provides nucleic acid molecules encoding any of the HCVR, LCVR or CDR sequences of the anti-APLP2/anti-HER2 bispecific antigen-binding molecules disclosed herein, including nucleic acid molecules comprising the polynucleotide sequences as set forth in Tables 1 and 2 herein, as well as nucleic acid molecules comprising two or more of the polynucleotide sequences as set forth in Tables 1 and 2 in any functional combination or arrangement thereof, such as the combinations found in Table 3. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

The present invention includes anti-APLP2/anti-HER2 bispecific antigen-binding molecules wherein any of the aforementioned antigen-binding domains that specifically bind APLP2 are combined, connected or otherwise associated with any of the aforementioned antigen-binding domains that specifically bind HER2 to form a bispecific antigen-binding molecule that binds APLP2 and HER2.

The present invention includes anti-APLP2/anti-HER2 bispecific antigen-binding molecules having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

According to another aspect, the present invention provides antibody-drug conjugates comprising an anti-HER2×APLP2 antibody or antigen-binding fragment thereof and a therapeutic agent (e.g., a cytotoxic agent). In some embodiments, the antibody or antigen-binding fragment and the cytotoxic agent are covalently attached via a linker, as discussed herein. In various embodiments, the anti-HER2×APLP2 antibody or antigen-binding fragment can be any of the anti-HER2×APLP2 antibodies or fragments described herein.

In some embodiments, the cytotoxic agent is selected from an auristatin, a maytansinoid, a tubulysin, a tomaymycin, calicheamicin, or a dolastatin derivative. In some cases, the cytotoxic agent is an auristatin selected from MMAE or MMAF, or a maytansinoid selected from DM1 or DM4. In some embodiments, the cytotoxic agent is a maytansinoid having the structure of Formulae, as discussed herein.

In some embodiments, the cytotoxic agent is a maytansinoid having the structure:

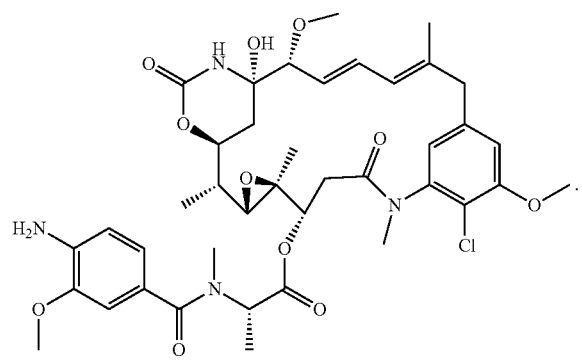 [SMILES: COc1cc(C(=O)N(C)[C@@H](C)C(=O)O[C@H]2CC(=O)N(C)c3cc(cc(OC)c3Cl)C/C(C)=C/C=C/[C@@H](OC)[C@@]3(O)C[C@H](OC(=O)N3)[C@@H](C)[C@@H]3O[C@@]23C)ccc1N]

In some embodiments, the cytotoxic agent is a maytansinoid having the structure:

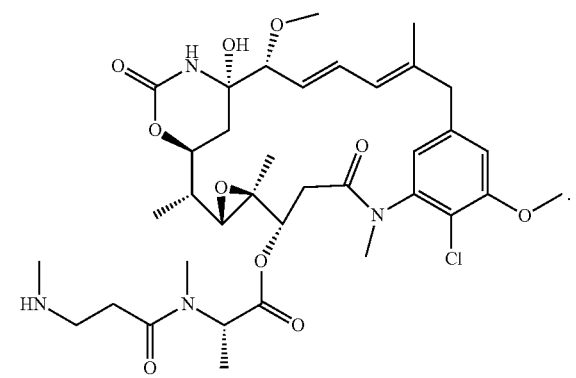 [SMILES: CNCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In some embodiments, the antibody-drug conjugate comprises an anti-HER2×anti-APLP2 antigen-binding protein or an anti-HER2 antibody, or fragment thereof, and

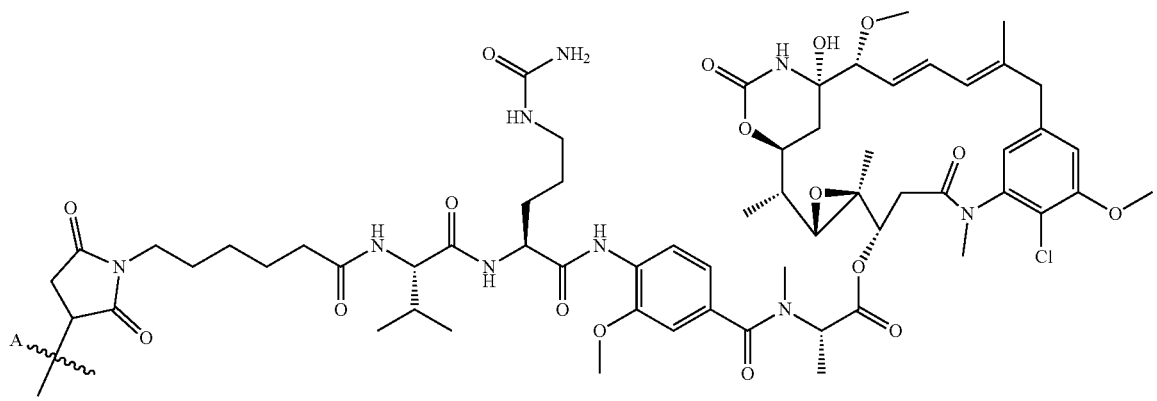

wherein

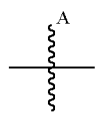

is a bond to the antibody or fragment thereof.

In some embodiments, the antibody-drug conjugate comprises an anti-HER2×anti-APLP2 antigen-binding protein or an anti-HER2 antibody, or fragment thereof, and

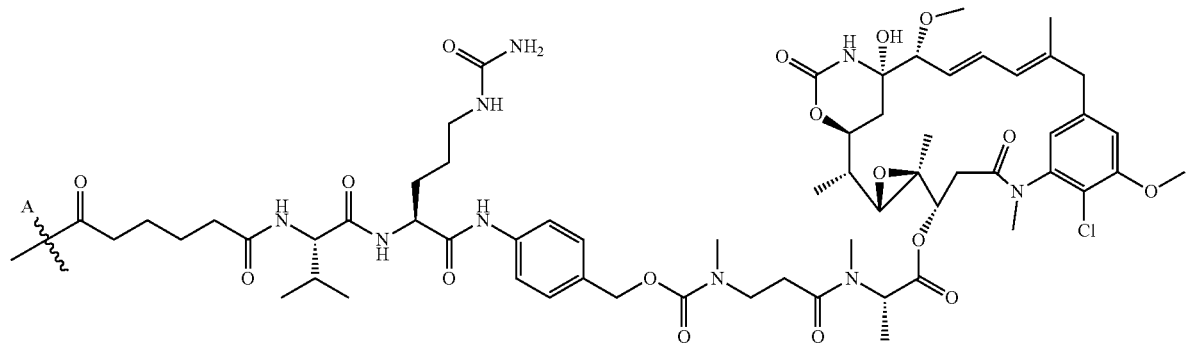

wherein

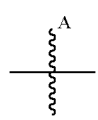

20 is a bond to the antibody or fragment thereof.

In some embodiments, the antibody-drug conjugate comprises an anti-HER2×anti-APLP2 antigen-binding protein or an anti-HER2 antibody, or fragment thereof, and

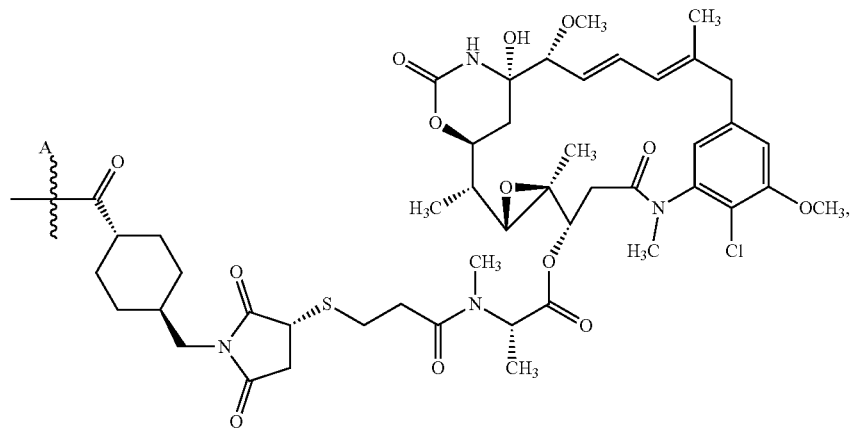

25 or

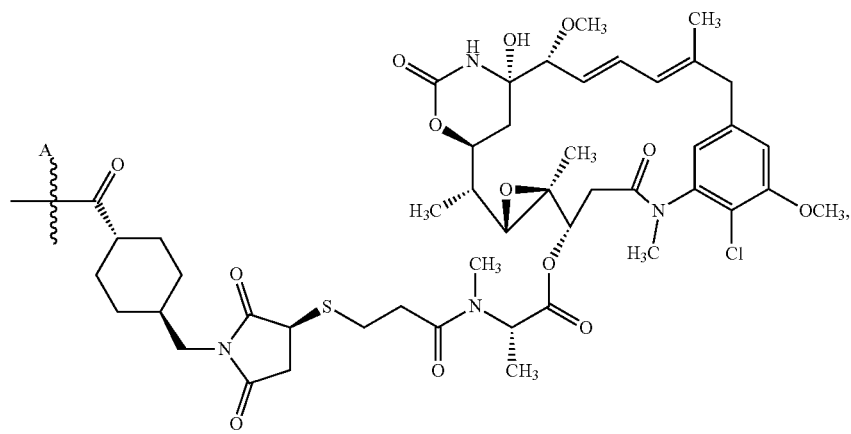

65 or
a mixture thereof, wherein

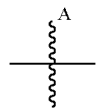

is a bond to the antibody or fragment thereof.

In some embodiments, the bond contacts the antibody or fragment thereof via a sulfur constituent of a cysteine residue.

In some embodiments, the bond contacts the antibody or fragment thereof via a nitrogen constituent of a lysine residue.

In any of the various embodiments of the antibody-drug conjugates discussed above or herein, the antibody-drug conjugate can comprise from 1 to 10 cytotoxic agents per anti-HER2×anti-APLP2 antigen-binding protein or anti-HER2 antibody, or fragment thereof.

In another aspect, the invention provides a pharmaceutical composition comprising an anti-APLP2/anti-HER2 bispecific antigen-binding molecule as disclosed herein and a pharmaceutically acceptable carrier. In a related aspect, the invention features a composition which is a combination of an anti-APLP2/anti-HER2 bispecific antigen-binding molecule and a second therapeutic agent. In one embodiment, the second therapeutic agent is any agent that is advantageously combined with an anti-APLP2/anti-HER2 bispecific antigen-binding molecule. Exemplary agents that may be advantageously combined with an anti-APLP2/anti-HER2 bispecific antigen-binding molecule are discussed in detail elsewhere herein.

In yet another aspect, the invention provides therapeutic methods for targeting/killing tumor cells expressing HER2 using an anti-APLP2/anti-HER2 bispecific antigen-binding molecule of the invention, wherein the therapeutic methods comprise administering a therapeutically effective amount of a pharmaceutical composition comprising an anti-APLP2/anti-HER2 bispecific antigen-binding molecule of the invention to a subject in need thereof.

The present invention also includes the use of an anti-APLP2/anti-HER2 bispecific antigen-binding molecule of the invention in the manufacture of a medicament for the treatment of a disease or disorder related to or caused by HER2-expressing cells.

Other embodiments will become apparent from a review of the ensuing detailed description.

BRIEF DESCRIPTION OF THE DRAWINGS

FIG. 10 provides the pharmacokinetic profiles of bispecific anti-HER2×APLP2 antibododies (25014, 25018, 252020) adn isotype control antibodies in APLP2hu/hu mice.

DETAILED DESCRIPTION

Figure 1:
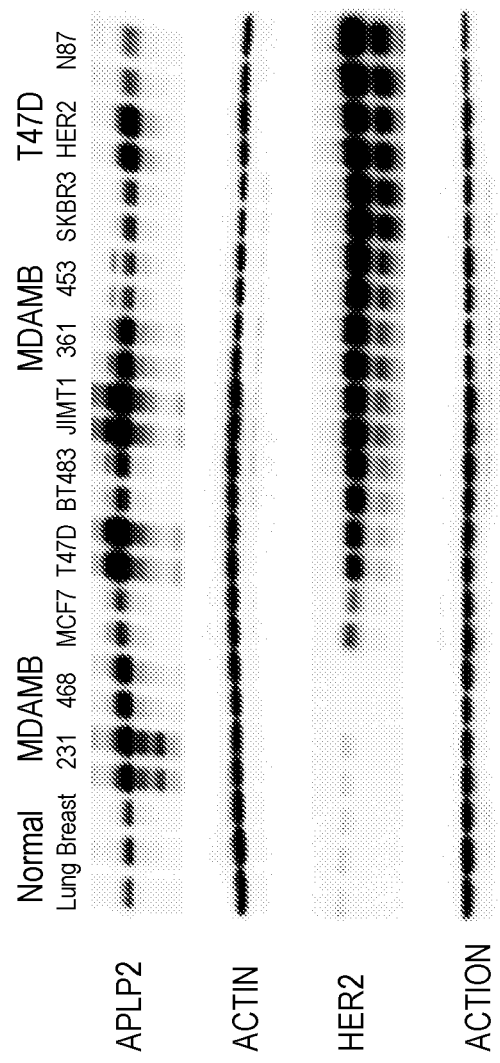
FIG. 1 shows Western blots of various tissues stained with anti-APLP2, anti-HER2, or anti-GAPDH antibodies

Provided herein is a demonstration that bispecific anti-HER2×APLP2 antibodies increased the internalization, lysosomal trafficking and degradation of HER2. Moreover, bispecific anti-HER2×APLP2 antibody drug conjugates (ADCs) were significantly more potent than T-DM1 in vitro and in vivo. Additionally, the low affinity of the APLP2 arm resulted in the bispecific anti-HER2×APLP-ADC displaying minimal internalization and cytotoxicity of cells lacking or having minimal HER2 expression. APLP2 was found to be expressed in most of the breast cancer cell lines, PDX models and patient samples tested (data not shown), suggesting that bispecific anti-HER2×APLP2-ADC could benefit a broad range of HER2-positive breast cancer patients, including those considered to be IHC 2+.

Before the present invention is described in detail, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. The term "about," when used in reference to a particular recited numerical value, means that the value may vary from the recited value by no more than 1%. For example, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "APLP2," includes a protein that in humans is encoded by the APLP2 gene and has an amino acid sequence set forth as SEQ ID NO: 50. APLP2 is ubiquitously expressed and is an important modulators of glucose and insulin homeostasis. All references to proteins, polypeptides and protein fragments herein are intended to refer to the human version of the respective protein, polypeptide or protein fragment unless explicitly specified as being from a non-human species. Thus, the expression "APLP2" means human APLP2 unless specified as being from a non-human species, e.g., "mouse APLP2," "monkey APLP2," etc.

The phrase "an antibody that binds APLP2" or an "anti-APLP2 antibody" includes antibodies and antigen-binding fragments thereof that specifically recognize a single APLP2 subunit (e.g., epsilon, delta, gamma or zeta), as well as antibodies and antigen-binding fragments thereof that specifically recognize a dimeric complex of two APLP2 subunits (e.g., gamma/epsilon, delta/epsilon, and zeta/zeta APLP2 dimers). The antibodies and antigen-binding fragments of the present invention may bind soluble APLP2 and/or cell surface expressed APLP2. Soluble APLP2 includes natural APLP2 proteins as well as recombinant APLP2 protein variants such as, e.g., monomeric and dimeric APLP2 constructs, that lack a transmembrane domain or are otherwise unassociated with a cell membrane.

The expression "cell surface-expressed APLP2" refers to one or more APLP2 protein(s) that is/are expressed on the surface of a cell in vitro or in vivo, such that at least a portion of a APLP2 protein is exposed to the extracellular side of the cell membrane and is accessible to an antigen-binding portion of an antibody. "Cell surface-expressed APLP2" includes APLP2 proteins contained within the context of a functional T cell receptor in the membrane of a cell. The expression "cell surface-expressed APLP2" includes APLP2 protein expressed as part of a homodimer or heterodimer on the surface of a cell (e.g., gamma/epsilon, delta/epsilon, and zeta/zeta APLP2 dimers). The expression, "cell surface-expressed APLP2" also includes a APLP2 chain (e.g., APLP2-epsilon, APLP2-delta or APLP2-gamma) that is expressed by itself, without other APLP2 chain types, on the surface of a cell. A "cell surface-expressed APLP2" can comprise or consist of a APLP2 protein expressed on the surface of a cell which normally expresses APLP2 protein. Alternatively, "cell surface-expressed APLP2" can comprise or consist of APLP2 protein expressed on the surface of a cell that normally does not express human APLP2 on its surface but has been artificially engineered to express APLP2 on its surface.

The expression "HER2" or "human epidermal growth factor receptor 2" refers to a member of the human epidermal growth factor receptor family. Amplification or overexpression of this oncogene has been shown to play an important role in the development and progression of certain aggressive types of breast cancer. In recent years the protein has become an important biomarker and target of therapy for approximately 30% of breast cancer patient. The amino acid sequence of HER2 is set forth as SEQ ID NO: 49. All references to proteins, polypeptides and protein fragments herein are intended to refer to the human version of the respective protein, polypeptide or protein fragment unless explicitly specified as being from a non-human species. Thus, the expression "HER2" means human HER2 unless specified as being from a non-human species, e.g., "mouse HER2," "monkey HER2," etc.

The phrase "an antibody that binds HER2" or an "anti-HER2 antibody" includes antibodies and antigen-binding fragments thereof that specifically recognize HER2.

The term "antigen-binding molecule" includes antibodies and antigen-binding fragments of antibodies, including, e.g., bispecific antibodies.

The term "avidity" refers to the ability of an antigen-binding molecule to reach a threshold of target engagement in order to achieve its desired effect. The phrase "avidity-driven binding" or "avidity-driven pairing" in the context of multiple target antigens and a multispecific antigen-binding molecule refers to the mechanism of action wherein the multispecific antigen-binding molecule provides at least two monovalent binding arms, and a first binding arm (or arms) binds to a first target antigen with high affinity. A second binding arm (or arms) binds a second target antigen with low affinity such that the second binding arm does not bind the second target antigen unless both antigens are in proximity to each other, such as present on the same cell. Thus, the high affinity binding to the first target antigen increases the avidity of the low affinity arm for the second binding arm and mediates binding to the second target (Rhoden, J. J., et al., May 20, 2016, *J Biol Chem.* 291, 11337-11347, first published on Mar. 28, 2016 doi: 10.1074/jbc.M116.714287; Jarantow, S. W., et al., Oct. 9, 2015, *J Biol Chem.* 290(41): 24689-704. doi: 10.1074/jbc.M115.651653. Epub 2015 Aug. 10). In one example, HER2×APLP2 bispecific antibodies display high HER2 affinity (e.g. 3-5 nM) and low APLP2 affinity (e.g. 145-976 nM). The proposed mechanism of action provides a HER2×APLP2 bispecific antibody (bsAb) that binds to HER2-positive tumor cells using the high affinity HER2 arm. This increases the avidity of the low affinity APLP2 arm for APLP2 and mediates binding to the second target to provide the desired internalization of HER2. Thus, upon APLP2 internalization, the entire complex (i.e., APLP2 target, HER2×APLP2 bsAb and HER2 target) is internalized for lysosomal degradation.

It was observed that the extent to which a HER2×APLP2 bsAb interacts with target cells is determined by its interaction with HER2. Without being bound to any one theory, the initial interaction between a high-affinity HER2 arm of the HER2×APLP2 bsAb and HER2 receptor increases the local cell-surface concentration of the bsAb. Subsequently, bsAb contacts APLP2 with its low-affinity APLP2 arm, whereupon dual-receptor avidity results in the formation of an APLP2-HER2×APLP2 bsAb-HER2 complex; the complex subsequently undergoes APLP2-mediated internalization from the surface into lysosomal compartment of the cell.

The term "antibody" refers to any antigen-binding molecule or molecular complex comprising at least one complementarity determining region (CDR) that specifically binds to or interacts with a particular antigen (e.g., HER2 or APLP2). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-HER2 antibody or anti-APLP2 antibody (or antigen-binding portion thereof) may be identical to the human germline sequences, or may be naturally or artificially modified. An amino acid consensus sequence may be defined based on a side-by-side analysis of two or more CDRs.

The term "antibody" also includes antigen-binding fragments of full antibody molecules. The terms "antigen-binding portion" of an antibody, "antigen-binding fragment" of an antibody, and the like include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment".

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$—$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-HER2 monospecific antibodies or anti-HER2/anti-APLP2 bispecific antibodies of the invention are human antibodies. The term "human antibody" refers to antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody" is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody" refers to an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention also includes one-arm antibodies that bind HER2. The term "one-arm antibody" refers to an antigen-binding molecule comprising a single antibody heavy chain and a single antibody light chain. The one-arm antibodies of the present invention may comprise any of the HCVR/LCVR or CDR amino acid sequences as set forth in Table 1.

The anti-HER2 or anti-HER2/anti-APLP2 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-HER2 or anti-HER2/anti-APLP2 antibodies comprising variants of any of the HCVR, LCVR, and/or CDR amino acid sequences disclosed herein having one or more conservative substitutions. For example, the present invention includes anti-HER2 or anti-HER2/anti-APLP2 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein or as described in Tables 2 and 3 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Germline Mutations

The anti-APLP2 antibodies disclosed herein may comprise one or more amino acid substitutions, insertions and/or deletions in the framework and/or CDR regions of the heavy chain variable domains as compared to the corresponding germline sequences from which the antibodies were derived.

The present invention also includes anti-APLP2 antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"), and having weak or no detectable binding to a APLP2 antigen. Several such exemplary antibodies that recognize APLP2 are described in Table 2 herein.

Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be tested for one or more desired properties such as, improved binding specificity, weak or reduced binding affinity, improved or enhanced pharmacokinetic properties, reduced immunogenicity, etc. Antibodies and antigen-binding fragments obtained in this general manner given the guidance of the present disclosure are encompassed within the present invention.

The present invention also includes anti-APLP2 and/or anti-HER2 antibodies comprising variants of any of the HCVR, LCVR, and/or CDR amino acid sequences disclosed herein having one or more conservative substitutions. For example, the present invention includes anti-APLP2 and/or anti-HER2 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Tables 1, 2, and 3 herein.

The antibodies and bispecific antigen-binding molecules of the present invention comprise one or more amino acid substitutions, insertions and/or deletions in the framework and/or CDR regions of the heavy and light chain variable domains as compared to the corresponding germline sequences from which the individual antigen-binding domains were derived, while maintaining or improving the desired weak-to-no detectable binding to, e.g., APLP2. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein, i.e. the amino acid substitution maintains or improves the desired weak to no detectable binding affinity in the case of anti-APLP2 binding molecules. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

The present invention also includes antigen-binding molecules comprising an antigen-binding domain with an HCVR and/or CDR amino acid sequence that is substantially identical to any of the HCVR and/or CDR amino acid sequences disclosed herein, while maintaining or improving the desired weak affinity to APLP2 antigen. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

Once obtained, antigen-binding domains that contain one or more germline mutations were tested for decreased binding affinity utilizing one or more in vitro assays. Although antibodies that recognize a particular antigen are typically screened for their purpose by testing for high (i.e. strong) binding affinity to the antigen, the antibodies of the present invention exhibit weak binding or no detectable binding. Bispecific antigen-binding molecules comprising one or more antigen-binding domains obtained in this general manner are also encompassed within the present invention and were found to be advantageous as avidity-driven tumor therapies.

Unexpected benefits, for example, improved pharmacokinetic properties and low toxicity to the patient may be realized from further modifying the antibodies of the invention by the methods described herein.

Binding Properties of the Antibodies

The term "binding" in the context of the binding of an antibody, immunoglobulin, antibody-binding fragment, or Fc-containing protein to either, e.g., a predetermined antigen, such as a cell surface protein or fragment thereof, typically refers to an interaction or association between a minimum of two entities or molecular structures, such as an antibody-antigen interaction.

For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen as the ligand and the antibody, Ig, antibody-binding fragment, or Fc-containing protein as the analyte (or antiligand). Cell-based binding strategies, such as fluorescent-activated cell sorting (FACS) binding assays, are also routinely used and provide binding characterization data with respect to cell-surface expressed proteins. FACS data correlates well with other methods such as radioligand competition binding and SPR (Benedict, CA, *J Immunol Methods.* 1997, 201(2):223-31; Geuijen, C A, et al. *J Immunol Methods.* 2005, 302(1-2):68-77).

Accordingly, the antibody or antigen-binding protein of the invention binds to the predetermined antigen or cell surface molecule (receptor) having an affinity corresponding to a $K_D$ value that is at least ten-fold lower than its affinity for binding to a non-specific antigen (e.g., BSA, casein). According to the present invention, the affinity of an antibody corresponding to a $K_D$ value that is equal to or less than ten-fold lower than a non-specific antigen may be considered non-detectable binding, however such an antibody may be paired with a second antigen binding arm for the production of a bispecific antibody of the invention.

The term "$K_D$" or "KD" in molar (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

In some embodiments, the bispecific antigen-binding molecule, or conjugate thereof, binds to HER2 with a binding affinity ($K_D$ value) greater than 10-fold its binding affinity to APLP2. As such, the bispecific molecule has a much stronger binding affinity to HER2 than its binding affinity to APLP2. In some cases, the binding affinity is measured by a surface plasmon resonance assay at 37° C., or equivalent assay.

The term "$k_d$" (sec-1 or 1/s) refers to the dissociation rate constant of a particular antibody-antigen interaction, or the dissociation rate constant of an antibody or antibody-binding fragment. Said value is also referred to as the $k_{off}$ value.

The term "$k_a$" (M-1×sec-1 or 1/M) refers to the association rate constant of a particular antibody-antigen interaction, or the association rate constant of an antibody or antibody-binding fragment.

The term "$K_A$" (M-1 or 1/M) refers to the association equilibrium constant of a particular antibody-antigen interaction, or the association equilibrium constant of an antibody or antibody-binding fragment. The association equilibrium constant is obtained by dividing the $k_a$ by the $k_d$.

The term "EC50" or "$EC_{50}$" refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. In certain embodiments, the $EC_{50}$ value equals the concentration of an antibody of the invention that gives half-maximal binding to cells expressing APLP2 or tumor-associated antigen, as determined by e.g. a FACS binding assay. Thus, reduced or weaker binding is observed with an increased $EC_{50}$, or half maximal effective concentration value.

In one embodiment, decreased binding can be defined as an increased $EC_{50}$ antibody concentration which enables binding to the half-maximal amount of target cells.

Bispecific Antigen-Binding Molecules

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-HER2 monospecific antibodies or anti-HER2/anti-APLP2 bispecific antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second or additional binding specificity.

Use of the expression "anti-APLP2 antibody" or "anti-HER2 antibody" herein is intended to include both monospecific anti-APLP2 or anti-HER2 antibodies as well as bispecific antibodies comprising a APLP2-binding arm and a HER2-binding arm. Thus, the present invention includes bispecific antibodies wherein one arm of an immunoglobulin binds human APLP2, and the other arm of the immunoglobulin is specific for human HER2. The APLP2-binding arm can comprise any of the HCVR/LCVR or CDR amino acid sequences as set forth in Tables 1, 2 and 3 herein.

In certain embodiments, the APLP2-binding arm binds to human APLP2 and induces internalization of the APLP2 and antibody bound thereto. In certain embodiments, the APLP2-binding arm binds weakly to human APLP2 and induces internalization the APLP2 and antibody bound thereto. In other embodiments, the APLP2-binding arm binds weakly to human APLP2 and induces tumor-associated antigen-expressing cell killing in the context of a bispecific or multispecific antibody. In other embodiments, the APLP2-binding arm binds or associated weakly with human and cynomolgus (monkey) APLP2, yet the binding interaction is not detectable by in vitro assays known in the art. The HER2-binding arm can comprise any of the HCVR/LCVR or CDR amino acid sequences as set forth in Table 1 herein. The HER2-binding arm can comprise any anti-HER2 antibodies that have a binding affinity less than 10 nM KD, as measured in an in vitro affinity binding assay, such as the surface plasmon resonance assay described in Example 4 herein.

According to certain exemplary embodiments, the present invention includes bispecific antigen-binding molecules that specifically bind APLP2 and HER2. Such molecules may be referred to herein as, e.g., "anti-APLP2/anti-HER2," or "anti-APLP2×HER2" or "APLP2×HER2" bispecific molecules, or other similar terminology (e.g., anti-HER2/anti-APLP2).

The term "HER2" refers to the human HER2 protein unless specified as being from a non-human species (e.g., "mouse HER2," "monkey HER2," etc.). The human HER2 protein has the amino acid sequence shown in SEQ ID NO: 49.

The aforementioned bispecific antigen-binding molecules that specifically bind APLP2 and HER2 may comprise an anti-APLP2 antigen-binding molecule which binds to APLP2 with a weak binding affinity such as exhibiting a $K_D$ of greater than about 40 or 50 nM, as measured by an in vitro affinity binding assay. In some cases, the APLP2 binding arm binds APLP2 with a $K_D$ or $EC_{50}$ greater than about 100 nM, greater than about 200 nM, greater than about 300 nM, greater than about 400 nM, greater than about 500 nM, or greater than about 1 µM (e.g., as measures in a surface plasmon resonance assay). In some cases, the first antigen-binding domain specifically binds APLP2 (e.g., either or both of human APLP2 and cynomolgus APLP2 with weak or no measurable affinity).

The bispecific antigen-binding molecules that specifically bind APLP2 and HER2 may binds to APLP2 with a more than 10-fold weaker binding than the bispecific antigen-binding molecule binds to HER2, as measured by an in vitro binding assay. In some cases, the bispecific antigen-binding molecule binds to APLP2 with a $K_D$ or $EC_{50}$ that is more than about 20-fold weaker, or 25-fold, 30-fold, 35-fold, 40-fold, 50-fold, 60-fold, 70-fold, 80-fold, 90-fold, 100-fold, 150-fold or 200-fold weaker, as measured by an in vitro binding assay, such as a surface plasmon resonance assay or a cell-based binding assay (i.e. FACS).

The expression "antigen-binding molecule" refers to a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

The expression "bispecific antigen-binding molecule" refers to a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., APLP2), and the second antigen-binding domain specifically binds a second, distinct antigen (e.g., HER2).

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen-binding domain (e.g., a bispecific antibody), the CDRs of the first antigen-binding domain may be designated with the prefix "A1" and the CDRs of the second antigen-binding domain may be designated with the prefix "A2". Thus, the CDRs of the first antigen-binding domain may be referred to herein as A1-HCDR1, A1-HCDR2, and A1-HCDR3; and the CDRs of the second antigen-binding domain may be referred to herein as A2-HCDR1, A2-HCDR2, and A2-HCDR3.

The first antigen-binding domain and the second antigen-binding domain may be directly or indirectly connected to one another to form a bispecific antigen-binding molecule of the present invention. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. A "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of from 1 to about 200 amino acids in length containing at least one cysteine residue. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

The present invention also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). See, for example, U.S. Pat. No. 8,586,713. Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 $C_H2$]-[IgG4 $C_H3$]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 $C_H2$]-[IgG1 $C_H3$]. These and other examples of chimeric Fc domains that can be included in any of the antigen-binding molecules of the present invention are described in US Publication 2014/0243504, published Aug. 28, 2014, which is herein incorporated in its entirety. Chimeric Fc domains having these general structural arrangements, and variants thereof, can have altered Fc receptor binding, which in turn affects Fc effector function.

In certain embodiments, the invention provides an antibody heavy chain wherein the heavy chain constant region (CH) region comprises an amino acid sequence at least 95%, at least 96%, at least 97%, at least 98%, at least 99% identical to any one of SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO:65, or SEQ ID NO:78. In some embodiments, the heavy chain constant region (CH) region comprises an amino acid sequence selected from the group consisting of SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO:65, or SEQ ID NO:78.

In other embodiments, the invention provides an antibody heavy chain wherein the Fc domain comprises an amino acid sequence at least 95%, at least 96%, at least 97%, at least 98%, at least 99% identical to any one of SEQ ID NO: 66, SEQ ID NO: 67 SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO:75, SEQ ID NO:76, or SEQ ID NO:77. In some embodiments, the Fc domain comprises an amino acid sequence selected form the group consisting of SEQ ID NO: 66, SEQ ID NO: 67 SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO:75, SEQ ID NO:76, or SEQ ID NO:77.

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germline sequences available from, for example, public antibody sequence databases. The antigen-binding molecules of the present invention may comprise antigen-binding domains which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

The present invention also includes antigen-binding molecules wherein one or both antigen-binding domains comprise variants of any of the HCVR, LCVR, and/or CDR amino acid sequences disclosed herein having one or more conservative substitutions. For example, the present invention includes antigen-binding molecules comprising an antigen-binding domain having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443-1445, herein incorporated by reference. A "moderately conservative" replacement is any change having a nonnegative value in the PAM250 log-likelihood matrix.

The present invention also includes antigen-binding molecules comprising an antigen-binding domain with an HCVR, LCVR, and/or CDR amino acid sequence that is substantially identical to any of the HCVR, LCVR, and/or CDR amino acid sequences disclosed herein. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) *Methods Mol. Biol.* 24: 307-331, herein incorporated by reference.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) *J. Mol. Biol.* 215:403-410 and Altschul et al. (1997) *Nucleic Acids Res.* 25:3389-402, each herein incorporated by reference.

pH-Dependent Binding

The present invention includes anti-HER2 antibodies, and anti-APLP2/anti-HER2 bispecific antigen-binding molecules, with pH-dependent binding characteristics. For example, an anti-HER2 antibody of the present invention may exhibit reduced binding to HER2 at acidic pH as compared to neutral pH. Alternatively, anti-HER2 antibodies of the invention may exhibit enhanced binding to HER2 at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. The expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to HER2 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments of the present invention, anti-HER2 antibodies, and anti-APLP2/anti-HER2 bispecific antigen-binding molecules, are provided comprising an Fc domain comprising one or more mutations which enhance or diminish antibody binding to the FcRn receptor, e.g., at acidic pH as compared to neutral pH. For example, the present invention includes antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-HER2 antibodies, and anti-APLP2/anti-HER2 bispecific antigen-binding molecules, comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies and Bispecific Antigen-Binding Molecules The present invention includes antibodies and antigen-binding fragments thereof that bind human HER2 with high affinity (e.g., nanomolar to sub-nanomolar $K_D$ values).

The present invention also includes anti-APLP2/anti-HER2 bispecific antigen-binding molecules which inhibit tumor growth in immunocompromised mice bearing human breast cancer xenografts. (see, e.g., Examples 12 and 13).

The present invention includes antibodies and antigen-binding fragments thereof that bind human APLP2 with medium or low affinity, depending on the therapeutic context and particular targeting properties that are desired. For example, in the context of a bispecific antigen-binding molecule, wherein one arm binds APLP2 and another arm binds a target antigen (e.g., HER2), it may be desirable for the target antigen-binding arm to bind the target antigen with high affinity while the anti-APLP2 arm binds APLP2 with only moderate or low affinity. In this manner, preferential targeting of the antigen-binding molecule to cells expressing the target antigen may be achieved while avoiding general/untargeted APLP2 binding and the consequent adverse side effects associated therewith.

The present invention includes bispecific antigen-binding molecules (e.g., bispecific antibodies) which are capable of simultaneously binding to human APLP2 and a human HER2. The binding arm that interacts with cells that express APLP2 may have weak to no detectable binding as measured in a suitable in vitro binding assay. The extent to which a bispecific antigen-binding molecule binds cells that express APLP2 and/or HER2 can be assessed by fluorescence activated cell sorting (FACS).

The present invention also includes antibodies, antigen-binding fragments, and bispecific antibodies thereof which bind to HER2-expressing cells and cell lines (e.g., ductal breast adenocarcinoma T47D cells), with an $EC_{50}$ value of between about 1 nM and 50 nM, as determined using a FACS binding assay which measures antibody interaction with cell membrane bound antigen, or a substantially similar assay. In certain embodiments, the antibodies, antigen-binding fragments, and bispecific antibodies thereof which bind to HER2-expressing cells and cell lines (e.g., T47D cells), with an $EC_{50}$ value of about 50 nM, of about 40 nM, of about 30 nM, of about 20 nM, of about of less than about 15 nM, of about 10 nM, of about 5 nM, of about 4 nM, of about 3 nM, or of about 2 nM, of about 1 nM, as determined using a FACS binding assay or a substantially similar assay.

The present invention includes antibodies, antigen-binding fragments, and bispecific antibodies thereof that bind human APLP2 with weak (i.e. low) or even no detectable affinity. According to certain embodiments, the present invention includes antibodies and antigen-binding fragments of antibodies that bind human APLP2 (e.g., at 37° C.) with a $K_D$ of greater than about 100 nM as measured by surface plasmon resonance. In certain embodiments, the antibodies or antigen-binding fragments of the present invention bind APLP2 with a $K_D$ of greater than about greater than about 110 nM, at least 120 nM, greater than about 130 nM, greater than about 140 nM, greater than about 150 nM, at least 160 nM, greater than about 170 nM, greater than about 180 nM, greater than about 190 nM, greater than about 200 nM, greater than about 250 nM, greater than about 300 nM, greater than about 400 nM, greater than about 500 nM, greater than about 600 nM, greater than about 700 nM, greater than about 800 nM, greater than about 900 nM, or greater than about 1 µM, or with no detectable affinity, as measured by surface plasmon resonance (e.g., mAb-capture or antigen-capture format), or a substantially similar assay.

The present invention includes antibodies, antigen-binding fragments, and bispecific antibodies thereof that bind monkey (i.e. cynomolgus) APLP2 with weak (i.e. low) or even no detectable affinity.

The present invention includes anti-APLP2/anti-HER2 bispecific antigen-binding molecules which bind to and are internalized by human HER2 expressing cells (e,g., T47D cells), as measured by an assay format as defined by Example 3 herein or a substantially similar assay. The present invention includes anti-APLP2/anti-HER2 bispecific antigen-binding molecules which are specific for binding to human HER2. In certain embodiments, the anti-APLP2/anti-HER2 bispecific antigen-binding molecules of the present invention bind human HER2 transiently expressed in HEK293 cells, as measured by an assay format as defined by Example 3 herein or a substantially similar assay. In certain embodiments, the anti-APLP2/anti-HER2 bispecific antigen-binding molecules of the present invention do not bind human HER1, human HER2, or human HER4 transiently expressed in HEK293 cells, as measured by an assay format as defined by Example 3 herein or a substantially similar assay.

The present invention includes anti-APLP2/anti-HER2 bispecific antigen-binding molecules which are capable of inhibiting HER2-expressing (e.g. JIMT-1) tumor growth (see, e.g., Example 10). For example, according to certain embodiments, anti-APLP2/anti-HER2 bispecific antigen-binding molecules are provided, wherein a single administration e.g., at a dose of about 0.1 mg/kg or about 0.01 mg/kg) causes a reduction in the tumor size compared to animals administered a isotype control bispecific antibody, when measured 46 days post-tumor implantation, as detected in a subject using standard caliper measurement methods, e.g., as set forth in Example 10, herein.

The present invention also includes anti-HER2 antibody drug conjugates which inhibit tumor growth in in vivo HER2 positive breast cancer xenograft models (see, e.g., Examples 12 and 13, or in a substantially similar assay). In certain embodiments, anti-HER2 antibody drug conjugates with Compound I are provided, wherein one dose at 10, 20, or 40 mg/kg administered on day 13 after tumor implantation, inhibit tumor growth in in vivo HER2 positive breast cancer xenograft models. In certain embodiments, anti-HER2 antibody drug conjugates with Compound I are provided wherein one dose at 5 or 20 mg/kg administered on day 14 after implantation, inhibit JIMT-1 and/or MDA-MB-361 tumor growth in in vivo HER2 positive breast cancer xenograft models. In certain embodiments, anti-HER2 antibody drug conjugates with Compound I are provided wherein one dose at 150 µg/kg administered on day 17 after implantation, inhibit JIMT-1 and/or MDA-MB-361 tumor growth in in vivo HER2 positive breast cancer xenograft models. In other embodiments, anti-HER2 antibody drug conjugates with Compound II are provided wherein one dose of at least 2.5 mg/kg administered on day 29 after implantation, inhibits JIMT-1 and/or MDA-MB-361 tumor growth in in vivo HER2 positive breast cancer xenograft models.

Epitope Mapping and Related Technologies

The epitope on APLP2 and/or HER2 to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a APLP2 or HER2 protein. Alternatively, the epitope may consist of a plurality of non-contiguous amino acids (or amino acid sequences) of APLP2 or HER2. The antibodies of the invention may interact with amino acids contained within a single APLP2 chain (e.g., APLP2-epsilon, APLP2-delta or APLP2-gamma), or may interact with amino acids on two or more different APLP2 chains. The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography of the antigen/antibody complex may also be used for epitope mapping purposes.

The present invention further includes anti-HER2 antibodies that bind to the same epitope as any of the specific exemplary antibodies described herein (e.g. antibodies comprising any of the amino acid sequences as set forth in Table 1 herein). Likewise, the present invention also includes anti-HER2 antibodies that compete for binding to HER2 with any of the specific exemplary antibodies described herein (e.g. antibodies comprising any of the amino acid sequences as set forth in Table 1 herein).

The present invention also includes bispecific antigen-binding molecules comprising a first antigen-binding domain that specifically binds human APLP2 and/or cynomolgus APLP2 with low or detectable binding affinity, and a second antigen binding domain that specifically binds human HER2, wherein the first antigen-binding domain binds to the same epitope on APLP2 as any of the specific exemplary APLP2-specific antigen-binding domains described herein (e.g. antibodies comprising any of the amino acid sequences as set forth in Table 2 herein), and/or wherein the second antigen-binding domain binds to the same epitope on HER2 as any of the specific exemplary HER2-specific antigen-binding domains described herein.

Likewise, the present invention also includes bispecific antigen-binding molecules comprising a first antigen-binding domain that specifically binds human APLP2, and a second antigen binding domain that specifically binds human HER2, wherein the first antigen-binding domain competes for binding to APLP2 with any of the specific exemplary APLP2-specific antigen-binding domains described herein, and/or wherein the second antigen-binding domain competes for binding to HER2 with any of the specific exemplary HER2-specific antigen-binding domains described herein.

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on HER2 (or APLP2) as a reference bispecific antigen-binding molecule of the present invention, the reference bispecific molecule is first allowed to bind to a HER2 protein (or APLP2 protein). Next, the ability of a test antibody to bind to the HER2 (or APLP2) molecule is assessed. If the test antibody is able to bind to HER2 (or APLP2) following saturation binding with the reference bispecific antigen-binding molecule, it can be concluded that the test antibody binds to a different epitope of HER2 (or APLP2) than the reference bispecific antigen-binding molecule. On the other hand, if the test antibody is not able to bind to the HER2 (or APLP2) molecule following saturation binding with the reference bispecific antigen-binding molecule, then the test antibody may bind to the same epitope of HER2 (or APLP2) as the epitope bound by the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a HER2 protein (or APLP2 protein) under saturating conditions followed by assessment of binding of the test antibody to the HER2 (or APLP2) molecule. In a second orientation, the test antibody is allowed to bind to a HER2 (or APLP2) molecule under saturating conditions followed by assessment of binding of the reference antigen-binding molecule to the HER2 (or APLP2) molecule. If, in both orientations, only the first (saturating) antigen-binding molecule is capable of binding to the HER2 (or APLP2) molecule, then it is concluded that the test antibody and the reference antigen-binding molecule compete for binding to HER2 (or APLP2). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., APLP2 and HER2), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., APLP2 or HER2) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to isolate heavy chain and light chain variable regions to produce fully human bispecific antigen-binding molecules. As such, the fully human bispecific antigen-binding molecules comprise two different heavy chains that associate with the same light chain. (See, e.g., US 2011/0195454). Fully human refers to an antibody, or antigen-binding fragment or immunoglobulin domain thereof, comprising an amino acid sequence encoded by a DNA derived from a human sequence over the entire length of each polypeptide of the antibody or antigen-binding fragment or immunoglobulin domain thereof. In some instances, the fully human sequence is derived from a protein endogenous to a human. In other instances, the fully human protein or protein sequence comprises a chimeric sequence wherein each component sequence is derived from human sequence. While not being bound by any one theory, chimeric proteins or chimeric sequences are generally designed to minimize the creation of immunogenic epitopes in the junctions of component sequences, e.g. compared to any wild-type human immunoglobulin regions or domains.

Bispecific antigen-binding molecules may be constructed with one heavy chain having a modified Fc domain that abrogates its binding to Protein A, thus enabling a purification method that yields a heterodimeric protein. See, for example, U.S. Pat. No. 8,586,713. As such, the bispecific antigen-binding molecules comprise a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation/modification that reduces or abolishes Protein A binding such as an H95R modification (by IMGT exon numbering; H435R by EU numbering). The second $C_H3$ may further comprise a Y96F modification (by IMGT; Y436F by EU).

Bioequivalents

The present invention encompasses antigen-binding molecules having amino acid sequences that vary from those of the exemplary molecules disclosed herein but that retain the ability to bind APLP2 and/or HER2. Such variant molecules may comprise one or more additions, deletions, or substitutions of amino acids when compared to parent sequence, but exhibit biological activity that is essentially equivalent to that of the described bispecific antigen-binding molecules.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary bispecific antigen-binding molecules set forth herein comprising amino acid changes which modify the glycosylation characteristics of the molecules, e.g., mutations which eliminate or remove glycosylation.

Species Selectivity and Species Cross-Reactivity

According to certain embodiments of the invention, antigen-binding molecules are provided which bind to human APLP2 but not to APLP2 from other species. Also provided are antigen-binding molecules which bind to human HER2 but not to HER2 from other species. The present invention also includes antigen-binding molecules that bind to human APLP2 and to APLP2 from one or more non-human species; and/or antigen-binding molecules that bind to human HER2 and to HER2 from one or more non-human species.

According to certain exemplary embodiments of the invention, antigen-binding molecules are provided which bind to human APLP2 and/or human HER2 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee APLP2 and/or HER2. For example, in a particular exemplary embodiment of the present invention bispecific antigen-binding molecules are provided comprising a first antigen-binding domain that binds human APLP2 and cynomolgus APLP2, and a second antigen-binding domain that specifically binds human HER2.

Antibody-Drug Conjugates (ADCs)

The present invention provides antibody-drug conjugates (ADCs) comprising an anti-HER2×anti-APLP2 antibody or antigen-binding fragments thereof conjugated to a therapeutic moiety such as a cytotoxic agent, a chemotherapeutic drug, immunosuppressant or a radioisotope. Anti-HER2 antibodies, or antigen-binding fragments thereof, conjugated to a therapeutic moiety are also provided. In general terms, the ADCs comprise: A-[L-P]y, in which A is an antigen-binding molecule, e.g. an anti-HER2×anti-APLP2 antibody, or a fragment thereof (e.g., a fragment comprising at least a HCDR3 selected from any of the HCDR3 amino acid sequences listed in Tables 1 or 2), L is a linker, P is the payload or therapeutic moiety (e.g., cytotoxic agent), and y is an integer from 1 to 30.

In various embodiments, the ADC comprises an anti-HER2×anti-APLP2 antibody or antigen-binding fragment thereof that comprises the CDRs of the HCVR arms and same LCVR arms having the amino acid sequences of the SEQ ID NOs set forth in Table 3 (e.g., having the HCVR1-HCVR2-LCVR SEQ ID NOs: 2-26-10; 2-34-10; 2-42-10; 18-26-10; 18-34-10; or 18-42-10) set forth in Table 3, or two specific HCVR/LCVR pairs (e.g., SEQ ID NOs: 2/10 and 26/10; 2/10 and 34/10; 2/10 and 42/10; 18/10 and 26/10; 18/10 and 34/10; or 18/10 and 42/10). In some cases, the anti-HER2×anti-APLP2 antibody or fragment comprises HC-CDRs and LC-CDRs with the amino acid sequences of the SEQ ID NOs (e.g., SEQ ID NOs: 4-6-8-12-14-16 and 28-30-32-12-14-16) set forth in Tables 1 and 2. In another embodiment, the ADC comprises an anti-HER2×anti-APLP2 antibody or antigen-binding fragment thereof that comprises the HCVR arms and same LCVR arm having the amino acid sequences of the SEQ ID NOs set forth in Table 3 (e.g., SEQ ID NOs2/10 and 26/10; 2/10 and 34/10; 2/10 and 42/10; 18/10 and 26/10; 18/10 and 34/10; or 18/10 and 42/10).

In various embodiments, the ADC comprises an anti-HER2 antibody or antigen-binding fragment thereof that comprises the CDRs of a HCVR and a LCVR having the amino acid sequences of the SEQ ID NOs (e.g., SEQ ID NOs: 2, 18 and 10) set forth in Table 1, or specific HCVR/LCVR pairs (e.g., SEQ ID NOs: 2/10 or 18/10). In some cases, the anti-HER2 antibody or fragment comprises CDRs with the amino acid sequences of the SEQ ID NOs (e.g., SEQ ID NOs: 4-6-8-12-14-16, 20-22-24-12-14-16) set forth in Table 1. In some cases, the anti-HER2 antibody or fragment comprises a HCVR and a LCVR having the amino acid sequences of the SEQ ID NOs (e.g., SEQ ID NOs: 2, 18 and 10) set forth in Table 1, or specific amino acid sequence pairs (e.g., SEQ ID NOs: 2/10 and 18/10).

Cytotoxic agents include any agent that is detrimental to the growth, viability or propagation of cells, including, but not limited to, tubulin-interacting agents and DNA-damaging agents. Examples of suitable cytotoxic agents and chemotherapeutic agents that can be conjugated to anti-HER2 antibodies in accordance with this aspect of the disclosure include, e.g., 1-(2chloroethyl)-1,2-dimethanesulfonyl hydrazide, 1,8-dihydroxy-bicyclo[7.3.1]trideca-4,9-diene-2,6-diyne-13-one, 1-dehydrotestosterone, 5-fluorouracil, 6-mercaptopurine, 6-thioguanine, 9-amino camptothecin, actinomycin D, amanitins, aminopterin, anguidine, anthracycline, anthramycin (AMC), auristatins, bleomycin, busulfan, butyric acid, calicheamicins (e.g., calicheamicin 71), camptothecin, carminomycins, carmustine, cemadotins, cisplatin, colchicin, combretastatins, cyclophosphamide, cytarabine, cytochalasin B, dactinomycin, daunorubicin, decarbazine, diacetoxypentyldoxorubicin, dibromomannitol, dihydroxy anthracin dione, disorazoles, dolastatin (e.g., dolastatin 10), doxorubicin, duocarmycin, echinomycins, eleutherobins, emetine, epothilones, esperamicin, estramustines, ethidium bromide, etoposide, fluorouracils, geldanamycins, gramicidin D, glucocorticoids, irinotecans, kinesin spindle protein (KSP) inhibitors, leptomycins, leurosines, lidocaine, lomustine (CCNU), maytansinoids, mechlorethamine, melphalan, mercatopurines, methopterins, methotrexate, mithramycin, mitomycin, mitoxantrone, N8-acetyl spermidine, podophyllotoxins, procaine, propranolol, pteridines, puromycin, pyrrolobenzodiazepines (PBDs), rhizoxins, streptozotocin, tallysomycins, taxol, tenoposide, tetracaine, thioepa chlorambucil, tomaymycins, topotecans, tubulysin, vinblastine, vincristine, vindesine, vinorelbines, and derivatives of any of the foregoing.

According to certain embodiments, the cytotoxic agent that is conjugated to an anti-HER2 antibody is a maytansinoid such as DM1 or DM4, a tomaymycin derivative, or a dolastatin derivative. According to certain embodiments, the cytotoxic agent that is conjugated to an anti-HER2 antibody is an auristatin such as MMAE, MMAF, or derivatives thereof. Other cytotoxic agents known in the art are contemplated within the scope of the present disclosure, including, e.g., protein toxins such ricin, *C. difficile* toxin, pseudomonas exotoxin, ricin, diphtheria toxin, botulinum toxin, bryodin, saporin, pokeweed toxins (i.e., phytolaccatoxin and phytolaccigenin), and others such as those set forth in Sapra et al., Pharmacol. & Therapeutics, 2013, 138:452-469.

In certain embodiments, the cytotoxic agent is a maytansinoid, e.g., derivative of maytansine. Suitable maytansinoids include DM1, DM4, or derivatives, stereoisomers, or isotopologues thereof. Suitable maytansinoids also include, but are not limited to, those disclosed in WO 2014/145090A1, WO 2015/031396A1, US 2016/0375147A1, and US 2017/0209591A1, incorporated herein by reference in their entireties.

In some embodiments, the maytansinoid has the following structure:

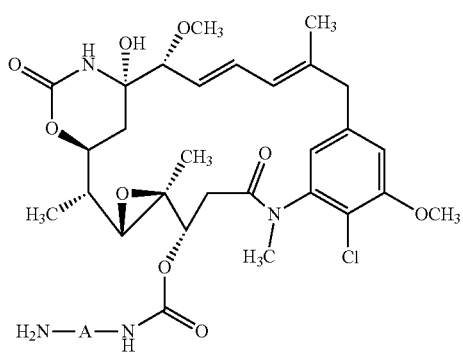

wherein A is an optionally substituted arylene or heteroarylene.

In some embodiments, the maytansinoid has the following structure:

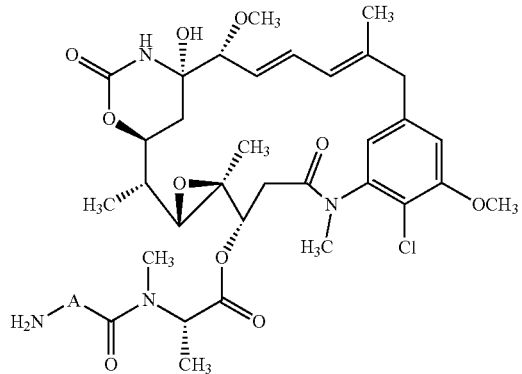

wherein A is an optionally substituted arylene or heteroarylene.

In some embodiments, the maytansinoid has the following structure:

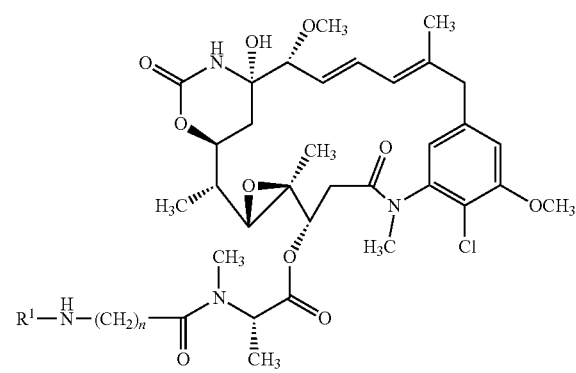

wherein n is an integer from 1-12 and $R^1$ is alkyl.

In some embodiments, the maytansinoid is:

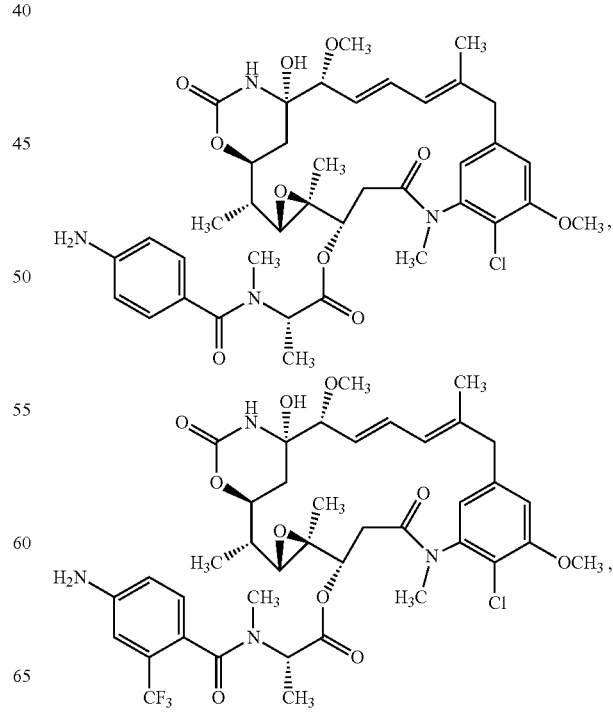

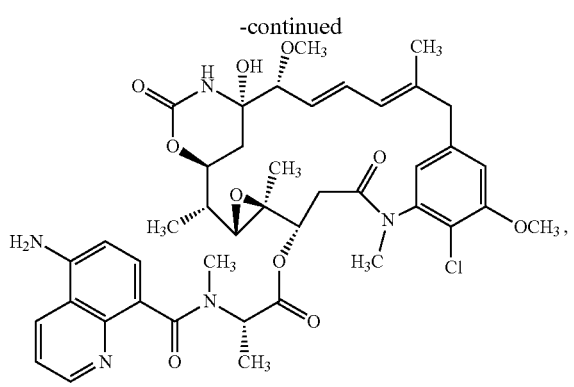
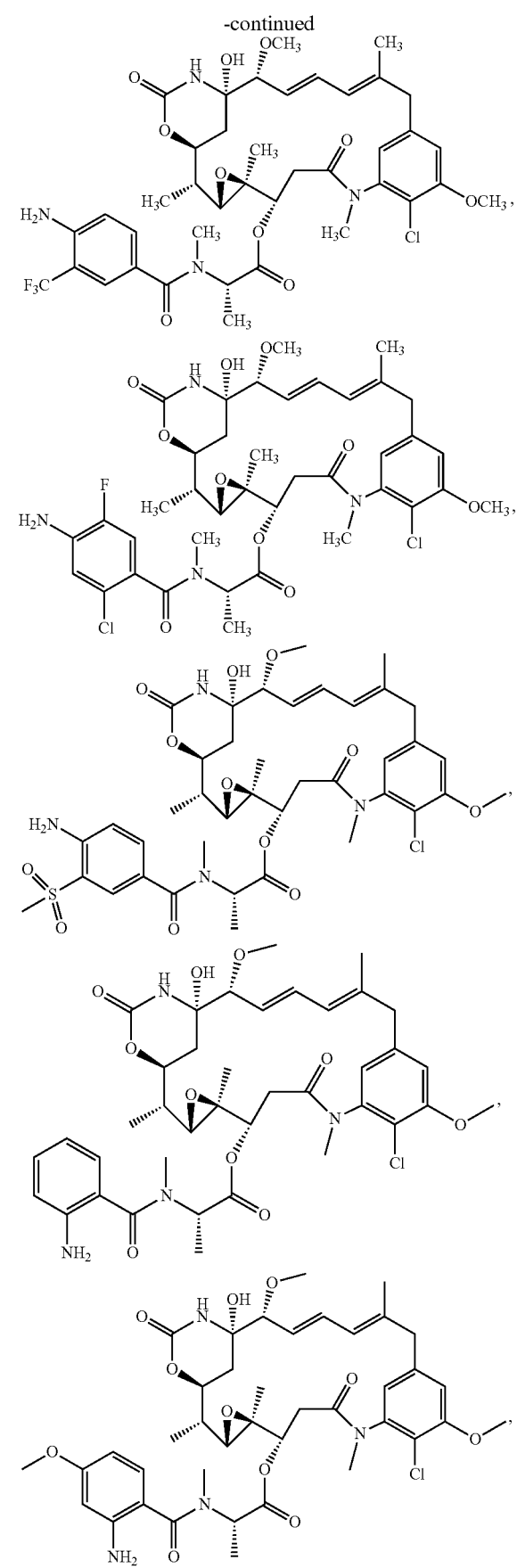

57
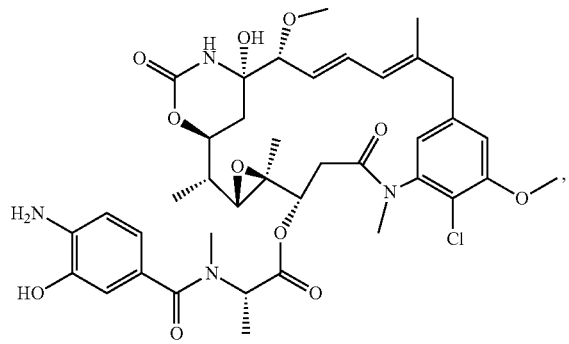
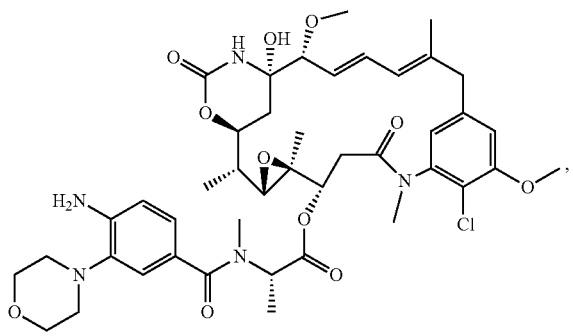
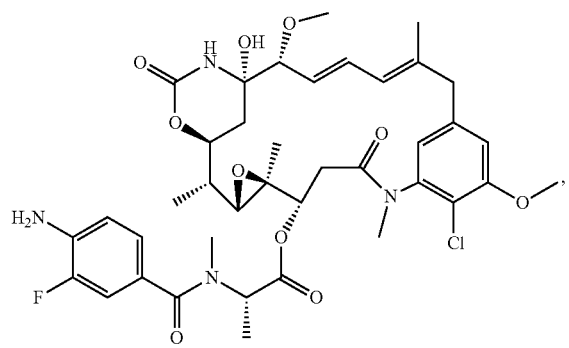
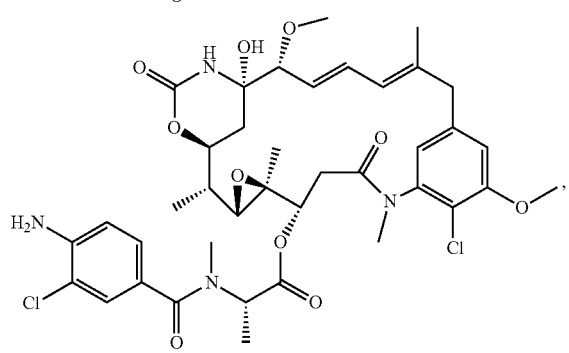
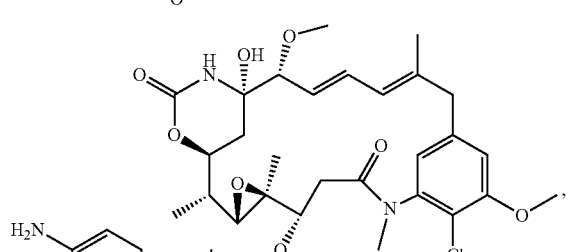
58
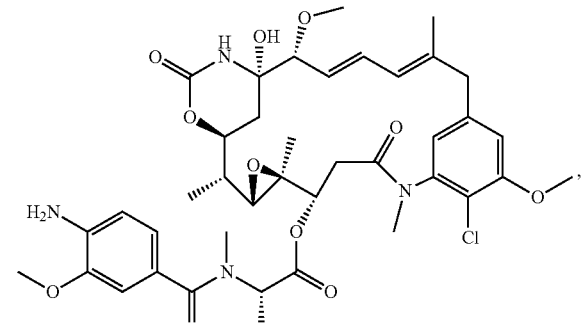
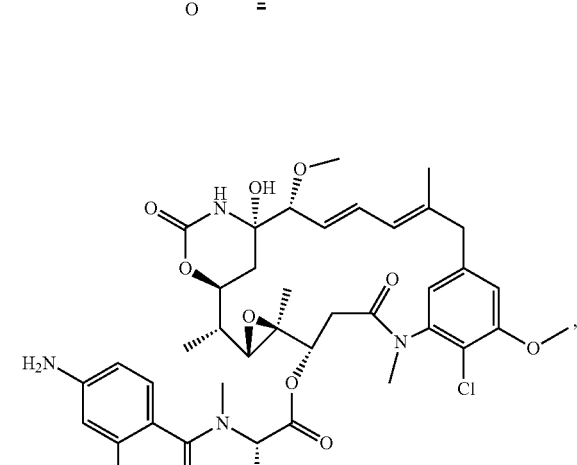
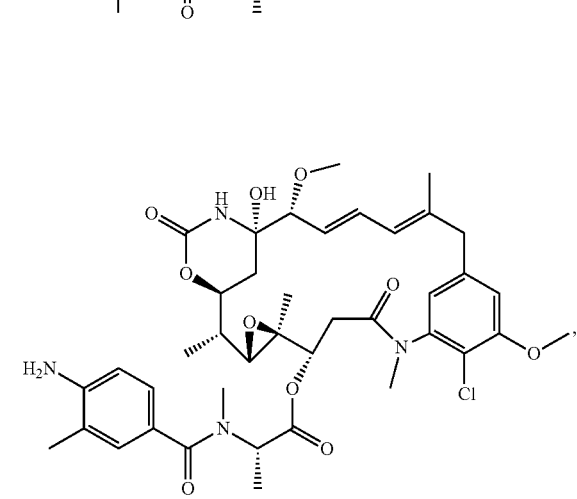
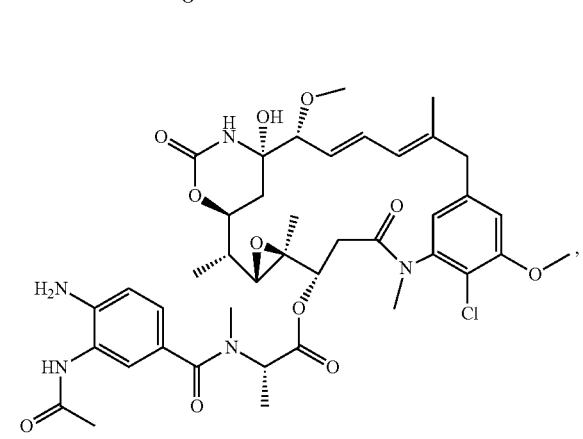

-continued
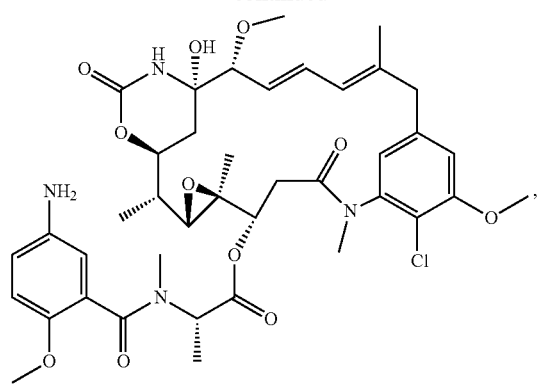
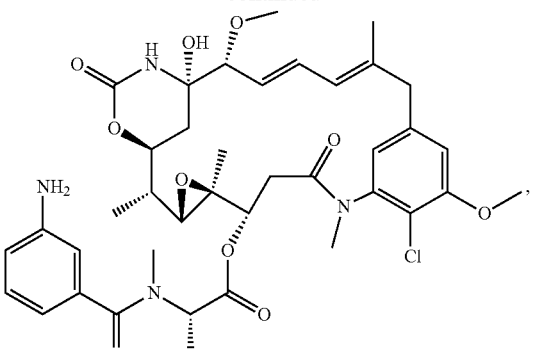
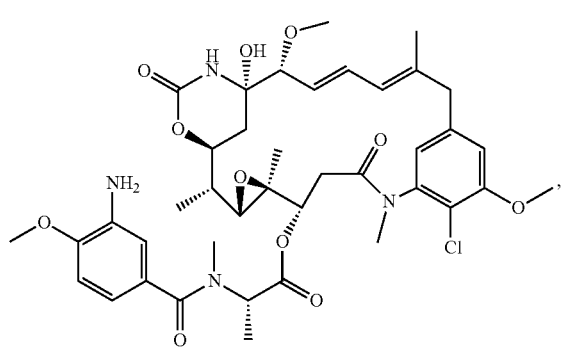
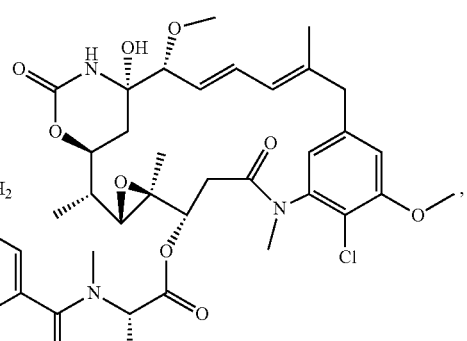
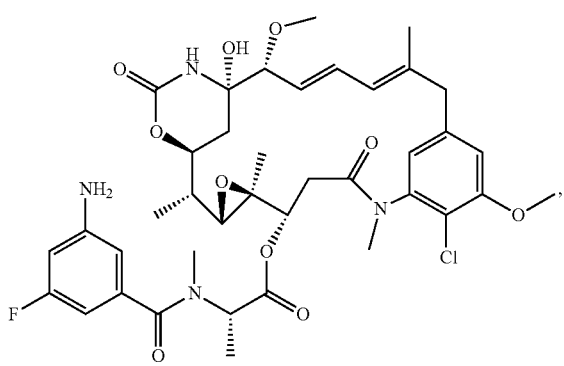
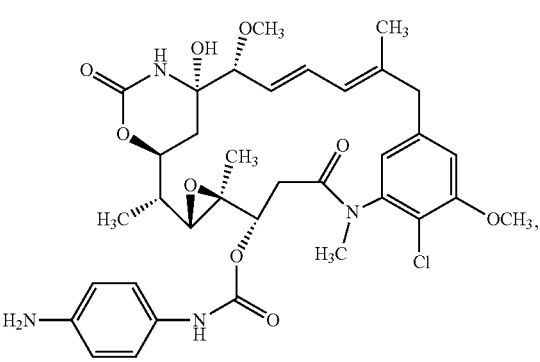
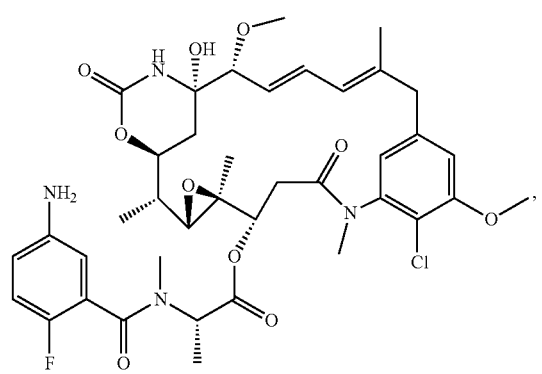
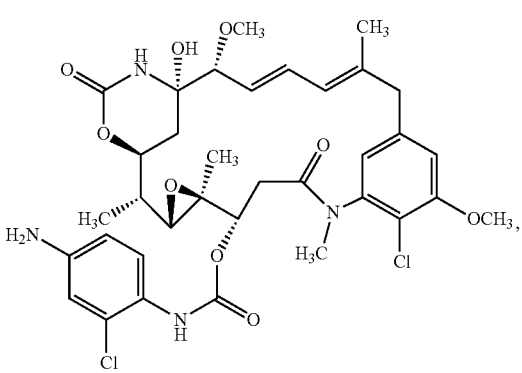

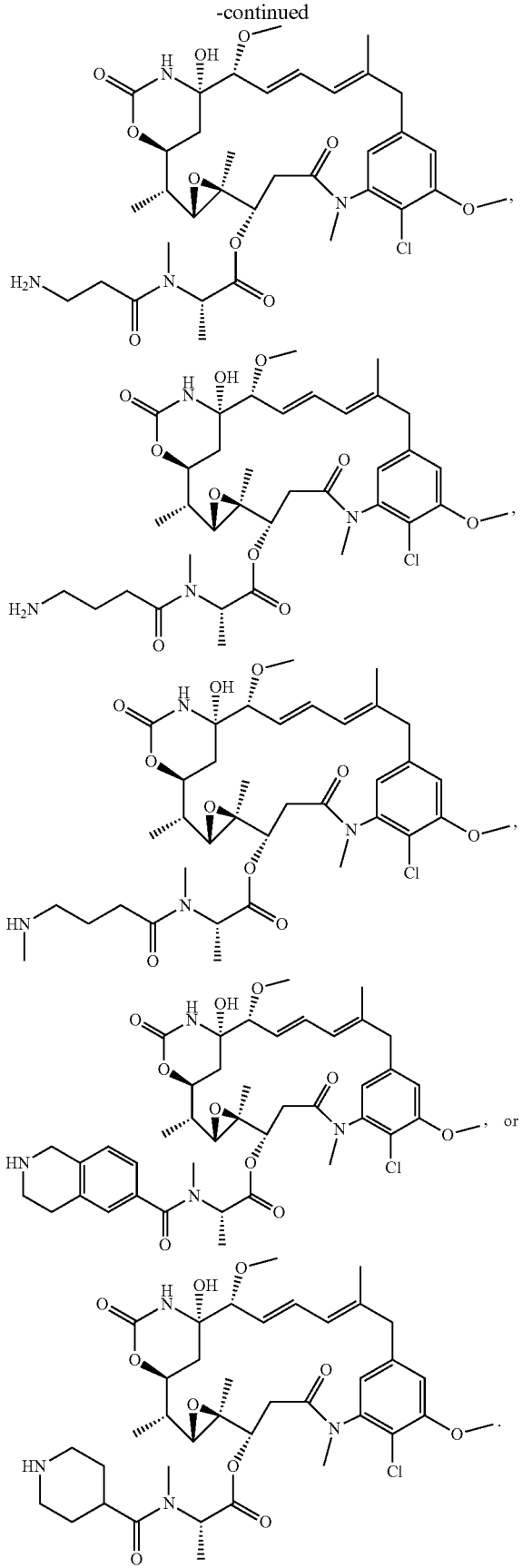

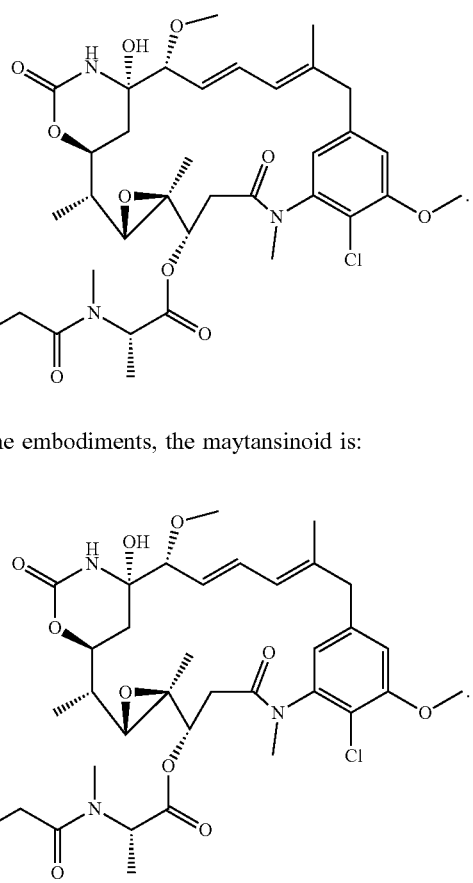

In some embodiments, the maytansinoid is:

In some embodiments, the maytansinoid is:

Also provided herein are antibody-radionuclide conjugates (ARCs) comprising anti-HER2 antibodies conjugated to one or more radionuclides. Exemplary radionuclides that can be used in the context of this aspect of the disclosure include, but are not limited to, e.g., $^{225}$Ac, $^{212}$Bi, $^{213}$Bi, $^{131}$I, $^{186}$Re, $^{227}$Th, $^{222}$Rn, $^{223}$Ra, $^{224}$Ra, and $^{90}$Y.

In certain embodiments provided herein, ADCs are provided comprising an anti-MET antibody or an anti-HER2× anti-APLP2 bispecific antigen-binding protein conjugated to a cytotoxic agent (e.g., any of the cytotoxic agents disclosed above) via a linker molecule. Linkers are any group or moiety that links, connects, or bonds the antibody or antigen-binding proteins described herein with a therapeutic moiety, e.g. cytotoxic agent. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. Generally, suitable binding agent linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers include linkers that are cleaved by intracellular metabolism following internalization, e.g., cleavage via hydrolysis, reduction, or enzymatic reaction. Non-cleavable linkers include linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citruline units, and para-aminobenzyl (PAB) units.

Any linker molecule or linker technology known in the art can be used to create or construct an ADC of the present disclosure. In certain embodiments, the linker is a cleavable linker. According to other embodiments, the linker is a non-cleavable linker. Exemplary linkers that can be used in the context of the present disclosure include, linkers that comprise or consist of e.g., MC (6-maleimidocaproyl), MP (maleimidopropanoyl), val-cit (valine-citrulline), val-ala (valine-alanine), val-gly (valine-glycine), dipeptide site in protease-cleavable linker, ala-phe (alanine-phenylalanine), dipeptide site in protease-cleavable linker, PAB (p-amino-benzyloxycarbonyl), SPP (N-Succinimidyl 4-(2-pyridylthio) pentanoate), SMCC (N-Succinimidyl 4-(N-maleimidomethyl)cyclohexane-1 carboxylate), SIAB (N-Succinimidyl (4-iodo-acetyl)aminobenzoate), and variants and combinations thereof. Additional examples of linkers that can be used in the context of the present disclosure are provided, e.g., in U.S. Pat. No. 7,754,681 and in Ducry, Bioconjugate Chem., 2010, 21:5-13, and the references cited therein, the contents of which are incorporated by reference herein in their entireties.

In certain embodiments, the linkers are stable in physiological conditions. In certain embodiments, the linkers are cleavable, for instance, able to release at least the payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety.

Suitable linkers also include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L- or D-α-amino acids. In some embodiments, the linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker comprises valine and citrulline. In some embodiments, the linker comprises lysine, valine, and citrulline. In some embodiments, the linker comprises lysine, valine, and alanine. In some embodiments, the linker comprises valine and alanine.

In some embodiments, the linker comprises a self-immolative group. The self-immolative group can be any such group known to those of skill. In particular embodiments, the self-immolative group isp-aminobenzyl (PAB), or a derivative thereof. Useful derivatives include p-aminobenzyloxycarbonyl (PABC). Those of skill will recognize that a self-immolative group is capable of carrying out a chemical reaction which releases the remaining atoms of a linker from a payload.

In some embodiments, the linker is:

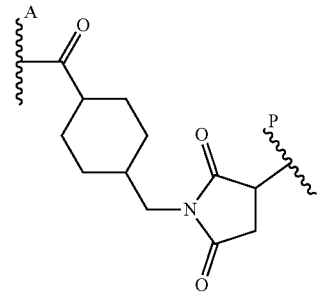

wherein

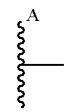

is a bond to the antibody or antigen-binding protein (e.g., via lysine residue) and

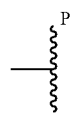

is a bond to the cytotoxic agent (e.g., DM1). In some embodiments, the linker is:

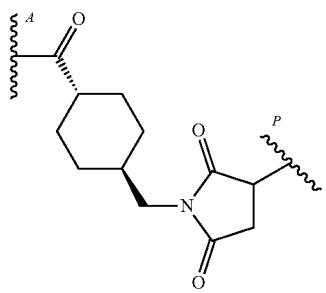

wherein

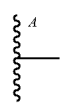

is a bond to the antibody or antigen-binding protein (e.g., via lysine residue) and

is a bond to the cytotoxic agent (e.g., DM1). In certain embodiments, the linker is:

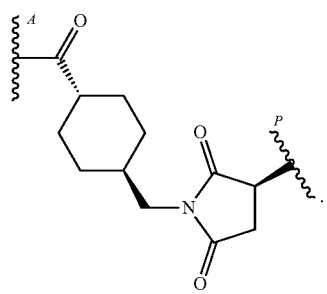

In certain embodiments, the linker is:

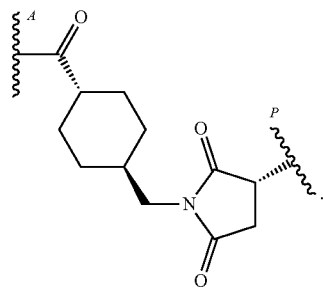

In some embodiments, the linker is derived from maleimidylmethyl-4-trans-cyclohexanecarboxysuccinate:

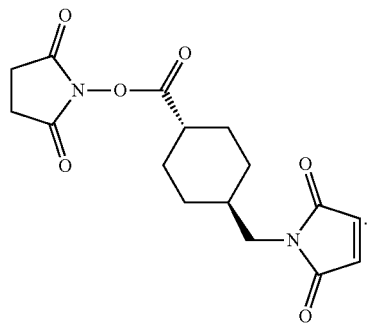 [SMILES: O=C1C=CC(=O)N1C[C@H]1CC[C@H](C(=O)ON2C(=O)CCC2=O)CC1]

In some embodiments, the linker is:

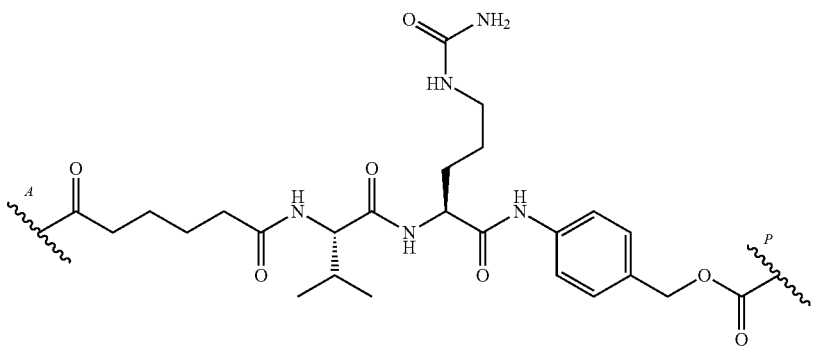

wherein

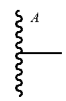

is a bond to the antibody or antigen-binding protein (e.g., via lysine residue) and

is a bond to the cytotoxic agent (e.g., a compound having the following formula:

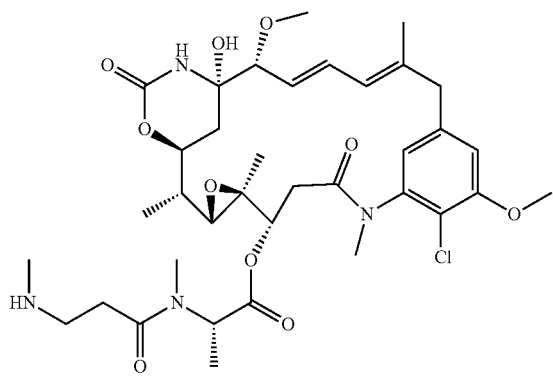

).

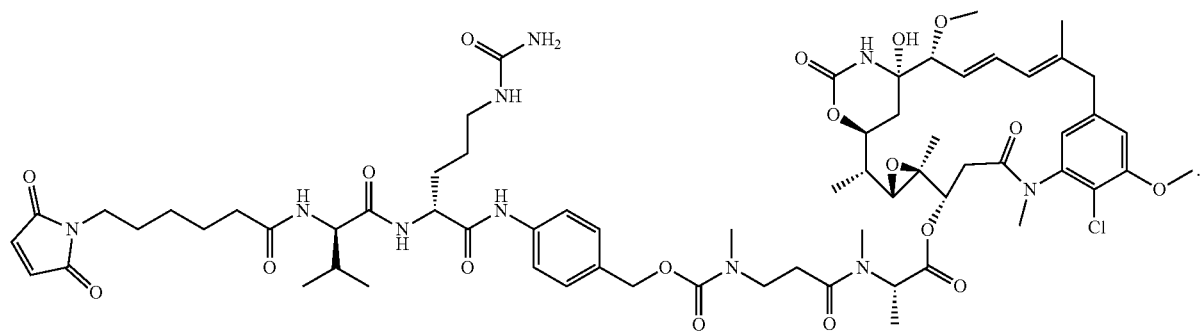

7

The present disclosure comprises ADCs in which a linker connects an anti-HER2×anti-APLP2 bispecific antigen-binding protein or anti-HER2 antibody to a drug or cytotoxin through an attachment at a particular amino acid within the antibody or antigen-binding molecule. Exemplary amino acid attachments that can be used in the context of this aspect, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; and US 2013/0101546), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA,* 2008, 105:12451-12456), formyl glycine (see, e.g., Carrico et al., *Nat. Chem. Biol.,* 2007, 3:321-322; Agarwal et al., *Proc. Natl. Acad. Sci., USA,* 2013, 110:46-51, and Rabuka et al., *Nat. Protocols,* 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan et al., *Food & Agriculture Immunol.,* 2001, 13:127-130) and disulfide linkers (see, e.g., WO 2013/085925, WO 2010/010324, WO 2011/018611, and Shaunak et al., *Nat. Chem. Biol.,* 2006, 2:312-313). Site specific conjugation techniques can also be employed to direct conjugation to particular residues of the antibody or antigen binding protein (see, e.g., Schumacher et al. *J Clin Immunol* (2016) 36(Suppl 1): 100). Site specific conjugation techniques, include, but are not limited to glutamine conjugation via transglutaminase (see e.g., Schibli, *Angew Chemie* Inter Ed. 2010, 49, 9995).

According to certain embodiments, the present disclosure provides ADCs, wherein an anti-HER2×anti-APLP2 bispecific antigen-binding protein or anti-HER2 antibody as described herein is conjugated to a linker-drug composition as set forth in International Patent Publication WO2014/145090, (e.g., compound "7," also referred to herein as "M0026" and depicted below), the disclosure of which is hereby incorporated by reference herein in its entirety:

Provided herein are also antibody-drug conjugates comprising the anti-HER2×anti-APLP2 bispecific antigen-binding proteins or anti-HER2 antibodies disclosed herein, where said anti-HER2×anti-APLP2 bispecific antigen-binding protein or anti-HER2 antibody is conjugated to a cytotoxic agent. In certain embodiments, the cytotoxic agent is a maytansinoid. In certain embodiments, the maytansinoid is a compound having the following formula:

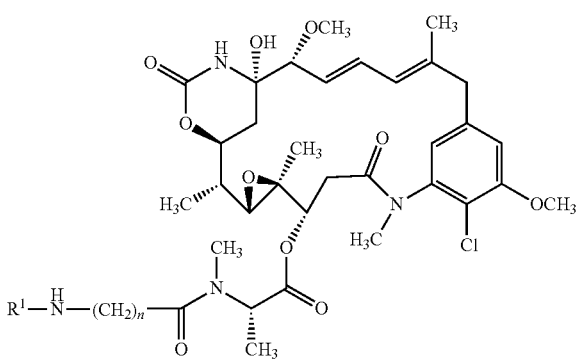

wherein n is an integer from 1-12 and $R^1$ is alkyl. In certain embodiments, the maytansinoid is

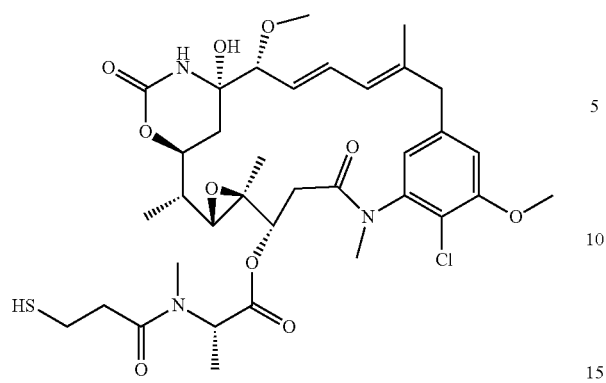

or

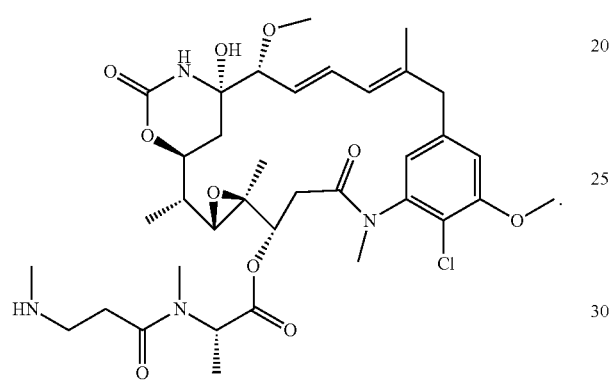

In certain embodiments, the cytotoxic agent is a maytansinoid, and the maytansinoid is covalently attached to the antibody via non-cleavable linker. In certain embodiments, the cytotoxic agent is a maytansinoid, and the maytansinoid is covalently attached to the antibody via cleavable linker.

In one embodiment, the antibody is conjugated to:

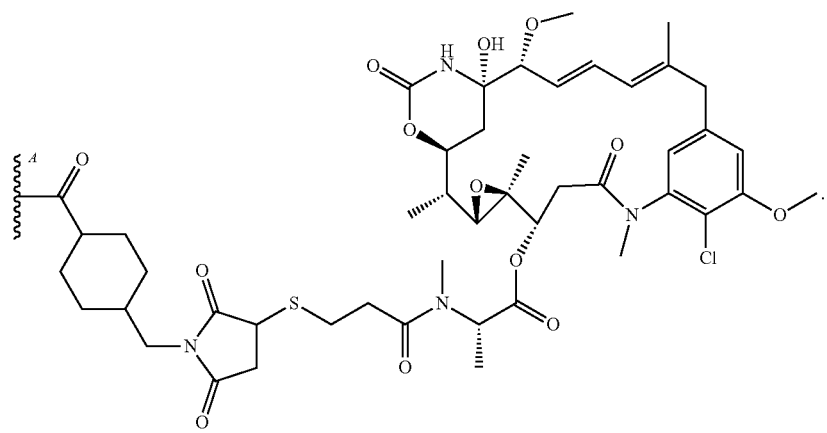

wherein

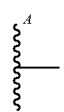

is a bond to the antibody.

In one embodiment, the antibody is conjugated to:
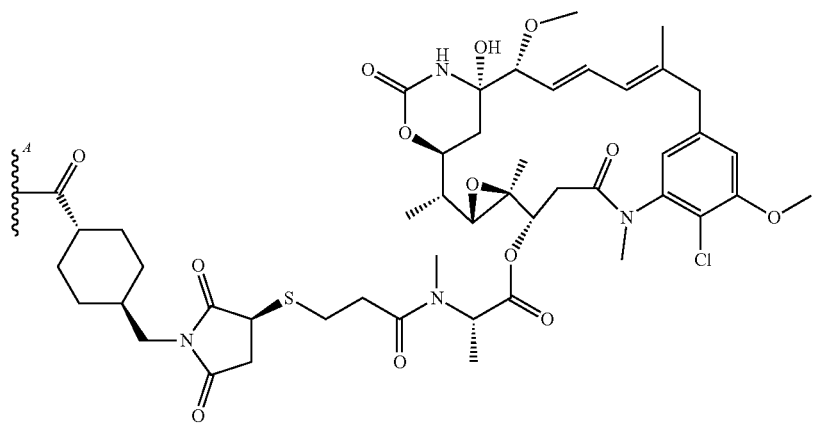
wherein
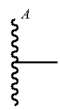
is a bond to the antibody.
In one embodiment, the antibody is conjugated to:
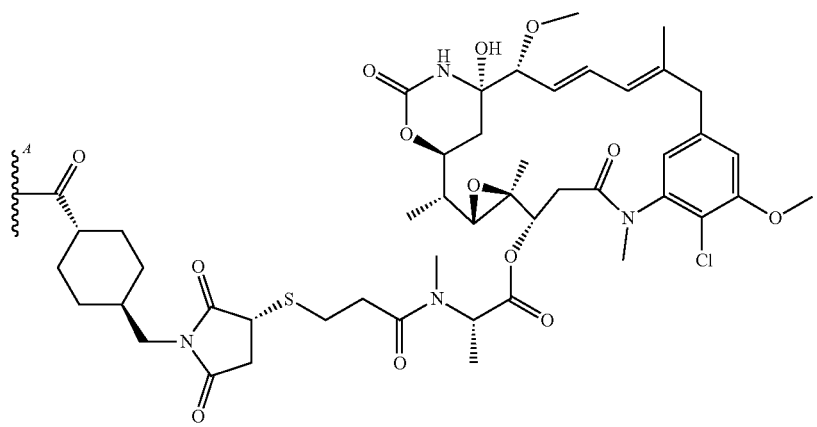
wherein
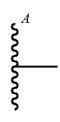
is a bond to the antibody.

In one embodiment, the antibody is conjugated to:

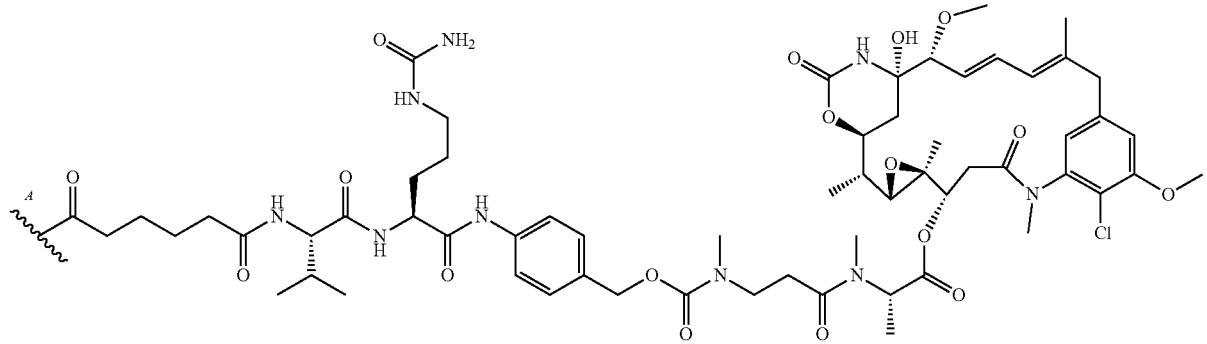

wherein

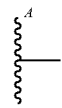

is a bond to the antibody.

In some embodiments, the conjugates have the following structure:

Ab-[L-Pay]$_n$ wherein:
Ab is an anti-HER2×anti-APLP2 bispecific antigen-binding protein or anti-HER2 antibody as described herein;
L is a linker;
Pay is a cytotoxic agent; and
n is an integer from 1-10.

In some embodiments, Ab is any of the antibodies or antigen-binding proteins described in Table 1 or 3.

In some embodiments, Payload is a maytansinoid.

In some embodiments, Pay is:

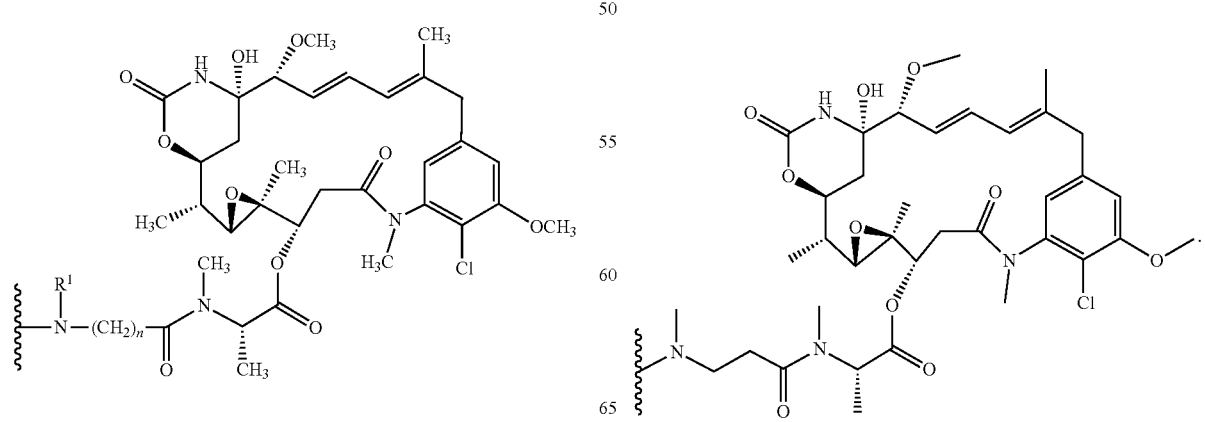

wherein R$^1$ is alkyl.

In some embodiments, Pay is:

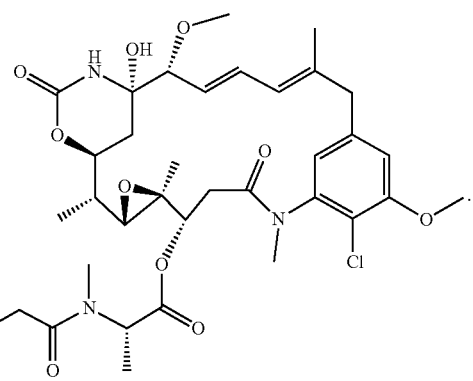

In some embodiments, Pay is:

In some embodiments, n is an integer from 2 to 5.
In some embodiments, -L-Pay is:
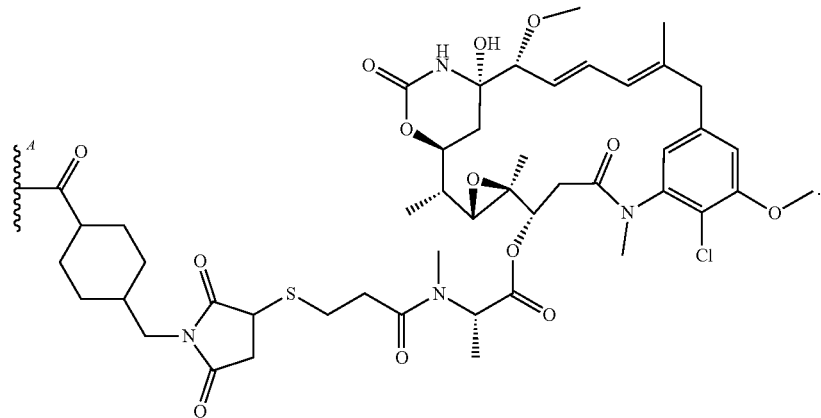
wherein
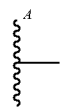
is a bond to the antibody.
In some embodiments, -L-Pay is:
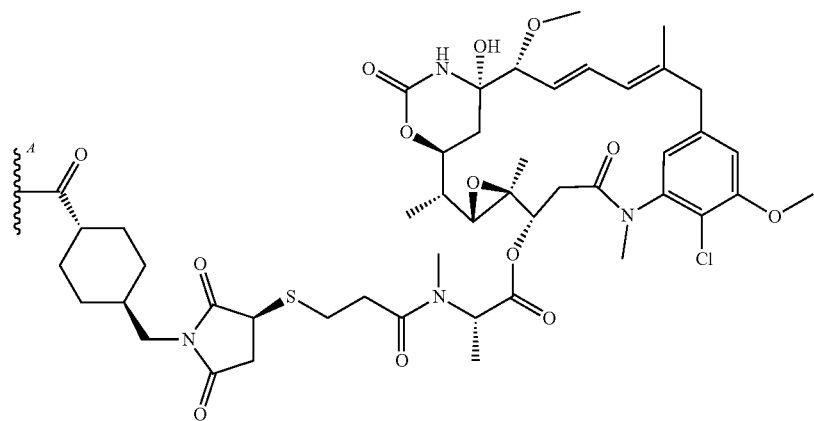
wherein
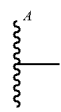
is a bond to the antibody.

In some embodiments, -L-Pay is
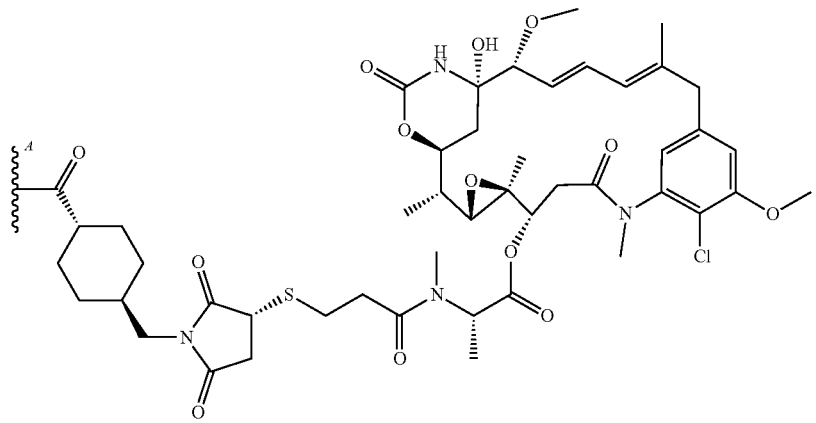
wherein
is a bond to the antibody.
In some embodiments, -L-Pay is:
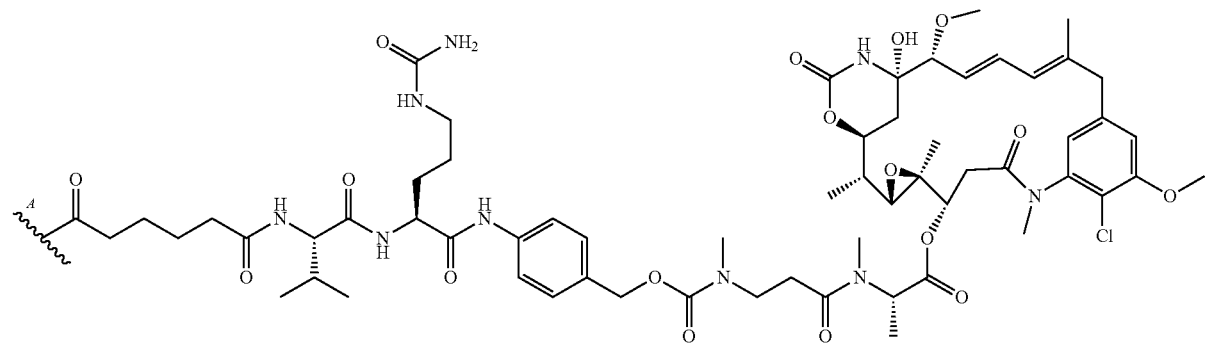
wherein
is a bond to the antibody.

In some embodiments, -L-Pay is:

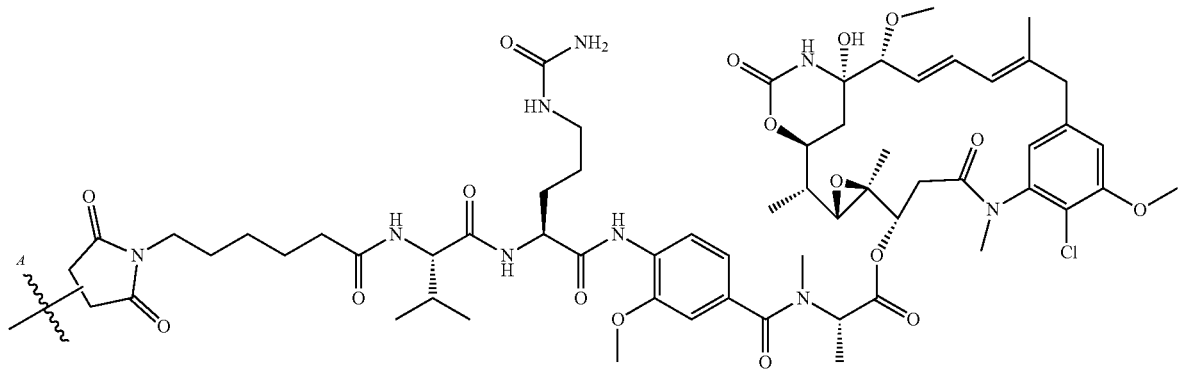

wherein

is a bond to the antibody.

The present invention provides antibody-drug conjugates (ADC) comprising an anti-HER2 antibody or antigen-binding fragments thereof and a therapeutic agent ("Pay") (e.g., a cytotoxic agent), such as but not limited to DM1. In some embodiments, the an anti-HER2 antibody or antigen-binding fragment and the cytotoxic agent (such as, but not limited to DM1) are covalently attached via a linker ("L"), such as but not limited to SMCC. In various embodiments, the ADC comprises
- an anti-HER2 antibody or antigen-binding fragment thereof that comprises the CDRs of a HCVR and a LCVR having the amino acid sequences of the SEQ ID NOs (e.g., SEQ ID NOs: 2, 18 and 10) set forth in Table 1, specific HCVR/LCVR pairs (e.g., SEQ ID NOs: 2/10 or 18/10), and/or CDRs with the amino acid sequences of the SEQ ID NOs (e.g., SEQ ID NOs: 4-6-8-12-14-16, 20-22-24-12-14-16) set forth in Table 1, and
- a maytansinoid, optionally DM1,
- optionally wherein the anti-HER2 antibody or antigen-binding fragment thereof and the maytansinoid are covalently attached via a linker, e.g., SMCC.

In some embodiments, the ADC comprises an anti-HER2 antibody or antigen-binding fragment thereof that comprises the CDRs of a HCVR and a LCVR having the amino acid sequences of the SEQ ID NOs (e.g., SEQ ID NOs: 2, 18 and 10) set forth in Table 1, specific HCVR/LCVR pairs (e.g., SEQ ID NOs: 2/10 or 18/10), and/or CDRs with the amino acid sequences of the SEQ ID NOs (e.g., SEQ ID NOs: 4-6-8-12-14-16, 20-22-24-12-14-16) set forth in Table 1, conjugated to

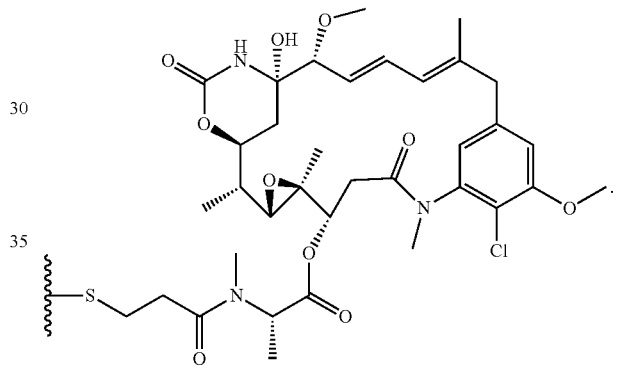

In some embodiments, the ADC comprises an anti-HER2 antibody or antigen-binding fragment thereof that comprises the CDRs of a HCVR and a LCVR having the amino acid sequences of the SEQ ID NOs (e.g., SEQ ID NOs: 2, 18 and 10) set forth in Table 1, specific HCVR/LCVR pairs (e.g., SEQ ID NOs: 2/10 or 18/10), and/or CDRs with the amino acid sequences of the SEQ ID NOs (e.g., SEQ ID NOs: 4-6-8-12-14-16, 20-22-24-12-14-16) set forth in Table 1, and

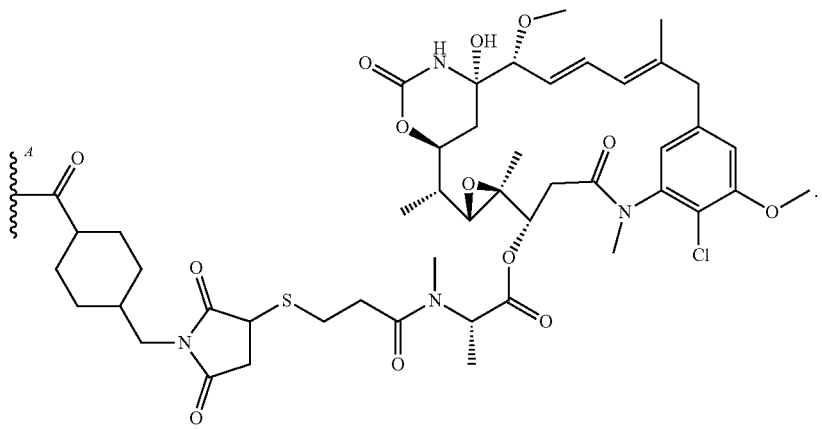

wherein

is a bond to the anti-HER2 antibody or antigen-binding fragment thereof.

In some embodiments, the ADC comprises an anti-HER2 antibody or antigen-binding fragment thereof that comprises the CDRs of a HCVR and a LCVR having the amino acid sequences of the SEQ ID NOs (e.g., SEQ ID NOs: 2, 18 and 10) set forth in Table 1, specific HCVR/LCVR pairs (e.g., SEQ ID NOs: 2/10 or 18/10), and/or CDRs with the amino acid sequences of the SEQ ID NOs (e.g., SEQ ID NOs: 4-6-8-12-14-16, 20-22-24-12-14-16) set forth in Table 1, and

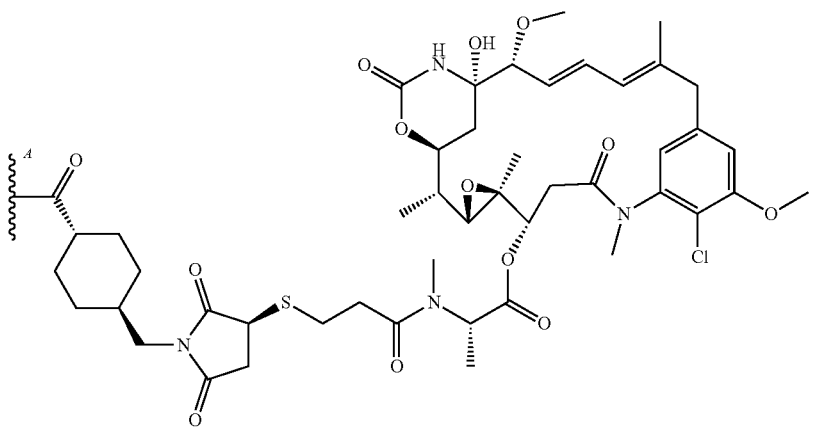

wherein

is a bond to the anti-HER2 antibody or antigen-binding fragment thereof.

In some embodiments, the ADC comprises an anti-HER2 antibody or antigen-binding fragment thereof that comprises the CDRs of a HCVR and a LCVR having the amino acid sequences of the SEQ ID NOs (e.g., SEQ ID NOs: 2, 18 and 10) set forth in Table 1, specific HCVR/LCVR pairs (e.g., SEQ ID NOs: 2/10 or 18/10), and/or CDRs with the amino acid sequences of the SEQ ID NOs (e.g., SEQ ID NOs: 4-6-8-12-14-16, 20-22-24-12-14-16) set forth in Table 1, and

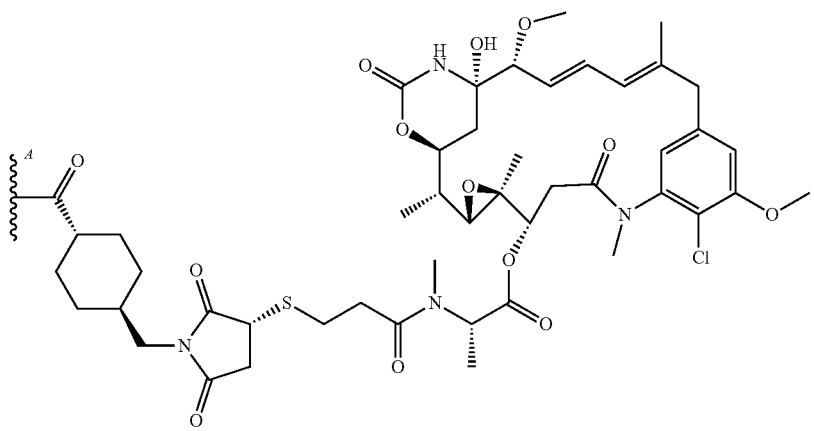

wherein

is a bond to the anti-HER2 antibody or antigen-binding fragment thereof.

In various embodiments, the ADC comprises an anti-HER2 antibody or antigen-binding fragment thereof that comprises the CDRs of a HCVR and a LCVR having the amino acid sequences of the SEQ ID NOs (e.g., SEQ ID NOs: 2, 18 and 10) set forth in Table 1, or specific HCVR/LCVR pairs (e.g., SEQ ID NOs: 2/10 or 18/10). In some cases, the anti-HER2 antibody or fragment comprises CDRs with the amino acid sequences of the SEQ ID NOs (e.g., SEQ ID NOs: 4-6-8-12-14-16, 20-22-24-12-14-16) set forth in Table 1. In some cases, the anti-HER2 antibody or fragment comprises a HCVR and a LCVR having the amino acid sequences of the SEQ ID NOs (e.g., SEQ ID NOs: 2, 18 and 10) set forth in Table 1, or specific amino acid sequence pairs (e.g., SEQ ID NOs: 2/10 and 18/10).

In various embodiments, the ADC comprises an anti-HER2×anti-APLP2 antibody or antigen-binding fragment thereof that comprises the CDRs of the HCVR arms and same LCVR arms having the amino acid sequences of the SEQ ID NOs set forth in Table 3 (e.g., having the HCVR1-HCVR2-LCVR SEQ ID NOs: 2-26-10; 2-34-10; 2-42-10; 18-26-10; 18-34-10; or 18-42-10) set forth in Table 3, or two specific HCVR/LCVR pairs (e.g., SEQ ID NOs: 2/10 and 26/10; 2/10 and 34/10; 2/10 and 42/10; 18/10 and 26/10; 18/10 and 34/10; or 18/10 and 42/10). In some cases, the anti-HER2×anti-APLP2 antibody or fragment comprises HC-CDRs and LC-CDRs with the amino acid sequences of the SEQ ID NOs (e.g., SEQ ID NOs: 4-6-8-12-14-16 and 28-30-32-12-14-16) set forth in Tables 1 and 2. In another embodiment, the ADC comprises an anti-HER2×anti-APLP2 antibody or antigen-binding fragment thereof that comprises the HCVR arms and same LCVR arm having the amino acid sequences of the SEQ ID NOs set forth in Table 3 (e.g., SEQ ID NOs2/10 and 26/10; 2/10 and 34/10; 2/10 and 42/10; 18/10 and 26/10; 18/10 and 34/10; or 18/10 and 42/10).

In some embodiments, the ADC comprises an anti-HER2×anti-APLP2 antibody or antigen-binding fragment thereof and a therapeutic agent ("Pay") (e.g., a cytotoxic agent), such as but not limited to DM1. In some embodiments, the an anti-HER2×anti-APLP2 antibody or antigen-binding fragment thereof and the cytotoxic agent (such as, but not limited to DM1) are covalently attached via a linker ("L"), such as but not limited to SMCC. In various embodiments, the ADC comprises an anti-HER2×anti-APLP2 antibody or antigen-binding fragment thereof that comprises the CDRs of the HCVR arms and same LCVR arms having the amino acid sequences of the SEQ ID NOs set forth in Table 3 (e.g., having the HCVR1-HCVR2-LCVR SEQ ID NOs: 2-26-10; 2-34-10; 2-42-10; 18-26-10; 18-34-10; or 18-42-10), two specific HCVR/LCVR pairs (e.g., SEQ ID NOs: 2/10 and 26/10; 2/10 and 34/10; 2/10 and 42/10; 18/10 and 26/10; 18/10 and 34/10; or 18/10 and 42/10), HC-CDRs and LC-CDRs with the amino acid sequences of the SEQ ID NOs set forth in Tables 1 and 2 (e.g., SEQ ID NOs: 4-6-8-12-14-16 and 28-30-32-12-14-16), and/or the HCVR arms and same LCVR arm having the amino acid sequences of the SEQ ID NOs set forth in Table 3 (e.g., SEQ ID NOs2/10 and 26/10; 2/10 and 34/10; 2/10 and 42/10; 18/10 and 26/10; 18/10 and 34/10; or 18/10 and 42/10), and a maytansinoid, optionally DM1, optionally wherein the anti-HER2×anti-APLP2 antibody or antigen-binding fragment thereof and the maytansinoid are covalently attached via a linker, e.g., SMCC.

In some embodiments, the ADC comprises an anti-HER2×anti-APLP2 antibody or antigen-binding fragment thereof that comprises the CDRs of the HCVR arms and same LCVR arms having the amino acid sequences of the SEQ ID NOs set forth in Table 3 (e.g., having the HCVR1-HCVR2-LCVR SEQ ID NOs: 2-26-10; 2-34-10; 2-42-10; 18-26-10; 18-34-10; or 18-42-10), two specific HCVR/LCVR pairs (e.g., SEQ ID NOs: 2/10 and 26/10; 2/10 and 34/10; 2/10 and 42/10; 18/10 and 26/10; 18/10 and 34/10; or 18/10 and 42/10), HC-CDRs and LC-CDRs with the amino acid sequences of the SEQ ID NOs set forth in Tables 1 and 2 (e.g., SEQ ID NOs: 4-6-8-12-14-16 and 28-30-32-12-14-16), and/or the HCVR arms and same LCVR arm having the amino acid sequences of the SEQ ID NOs set forth in Table 3 (e.g., SEQ ID NOs2/10 and 26/10; 2/10 and 34/10; 2/10 and 42/10; 18/10 and 26/10; 18/10 and 34/10; or 18/10 and 42/10) conjugated to

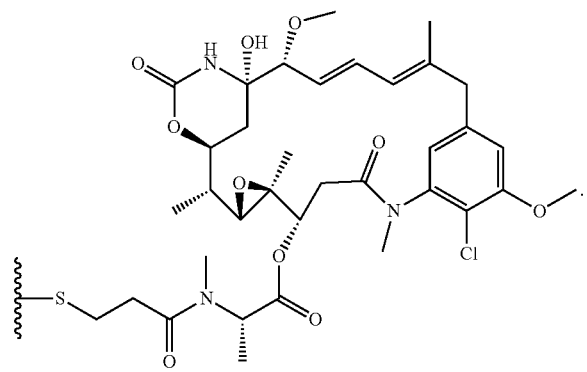 [SMILES: *SCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In some embodiments, the ADC comprises an anti-HER2×anti-APLP2 antibody or antigen-binding fragment thereof that comprises the CDRs of the HCVR arms and same LCVR arms having the amino acid sequences of the SEQ ID NOs set forth in Table 3 (e.g., having the HCVR1-HCVR2-LCVR SEQ ID NOs: 2-26-10; 2-34-10; 2-42-10; 18-26-10; 18-34-10; or 18-42-10), two specific HCVR/LCVR pairs (e.g., SEQ ID NOs: 2/10 and 26/10; 2/10 and 34/10; 2/10 and 42/10; 18/10 and 26/10; 18/10 and 34/10; or 18/10 and 42/10), HC-CDRs and LC-CDRs with the amino acid sequences of the SEQ ID NOs set forth in Tables 1 and 2 (e.g., SEQ ID NOs: 4-6-8-12-14-16 and 28-30-32-12-14-16), and/or the HCVR arms and same LCVR arm having the amino acid sequences of the SEQ ID NOs set forth in Table 3 (e.g., SEQ ID NOs2/10 and 26/10; 2/10 and 34/10; 2/10 and 42/10; 18/10 and 26/10; 18/10 and 34/10; or 18/10 and 42/10), and

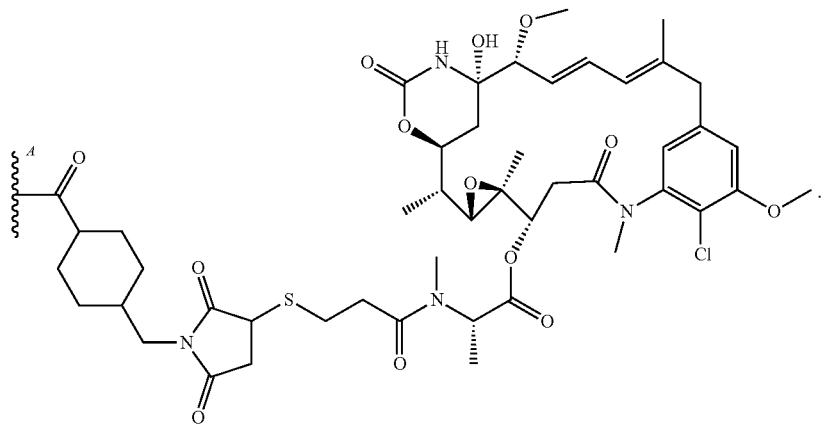

wherein

is a bond to the anti-HER2×anti-APLP2 antibody or antigen-binding fragment thereof.

In some embodiments, the ADC comprises an anti-HER2×anti-APLP2 antibody or antigen-binding fragment thereof that comprises the CDRs of the HCVR arms and same LCVR arms having the amino acid sequences of the SEQ ID NOs set forth in Table 3 (e.g., having the HCVR1-HCVR2-LCVR SEQ ID NOs: 2-26-10; 2-34-10; 2-42-10; 18-26-10; 18-34-10; or 18-42-10), two specific HCVR/LCVR pairs (e.g., SEQ ID NOs: 2/10 and 26/10; 2/10 and 34/10; 2/10 and 42/10; 18/10 and 26/10; 18/10 and 34/10; or 18/10 and 42/10), HC-CDRs and LC-CDRs with the amino acid sequences of the SEQ ID NOs set forth in Tables 1 and 2 (e.g., SEQ ID NOs: 4-6-8-12-14-16 and 28-30-32-12-14-16), and/or the HCVR arms and same LCVR arm having the amino acid sequences of the SEQ ID NOs set forth in Table 3 (e.g., SEQ ID NOs2/10 and 26/10; 2/10 and 34/10; 2/10 and 42/10; 18/10 and 26/10; 18/10 and 34/10; or 18/10 and 42/10), and wherein

is a bond to the anti-HER2×anti-APLP2 antibody or antigen-binding fragment thereof.

In some embodiments, the ADC comprises an anti-HER2×anti-APLP2 antibody or antigen-binding fragment thereof that comprises the CDRs of the HCVR arms and same LCVR arms having the amino acid sequences of the SEQ ID NOs set forth in Table 3 (e.g., having the HCVR1-HCVR2-LCVR SEQ ID NOs: 2-26-10; 2-34-10; 2-42-10; 18-26-10; 18-34-10; or 18-42-10), two specific HCVR/LCVR pairs (e.g., SEQ ID NOs: 2/10 and 26/10; 2/10 and 34/10; 2/10 and 42/10; 18/10 and 26/10; 18/10 and 34/10; or 18/10 and 42/10), HC-CDRs and LC-CDRs with the amino acid sequences of the SEQ ID NOs set forth in Tables 1 and 2 (e.g., SEQ ID NOs: 4-6-8-12-14-16 and 28-30-32-12-14-16), and/or the HCVR arms and same LCVR arm having the amino acid sequences of the SEQ ID NOs set forth in Table 3 (e.g., SEQ ID NOs2/10 and 26/10; 2/10 and 34/10; 2/10 and 42/10; 18/10 and 26/10; 18/10 and 34/10; or 18/10 and 42/10), and

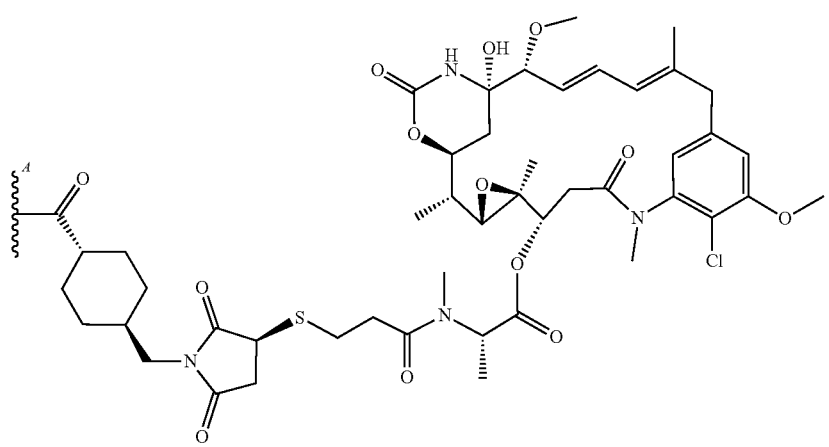

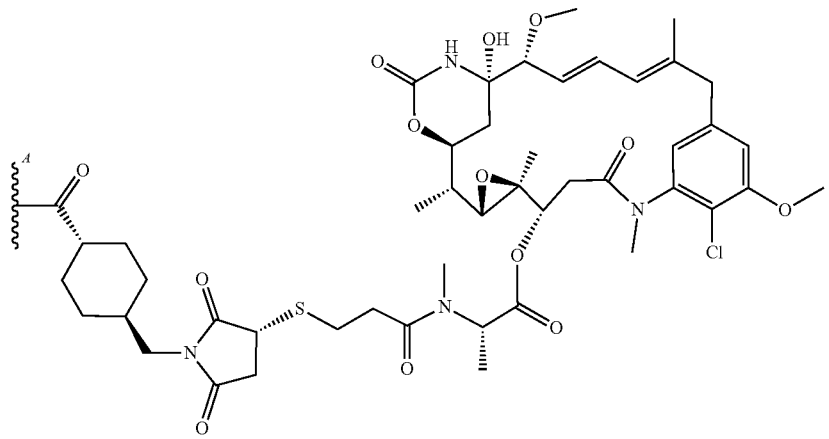

wherein

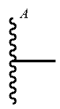

is a bond to the anti-HER2×anti-APLP2 antibody or antigen-binding fragment thereof.

The antibody drug conjugates described herein can be prepared using conjugation conditions known to those of ordinary skill in the art, (see, e.g., Doronina et al. *Nature Biotechnology* 2003, 21, 7, 778, which is incorporated herein by reference in its entirety). In some embodiments an anti-HER2×anti-APLP2 bispecific antigen-binding protein or anti-HER2 antibody drug conjugate is prepared by contacting an anti-HER2×anti-APLP2 bispecific antigen-binding protein or anti-HER2 antibody described herein with a compound comprising the desired linker and cytotoxic agent, wherein said linker possesses a moiety that is reactive with the antibody or antigen-binding protein, e.g., at the desired residue of the antibody or antigen-binding protein.

In some embodiments, provided herein are processes for preparing an antibody-drug conjugate comprising contacting an anti-HER2×anti-APLP2 bispecific antigen-binding protein or anti-HER2 antibody described herein with a compound having the following formula $A^1$:

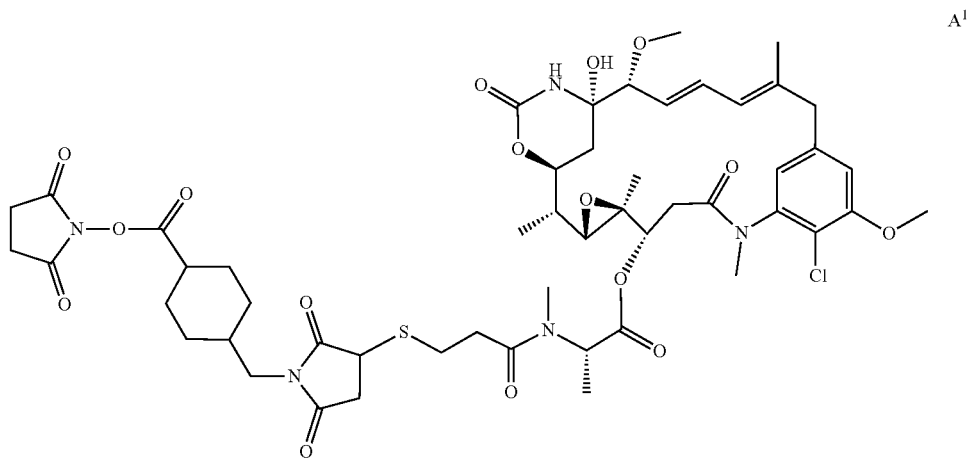 [SMILES: COc1cc2cc(c1Cl)N(C)C(=O)C[C@H](OC(=O)[C@H](C)N(C)C(=O)CCSC1CC(=O)N(CC3CCC(C(=O)ON4C(=O)CCC4=O)CC3)C1=O)[C@]1(C)O[C@H]1[C@H](C)[C@@H]1C[C@@](O)(NC(=O)O1)[C@H](OC)/C=C/C=C(\C)C2]

and aqueous diluent.

In some embodiments, the compound of formula $A^1$ is present in stoichiometric excess. In some embodiments, the compound of formula $A^1$ is present in 5-6 fold stoichiometric excess. In some embodiments, the aqueous diluent comprises HEPES. In some embodiments, the aqueous diluent comprises DMA.

In some embodiments, the compound of formula A¹ is a compound of formula A² or A³:

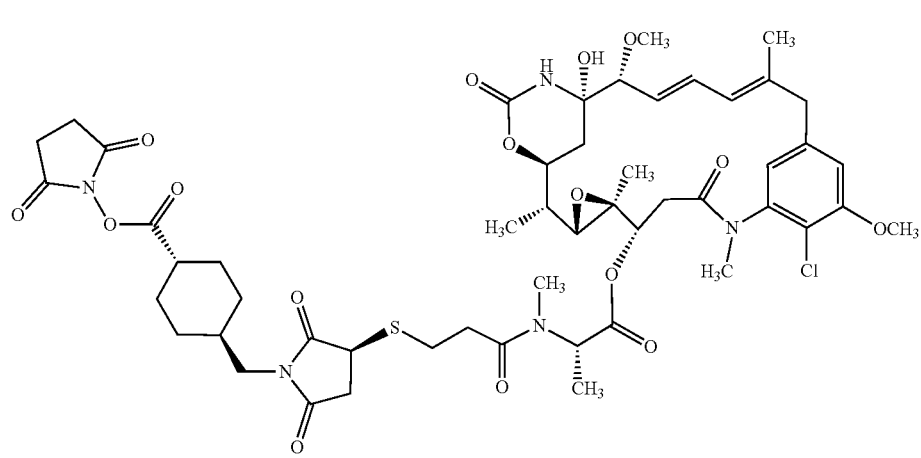

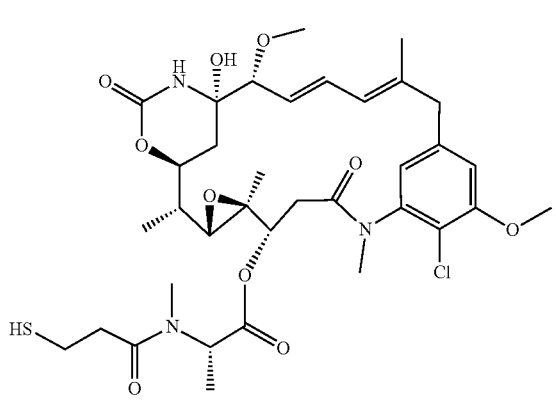

In some embodiments, the compound of formula A² is A³ stereomerically pure. In some embodiments, the compound of formula A¹ comprises a compound of formula A¹ or A², wherein the compound of A¹ or A² is present in a diastereomeric excess of more than 50%. In certain embodiments, the diastereomeric excess is more than 70%. In certain embodiments, the diastereomeric excess is more than 90%. In certain embodiments, the diastereomeric excess is more than 95%. Structures A¹, A² and A³ individually or collectively are known as SMCC-DM1.

The term "diastereomeric excess" refers to the difference between the mole fraction of the desired single diastereomer as compared to the remaining diastereomers in a composition. Diastereomeric excess is calculated as follows: (amount of single diastereomer)−(amount of other diastereomers)/1. For example, a composition that contains 90% of 1 and 10% of 2, 3, 4, or a mixture thereof has a diastereomeric excess of 80% [(90-10)/1]. A composition that contains 95% of 1 and 5% of 2, 3, 4, or a mixture thereof has a diastereomeric excess of 90% [(95-5)/1]. A composition that contains 99% of 1 and 1% of 2, 3, 4, or a mixture thereof has a diastereomeric excess of 98% [(99-1)/1]. The diastereomeric excess can similarly be calculated for any one of 1, 2, 3, or 4.

In some embodiments, the compound of formula A¹ is prepared by contacting a compound of formula (a):

with a compound of formula (b):

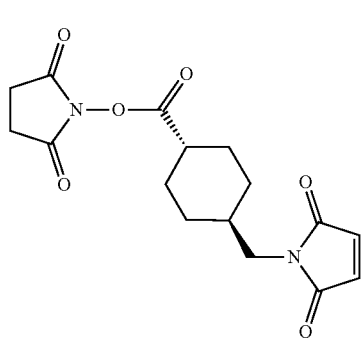

in the presence of silica gel and diluent. In some embodiments, the diluent comprises an organic solvent and water.

Provided herein is also the product prepared by the process of: (i) contacting a compound of formula (a):

(a)

with a compound of formula (b):

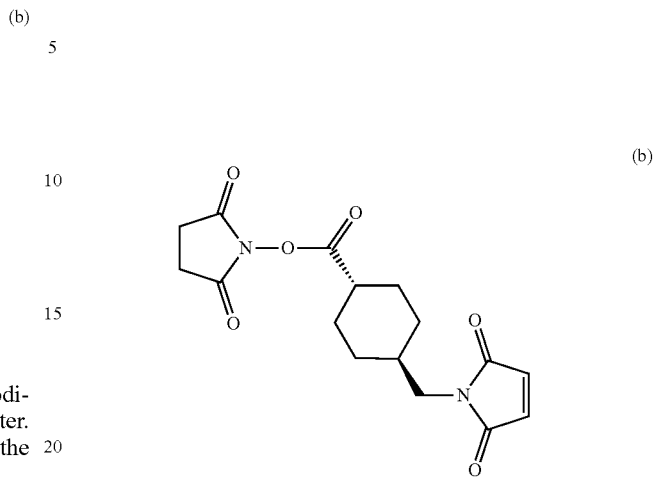

in the presence of silica gel and diluent to synthesize an intermediate; and (ii) contacting an anti-HER2×anti-APLP2 bispecific antigen-binding protein or anti-HER2 antibody described herein with the intermediate and aqueous diluent.

In some embodiments, provided herein are processes for preparing an antibody-drug conjugate comprising contacting an anti-HER2×anti-APLP2 bispecific antigen-binding protein or anti-HER2 antibody described herein with a compound having the following formula B:

B

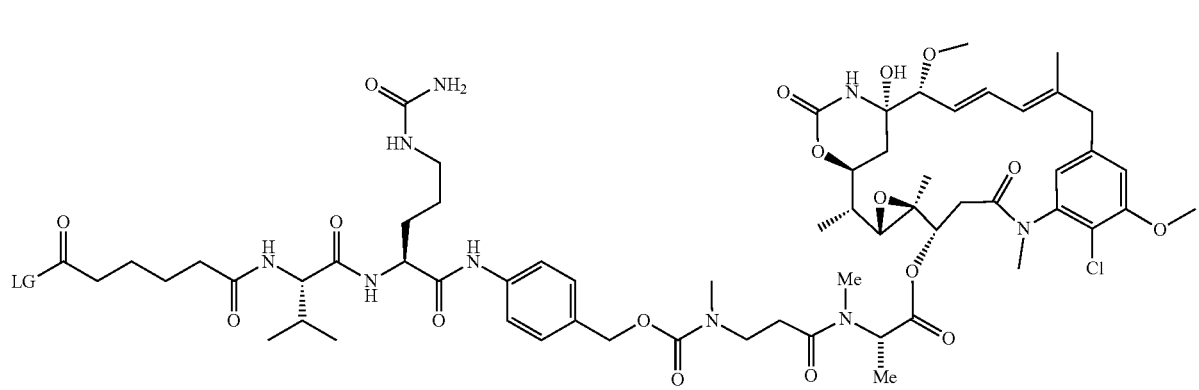

wherein LG is a leaving group, and aqueous diluent.

In some embodiments, the compound of formula B is present in stoichiometric excess. In some embodiments, the compound of formula B is present in 5-6 fold stoichiometric excess. In some embodiments, the aqueous diluent comprises HEPES. In some embodiments, the aqueous diluent comprises DMA. In some embodiments, the —C(O)-LG is an ester, e.g., NHS or pentafluorophenyl ester.

In some embodiments, the compound of formula B is a compound of formula B¹ known as Compound I:

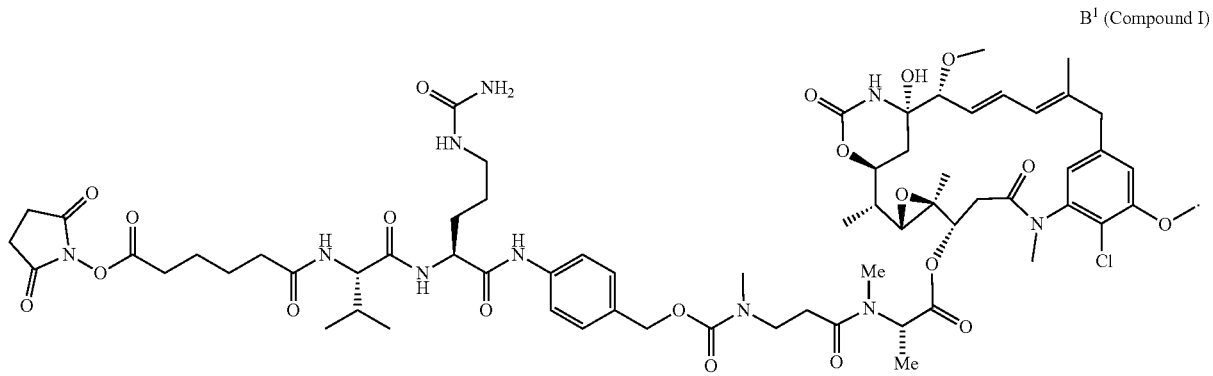

B¹ (Compound I)

In some embodiments, the compound of formula C is known as Compound II:

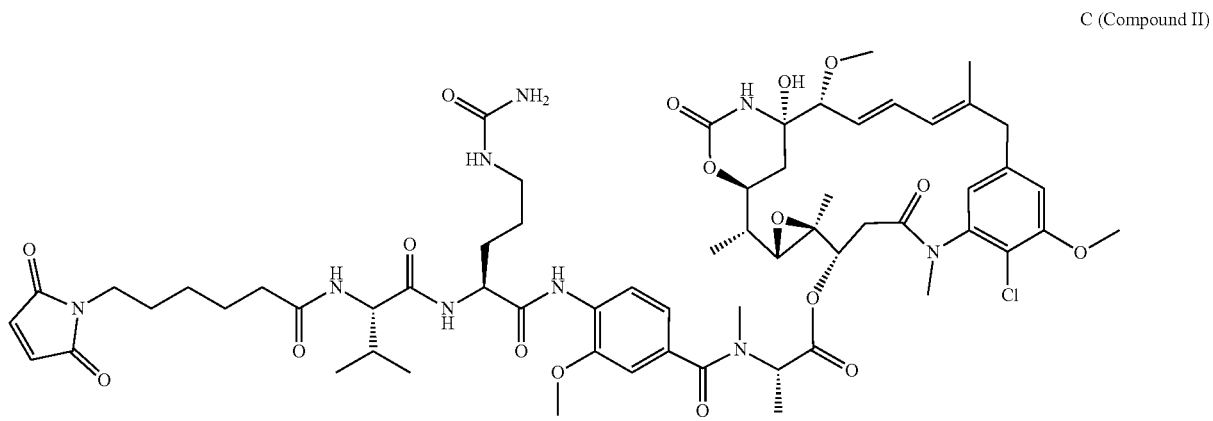 [SMILES: COc1cc(C(=O)N(C)[C@@H](C)C(=O)O[C@H]2CC(=O)N(C)c3cc(cc(OC)c3Cl)C/C(C)=C/C=C/[C@@H](OC)[C@@]3(O)C[C@H](OC(=O)N3)[C@@H](C)[C@@H]3O[C@@]23C)ccc1NC(=O)[C@H](CCCNC(N)=O)NC(=O)[C@@H](NC(=O)CCCCCN1C(=O)C=CC1=O)C(C)C]

C (Compound II)

Drug-to-antibody ratio (DAR) is the average number of drugs conjugated to the antibody or antigen-binding fragment, which has an important effect on the efficacy, potency and pharmacokinetics of the ADC. In various embodiments, the DAR is from 1, 2, 3, 4, 5, 6, 7, or 8 drug molecules per antibody. In some embodiments, the DAR is from 1 to 4. In certain embodiments, the DAR is from 2 to 4. In some cases, the DAR is from 2 to 3. In certain cases, the DAR is from 3 to 4. In some embodiments, the DAR is from 1 to 10, 1 to 20 or 1 to 30 (i.e., from 1 to 30 drug molecules per antibody or antigen-binding fragment thereof).

Therapeutic Formulation and Administration

The present invention provides pharmaceutical compositions comprising the antigen-binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like. The preferred dose is typically calculated according to body weight or body surface area. When a bispecific antigen-binding molecule of the present invention is used for therapeutic purposes in an adult patient, it may be advantageous to intravenously administer the bispecific antigen-binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antigen-Binding Molecules

The present invention includes methods comprising administering to a subject in need thereof a therapeutic composition comprising an anti-HER2 antibody or antigen-binding fragment thereof, or a bispecific antigen-binding molecule that specifically binds APLP2 and HER2. The therapeutic composition can comprise any of the antibodies or bispecific antigen-binding molecules as disclosed herein and a pharmaceutically acceptable carrier or diluent. The expression "a subject in need thereof" means a human or non-human animal that exhibits one or more symptoms or indicia of cancer (e.g., a subject expressing a tumor or suffering from any of the cancers mentioned herein below), or who otherwise would benefit from an inhibition or reduction in HER2 activity or a depletion of HER2+ cells (e.g., breast cancer cells).

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the anti-HER2 antibodies or the anti-APLP2/anti-HER2 bispecific antigen-binding molecules of the present invention may be used for the treatment, prevention and/or amelioration of any disease or disorder associated with or mediated by HER2 expression or activity or the proliferation of HER2+ cells. The mechanism of action by which the therapeutic methods of the invention are achieved include killing of the cells expressing HER2 in the presence of effector cells, for example, by CDC, apoptosis, ADCC, phagocytosis, or by a combination of two or more of these mechanisms. Cells expressing HER2 which can be inhibited or killed using the bispecific antigen-binding molecules of the invention include, for example, breast tumor cells.

The antigen-binding molecules of the present invention may be used to treat, e.g., primary and/or metastatic tumors arising in the prostate, bladder, cervix, lung, colon, kidney, breast, pancreas, stomach, uterus, and/or ovary. In certain embodiments, the bispecific antigen-binding molecules of the invention are used to treat one or more of the following cancers: prostate cancer, bladder cancer, cervical cancer, lung cancer, colon cancer, kidney cancer, breast cancer, pancreatic cancer, stomach cancer, uterine cancer, and ovarian cancer. According to certain embodiments of the present invention, the anti-HER2 antibodies or anti-HER2/anti-APLP2 bispecific antibodies are useful for treating a patient afflicted with a breast cancer cell that is IHC2+ or more. According to other related embodiments of the invention, methods are provided comprising administering an anti-HER2 antibody or an anti-APLP2/anti-HER2 bispecific antigen-binding molecule as disclosed herein to a patient who is afflicted with a breast cancer cell that is IHC2+ or more. Analytic/diagnostic methods known in the art, such as tumor scanning, etc., may be used to ascertain whether a patient harbors a tumor that is castrate-resistant.

The present invention also includes methods for treating residual cancer in a subject. The term "residual cancer" means the existence or persistence of one or more cancerous cells in a subject following treatment with an anti-cancer therapy.

According to certain aspects, the present invention provides methods for treating a disease or disorder associated with HER2 expression (e.g., breast cancer) comprising administering one or more of the anti-HER2 or bispecific antigen-binding molecules described elsewhere herein to a subject after the subject has been determined to have breast cancer (e.g., and IHC2+ breast cancer). For example, the present invention includes methods for treating breast cancer comprising administering an anti-HER2 antibody or an anti-APLP2/anti-HER2 bispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received hormone therapy (e.g., anti-androgen therapy).

Combination Therapies and Formulations

The present invention provides methods which comprise administering a pharmaceutical composition comprising any of the exemplary antibodies and bispecific antigen-binding molecules described herein in combination with one or more additional therapeutic agents. Exemplary additional therapeutic agents that may be combined with or administered in combination with an antigen-binding molecule of the present invention include, e.g., an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody), a VEGF antagonist (e.g., a VEGF-Trap, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 (PSMA) antagonist, a PRLR antagonist (e.g., an anti-PRLR antibody), a HER1 or HER2 antagonist (e.g., an anti-HER1 antibody or an anti-HER2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin antibody), etc. Other agents that may be beneficially administered in combination with the antigen-binding molecules of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present invention (e.g., pharmaceutical compositions comprising an anti-APLP2/anti-HER2 bispecific antigen-binding molecule as disclosed herein) may also be administered as part of a therapeutic regimen comprising one or more therapeutic combinations selected from "ICE": ifosfamide (e.g., Ifex®), carboplatin (e.g., Paraplatin®), etoposide (e.g., Etopophos®, Toposar®, VePesid®, VP-16); "DHAP": dexamethasone (e.g., Decadron®), cytarabine (e.g., Cytosar-U®, cytosine arabinoside, ara-C), cisplatin (e.g., Platinol®-AQ); and "ESHAP": etoposide (e.g., Etopophos®, Toposar®, VePesid®, VP-16), methylprednisolone (e.g., Medrol®), high-dose cytarabine, cisplatin (e.g., Platinol®-AQ).

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvIII, cMet, IGF1R, B-raf, PDGFR-α, PDGFR-β, FOLH1 (PSMA), PRLR, HER1, HER2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, corticosteroids and/or NSAIDs. The antigen-binding molecules of the invention may also be administered as part of a treatment regimen that also includes radiation treatment and/or conventional chemotherapy.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen-binding molecule of the present invention is co-formulated with one or more of the additional therapeutically active component(s) as described elsewhere herein.

Administration Regimens

According to certain embodiments of the present invention, multiple doses of an antigen-binding molecule (e.g., an anti-HER2 antibody or a bispecific antigen-binding molecule that specifically binds HER2 and APLP2) may be administered to a subject over a defined time course. The methods according to this aspect of the invention comprise sequentially administering to a subject multiple doses of an antigen-binding molecule of the invention. The phrase "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose", in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule (e.g., an anti-HER2 antibody or a bispecific antigen-binding molecule that specifically binds HER2 and APLP2). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-HER2 antibodies of the present invention may also be used to detect and/or measure HER2, or HER2-expressing cells in a sample, e.g., for diagnostic purposes. For example, an anti-HER2 antibody, or fragment thereof, may be used to diagnose a condition or disease characterized by aberrant expression (e.g., over-expression, under-expression, lack of expression, etc.) of HER2. Exemplary diagnostic assays for HER2 may comprise, e.g., contacting a sample, obtained from a patient, with an anti-HER2 antibody of the invention, wherein the anti-HER2 antibody is labeled with a detectable label or reporter molecule. Alternatively, an unlabeled anti-HER2 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Another exemplary diagnostic use of the anti-HER2 antibodies of the invention includes $^{89}$Zr-labeled, such as $^{89}$Zr-desferrioxamine-labeled, antibody for the purpose of noninvasive identification and tracking of tumor cells in a subject (e.g. positron emission tomography (PET) imaging). (See, e.g., Tavare, R. et al. Cancer Res. 2016 Jan. 1; 76(1):73-82; and Azad, B B. et al. Oncotarget. 2016 Mar. 15; 7(11):12344-58.) Specific exemplary assays that can be used to detect or measure HER2 in a sample include enzyme-linked immunosorbent assay (ELISA), radioimmunoassay (RIA), and fluorescence-activated cell sorting (FACS).

Samples that can be used in HER2 diagnostic assays according to the present invention include any tissue or fluid sample obtainable from a patient which contains detectable quantities of HER2 protein, or fragments thereof, under normal or pathological conditions. Generally, levels of HER2 in a particular sample obtained from a healthy patient (e.g., a patient not afflicted with a disease or condition associated with abnormal HER2 levels or activity) will be measured to initially establish a baseline, or standard, level of HER2. This baseline level of HER2 can then be compared against the levels of HER2 measured in samples obtained from individuals suspected of having a HER2 related disease (e.g., a tumor containing HER2-expressing cells) or condition.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Anti-HER2, Anti-APLP2, and Anti-HER2×APLP2 Antibodies

Anti-HER2 or anti-APLP2 antibodies were obtained by immunizing a mouse (e.g., an engineered mouse comprising DNA encoding human immunoglobulin heavy and human kappa light chain variable regions), with either the extracellular domain of human HER2 (amino acids of T23-T652 of amino acid sequence NP_004439.2 (SEQ ID NO:51)) or the extracellular domain of human APLP2 (amino acids G32-S692 of the amino acid sequence NP_001633.1 (SEQ ID NO: 52)), respectively. The amino acid sequences of the human HER2 and human APLP2 antigens are respectively set forth as SEQ ID NO:49 and SEQ ID NO:50.

Following immunization, splenocytes were harvested from each mouse and either (1) fused with mouse myeloma cells to preserve their viability and form hybridoma cells and screened for human HER2 specificity, or (2) B-cell sorted (as described in US 2007/0280945A1) using a either a human HER2 fragment or a human APLP2 fragment as the sorting reagent that binds and identifies reactive antibodies (antigen-positive B cells).

Chimeric antibodies to human HER2 or human APLP2 were initially isolated having a human variable region and a mouse constant region. Bispecific antibodies comprising an anti-HER2-specific binding domain and an anti-APLP2-specific binding domain were recombinantly constructed by standard molecular cloning methodologies and expressed in CHO cells, wherein the anti-HER2 antigen binding domain and the anti-APLP2 antigen binding domain each comprise different, distinct heavy chain variable regions (HCVRs) paired with a common light chain variable region (LCVR). In exemplified bispecific antibodies, the molecules were constructed utilizing a heavy chain from an anti-HER2 antibody, a heavy chain from an anti-APLP2 antibody and a light chain common to both the anti-HER2 and anti-APLP2 antibodies (see, e.g. SEQ ID NO: 10), and expressed in CHO cells. In some instances, the bispecific antibodies may be constructed utilizing a heavy chain from an anti-HER2 antibody; a heavy chain from an anti-APLP2 antibody; and a light chain from an anti-HER2 antibody, a light chain from an anti-APLP2 antibody, or another antibody light chain known to be promiscuous or pair effectively with a variety of heavy chain arms, e.g., such as Vκ1-39Jκ5 or Vκ3-20Jκ1 (see e.g. US 2011/0195454).

The antibodies were characterized and selected for desirable characteristics, including affinity, selectivity, etc.

If necessary, mouse constant regions were replaced with a desired human constant region, for example wild-type human CH or modified human CH (e.g. IgG1, IgG2 or IgG4 isotypes), and light chain constant region (CL), to generate a fully human anti-HER2, a fully human anti-APLP2 antibody, or a fully human bispecific anti-HER2×APLP2 antibody. While the constant region selected may vary according to specific use, high affinity antigen-binding and target specificity characteristics reside in the variable region. Antibody name designations or ID numbers starting with "H4" or "H4H" denote fully human antibodies. Antibodies were identified by the B-cell sorting method and are designated with antibody ID numbers ending with "P" or "P2". Bispecific antibodies are designated with antibody ID numbers ending with "D".

Certain biological properties of the exemplary anti-HER2, anti-APLP2, and anti-HER2×APLP2 antibodies generated in accordance with the methods of this Example are described in detail in the Examples set forth below.

Example 2: Characterization of Antibodies

Example 2.1 Characterization of Anti-HER2 Antibodies

Heavy and Light Chain Variable Region Amino Acid and Nucleic Acid Sequences of Anti-HER2 Antibodies Table 1 sets forth sequence identifiers of a nucleic acid (NA) sequence encoding, and in parentheses an amino acid (AA) sequence of, a heavy or light chain variable region (HCVR or LCVR, respectively), or a heavy or light chain CDR (HCDR and LCDR, respectively) of selected anti-HER2 antibodies used to generate bispecific anti-HER2×APLP2 antibodies disclosed herein.

TABLE 1 anti-HER2 Sequence Identifiers

| Antibody Designation | SEQ ID NOs: | | | | | | | |
|---|---|---|---|---|---|---|---|---|
| | HCVR NA (AA) | HCDR1 NA (AA) | HCDR2 NA (AA) | HCDR3 NA (AA) | LCVR NA (AA) | LCDR1 NA (AA) | LCDR2 NA (AA) | LCDR3 NA (AA) |
| H4H13050P2 | 1 (2) | 3 (4) | 5 (6) | 7 (8) | 9 (10) | 11 (12) | 13 (14) | 15 (16) |
| H4H13055P2 | 17 (18) | 19 (20) | 21 (22) | 23 (24) | 9 (10) | 11 (12) | 13 (14) | 15 (16) |

Example 2.2 Characterization of Anti-APLP2 Antibodies

Heavy and Light Chain Variable Region Amino Acid and Nucleic Acid Sequences of Anti-APLP2 Antibodies Table 2 sets forth sequence identifiers of a nucleic acid (NA) sequence encoding, and in parentheses an amino acid (AA) sequence of, a heavy or light chain variable region (HCVR or LCVR, respectively), or a heavy or light chain CDR (HCDR and LCDR, respectively) of selected anti-APLP2 antibodies used to generate bispecific anti-HER2×APLP2 antibodies disclosed herein.

TABLE 2 anti-APLP2 Sequence Identifiers

| Antibody Designation | SEQ ID NOS: | | | | | | | |
|---|---|---|---|---|---|---|---|---|
| | HCVR NA (AA) | HCDR1 NA (AA) | HCDR2 NA (AA) | HCDR3 NA (AA) | LCVR NA (AA) | LCDR1 NA (AA) | LCDR2 NA (AA) | LCDR3 NA (AA) |
| H4xH21362P2 | 25 (26) | 27 (28) | 29 (30) | 31 (32) | 9 (10) | 11 (12) | 13 (14) | 15 (16) |
| H4xH21387P2 | 33 (34) | 35 (36) | 37 (38) | 39 (40) | 9 (10) | 11 (12) | 13 (14) | 15 (16) |

TABLE 2-continued anti-APLP2 Sequence Identifiers

| | SEQ ID NOS: | | | | | | | |
|---|---|---|---|---|---|---|---|---|
| Antibody Designation | HCVR NA (AA) | HCDR1 NA (AA) | HCDR2 NA (AA) | HCDR3 NA (AA) | LCVR NA (AA) | LCDR1 NA (AA) | LCDR2 NA (AA) | LCDR3 NA (AA) |
| H4xH21371P2 | 41 (42) | 43 (44) | 45 (46) | 47 (48) | 9 (10) | 11 (12) | 13 (14) | 15 (16) |

Example 2.3 Characterization of Anti-HER2×APLP2 Antibodies

Heavy and Light Chain Variable Region Amino Acid and Nucleic Acid Sequences of Anti-HER2×APLP2 Antibodies Described herein are bispecific antigen-binding molecules that bind HER2 and APLP2; such bispecific antigen-binding molecules are also referred to herein as bispecific "anti-HER2/anti-APLP2" or "anti-HER2×APLP2" antibodies, antigen binding proteins, or molecules. The anti-HER2 portion of the anti-HER2/anti-APLP2 bispecific molecule is useful for targeting tumor cells that express human epidermal growth factor receptor 2 (HER2), and the anti-APLP2 portion of the bispecific molecule is useful for mediating internalization of HER2 into the lysosome and mediating HER2 degradation.

The bispecific antibodies described in the following examples consist of anti-HER2 and anti-APLP2 binding arms having varying binding affinities to the extracellular portions of human HER2 and human APLP2 (see Examples 1-2 above). Exemplified bispecific antibodies were manufactured having a wild-type kappa CL and a modified (chimeric) IgG4 CH domain as set forth in US Patent Application Publication No. US20140243504A1, published on Aug. 28, 2014.

A summary of the component parts of the antigen-binding domains of the various anti-HER2×APLP2 bispecific antibodies constructed is set forth in Table 3.

identifiers for the various heavy chain variable regions, and their corresponding CDRs, of the anti-HER2 arms (i.e. HCVRs are derived from H4H13050P2 or H4H13055P2) to construct the bispecific antibodies of characterized in Table 3. Table 2 sets forth the nucleic acid and amino acid sequence identifiers for the various heavy chain variable regions, and their corresponding CDRs, of the anti-APLP2 arms of the bispecific antibodies of this Example.

Example 2.4 Characterization of Control Antibodies

Isotype Control Antibody, referred to in the Examples hereinbelow, is an isotype matched (modified IgG4) antibody that interacts with an irrelevant antigen, i.e. FelD1 (cat allergy) antigen, with no cross-reactivity to human APLP2 or HER2.

HER2/T Control Antibody, referred to in the Examples hereinbelow, is a recombinantly made anti-HER2 antibody derived from the antibody known as trastuzumab.

Bispecific anti-FelD1×APLP2, referred to as H4H28697D, was constructed by way of the same methods described herein with a first heavy chain arm that binds to FelD1 derived from the isotype control antibody referred to hereinabove and a second heavy chain arm that binds to APLP2 derived from H4H13055P parental antibody.

Example 3: Biacore $K_D$ Binding to Soluble Truncated Human HER2 or APLP2 Protein Equilibrium dissociation constants ($K_D$ values) for HER2 and APLP2 binding to purified anti-HER2×APLP2 bispecific and parental antibodies were determined using a real-time surface plasmon resonance biosensor using a Biacore 4000 instrument. The Biacore sensor surface was first derivatized by amine coupling with a monoclonal mouse anti-human Fc antibody (GE, Cat #BR-1008-39) to capture anti-HER2×APLP2 bispecific monoclonal antibodies. All binding studies were performed in 0.01M Hepes pH 7.4, 0.15M NaCl, 1 mM $CaCl_2$), 0.5 mM MgCl2, and 0.05% v/v Surfactant Tween-20 (HBS-P running buffer) at 37° C. Different concentrations of reagents, either human HER2

TABLE 3

| Bispecific Antibody Identifier | Anti-HER2 Antigen-Binding Domain Heavy Chain Variable Region | Anti-APLP2 Antigen-Binding Domain Heavy Chain Variable Region | Common Light Chain Variable Region |
|---|---|---|---|
| H4H25017D | H4H13050P2 (SEQ ID NO: 2) | H4xH21362P2 (SEQ ID NO: 26) | (SEQ ID NO: 10) |
| H4H25019D | | H4xH21387P2 (SEQ ID NO: 34) | |
| H4H25021D | | H4xH21371P2 (SEQ ID NO: 42) | |
| H4H25014D | H4H13055P2 (SEQ ID NO: 18) | H4xH21362P2 (SEQ ID NO: 26) | |
| H4H25018D | | H4xH21387P2 (SEQ ID NO: 34) | |
| H4H25020D | | H4xH21371P2 (SEQ ID NO: 42) | |

The light chain listed in Table 3 was common to both the HER2 and APLP2 targeting arms of the bispecific antibodies. Table 1 sets forth nucleic acid and amino acid sequence extracellular domain expressed with a C-terminal myc-myc-hexahistidine tag (hHER2-MMH; SEQ ID NO: 53) or human APLP2 extracellular domain expressed with a C-terminal myc-myc-hexahistidine tag (hAPLP2-MMH; SEQ ID NO: 54) in HBS-P running buffer (ranging from 300 nM to 3.7 nM, 3-fold dilutions) were injected over the anti-HER2×APLP2 bispecific antibody captured surface for 4 minutes at a flow rate of 30 μL/minute and their dissociation in HBS-P running buffer was monitored for 10 minutes. Kinetic association rate constant (ka) and dissociation rate constant (kd) were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D(M) = \frac{kd}{ka},$$

and $$t\ 1/2(\min) = \frac{\ln(2)}{60 * kd}$$

Binding kinetic parameters for hHER2-MMH, or hAPLP2-MMH binding to different anti-HER2×APLP2 bispecific antibodies of the invention and their parental antibodies at 37° C. are shown in Tables 4 and 5. At 37° C., hHER2-MMH bound to all of the anti-HER2×APLP2 bispecific antibodies of the invention with $K_D$ values ranging from 3.37 nM to 5.15 nM, as shown in Table 4. hHER2-MMH bound to all of the anti-HER2 parental antibodies with $K_D$ values of 4.11 nM and 5.20 nM. None of the anti-APLP2 parental antibodies demonstrated binding to hHER2-MMH. At 37° C., hAPLP2-MMH bound to all of the anti-HER2×APLP2 bispecific antibodies of the invention with $K_D$ values ranging from 145 nM to 976 nM, as shown in Table 5A. hAPLP2-MMH bound to all of the anti-APLP2 parental antibodies with $K_D$ values ranging from 145 nM to 899 nM. None of the anti-HER2 parental antibodies demonstrated binding to hAPLP2-MMH. At 25° C., hAPLP2-MMH bound to all of the anti-HER2×APLP2 bispecific antibodies of the invention with KD values ranging from 8.5 nM to 17.2 nM, as shown in Table 5B. hAPLP2-MMH bound to all of the anti-APLP2 parental antibodies with KD values ranging from 11.2 nM to 21.7 nM.

TABLE 4

Binding Kinetics parameters of anti-HER2 × APLP2 bispecific and parental antibodies binding to hHER2-MMH at 37° C.

| Antibody | mAb Capture Level (RU) | 100 nM hHER2-MMH Bound (RU) | $k_a$ (1/Ms) | $k_d$ (1/s) | $K_D$ (M) | t½ (min) |
|---|---|---|---|---|---|---|
| H4H13055P2 | 526 ± 1.3 | 299 | 2.11E+05 | 8.69E−04 | 4.11E−09 | 13 |
| H4H25014D | 483 ± 4.5 | 153 | 2.17E+05 | 7.31E−04 | 3.37E−09 | 16 |
| H4H25018D | 467 ± 0.7 | 149 | 2.13E+05 | 8.95E−04 | 4.21E−09 | 13 |
| H4H25020D | 465 ± 3.4 | 164 | 2.19E+05 | 9.19E−04 | 4.20E−09 | 13 |
| H4H13050P2 | 535 ± 2.9 | 257 | 1.82E+05 | 9.47E−04 | 5.20E−09 | 12 |
| H4H25017D | 497 ± 4.3 | 150 | 1.86E+05 | 9.00E−04 | 4.85E−09 | 13 |
| H4H25019D | 517 ± 1.4 | 171 | 2.05E+05 | 1.06E−03 | 5.15E−09 | 11 |
| H4H25021D | 499 ± 2 | 142 | 1.89E+05 | 9.73E−04 | 5.15E−09 | 12 |
| H4 × H21362P2 | 538 ± 7.4 | 1 | NB | NB | NB | NB |
| H4 × H21371P2 | 497 ± 3.8 | 0 | NB | NB | NB | NB |
| H4 × H21387P2 | 498 ± 2 | 0 | NB | NB | NB | NB |

*NB indicates that under the experimental conditions, hHER2-MMH reagent did not bind to the captured antibody

TABLE 5A

Binding Kinetics parameters of anti-HER2 × APLP2 bispecific and parental antibodies binding to hAPLP2-MMH at 37° C.

| Antibody | mAb Capture Level (RU) | 100 nM hAPLP2-MMH Bound (RU) | $k_a$ (1/Ms) | $k_d$ (1/s) | $K_D$ (M) | t½ (min) |
|---|---|---|---|---|---|---|
| H4 × H21387P2 | 495 ± 4.9 | 114 | 8.08E+04 | 1.01E−02 | 1.24E−07 | 1.1 |
| H4H25018D | 467 ± 1.2 | 49 | 6.50E+04 | 9.41E−03 | 1.45E−07 | 1.2 |
| H4H25019D | 516 ± 2.2 | 48 | 5.61E+04 | 1.03E−02 | 1.83E−07 | 1.1 |
| H4 × H21362P2 | 538 ± 9.6 | 34 | 4.88E+04 | 8.60E−03 | 1.76E−07 | 1.3 |
| H4H25014D | 480 ± 4.7 | 23 | 4.44E+04 | 1.04E−02 | 2.35E−07 | 1.1 |
| H4H25017D | 498 ± 5.8 | 13 | 3.47E+04 | 9.77E−03 | 2.81E−07 | 1.2 |
| H4 × H21371P2 | 501 ± 12 | 48 | 4.09E+05 | 3.68E−01 | 8.99E−07 | 0.03 |
| H4H25020D | 461 ± 6.4 | 30 | 3.98E+05 | 3.36E−01 | 8.44E−07 | 0.03 |
| H4H25021D | 498 ± 7.8 | 24 | 2.87E+05 | 2.80E−01 | 9.76E−07 | 0.04 |
| H4H13055P2 | 525 ± 1.9 | 0 | NB | NB | NB | NB |
| H4H13050P2 | 534 ± 3.7 | −3 | NB | NB | NB | NB |

*NB indicates that under the experimental conditions, hAPLP2-MMH reagent did not bind to the captured antibody Note that two bispecific antibodies (H4H25018D and H4H25019D) bind to APLP2 with low affinity within the range of 100 to 200 nM, while their binding affinity to HER2 is less than 10 nM (4.21 and 5.15 nM, respectively). Two bispecific antibodies (H4H25014D and H4H25017D) bind to APLP2 with moderately low affinity within the range of 200 to 300 nM, while their binding affinity to HER2 remains less than 10 nM, even less than 5 nM (3.37 and 4.85 nM, respectively). Finally, two bispecific antibodies (H4H25020D and H4H25021D) exhibit very low binding affinity to APLP2 within the range of 800 nM to 1 µM, and still exhibit strong binding affinity to HER2 at less than 10 nM (4.20 and 5.15 nM, respectively). See both Tables 4 and 5.

TABLE 5B

Binding Kinetics parameters of anti-HER2 × APLP2 bispecific and parental antibodies binding to hAPLP2-MMH at 25° C.

| Antibody | mAb Capture Level (RU) | 90 nM hAPLP2-MMH Bound (RU) | $k_a$ (1/Ms) | $k_d$ (1/s) | $K_D$ (M) | t½ (min) |
|---|---|---|---|---|---|---|
| H4 × H21362P2 | 427.2 ± 3.8 | 36.6 | 9.49E+04 | 1.06E−03 | 1.12E−08 | 10.9 |
| H4 × H21371P2 | 302.8 ± 2.4 | 52.1 | 1.01E+06 | 2.20E−02 | 2.17E−08 | 0.5 |
| H4 × H21387P2 | 276.9 ± 2.2 | 60.5 | 9.29E+04 | 1.05E−03 | 1.13E−08 | 11.0 |
| H4H25014D | 311.4 ± 1.1 | 17.1 | 9.48E+04 | 9.46E−04 | 9.98E−09 | 12.2 |
| H4H25017D | 349.6 ± 4.2 | 13.4 | 9.20E+04 | 7.82E−04 | 8.50E−09 | 14.8 |
| H4H25018D | 303.1 ± 2.8 | 30.2 | 1.10E+05 | 1.71E−03 | 1.56E−08 | 6.8 |
| H4H25018D | 346.1 ± 4.3 | 36.6 | 9.03E+04 | 1.50E−03 | 1.66E−08 | 7.7 |
| H4H25019D | 319.4 ± 3.3 | 30.6 | 9.09E+04 | 1.33E−03 | 1.46E−08 | 8.7 |
| H4H25019D | 329 ± 3.3 | 31.0 | 1.00E+05 | 1.73E−03 | 1.72E−08 | 6.7 |

Example 4: Relative Expression of HER2 and APLP2 in Cancer Cell Lines and Normal Primary Cultures To determine the relative expression of HER2 and APLP2 in eleven (11) cancer cell lines [MDA-MB-468 (ATCC, Cat #HTB-132), T47D (ATCC, Cat #HTB-133), T7D overexpressing transgenic HER2 and Cas9, MCF7 (ATCC, Cat #HTB-22), JIMT-1 (DSMZ, Cat #ACC589), BT483 (ATCC, Cat #HTB-121), MDA-MB-361 (ATCC, Cat #HTB-27), MDA-MB-231 (ATCC, Cat #HTB-26), MDA-MB-453 (ATCC, Cat #HTB-131), SK-BR3 (ATCC, Cat #HTB-30) and NCI-N87 (ATCC, Cat #CRL5822) and two (2) normal primary cultures [Normal Lung Epithelium (NLE; ATCC, Cat #PCS-300-010) and Normal Breast Epithelium (NBE; ATCC, Cat #PCS-600-010)], western blot analysis was performed. For the analysis, cells were plated on 6-well, cell culture plates at 1×10⁶ cells/well in their appropriate culture media, which is described for each cell line/culture in Table 6, and incubated overnight at 37° C. in 5% Co₂.

TABLE 6

Media Composition for each cell type tested

| Cell type | Media composition |
|---|---|
| NLE | 40% DMEM + 10% FBS + 40% Basal Epithelium Medium (ATCC, Cat# PCS-600-030) |
| NBE | Basal Epithelium Medium (ATCC, Cat# PCS-600-030) |
| T47D | RPMI 1640 + 10% FBS + 1 mM Sodium Pyruvate + 10 mM HEPES + 10 ug/mL Insulin + 5 mL Penicillin/Streptomycin/Glutamine |
| T47D/HER2 | RPMI 1640 + 10% FBS + 1 mM Sodium Pyruvate + 10 mM HEPES + 10 ug/mL Insulin + 5 mL Penicillin/Streptomycin/Glutamine + Blasticidin (10 ug/ml) + Hygromycin (100 ug/ml) |
| MCF7 | MEM 10% + 10 ug/mL Insulin |
| JIMT-1 | DMEM + 10% FBS + 10 ug/mL Insulin |
| BT483 | RPMI 1640 + 20% FBS + 10 ug/mL Insulin |
| MDA-MB-231 | DMEM + 10% FBS |
| MDA-MB-468 | DMEM + 10% FBS |
| MDA-MB-361 | DMEM + 10% FBS |
| MDA-MB-453 | DMEM + 10% FBS |
| SK-BR3 | McCoy's 5a-10% FBS |
| NCI N87 | RPMI 1640 + 10% FBS |

After the incubation, cells were washed once with DPBS in culture media (DPBS/CM), and placed on ice. Subsequently, the DPBS/CM was replaced with 150 uL of lysis buffer [consisting of 13 mL 1×RIPA buffer (Boston Bioproducts, Cat #BP-116), 200 uL protease inhibitor (Thermo Fisher, Cat #1861280), 5 mL 4× Laemmli (Invitrogen, Cat #NP0007), and 2 mL 10× Reducing agent (Invitrogen, Cat #NP0009)]. Cells were subsequently scraped, and then the samples were transferred to 1.2 mL deep 96-well plates covered with film with one hole/well. The plates were sonicated ten times (1 second each time) at 50% power. After sonication, the plates were boiled in a water bath at 80° C. for 10 minutes. The samples were subsequently frozen. Later, the samples were thawed and 20 uL of each sample was loaded into a Wedged 4-12% TRIS-Glycine gel (Invitrogen, Cat #XPO4125BOX) and ran at 150V for 1-1.5 hours. The gel was then transferred into PVDF membranes (ThermoFisher, Cat #IB24001) with iBlot2 dry blotting system (ThermoFisher, Cat #IB21001). The membrane was then blocked with 5% milk (BioRad, Cat #170-6404) in TRIS buffered saline (TBS; ThermoFisher, Cat #28376) for 1-3 hours at room temperature. Primary antibody [either rabbit-anti-HER2 antibody (Dako, Cat #A048529) or mouse-anti-APLP2 antibody (Millipore, Cat #MABN782)] in a solution containing 2.5% milk and 0.1% Tween (Sigma, Cat #P8074) in TBS, was then added to the membrane and incubated at 4° C. overnight. The membrane was then washed 3 times with TBS for 5 minutes at room temperature. After, either an anti-rabbit-HRP antibody (Promega, #W401B) or an anti-mouse-HRP antibody (Promega, Cat #W402B), along with an anti-Actin-HRP antibody (Santa Cruz, Cat #sc-47779) in a solution containing 2.5% milk and 0.1% Tween in TBS was then added to the membrane and incubated at room temperature for 1 hour. The membrane was then washed 2 times with TBS containing 0.1% Tween at room temperature for 5 minutes, and then washed 2 more times with TBS room temperature for 5 minutes. The blot was then developed with ECL Detection Reagent (GE healthcare, Cat #RPN2106) and imaged with an Azure C300 imager. Band quantification (mean fluorescence intensity minus background) was performed using ImageJ software. For quantification, the HER2/actin and APLP2/actin ratios were determined and subsequently normalized to the highest value, which was SK-BR-3 for HER2/Actin and JIMT-1 for APLP2/Actin. (See FIG. 1.)

The HER2 and APLP2 expression levels relative to Actin levels in eleven (11) cancer cell lines and two (2) normal primary cultures are shown in Table 7.

TABLE 7

Relative expression of HER2 and APLP2 as compared to Actin by eleven (11) cancer cell lines and two (2) normal primary cultures

| Cell Line | Normalized APLP2/Actin | Normalized HER2/Actin |
|---|---|---|
| Normal Lung | 19% | 1% |
| Normal Breast | 27% | 1% |
| MDA-MB-231 | 86% | 2% |
| MDA-MB-468 | 65% | 0.1% |
| MCF7 | 42% | 17% |
| T47D | 100% | 36% |
| BT483 | 49% | 43% |
| JIMT-1 | 95% | 50% |
| MDA-MB-361 | 86% | 66% |
| MDA-MB-453 | 33% | 70% |
| SKBR3 | 44% | 86% |
| T47D/HER2 | 85% | 84% |
| N87 | 39% | 100% |

Example 5: Binding of Bispecific Anti-HER2×APLP2 Antibodies to HER2-Expressing Cells is Mediated by and Dependent on the Anti-HER2 Arm To test the ability of bispecific anti-HER2×APLP2 molecules described herein to bind to cells lines expressing various levels of HER2, a high content imaging assay was performed. For the assay, 8 cancer cell lines [MDA-MB-468 (ATCC, HTB-132), T47D (ATCC, HTB-133), MCF-7 (ATCC, HTB-22), JIMT-1(DSMZ, ACC589), BT-483 (ATCC, HTB-121), MDA-MB-361 (ATCC, HTB-27), MDA-MB-453 (ATCC, HTB-131), and SK-BR-3 (ATCC, HTB-30)] and 2 normal primary cultures [Normal Lung Epithelium (NLE; ATCC®, Cat #PCS-300-010) and Normal Breast Epithelium (NBE; ATCC®, Cat #PCS-600-010)] were used. Cells were plated on collagen-coated, black wall, 96-well, optical plates (Greiner, Cat #655936) at $2.5 \times 10^5$ cells per well in their appropriate culture media, which is described for each cell line/culture in Table 6, and incubated overnight at 37° C. in 5% $CO_2$.

Figure 2:
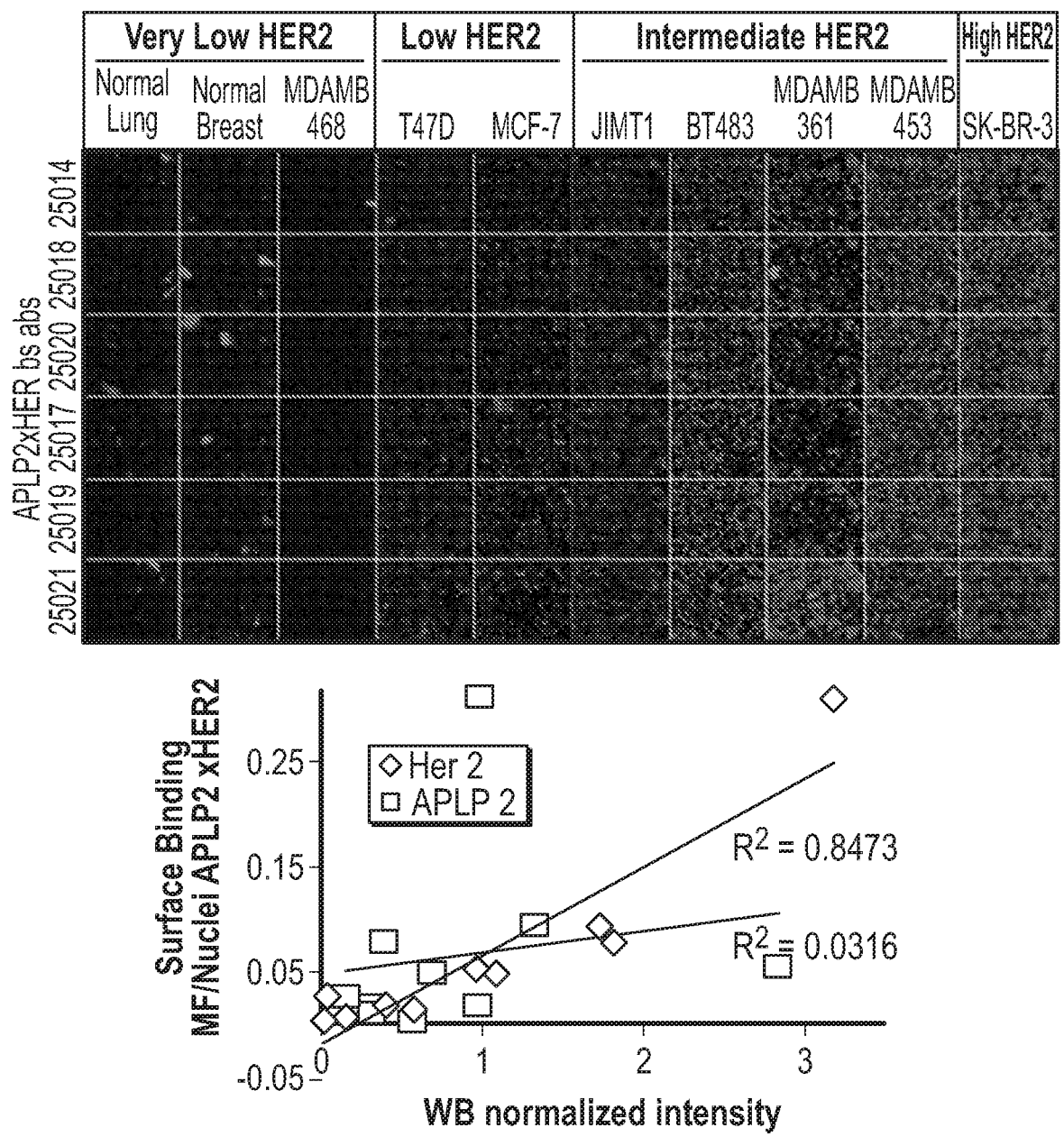
FIG. 2 shows the binding of bispecific anti-HER2×APLP2 antibodies to breast cancer cells expressing from very low to high levels of HER2 (top panel) and the correlation of anti-HER2×APLP2 antibody cell surface binding (MFI/Nuclei. APLP2×HER2 (H4H25018D); y-axis) with HER2 or APLP2 total cellular expression (Western blot (WB) normalized intensity; x-axis) (bottom panel).

The following day, cells were incubated for 1 hour with 10 ug/mL of Alexa647 labeled (Thermo, Cat #A37573) bispecific anti-HER2×APLP2 molecules (H4H25014D, H4H25018D, H4H25020D, H4H25017D, H4H25019D, and H4H25021D) in 50 μL of DMEM at 4° C. After, cells were washed twice with cold DMEM+10% FBS. To the cold DMEM+10% FBS, 100 μL of a solution composed of 8% paraformaldehyde (Electron Microcopy Sciences, Cat #15710)+0.15% Saponin (Sigma, Cat #S4521)+20 ug/ml Hoechst (Lifetech, #H3569) in DPBS/CM was added and incubated for 20 minutes at room temperature to fix and permeabilize cells while staining their nuclei. After, the solution was replaced with DPBS/CM. Binding of the bispecific antibodies to each of the cell types was measured using an Image Xpress$^{Micro}$ automatic microscope (Molecular Devices). Binding of fluorescently-labeled APLP2× HER2 bispecific antibodies to cells (Table 8) was directly proportional to the ITER2 expression levels determined in Example 4. (See also FIG. 2.)

TABLE 8

Bispecific anti-HER2 × APLP2 bispecific antibodies bind to 8 cancer cell lines and 2 normal primary cultures with varying affinities. The signal of antibody binding (mean intensity fluorescence of Alexa647) divided by the nuclei signals was determined for each condition using MetaXpress software (Molecular Devices). Values were normalized to the cell line displaying the highest antibody binding signal.

| Bispecific Antibody | Cell line tested | Antibody bound (% of highest) |
|---|---|---|
| H4H25014D | NBE | 5% |
| H4H25014D | 468 | 2% |
| H4H25014D | T47D | 6% |
| H4H25014D | MCF7 | 5% |
| H4H25014D | JIMT-1 | 17% |
| H4H25014D | BT483 | 13% |
| H4H25014D | MDA-MB-361 | 30% |
| H4H25014D | MDA-MB-453 | 25% |
| H4H25014D | SKBR3 | 100% |
| H4H25014D | NLE | 4% |
| H4H25018D | NBE | 9% |
| H4H25018D | MDA-MB-468 | 1% |
| H4H25018D | T47D | 5% |
| H4H25018D | MCF7 | 6% |
| H4H25018D | JIMT-1 | 17% |
| H4H25018D | BT483 | 16% |
| H4H25018D | MDA-MB-361 | 30% |
| H4H25018D | MDA-MB-453 | 25% |

TABLE 8-continued

Bispecific anti-HER2 × APLP2 bispecific antibodies bind to 8 cancer cell lines and 2 normal primary cultures with varying affinities. The signal of antibody binding (mean intensity fluorescence of Alexa647) divided by the nuclei signals was determined for each condition using MetaXpress software (Molecular Devices). Values were normalized to the cell line displaying the highest antibody binding signal.

| Bispecific Antibody | Cell line tested | Antibody bound (% of highest) |
|---|---|---|
| H4H25018D | SKBR3 | 100% |
| H4H25018D | NLE | 3% |
| H4H25020D | NBE | 8% |
| H4H25020D | MDA-MB-468 | 1% |
| H4H25020D | T47D | 5% |
| H4H25020D | MCF7 | 5% |
| H4H25020D | JIMT-1 | 18% |
| H4H25020D | BT483 | 15% |
| H4H25020D | MDA-MB-361 | 27% |
| H4H25020D | MDA-MB-453 | 24% |
| H4H25020D | SKBR3 | 100% |
| H4H25020D | NLE | 6% |
| H4H25017D | NBE | 10% |
| H4H25017D | MDA-MB-468 | 1% |
| H4H25017D | T47D | 7% |
| H4H25017D | MCF7 | 9% |
| H4H25017D | JIMT-1 | 17% |
| H4H25017D | BT483 | 22% |
| H4H25017D | MDA-MB-361 | 35% |
| H4H25017D | MDA-MB-453 | 31% |
| H4H25017D | SKBR3 | 100% |
| H4H25017D | NLE | 4% |
| H4H25019D | NBE | 6% |
| H4H25019D | MDA-MB-468 | 1% |
| H4H25019D | T47D | 9% |
| H4H25019D | MCF7 | 7% |
| H4H25019D | JIMT-1 | 15% |
| H4H25019D | BT483 | 22% |
| H4H25019D | MDA-MB-361 | 32% |
| H4H25019D | MDA-MB-453 | 30% |
| H4H25019D | SKBR3 | 100% |
| H4H25019D | NLE | 2% |
| H4H25021D | NBE | 8% |
| H4H25021D | MDA-MB-468 | 1% |
| H4H25021D | T47D | 8% |
| H4H25021D | MCF7 | 7% |
| H4H25021D | JIMT-1 | 17% |
| H4H25021D | BT483 | 22% |
| H4H25021D | MDA-MB-361 | 37% |
| H4H25021D | MDA-MB-453 | 28% |
| H4H25021D | SKBR3 | 100% |
| H4H25021D | NLE | 7% |

To test the contribution of binding of each arm of the bispecific anti-HER2×APLP2 binding proteins described herein to cells expressing both HER2 and APLP2, a competition binding assay was performed using a MDA-MB-361 (ATCC, Cat #HTB-27) breast cancer cell line. For the assay, cells were plated on collagen-coated, black wall, 96-well, optical plates (Greiner, Cat #655936) at 2.5×10$^5$ cells per well in their appropriate culture media (described in previous examples), and incubated overnight at 37° C. in 5% CO$_2$. The next day, the cells were placed in refrigeration at 4° C. for 30 minutes. A solution of 67 µM of Alexa647 (Thermo, Cat #A37573) labeled bispecific anti-HER2× APLP2 antibody (H4H25014D, H4H25018D, H4H25020D, H4H25017D, H4H25019D, or H4H25021D) or no antibody (blank) in DMEM containing 10% FBS at 4° C. was prepared. To each antibody solution, either PBS alone, human HER2 extracellular domain expressed with a C-terminal myc-myc-hexahistidine tag (hHER2-MMH; SEQ ID NO: 53) alone, human APLP2 extracellular domain expressed with a C-terminal myc-myc-hexahistidine tag (hAPLP2-MMH; SEQ ID NO: 54) alone, or the combination of hHER2-MMH and hAPLP2-MMH was added at a concentration of 333 mM. After incubation, and removal of culture media, 50 µL/well of the bispecific antibody and soluble protein solutions were added to the cells for 30 minutes at 4° C. The cells were subsequently washed with 150 µL/well of DMEM containing 10% FBS at 4° C. for 10 minutes. Following this wash, 50 µL of fixing buffer [containing 9 mL PBS in culture media (PBS/CM), 3 mL of 16% paraformaldehyde (Electron Microscopy Sciences, Cat #15710) and 10 µg/ml of Hoechst (final concentration); (Lifetech, Cat #H3569)] was added to each well and incubated for 20 minutes at room temperature. The fixing buffer was then removed, 100 uL of DPBS/CM was added and allowed to incubate for approximately 20 minutes at room temperature prior to image acquisition. Binding of the bispecific antibodies to each of the cell types was measured using an Image Xpress$^{Micro}$ automatic microscope (Molecular Devices). Data acquired was analyzed using MetaXpress software (Molecular Devices). The binding signal of the bispecific antibodies was normalized to the signal obtained when no bispecific antibody was present (referred as blank).

Figure 3:
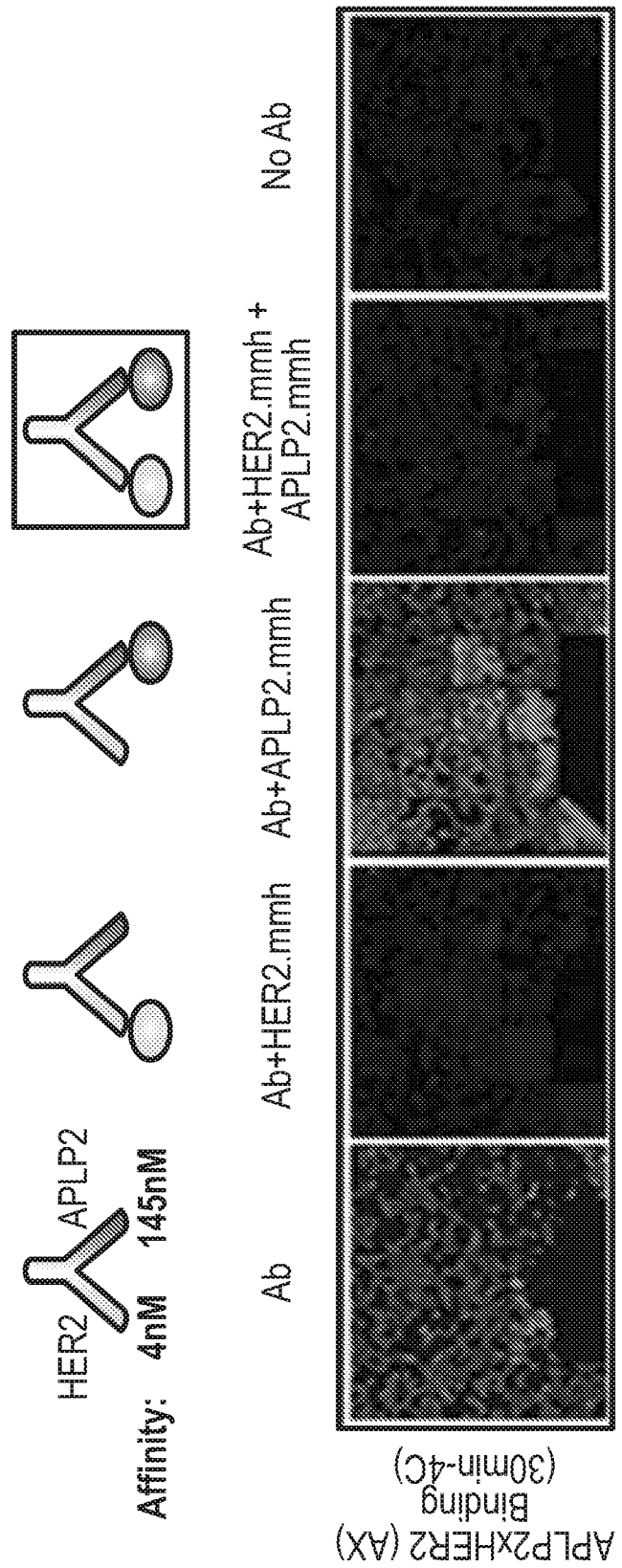
FIG. 3 shows the binding of a bispecific anti-HER2×APLP2 antibody to HER2 expressing MDA-MB-361 cells in the absence or presence of soluble HER2 (HER2.mmh) and/or APLP2 (APLP2.mmh)

Although the presence of soluble hHER2-M3 significantly inhibited binding of each tested bispecific anti-HER2×APLP2 antibody to MDA-MB-361 breast cancer cells, such effect was not seen with soluble hAPLP2-MMH. (See Table 9 below, and also FIG. 3).

TABLE 9

Binding of anti-HER2 × APLP2 bispecific antibodies to MDA-MB-361 breast cancer cell lines in the presence or absence of soluble HER2 and APLP2 reagents

| Bispecific antibody | Reagent used for blocking | Bispecific antibody signal (Fold over blank) |
|---|---|---|
| H4H25014D | No Block | 14 |
| H4H25014D | hHER2-MMH | 3 |
| H4H25014D | hAPLP2-MMH | 13 |
| H4H25014D | hHER2-MMH + hAPLP2-MMH | 5 |
| H4H25014D | Blank | 1 |
| H4H25018D | No Block | 14 |
| H4H25018D | hHER2-MMH | 5 |
| H4H25018D | hAPLP2-MMH | 14 |
| H4H25018D | hHER2-MMH + hAPLP2-MMH | 5 |
| H4H25018D | Blank | 1 |
| H4H25020D | No Block | 15 |
| H4H25020D | hHER2-MMH | 6 |
| H4H25020D | hAPLP2-MMH | 16 |
| H4H25020D | hHER2-MMH + hAPLP2-MMH | 7 |
| H4H25020D | Blank | 1 |
| H4H25017D | No Block | 14 |
| H4H25017D | hHER2-MMH | 3 |
| H4H25017D | hAPLP2-MMH | 13 |
| H4H25017D | hHER2-MMH + hAPLP2-MMH | 5 |
| H4H25017D | Blank | 1 |
| H4H25019D | No Block | 14 |
| H4H25019D | hHER2-MMH | 7 |
| H4H25019D | hAPLP2-MMH | 13 |
| H4H25019D | hHER2-MMH + hAPLP2-MMH | 4 |
| H4H25019D | Blank | 1 |
| H4H25021D | No Block | 16 |
| H4H25021D | hHER2-MMH | 6 |
| H4H25021D | hAPLP2-MMH | 16 |
| H4H25021D | hHER2-MMH + hAPLP2-MMH | 6 |
| H4H25021D | Blank | 1 |

These data indicate that the binding of the bispecific anti-HER2×APLP2 antibodies described herein is largely mediated by the anti-HER2 arm, not the anti-APLP2 arm. Thus, it is expected that a bispecific antigen-binding molecule having the described properties including lower binding to APLP2 will bind with specificity to cells expressing both APLP2 and ITER2, yet will diminish binding to cells expressing only APLP2.

Example 6: APLP2, but not HER2, is Rapidly Internalized and Degraded

The ability of APLP2 and ITER2 antibodies to internalize on T47D cells (ATCC, HTB-133) was tested on T47D cells cultured in media according to Table 6. T47D cells were plated on collagen-coated 96-well optical plates (Greiner, Cat #655936) at 50,000 cells/well in media and incubated overnight at 37° C. in 5% $CO_2$. The following day, cells were incubated with 1 mg/ml Fluorescein-labeled dextran for 60 min at 37 C. CF594-labeled anti-APLP2 (R&D MAB49451) or anti-HER2 (HER2/T control) antibodies were incubated at 67 nM with the dextran for 5, 10, 20, 30, 45 or 60 min, after which cells were washed once and incubated for 10 minutes with warm (37° C.) media. Afterwards, cells were fixed with 4% PFA in DPBS+Calcium/Magnesium (CM) for 10 min at room temperature and washed twice with DPBS/CM.

Acquisition was performed with LSM780 Zeiss Confocal Microscope. Acquired images were analyzed using Zeiss Zen software. The trafficking of internalized antibodies to the lysosomes was quantified by the colocalization of the antibody pixels with fluorescent dextran pixels in confocal stacks. The amount of time (minutes) for the antibodies to colocalize with lysosomes is shown in Table 10.

TABLE 10

Internalization of anti-APLP2 and anti-HER2 antibodies into lysosomes

| | | Antibody colocalizing with Lysosomes (% pixels) | |
|---|---|---|---|
| Target | Minutes | Average | Standard Error |
| APLP2 | 15.6 | 6% | 1% |
| APLP2 | 20.6 | 23% | 2% |
| APLP2 | 30.6 | 47% | 4% |
| APLP2 | 40.6 | 67% | 3% |
| APLP2 | 55.6 | 81% | 2% |
| APLP2 | 70.6 | 89% | 1% |
| HER2 | 15.6 | 7% | 2% |
| HER2 | 20.6 | 10% | 2% |
| HER2 | 30.6 | 11% | 2% |
| HER2 | 40.6 | 12% | 2% |
| HER2 | 55.6 | 16% | 2% |
| HER2 | 70.6 | 17% | 2% |

Additionally, the degradation rates of APLP2 and HER2 was tested on T47D cells. For the assay, T47D cells were plate at $10^6$ cells/well in 6 well plates (Corning #3516). The cells were allowed to grow overnight at 37° C. in 5% $CO_2$ in media consisting of RPMI 1640+10% FBS+1 mM sodium pyruvate+10 mM HEPES+10 ug/mL Insulin+5 mL Penicillin/Streptomycin/Glutamine. The following day, cells were treated with 50 ug/ml cycloheximide (Sigma #C4859-1ML) for 0, 0.5, 1.5, 2.5, 3.5, 4.5 and 5.5 hours. After the incubation, cells were washed once with 1 ml of DPBS/CM, and subsequently placed on ice and then the DPBS/CM was replaced with 800 uL of lysis buffer [1×RIPA (Boston Bioproducts, Cat #BP-116)+Protease inhibitor (Thermo Fisher, 1861280), cells were scraped and lysates were transferred to 1.5 ml Eppendorf tubes. Afterwards, the samples were sonicated with 25 pulses, 1 sec each at 50% power. Afterwards, the samples were frozen at −20° C. The samples were later thawed and 52 ul of each sample was mixed with 20 ul 4× Laemmli (Invitrogen, NP0007)+8 uL 10× Reducing agent (Invitrogen, Cat #NP0009)]. Samples were boiled at 95° C. for 10 minutes, centrifuged at 14000 RPM for 10 minutes at room temperature. 40 uL of each sample was loaded into three Wedged 4-20% TRIS-Glycine gels (Invitrogen, XPO4125BOX) and ran at 150V. The gels were then transferred into two PVDF membranes (ThermoFisher, IB24001) with iBlot2 dry blotting system (ThermoFisher, 1321001). The membranes were then blocked with 5% milk (BioRad, Cat #170-6404) in TBS for 3 hours at room temperature. Primary antibodies, rabbit-anti-HER2 antibody (Dako, Cat #A048529) or rabbit-anti-APLP2 antibody (abcam, Cat #ab140624) in 2.5% Milk+0.1% Tween (Sigma, Cat #P8074) in TRIS buffered saline (TBS; ThermoFisher, Cat #28376), were then added to the membranes and incubated at 4° C. overnight. The membranes were then washed 3 times with TBS for 5 minutes at room temperature. After, anti-rabbit-HRP antibodies (Promega, #W4011) and anti-actin-HRP antibody (Santa Cruz, Cat #sc-47779) in 2.5% Milk+0.1% Tween in TBS were added to the membranes and incubated at room temperature for 1 hour. The membranes were then washed 2 times with TBS+0.1% Tween at room temperature for 5 minutes, and then washed 2 more times with TBS room temperature for 5 minutes. The blot was then developed with ECL Detection Reagent (GE healthcare, Cat #RPN2106) and imaged with Azure C300 imager. Band quantification (mean fluorescence intensity minus background) was performed using ImageJ. Table 11 summarizes HER2, APLP, or T47D cells after cycloheximide (CHX) treatment normalized to cells having no CHX contact.

TABLE 11

APLP2 and HER2 turnover in T47D cells.

| CHX treatment (hours) | Normalized HER2 expression | Normalized APLP2 expression |
| --- | --- | --- |
| 0 | 100% | 100% |
| 0.5 | 57% | 41% |
| 1.5 | 78% | 22% |
| 2.5 | 68% | 9% |
| 3.5 | 64% | 7% |
| 4.5 | 88% | 8% |
| 5.5 | 78% | 6% |

Figure 4:
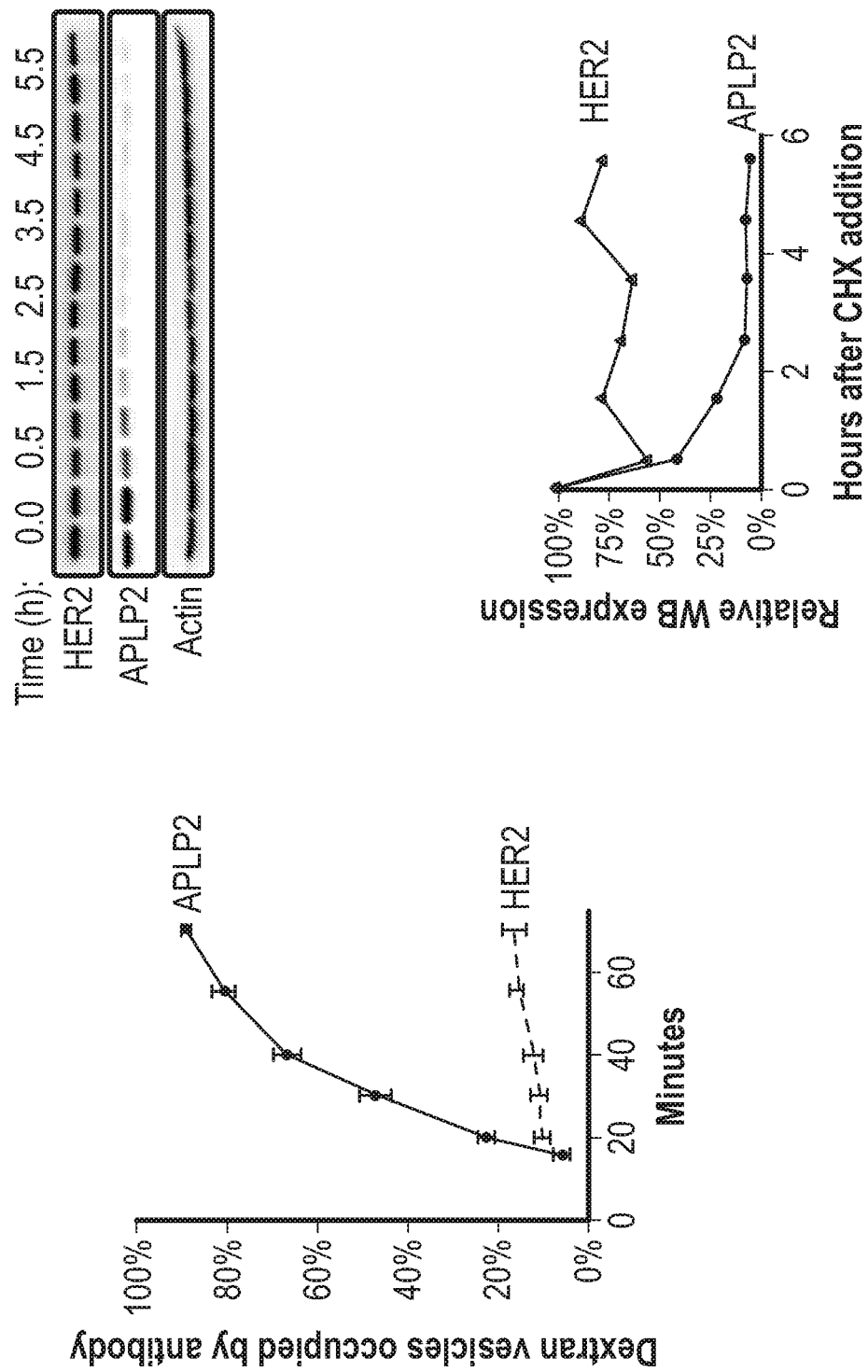
FIG. 4 shows the lysosomal internalization of cell receptors APLP2 and HER2 after binding with corresponding monospecific antibodies (top panel) and degradation of APLP2 and HER2 receptors following the addition of protein synthesis inhibitor Cyclohexamide (CHX) (bottom panel).

As shown in Table 10, lysosomal trafficking of APLP2 was significantly faster than that of HER2. As shown in Table 11, APLP2, but not HER2, underwent rapid turnover. Cycloheximide treatment induced only 22% HER2 degradation was seen after 5.5 hours, while 94% APLP2 degradation was seen in the same amount of time. Eighty-eight percent of APLP2 was degraded in only 1.5 hours (see also FIG. 4).

Example 7: Degradation of Cell-Surface Expressed HER2 after Binding of Bispecific Anti-HER2×APLP2 Antibodies The ability of bispecific anti-HER2×APLP2 binding proteins or appropriate binding protein controls to degrade HER2 was tested on T47D cells, which expresses lower levels of HER2 compared to mammary tumor cell lines listed in Table 7. For the assay, T47D cells were plated at 25,000 cells/well in collagen-coated, 96-well, optical plates (Greiner, Cat #655936). The cells were incubated at 37° C. in 5% $CO_2$ in media consisting of RPMI 1640+10% FBS+1 mM sodium pyruvate+10 mM HEPES+10 ug/mL Insulin+5 mL Penicillin/Streptomycin/Glutamine. The following day, bispecific anti-HER2×APLP2 binding proteins (H4H25018D, H4H25019D, H4H25014D, H4H25020D, H4H25017D, and H4H25021D), monospecific anti-HER2 binding proteins (HER2/T control and H4H13055P) or isotype control binding proteins were added to cells at final concentration of 10 μg/mL. The binding proteins were incubated on cells for 4 hours at 37° C. in 5% $CO_2$. After the incubation, cells were washed once with 100 μL of a solution of DPBS with calcium and magnesium (DPBS/CM) on ice, after which the DPBS/CM solution was replaced with 80 μL of lysis buffer [6500 uL 1×RIPA (Boston Bioproducts, Cat #BP-116), 65 uL protease inhibitor (Thermo Fisher, 1861280), 2500 uL of 4× Laemmli (Invitrogen, NP0007) and 1000 μL 10× Reducing agent (Invitrogen, Cat #NP0009)]. After addition of the buffer, the plate was incubated on an orbital plate shaker (Scientific Industries, SI 0401) at medium speed (~1250 RPM) at 4° C. for 30 minutes. Afterwards, the samples were frozen at −20° C. The samples were later thawed, centrifuged at 4000 RPM for 10 minutes at 4° C., then transferred to a PCR plate and boiled in thermocycler at 85° C. for 10 minutes. The samples were then centrifuged at 4000 RPM for 10 seconds at 4° C. 40 μL of each sample was loaded into a Wedged 4-12% TRIS-Glycine gel (Invitrogen, XPO4125BOX) and ran at 150V. The gel was then transferred into PVDF membranes (ThermoFisher, IB24001) with iBlot2 dry blotting system (ThermoFisher, IB21001). The membrane was then blocked with 5% milk (BioRad, Cat #170-6404) in TRIS-buffered saline (TBS; ThermoFisher, Cat #28376) for 1-3 hours at room temperature. Membrane was incubated overnight at 4° C. with primary rabbit-anti-HER2 antibody (Dako, Cat #A048529) in TBS containing 2.5% Milk+0.1% Tween (Sigma, Cat #P8074). The membrane was subsequently washed 3 times with TBS for 5 minutes at room temperature. After, anti-rabbit-HRP antibody (Promega, #W401B) and anti-Actin-HRP antibody (Santa Cruz, Cat #sc-47779) in 2.5% Milk+0.1% Tween in TBS were added to the membrane and incubated at room temperature for 1 hour. The membrane was then washed 2 times with TBS+0.1% Tween at room temperature for 5 minutes, and then washed 2 more times with TBS room temperature for 5 minutes. The blot was then developed with ECL Detection Reagent (GE healthcare, Cat #RPN2106) and imaged with Azure C300 imager. Band quantification (mean fluorescence intensity minus background) was performed using ImageJ.

Figure 5:
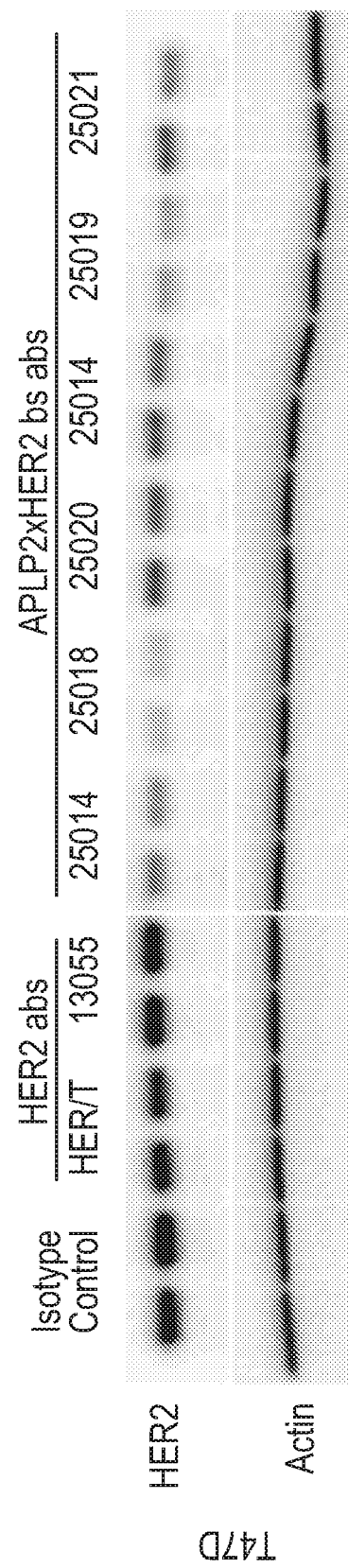
FIG. 5 shows a Western blot of total lysates from T47D breast cancer cell line stained with anti-HER2 or anti-Actin antibodies after incubation with control antibodies, anti-HER2 antibodies, or bispecific anti-HER2×APLP2 antibodies (25014, 25018, 25020, 25017, 25019, and 25021).

As shown in Table 12, bispecific anti-HER2×APLP2 binding proteins (H4H25018D, H4H25019D, H4H25014D, H4H25020D, H4H25017D, and H4H25021D) induced HER2 degradation with approximately 12% to 38% of the HER2 expression remaining on T47D cells. In contrast, monospecific anti-HER2 antibodies, the HER2/T control and H4H13055P (from which the anti-HER2 binding arm of test antibodies H4H25014D, H4H25020D, and H4H25021D are derived) induced HER2 degradation with approximately 73% and 90%, respectively, of the HER2 expression remaining on T47D cells. The isotype control did not induce any HER2 degradation. See also FIG. 5.

TABLE 12

HER2 degradation on T47D cells by bispecific anti-HER2 × APLP2 molecules

T47D Cells

| Antibody or bispecific tested | Target | Average HER2 relative expression | Standard Error |
|---|---|---|---|
| Isotype control | FelD1 | 100% | 9.9% |
| HER2/T control | HER2 | 73% | 6.8% |
| H4H13055P | HER2 | 90% | 3.8% |
| H4H25014D | APLP2 × HER2 | 28% | 2.6% |
| H4H25018D | APLP2 × HER2 | 12% | 0.4% |
| H4H25020D | APLP2 × HER2 | 38% | 1.7% |
| H4H25017D | APLP2 × HER2 | 34% | 3.6% |
| H4H25019D | APLP2 × HER2 | 19% | 0.5% |
| H4H25021D | APLP2 × HER2 | 28% | 5.7% |

Most notably, the two anti-APLP2×HER2 bispecific antibodies, H4H25018D and H4H25019D, that contain the H4×H21387P2 APLP2 arm and have binding affinities to APLP2 between 100 and 200 nM, induced HER2 degradation most efficiently in T47D cells compared to the other bispecific antibodies, with cells exhibiting a remaining HER2 expression of less than 20%. HER2 degradation by monospecific antibodies (HER2/T and H4H13055P parental antibody) was more than 50% less efficient than that of the bispecific antibodies H4H25018D and H4H25019D.

Example 8: The Affinity of the APLP2 Arm to APLP2 Modulates the Efficiency of Bispecific Anti-HER2×APLP2 Antibody Internalization The ability of a subset of bispecific anti-HER2×APLP2 antibodies to internalize on MDA-MB-361 cell monolayers or MDA-MB-361 tumor spheroids was tested. For the assays, MDA-MB-361 cells (ATCC, Cat #HTB-27) were respectively plated on collagen-coated 96-well optical plates (Greiner, Cat #655936) at 25,000 cells/well or on Corning® 96 Well Black Clear Round Bottom Ultra Low Attachment Spheroid Microplate (Corning #4520) at 1,000 cells/well in DMEM containing 10% FBS and incubated overnight (for cells) or three days (for tumor spheroids) at 37° C. in 5% $CO_2$. Following incubation, cells were incubated for 30 minutes with cold (4° C.) media, and spheroids were incubated for 3 hours with warm (37° C.) media, each medium containing 10 μg/mL of Alexa647 (Thermo, Cat #A37573) labeled anti-HER2×APLP2 binding proteins (H4H25014D, H4H25018D or H4H25020D). After, cells were washed once or twice with cold (4° C.) media.

After the wash, cells were placed in Basal Epithelium Medium (ATCC, Cat #PCS-600-030) at room temperature and then live image acquisition was started 1-2 minutes later on a Zeiss Spinning Disc Confocal Microscope. Spheroids were fixed with 40 PFA+0.0750 Saponin+10 μg/ml Hoechst, which was subsequently washed DPBS. Confocal images from the center of the spheroids were acquired on a Zeiss Spinning Disc Confocal Microscope. Acquired images were analyzed using Zeiss Zen software. The amount of bispecific internalized into MDA-MB-361 cells, expressed in arbitrary units, are shown in Table 13 on a per minute basis.

TABLE 13

Amount of internalized bispecific anti-HER2 × APLP2 antibodies by MDA-MB-361 cells Integrated fluorescence of internalized vesicles

| Minutes | H4H25018D | H4H25020D | H4H25014D |
|---|---|---|---|
| 1 | 0.0E+00 | 0.0E+00 | 0.0E+00 |
| 2 | 0.0E+00 | 3.7E+04 | 3.3E+04 |
| 3 | 8.2E+03 | 2.2E+04 | 1.2E+03 |
| 4 | 3.6E+04 | 2.9E+04 | 6.3E+03 |
| 5 | 1.2E+05 | 3.3E+04 | 4.4E+04 |
| 6 | 1.6E+05 | 2.8E+04 | 3.0E+05 |
| 7 | 2.5E+05 | 9.4E+03 | 2.4E+05 |
| 8 | 3.2E+05 | 3.2E+03 | 2.0E+05 |
| 9 | 4.3E+05 | 1.9E+04 | 1.4E+05 |
| 10 | 5.2E+05 | 5.5E+03 | 1.7E+05 |
| 11 | 6.0E+05 | 9.5E+03 | 1.7E+05 |
| 12 | 6.2E+05 | 1.7E+04 | 2.2E+05 |
| 13 | 6.3E+05 | 1.9E+04 | 2.3E+05 |
| 14 | 5.8E+05 | 5.8E+04 | 3.2E+05 |
| 15 | 5.0E+05 | 7.9E+04 | 3.4E+05 |
| 16 | 5.5E+05 | 6.8E+04 | 2.7E+05 |
| 17 | 9.6E+05 | 1.8E+05 | 4.2E+05 |
| 18 | 8.0E+05 | 1.7E+05 | 4.2E+05 |
| 19 | 9.6E+05 | 1.5E+05 | 4.2E+05 |
| 20 | 7.7E+05 | 1.5E+05 | 4.4E+05 |
| 21 | 1.0E+06 | 1.2E+05 | 4.9E+05 |
| 22 | 8.2E+05 | 1.2E+05 | 4.3E+05 |
| 23 | 9.6E+05 | 7.1E+04 | 4.8E+05 |
| 24 | 9.9E+05 | 2.3E+04 | 5.3E+05 |
| 25 | 1.1E+06 | 6.5E+03 | 4.0E+05 |
| 26 | 1.2E+06 | 2.1E+03 | 5.6E+05 |
| 27 | 1.2E+06 | 0.0E+00 | 5.7E+05 |
| 28 | 1.3E+06 | 3.7E+03 | 6.2E+05 |
| 29 | 1.3E+06 | 2.7E+04 | 5.5E+05 |
| 30 | 1.6E+06 | 3.9E+03 | 7.1E+05 |
| 31 | 1.6E+06 | 6.4E+03 | 7.1E+05 |
| 32 | 1.6E+06 | 1.0E+04 | 7.6E+05 |
| 33 | 1.6E+06 | 2.8E+04 | 8.1E+05 |
| 34 | 1.5E+06 | 8.6E+04 | 8.6E+05 |
| 35 | 1.7E+06 | 9.2E+04 | 1.0E+06 |
| 36 | 1.9E+06 | 5.3E+04 | 1.0E+06 |
| 37 | 1.8E+06 | 5.9E+04 | 1.0E+06 |
| 38 | 1.9E+06 | 4.2E+04 | 9.8E+05 |
| 39 | 2.1E+06 | 3.4E+04 | 1.1E+06 |
| 40 | 2.0E+06 | 1.1E+04 | 1.1E+06 |
| 41 | 1.9E+06 | 2.4E+04 | 1.2E+06 |
| 42 | 1.9E+06 | 2.2E+04 | 1.2E+06 |
| 43 | 1.9E+06 | 2.8E+04 | 1.2E+06 |
| 44 | 1.9E+06 | 1.2E+04 | 1.2E+06 |
| 45 | 2.0E+06 | 1.7E+04 | 1.2E+06 |
| 46 | 2.0E+06 | 1.3E+04 | 1.5E+06 |
| 47 | 2.4E+06 | 1.5E+04 | 1.4E+06 |
| 48 | 2.4E+06 | 3.0E+04 | 1.5E+06 |
| 49 | 2.8E+06 | 2.2E+04 | 1.3E+06 |
| 50 | 2.8E+06 | 2.0E+04 | 1.4E+06 |
| 51 | 2.9E+06 | 3.0E+04 | 1.3E+06 |

TABLE 13-continued

Amount of internalized bispecific anti-HER2 × APLP2
antibodies by MDA-MB-361 cells Integrated fluorescence of internalized vesicles

| Minutes | H4H25018D | H4H25020D | H4H25014D |
|---|---|---|---|
| 52 | 2.8E+06 | 2.0E+04 | 1.3E+06 |
| 53 | 2.7E+06 | 1.2E+04 | 1.3E+06 |
| 54 | 2.9E+06 | 0.0E+00 | 1.3E+06 |
| 55 | 3.0E+06 | 5.8E+03 | 1.3E+06 |
| 56 | 2.9E+06 | 3.8E+03 | 1.8E+06 |
| 57 | 3.0E+06 | 2.1E+03 | 1.7E+06 |
| 58 | 3.0E+06 | 0.0E+00 | 1.8E+06 |
| 59 | 3.2E+06 | 4.2E+03 | 1.8E+06 |
| 60 | 3.2E+06 | 3.6E+03 | 1.5E+06 |
| 61 | 3.3E+06 | 2.1E+03 | 1.6E+06 |
| 62 | 3.2E+06 | 4.0E+03 | 1.6E+06 |
| 63 | 3.4E+06 | 6.1E+03 | 1.7E+06 |
| 64 | 3.3E+06 | 5.8E+03 | 1.7E+06 |
| 65 | 3.4E+06 | 9.9E+03 | 1.7E+06 |
| 66 | 3.2E+06 | 1.6E+04 | 1.6E+06 |
| 67 | 3.3E+06 | 1.9E+04 | 1.7E+06 |
| 68 | 3.2E+06 | 1.0E+04 | 1.6E+06 |
| 69 | 3.2E+06 | 0.0E+00 | 1.7E+06 |
| 70 | 3.1E+06 | 1.4E+04 | 1.6E+06 |
| 71 | 3.0E+06 | 6.8E+03 | 1.6E+06 |
| 72 | 2.9E+06 | 8.9E+03 | 1.6E+06 |
| 73 | 3.1E+06 | 2.6E+04 | 1.6E+06 |
| 74 | 3.1E+06 | 6.9E+03 | 1.6E+06 |
| 75 | 3.2E+06 | 3.7E+04 | 1.6E+06 |
| 76 | 3.0E+06 | 7.6E+04 | 1.6E+06 |
| 77 | 3.1E+06 | 6.2E+04 | 1.5E+06 |
| 78 | 2.9E+06 | 1.1E+05 | 1.4E+06 |
| 79 | 2.8E+06 | 1.1E+05 | 1.4E+06 |
| 80 | 2.8E+06 | 1.1E+05 | 1.5E+06 |
| 81 | 3.0E+06 | 1.1E+05 | 1.7E+06 |
| 82 | 3.0E+06 | 8.9E+04 | 1.5E+06 |
| 83 | 3.1E+06 | 9.3E+04 | 1.7E+06 |
| 84 | 2.9E+06 | 9.0E+04 | 1.6E+06 |
| 85 | 2.9E+06 | 9.3E+04 | 1.7E+06 |
| 86 | 2.9E+06 | 9.4E+04 | 1.7E+06 |
| 87 | 3.1E+06 | 1.1E+05 | 1.7E+06 |
| 88 | 2.8E+06 | 1.1E+05 | 1.7E+06 |
| 89 | 2.9E+06 | 1.2E+05 | 1.7E+06 |
| 90 | 2.6E+06 | 1.5E+05 | 1.8E+06 |
| 91 | 2.7E+06 | 1.2E+05 | 1.7E+06 |
| 92 | 3.0E+06 | 9.9E+04 | 1.8E+06 |
| 93 | 3.1E+06 | 1.3E+05 | 1.8E+06 |
| 94 | 2.8E+06 | 1.4E+05 | 2.0E+06 |
| 95 | 2.9E+06 | 1.4E+05 | 1.8E+06 |
| 96 | 3.0E+06 | 1.3E+05 | 2.0E+06 |
| 97 | 2.9E+06 | 1.3E+05 | 1.8E+06 |
| 98 | 2.9E+06 | 1.6E+05 | 1.9E+06 |
| 99 | 2.7E+06 | 1.8E+05 | 1.9E+06 |

Figure 6:
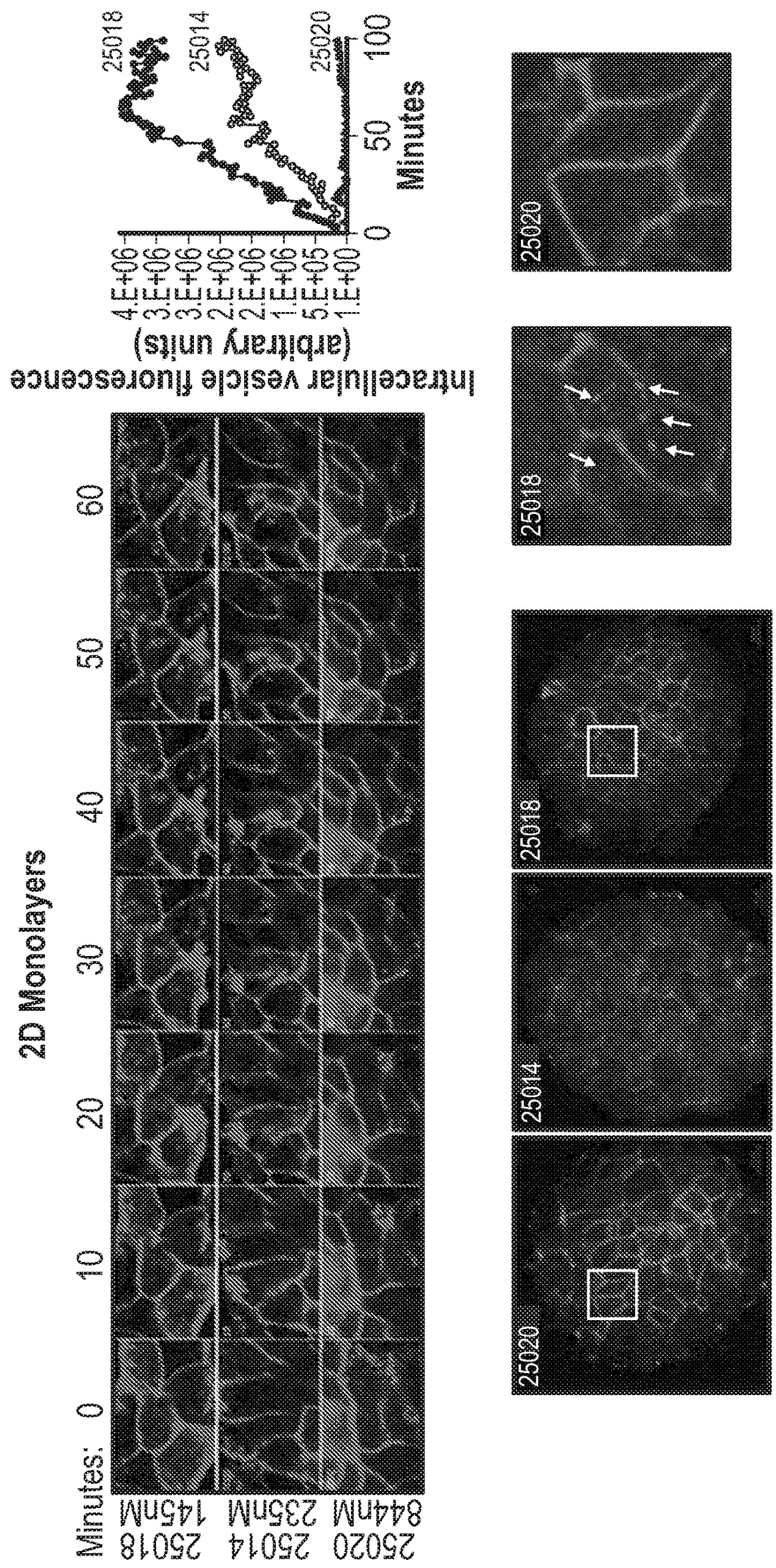
FIG. 6 shows internalization of bispecific anti-HER2×APLP2 antibodies (25014, 25018, 25020) by a breast cancer cell monolayer (top and middle panel) or a breast cancer cell spheroid (bottom panel).

As shown in Table 13, the three bispecific anti-HER2× APLP2 antibodies containing the same HER2 arm and different APLP2 arms internalized by cells and penetrated to the center of tumor spheroids. See FIG. 6. H4H25018D, which contains the H4xH21387P2 APLP2 arm, displayed the fastest internalization rate (Table 13) and more efficient internalization than H4H24020D evidenced by the presence of an increased number of intracellular vesicles (arrows). See FIG. 6 (bottom panel). Without wishing to be bound by theory, this data suggests that internalization of bispecific anti-HER2×APLP2 binding proteins may be dependent on the internalization kinetics of the APLP2 arm and a mechanism of action by which bispecific anti-HER2×APLP2 binding proteins bind to the cell surface using the HER2 arm and are subsequently internalized using the APLP2 arm.

Example 9: Generating and Characterizing Drug Conjugated Anti-HER2×APLP2 Binding Proteins Two methods of drug conjugation were used. In the first method, antibodies (10-20 mg/mL) in 50 mM HEPES, 150 mM NaCl, pH 8.0, and 10-15% (v/v) DMA were conjugated via lysines with a 5-6 fold excess of SMCC-DM1 or (Compound I, for 2 hours at ambient temperature. (See also the process comprising contacting an antibody or bispecific antigen-binding protein described herein with a compound having formula B as in PCT International Application No. PCT/US2017/061757, filed on Nov. 15, 2017.) In the second method, antibodies (10 mg/mL) in 50 mM HEPES, 150 mM NaCl, pH 7.5, were treated with 1 mM dithiothreitol at 37° C. for 30 minutes. After gel filtration (G-25, pH 4.5 sodium acetate), the maleimido linker payload derivative Compound II (see also compound 60 from WO2016160615) (1.2 equivalents/SH group) DMSO (10 mg/ml), was added to the reduced antibodies and the mixture adjusted to pH 7.0 with 1 M HEPES (pH 7.4) to conjugate to the reduced interchain cysteines.

Each conjugate was purified by size exclusion chromatography or extensive ultrafiltration and then sterile filtered. Protein concentrations were determined by UV spectral analysis. Size-exclusion HPLC established that all conjugates used were >95% monomeric. All conjugated antibodies were analyzed by UV for linker payload loading values (drug to antibody ratios; DAR values) according to Hamblett et al (American Association for Cancer Research. 2004 Oct. 15; 10(20):7063-70) and/or by or mass spectrometry using mass difference, native versus conjugated. The results are summarized in Table 14.

TABLE 14

Percent yield and payload to antibody ratios
for each of the antibody drug conjugates

| Antibody | Yield (%) | DAR (MS) | DAR (UV) |
|---|---|---|---|
| H4H25018D-SMCC-DM1 | 68 | 2.7 | 2.6 |
| H4H25019D-SMCC-DM1 | 68 | 2.6 | 2.9 |
| H4H25018D-Compound II | 72 | 3.6 | 4.0 |
| H4H25019D-Compound II | 36 | 0.7 | — |
| H4H25018D-Compound I | 50% | — | 3.6 |
| H4H25019D- Compound I | 25% | — | 4.5 |
| Isotype Control-SMCC-DM1 | 70% | 3.7 | 3.7 |
| Isotype Control REGN1945- Compound I | 70% | 2.3 | 2.5 |
| Isotype Control REGN1945- Compound II | 84% | 4.5 | — |

To determine the loading of the linker-payloads on the antibodies for the first method of conjugation, the conjugates were deglycosylated, and analyzed by LC-MS. Briefly, 50 μg of the conjugate was diluted with milli-Q water to a final concentration of 1 mg/mL. Ten L of PNGase F solution [PNGase F solution was prepared by adding 150 μL of PNGase F stock (New England Biolabs, Cat #P0704L) and 850 μL of milli-Q water and mixed well] was added to the diluted conjugate solution and then incubated at 37° C. overnight. Injections of 5 μL of each sample were made onto LC-MS (Waters Synat G2-Si) and eluted with 0.1 mL/minute of a gradient mobile phase 20-40% over 25 minutes (Mobile Phase A: 0.1% v/v formic acid in H20; Mobile Phase B: 0.1% v/v formic acid in Acetonitrile). The LC separation was achieved on a Waters Acquity BEH C4 column (1.0×50 mM, 1.7 μM) at 80° C. The mass spectrometry spectra were deconvoluted using Masslynx software and the drug to antibody ratio (DAR) was calculated using the following equations.

Relative percentage (%) of drug (Dn) by distribution peak intensity (PI):

$$Dn\% = PIn/\Sigma(PI0+PI1+PI2\ldots+PIi) \times 100$$
$$(n=0,1,2,3,\ldots,i)$$

Average DAR calculation:

$$DAR = \Sigma(1 \times D1\% + 2 \times D2\% + 3 \times D3\% + \ldots + i \times Di\%)$$

To determine the loading of the linker-payloads on the antibodies for the second method of conjugation, conjugates were deglycosylated, reduced, and analyzed by LC-MS. Briefly, 50 μg of the conjugate was diluted with milli-Q water to a final concentration of 1 mg/mL. Ten μL of PNGase F solution [PNGase F solution was prepared by adding 150 μL of PNGase F stock (New England Biolabs, Cat #P0704L) and 850 μL of milli-Q water and mixed well] was added to the diluted conjugate solution and then incubated at 37° C. overnight. 2.4 μL of 0.5 M TCEP was added to the sample such that the resulting material had a final TCEP concentration of 20 mM and this was then incubated at 50° C. for 30 minutes. Injections of 10 μL of each sample were made onto LC-MS (Waters Synat G2-Si) and eluted with 0.1 mL/minute of a gradient mobile phase 20-40% over 25 minutes (Mobile Phase A: 0.1% v/v formic acid in H20; Mobile Phase B: 0.1% v/v formic acid in Acetonitrile). The LC separation was achieved on Waters Acquity BEH C4 column (1.0×50 mM, 1.7 μM) at 80° C.

The mass spectrometry spectra were deconvoluted to identify light and heavy chain peaks represented by the light chain (L) with linker-payload values=0 and 1, and heavy chain (H) with linker-payload values=0, 1, 2, and 3. From the intensity values of each species, the drug to antibody ratio (DAR) was calculated using equation below for a homo- or heterodimer antibody conjugate. The intensity of each deconvoluted peak was used for the calculation.

$$DAR = 2 * \left[ \frac{L1}{L0 + L1} + \frac{H1 + 2*H2 + 3*H3}{H0 + H1 + H2 + H3} \right]$$

Example 10: In Vitro Cytotoxicity of SMCC-DM1, Compound I-, or Compound II-Conjugated Anti-HER2×APLP2 Binding Proteins To compare the $IC_{50}$ of bispecific HER2×APLP2 antibody drug conjugates (ADC) conjugated with either SMCC-DM1, Compound I or Compound II toxins, in vitro cytotoxicity assays were performed. The assays were conducted on JIMT-1 cells treated with decreasing ADC concentrations for 6 days and cell viability was measured after treatment by counting nuclei. For the assay, JIMT-1 (DSMZ, Cat #ACC589) were seeded at $3 \times 10^3$ cells/well on collagen-coated 96-well optical plates (Greiner, Cat #655936) and grown overnight in media containing DMEM, 10% FBS, and 10 ug/mL insulin at 37° C. in 5% $CO_2$. The following day either bispecific anti-HER2×APLP2 ADCs (H4H25018D-SMCC-DM1, H4H25019D-SMCC-DM1, H4H25018D-Compound I, H4H25019D-Compound I, H4H25018D-Compound II, H4H25019D-Compound II) or non-binding control antibodies conjugated with either SMCC-DM1, Compound I or Compound II were added to cells at final concentrations ranging from 66.67 nM to 0.01 nM in DMEM and 10% FBS and were then incubated for 6 days. After the incubation, 110 uL of a nuclei stain [50 mL of 8% paraformaldehyde with 0.15% Saponin (Sigma, Cat #S4521) and 20 ug/mL Hoechst (Lifetech, Cat #H3569)] were add to each well and incubated for 15-25 minutes at room temperature. Subsequently the media and stain were removed and the wells were washed once with DPBS with Calcium and Magnesium (DPBS/CM). After the washing, the wells were placed in DPBS/CM. Nine fields per well were then imaged using the 10× objective lens on an ImageXpress$^{Micro}$ automatic microscope (Molecular Devices). The nuclei were quantified from the acquired images using MetaXpress software (Molecular Devices). The $IC_{50}$ values were determined from a two-phase decay equation over a 10-point response curve (GraphPad Prism). All $IC_{50}$ values are expressed in nM concentration.

TABLE 15

Cytotoxicity of HER2 × APLP2 bispecific ADCs and controls conjugated with either DM1, Compound I or Compound II.

| Cell Line | HER2 expression | ADC tested | $IC_{50}$ (nM) |
|---|---|---|---|
| JIMT-1 | Intermediate | Isotype control-SMCC-DM1 | 15 |
| JIMT-1 | Intermediate | H4H25018D-SMCC-DM1 | 0.07 |
| JIMT-1 | Intermediate | H4H25019D-SMCC-DM1 | 0.13 |
| JIMT-1 | Intermediate | Isotype control-Compound I | >67 |
| JIMT-1 | Intermediate | H4H25018D-Compound I | 0.2 |
| JIMT-1 | Intermediate | H4H25019D-Compound I | 0.75 |
| JIMT-1 | Intermediate | Isotype control-Compound II | 32.5 |
| JIMT-1 | Intermediate | H4H25018D-Compound II | 0.3 |
| JIMT-1 | Intermediate | H4H25019D-Compound II | 0.9 |

As shown in Table 15, bispecific anti-HER2×APLP2 binding proteins conjugated with DM1 (H4H25018D-SMCC-DM1 and H4H25019D-SMCC-DM1) both demonstrated killing with $IC_{50}$ values of 0.07 nM and 0.13 nM, respectively. H4H25018D and H4H25019D conjugated with either Compound I or Compound II showed comparable $IC_{50}$ values to their respective DM1 conjugates. The non-binding control antibodies conjugated with either SMCC-DM1, Compound I or Compound II demonstrated less efficient killing, with $IC_{50}$ values ranging between 15 and >67 nM.

Example 11: Bispecific Anti-HER2×APLP2 ADCs Exhibit Greater Targeted Cytotoxicity to HER2 Expressing Cells Compared to Monospecific Anti-HER2 Antibodies Experiment 1

To test the ability of HER2×APLP2 bispecific antibody drug conjugates (ADC) of the invention to kill bioassay cells, in vitro cytotoxicity assays were performed. The assays were conducted on cells with varying levels of HER2 expression treated with decreasing ADC concentrations for 6 days and cell viability was measured after treatment by counting nuclei. For the assay, either MDA-MB-231 (ATCC, HTB-26), MDA-MB-468 (ATCC, Cat #HTB-132), MCF7 (ATCC, Cat #HTB-22), T47D cells (ATCC, HTB-133), JIMT-1(DSMZ, ACC589), MDA-MB-361 (ATCC, Cat #HTB-27), MDA-MB-453 (ATCC, Cat #HTB-131) or SKBR3(ATCC, HTB-30) were seeded at $3 \times 10^3$ cells/well on collagen-coated 96-well optical plates (Greiner, Cat #655936) and cultured in media according to Table 6 overnight at 37° C. in 5% $CO_2$. The following day bispecific anti-HER2×APLP2 ADCs (H4H25018D-SMCC-DM1 and H4H25019D-SMCC-DM1), bispecific anti-FelD1×APLP2 ADC (H4H28697D-SMCC-DM1), HER2/T control Ab-SMCC-DM1, or Isotype control-SMCC-DM1 were added to cells at final concentrations ranging from 66.67 nM to 0.01 nM in DMEM and 10% FBS and were then incubated for 6 days. After the incubation, 110 uL of a nuclei stain [50 mL of 8% paraformaldehyde with 0.15% Saponin (Sigma, Cat #S4521) and 20 ug/mL Hoecsht (Lifetech, Cat #H3569)] were add to each well and incubated for 15-25 minutes at room temperature. Subsequently the media and stain were removed and the wells were washed once with DPBS with Calcium and Magnesium (DPBS/CM). After the washing, the wells were placed in DPBS/CM. Nine fields per well were then imaged using the 10× objective lens on an Image Xpress$^{Micro}$ automatic microscope (Molecular Devices). Nuclei were quantified from the acquired images using MetaXpress software (Molecular Devices). The $IC_{50}$ values were determined from a two-phase decay equation over a 10-point response curve (GraphPad Prism). All $IC_{50}$ values are expressed in nM concentration. The data are summarized in Table 16A. See also FIG. 7.

TABLE 16A

Cytotoxicity of HER2 × APLP2 bispecific ADCs, FELD1 × APLP2 bispecific ADCs and controls on cell lines with varying HER2 expression.

| Cell Line | HER2 expression | ADC-Lot | Target | Drug | IC50 (nM) |
|---|---|---|---|---|---|
| MDA-MB-231 | Very Low | Isotype Control Ab-L65 | FelD1 | DM1 | 35 |
| MDA-MB-231 | Very Low | HER2/T-L86 | HER2 | DM1 | 25 |
| MDA-MB-231 | Very Low | H4H25018-L6 | APLP2 × HER2 | DM1 | 5 |
| MDA-MB-231 | Very Low | H4H25019-L6 | APLP2 × HER2 | DM1 | 9 |
| MDA-MB-231 | Very Low | H4H28697-L3 | APLP2 × FelD1 | DM1 | 5 |
| MDA-MB-468 | Very Low | Isotype Control Ab -L65 | FELD1 | DM1 | 18 |
| MDA-MB-468 | Very Low | HER/T-L86 | HER2 | DM1 | 10 |
| MDA-MB-468 | Very Low | H4H25018-L6 | APLP2 × HER2 | DM1 | 7.5 |
| MDA-MB-468 | Very Low | H4H25019-L6 | APLP2 × HER2 | DM1 | 8.5 |
| MDA-MB-468 | Very Low | H4H28697-L3 | APLP2 × FelD1 | DM1 | 2 |
| MCF-7 | Low | Isotype Control Ab -L65 | FELD1 | DM1 | 30 |
| MCF-7 | Low | HER/T -L86 | HER2 | DM1 | 10 |
| MCF-7 | Low | H4H25018-L4 | APLP2 × HER2 | DM1 | 2 |
| MCF-7 | Low | H4H25019-L4 | APLP2 × HER2 | DM1 | 2 |
| MCF-7 | Low | | APLP2 × FelD1 | DM1 | Not Determined |
| T47D | Low | Isotype Control Ab-L65 | FELD1 | DM1 | 50 |
| T47D | Low | HER/T-L86 | HER2 | DM1 | 40 |
| T47D | Low | H4H25018-L4 | APLP2 × HER2 | DM1 | 2 |
| T47D | Low | H4H25019-L4 | APLP2 × HER2 | DM1 | 2 |
| T47D | Low | | APLP2 × FelD1 | DM1 | Not Determined |
| JIMT-1 | Intermediate | Isotype Control Ab -L65 | FelD1 | DM1 | 30 |
| JIMT-1 | Intermediate | HER2/T-L81 | HER2 | DM1 | 5 |
| JIMT-1 | Intermediate | H4H25018-L6 | APLP2 × HER2 | DM1 | 0.3 |
| JIMT-1 | Intermediate | H4H25019-L6 | APLP2 × HER2 | DM1 | 0.8 |
| JIMT-1 | Intermediate | H4H28697-L3 | APLP2 × FelD1 | DM1 | 5 |
| MDA-MB-361 | Intermediate | Isotype Control Ab -L65 | FelD1 | DM1 | 8 |
| MDA-MB-361 | Intermediate | HER/T-L81 | HER2 | DM1 | 0.25 |
| MDA-MB-361 | Intermediate | H4H25018-L6 | APLP2 × HER2 | DM1 | 0.02 |
| MDA-MB-361 | Intermediate | H4H25019-L6 | APLP2 × HER2 | DM1 | 0.04 |
| MDA-MB-361 | Intermediate | H4H28697-L3 | APLP2 × FelD1 | DM1 | 2 |
| MDA-MB-453 | Intermediate | Isotype Control Ab -L65 | FelD1 | DM1 | 10 |
| MDA-MB-453 | Intermediate | HER/T-L81 | HER2 | DM1 | 0.6 |
| MDA-MB-453 | Intermediate | H4H25018-L6 | APLP2 × HER2 | DM1 | 0.03 |
| MDA-MB-453 | Intermediate | H4H25019-L6 | APLP2 × HER2 | DM1 | 0.06 |
| MDA-MB-453 | Intermediate | H4H28697-L3 | APLP2 × FelD1 | DM1 | 4 |
| SK-BR-3 | High | Isotype Control Ab -L65 | FelD1 | DM1 | 10 |
| SK-BR-3 | High | HER2/T-L86 | HER2 | DM1 | 0.1 |
| SK-BR-3 | High | H4H25018-L4 | APLP2 × HER2 | DM1 | 0.02 |
| SK-BR-3 | High | H4H25019-L4 | APLP2 × HER2 | DM1 | 0.03 |
| SK-BR-3 | High | | APLP2 × FelD1 | DM1 | Not Determined |

Figure 7:
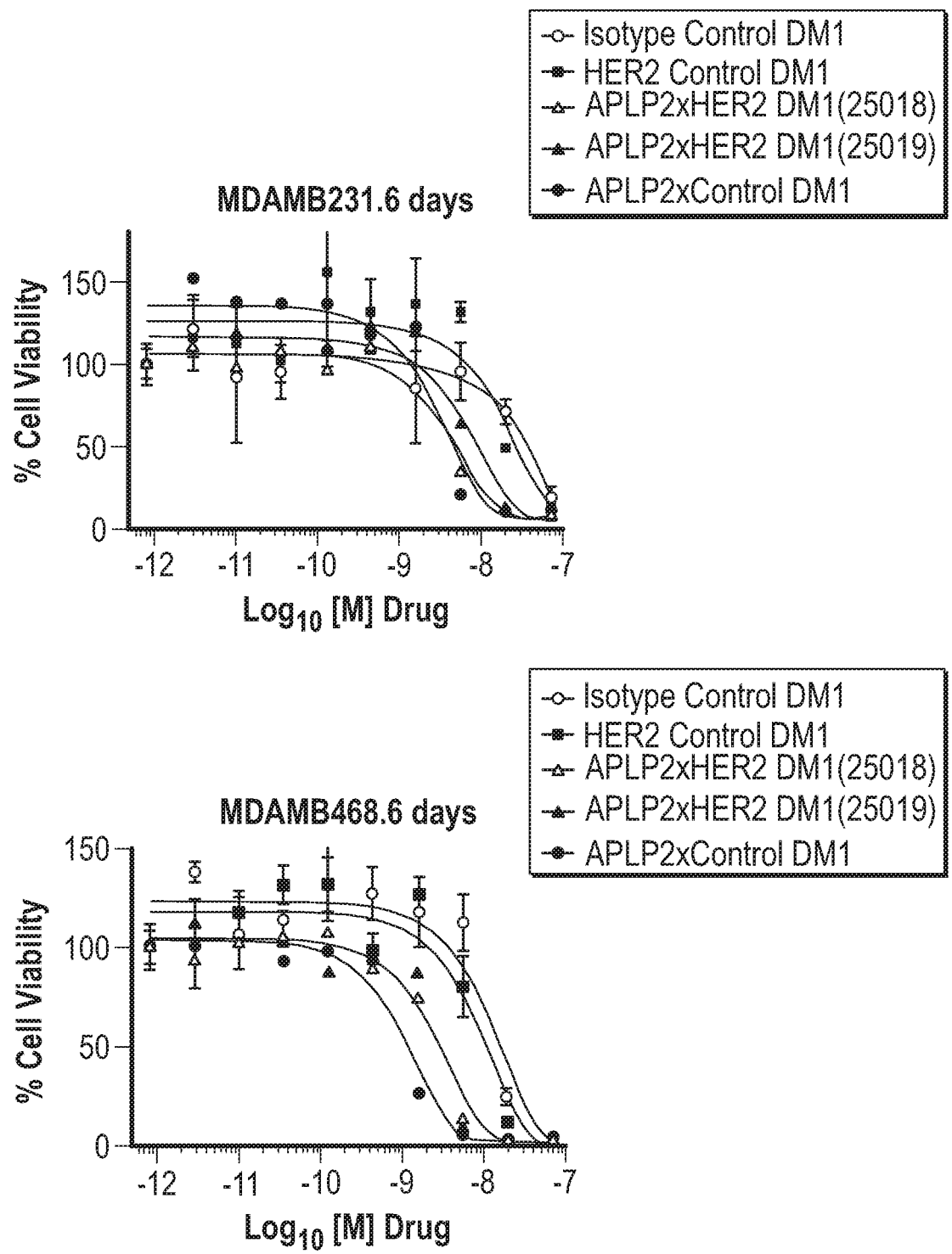
FIG. 7 shows in vitro killing curves in a panel of breast cancer cell lines of isotype control DM1-conjugated antibody, HER2/T control DM1-conjugated antibody, bispecific anti-HER2×APLP2 (25018 and 25019) DM1-conjugated antibodies and bispecific APLP2×Control DM1-conjugated antibody.
Figure 7:
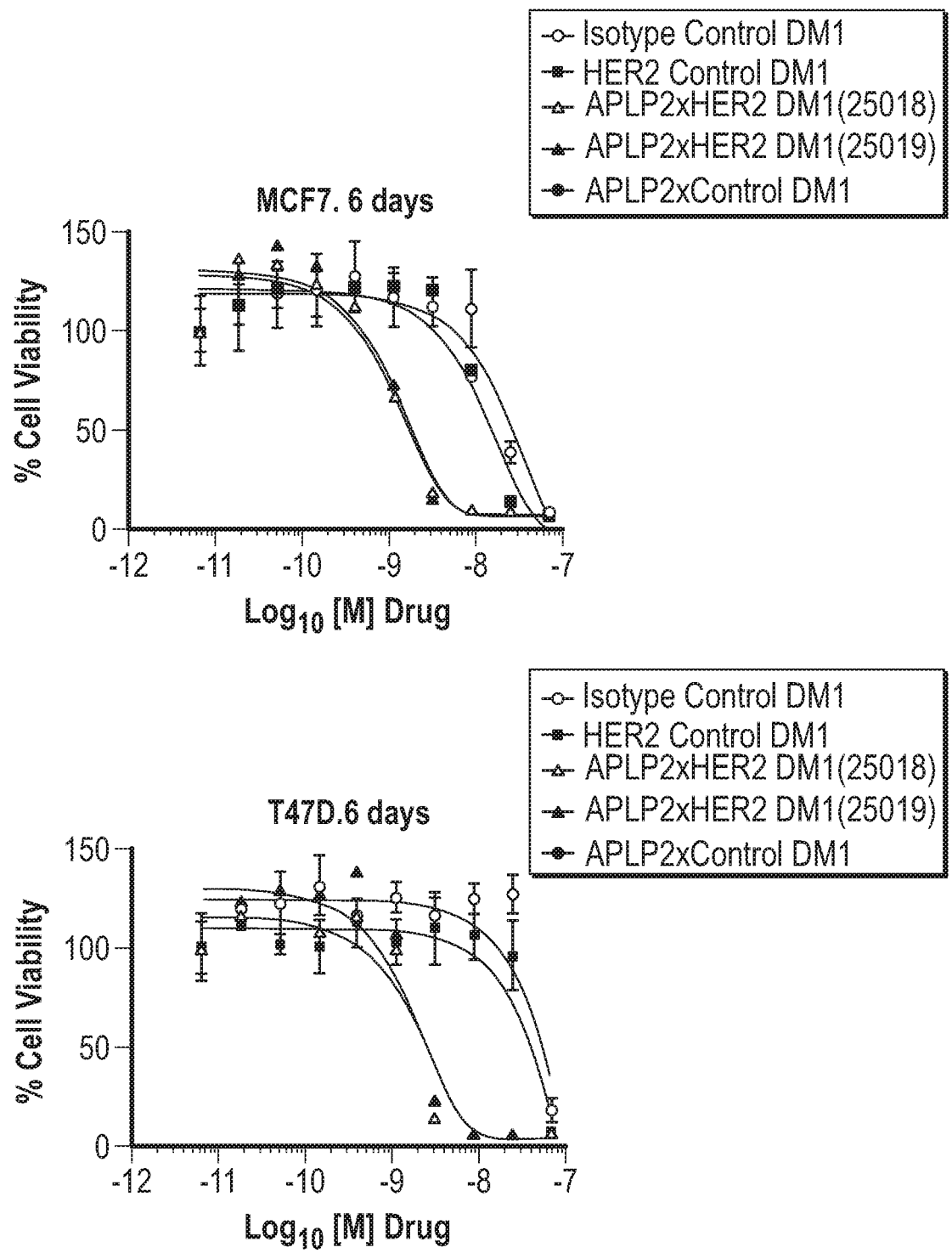
Figure 7:
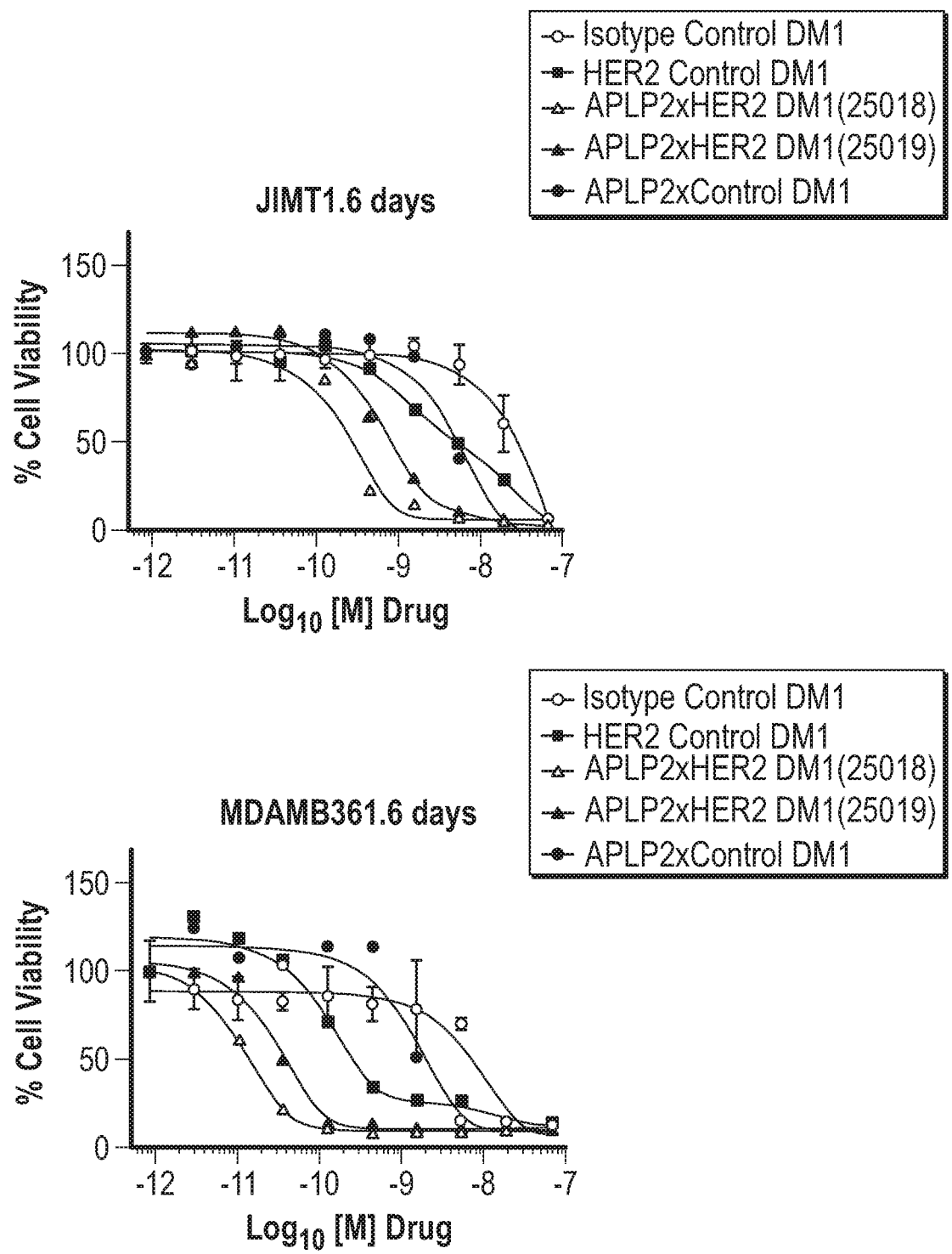
Figure 7:
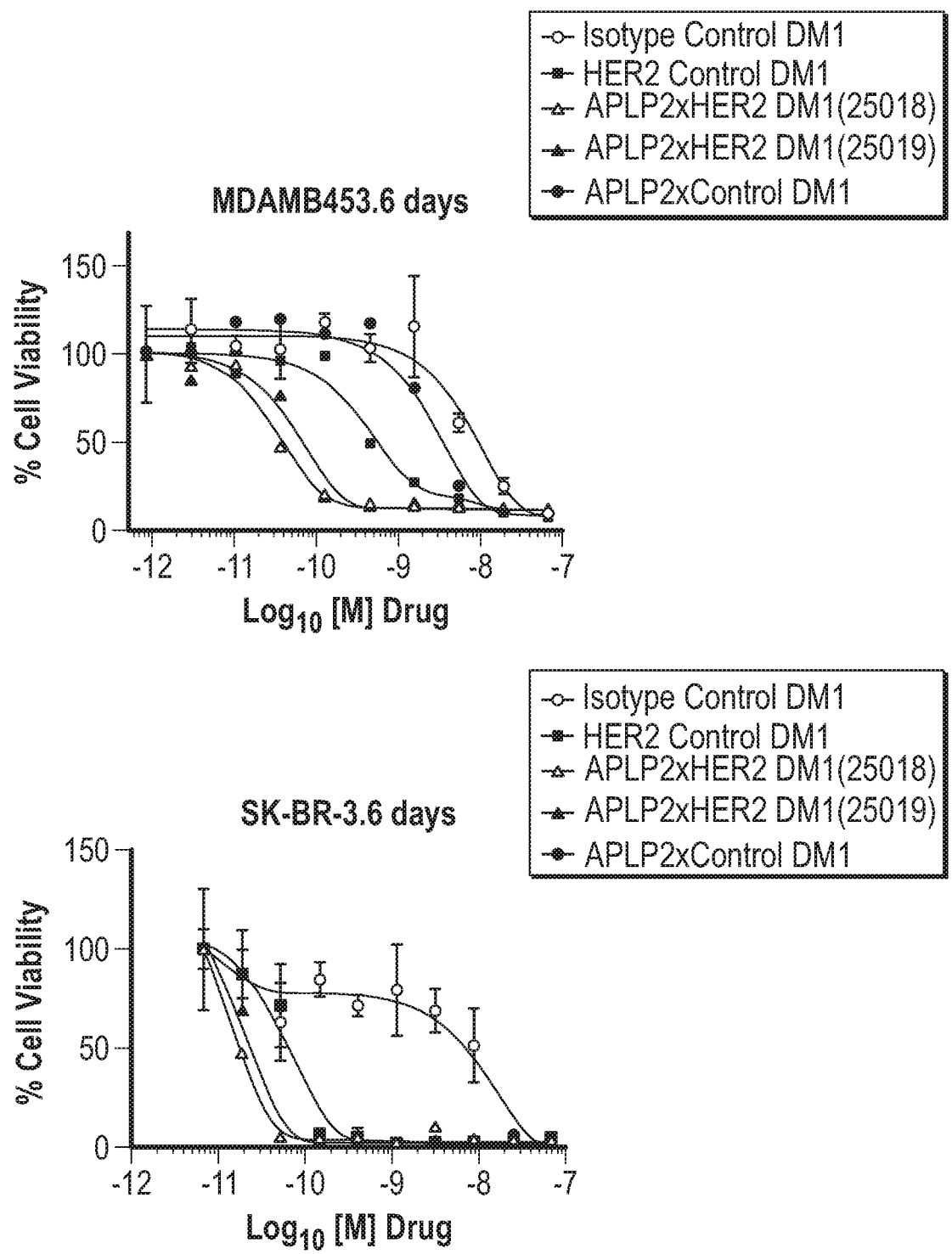

As shown in Table 16A and FIG. 7, in MDA-MB-231 and MDA-MB468 cells, which express very low HTER2 levels, anti-HER2×APLP2 binding protein ADCs, 1141125018D-DM1 and H4H25019D-SMCC-DM1, demonstrated killing with $IC_{50}$ values of 5-9 nM. In the same cells, the HER2/T control-SMCC-DM1 ADC demonstrated less efficient killing with an $IC_{50}$ value of 10-25 nM. The isotype control-SMCC-DM1 ADC demonstrated less efficient killing with an $IC_{50}$ value of 18-35 nM.

In MCF-7 and T47D cells, which express low HER2 levels, anti-HER2×APLP2 binding protein ADCs bispecific ADCs, H4H25018D-SMCC-DM1 and H4H25019D-SMCC-DM1, demonstrated killing with $IC_{50}$ values of 2 nM. In the same cells, the HER2/T control-SMCC-DM1 ADC demonstrated less efficient killing with an $IC_{50}$ value of 10-40 nM. The isotype control-SMCC-DM1 ADC demonstrated less efficient killing with an $IC_{50}$ value of 30-50 nM.

In JIMT-1, MDA-MB-361 and MDA-MB-453 cells, which express intermediate HER2 levels, anti-HER2×APLP2 binding protein ADCs, H4H25018D-SMCC-DM1 and H4H25019D-SMCC-DM1, demonstrated killing with $IC_{50}$ values between 0.03 and 0.8 nM. In the same cells, the HER2/T control-SMCC-DM1 ADC and the anti-FelD1×APLP2 ADC (H4H28697D-SMCC-DM1) demonstrated less efficient killing with $IC_{50}$ values of 0.25-5 nM and 2-5 nM, respectively. The isotype control-SMCC-DM1 ADC demonstrated less efficient killing with an $IC_{50}$ value of 8-30 nM.

In SK-BR-3 cells, which express high HER2 levels, anti-HER2×APLP2 binding protein ADCs, H4H25018D-SMCC-DM1 and H4H25019D-SMCC-DM1, both demonstrated killing with $IC_{50}$ values of 0.02 nM and 0.03 nM, respectively. In the same cells, the HER2/T control-SMCC-DM1 ADC demonstrated less efficient killing with an $IC_{50}$ value of 0.1 nM. The isotype control-SMCC-DM1 ADC demonstrated less efficient killing with an $IC_{50}$ value of 10 nM.

Anti-HER2×APLP2 binding protein ADCs, H4H25018D-SMCC-DM1 and H4H25019D-SMCC-DM1, induced more potent cell killing than HER2 control Ab-SMCC-DM1 ADC in all cell lines tested. Anti-HER2×APLP2 binding protein ADCs were not as efficient at killing cells expressing very low HER2 levels as they were killing cells with higher HER2 levels. Bispecific anti-FELD1×APLP2 binding proteins induced little killing of cell lines expressing intermediate HER2 levels, indicating that the APLP2 arm alone was not sufficient to drive efficient cell killing.

Experiment 2

To test the ability of HER2×APLP2 bispecific antibody drug conjugates (ADC) of the invention comprised of different APLP2 arms to kill bioassay cells, in vitro cytotoxicity assays were performed. The assays were conducted on cells with varying levels of HER2 expression treated with decreasing ADC concentrations for 6 days and cell viability was measured after treatment by measuring ATP production with Cell Titer Glow (Promega G7571).

For the assay, either MDA-MB-231 (ATCC, Cat #HTB-26), MCF7 (ATCC, Cat #HTB-22), T47D (ATCC, Cat #HTB-133), ZR75-1 (ATCC, Cat #CRL1500), JIMT1 (DSMZ, ACC589), MDA-MB-361 (ATCC, Cat #HTB-27), MDA-MB-453 (ATCC, Cat #HTB-131), SKBR3 (ATCC, Cat #HTB-30) or N87 (ATCC, CRL5822) were seeded at $3 \times 10^3$ cells/well on collagen-coated 96-well optical plates (Greiner, Cat #655936).

MDA-MB-231, MDA-MB-361 and MDA-MB-453 cells were cultured in media containing DMEM and 10% FBS. MCF-7 were cultured in media containing MEM, 10% FBS and 10 ug/mL Insulin. T47D cells were cultured in media containing RPMI1640, 10% FBS, Glutamine, 1 mM Sodium Pyruvate, 10 mM HEPES and 10 ug/mL Insulin. SKBR3 were cultured media containing McCoy with 10% FBS. ZR75-1 and N87 were cultured in media containing RPMI1640, 10% FBS. JIMT1 cells were cultured in media containing DMEM, 10% FBS, and 10 ug/mL insulin.

The following day either HER2×APLP2 bispecific ADCs (H4H25014D-DM1, H4H25018D-DM1 and H4H25020D-DM1), Exogenous target×APLP2 ADC (H4H28695D-DM1, H4H28697D-DM1 and H4H28696D-DM1), HER2 control Ab-DM1, or Isotype control-DM1 were added to cells at final concentrations ranging from 66.67 nM to 0.01 nM in DMEM and 10% FBS and were then incubated for 6 days. After the incubation, 100 uL of Cell Titer Glow solution (Promega, Cat #G7571) were added to each well and incubated for 5 minutes at room temperature in orbital shaker (400RPM). Luminescence was quantified in Spectramax M3 reader (Molecular Devices). The IC50 values were determined from a two-phase decay equation over a 10-point response curve (GraphPad Prism). All IC50 values are expressed in nM concentration.

As shown in Table 16B, in cell lines that express high HER2 levels (SKBR3 and N87) the HER2-ADC and the three HER2×APLP2 bispecific ADCs induced efficient cell killing to a similar extent with $IC_{50}$ values ranging from 0.004-0.05 nM, while the Isotype control-ADC induced inefficient cell killing with an $IC_{50}$ value of 7 nM. In cell lines that express intermediate HER2 levels (MDAMB453, MDAMB361, JIMT1 and ZR751) the HER2×APLP2 bispecific ADC with strong APLP2 arm, H4H25018D, induced more efficient cell killing, with $IC_{50}$ values ranging from 0.04-0.15 nM, than the HER2×APLP2 bispecific ADCs with moderate and weak APLP2 arms, H4H25014D and H4H25020D, which demonstrated killing with an $IC_{50}$ value of $IC_{50}$ 0.06-3 nM. In cell lines that express intermediate HER2 levels (MDAMB453, MDAMB361, JIMT1 and ZR751), the HER2-ADC induced less efficient cell killing than any of the three bispecifics. In these cells the isotype control-ADC induced inefficient cell killing with $IC_{50}$ values ranging from 1-30 nM. In cell lines that express low HER2 levels (T47D and MCF7) the isotype control-ADC, the HER2-ADC and the HER2×APLP2 bispecific ADCs with moderate and weak APLP2 arms induced inefficient cell killing with $IC_{50}$ values ranging from 10-70 nM. The HER2×APLP2 bispecific ADC with a strong APLP2 arm demonstrated slightly more potent killing than the other ADCs, however, the effect was limited with $IC_{50}$ values ranging from 3.5-5 nM. In the cell line expressing very low HER2 levels (MDAMB231), none of the ADCs induced efficient killing. In all cell lines tested, the moderate or weak monovalent APLP2-ADCs induced inefficient cell killing that overlapped with the isotype control-ADC with $IC_{50}$ values>6 nM, while the strong monovalent APLP2-ADC demonstrated limited killing effect with $IC_{50}$ values>2 nM.

TABLE 16B

Cytotoxicity of HER2 × APLP2 bispecific ADCs, Exogenous target × APLP2 bispecific ADCs with different APLP2 arms and controls on cell lines with varying HER2 expression.

| Cell Line | HER2 expression | ADC tested | $IC_{50}$ (nM) |
| --- | --- | --- | --- |
| MDAMB231 | Very Low HER2 | Isotype control-DM1 | 100.000 |
| MDAMB231 | Very Low HER2 | Anti-HER2 comparator-DM1 | 100.000 |
| MDAMB231 | Very Low HER2 | H4H25018D-DM1 | 40.000 |
| MDAMB231 | Very Low HER2 | H4H25014D-DM1 | 100.000 |
| MDAMB231 | Very Low HER2 | H4H25020D-DM1 | 100.000 |
| MDAMB231 | Very Low HER2 | H4H28695D-DM1 | 100.000 |

TABLE 16B-continued

Cytotoxicity of HER2 × APLP2 bispecific ADCs, Exogenous target × APLP2 bispecific ADCs with different APLP2 arms and controls on cell lines with varying HER2 expression.

| Cell Line | HER2 expression | ADC tested | IC$_{50}$ (nM) |
| --- | --- | --- | --- |
| MDAMB231 | Very Low HER2 | H4H28696D-DM1 | 100.000 |
| MDAMB231 | Very Low HER2 | H4H28697D-DM1 | 40.000 |
| MCF7 | Low HER2 | Isotype control-DM1 | 35.000 |
| MCF7 | Low HER2 | Anti-HER2 comparator-DM1 | 35.000 |
| MCF7 | Low HER2 | H4H25018D-DM1 | 5.000 |
| MCF7 | Low HER2 | H4H25014D-DM1 | 15.000 |
| MCF7 | Low HER2 | H4H25020D-DM1 | 10.000 |
| MCF7 | Low HER2 | H4H28695D-DM1 | 40.000 |
| MCF7 | Low HER2 | H4H28696D-DM1 | 35.000 |
| MCF7 | Low HER2 | H4H28697D-DM1 | 10.000 |
| T47D | Low HER2 | Isotype control-DM1 | 50.000 |
| T47D | Low HER2 | Anti-HER2 comparator-DM1 | 70.000 |
| T47D | Low HER2 | H4H25018D-DM1 | 3.500 |
| T47D | Low HER2 | H4H25014D-DM1 | 10.000 |
| T47D | Low HER2 | H4H25020D-DM1 | 40.000 |
| T47D | Low HER2 | H4H28695D-DM1 | 70.000 |
| T47D | Low HER2 | H4H28696D-DM1 | 10.000 |
| T47D | Low HER2 | H4H28697D-DM1 | 5.000 |
| ZR-75-1 | Intermediate HER2 | Isotype control-DM1 | 30.000 |
| ZR-75-1 | Intermediate HER2 | Anti-HER2 comparator-DM1 | 20.000 |
| ZR-75-1 | Intermediate HER2 | H4H25018D-DM1 | 0.100 |
| ZR-75-1 | Intermediate HER2 | H4H25014D-DM1 | 0.500 |
| ZR-75-1 | Intermediate HER2 | H4H25020D-DM1 | 2.000 |
| ZR-75-1 | Intermediate HER2 | H4H28695D-DM1 | 30.000 |
| ZR-75-1 | Intermediate HER2 | H4H28696D-DM1 | 20.000 |
| ZR-75-1 | Intermediate HER2 | H4H28697D-DM1 | 6.000 |
| JIMT1 | Intermediate HER2 | Isotype control-DM1 | 25.000 |
| JIMT1 | Intermediate HER2 | Anti-HER2 comparator-DM1 | 15.000 |
| JIMT1 | Intermediate HER2 | H4H25018D-DM1 | 0.150 |
| JIMT1 | Intermediate HER2 | H4H25014D-DM1 | 1.500 |
| JIMT1 | Intermediate HER2 | H4H25020D-DM1 | 3.000 |
| JIMT1 | Intermediate HER2 | H4H28695D-DM1 | 25.000 |
| JIMT1 | Intermediate HER2 | H4H28696D-DM1 | 30.000 |
| JIMT1 | Intermediate HER2 | H4H28697D-DM1 | 10.000 |
| MDAMB361 | Intermediate HER2 | Isotype control-DM1 | 10.000 |
| MDAMB361 | Intermediate HER2 | Anti-HER2 comparator-DM1 | 0.100 |
| MDAMB361 | Intermediate HER2 | H4H25018D-DM1 | 0.040 |
| MDAMB361 | Intermediate HER2 | H4H25014D-DM1 | 0.100 |
| MDAMB361 | Intermediate HER2 | H4H25020D-DM1 | 0.060 |
| MDAMB361 | Intermediate HER2 | H4H28695D-DM1 | 10.000 |
| MDAMB361 | Intermediate HER2 | H4H28696D-DM1 | 10.000 |
| MDAMB361 | Intermediate HER2 | H4H28697D-DM1 | 3.000 |
| MDAMB453 | Intermediate HER2 | Isotype control-DM1 | 20.000 |
| MDAMB453 | Intermediate HER2 | Anti-HER2 comparator-DM1 | 0.500 |
| MDAMB453 | Intermediate HER2 | H4H25018D-DM1 | 0.060 |
| MDAMB453 | Intermediate HER2 | H4H25014D-DM1 | 0.100 |
| MDAMB453 | Intermediate HER2 | H4H25020D-DM1 | 0.080 |
| MDAMB453 | Intermediate HER2 | H4H28695D-DM1 | 10.000 |
| MDAMB453 | Intermediate HER2 | H4H28696D-DM1 | 20.000 |
| MDAMB453 | Intermediate HER2 | H4H28697D-DM1 | 6.000 |
| SK-BR-3 | High HER2 | Isotype control-DM1 | 7.000 |
| SK-BR-3 | High HER2 | Anti-HER2 comparator-DM1 | 0.015 |
| SK-BR-3 | High HER2 | H4H25018D-DM1 | 0.004 |
| SK-BR-3 | High HER2 | H4H25014D-DM1 | 0.020 |
| SK-BR-3 | High HER2 | H4H25020D-DM1 | 0.008 |
| SK-BR-3 | High HER2 | H4H28695D-DM1 | 7.000 |
| SK-BR-3 | High HER2 | H4H28696D-DM1 | 7.000 |
| SK-BR-3 | High HER2 | H4H28697D-DM1 | 2.000 |
| NCI-N87 | High HER2 | Isotype control-DM1 | 7.000 |
| NCI-N87 | High HER2 | Anti-HER2 comparator-DM1 | 0.050 |
| NCI-N87 | High HER2 | H4H25018D-DM1 | 0.025 |
| NCI-N87 | High HER2 | H4H25014D-DM1 | 0.050 |
| NCI-N87 | High HER2 | H4H25020D-DM1 | 0.030 |
| NCI-N87 | High HER2 | H4H28695D-DM1 | 7.000 |
| NCI-N87 | High HER2 | H4H28696D-DM1 | 6.000 |
| NCI-N87 | High HER2 | H4H28697D-DM1 | 3.000 |

In conclusion, the HER2×APLP2-ADCs were as efficient as the HER2-ADC in high HER2-expressing cells and more efficient in intermediate HER2-expressing cells at killing the cell lines tested. In cells expressing low HER2 levels that are slightly higher than the HER2 expression in normal cells, the HER2×APLP2-ADCs demonstrated limited to no cell killing. The monovalent APLP2-ADCs were not sufficient to induce efficient cell killing in any cell line tested.

Figure 8:
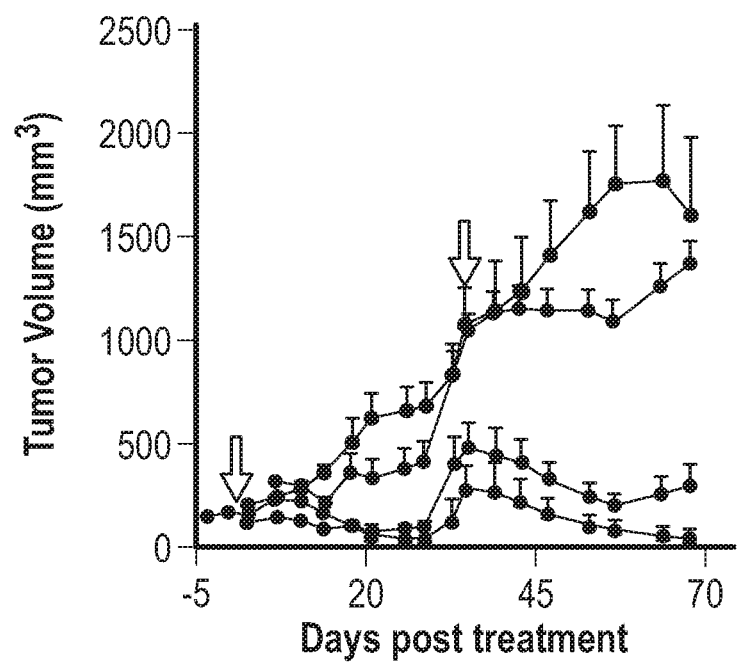
FIG. 8 provides JIMT-1 tumor volumes in mice treated with isotype control DM1-conjugated antibody, HER2/T control DM1-conjugated antibody, or bispecific anti-HER2×APLP2 (25018 or 25019) DM1-conjugated antibody.
Figure 8:
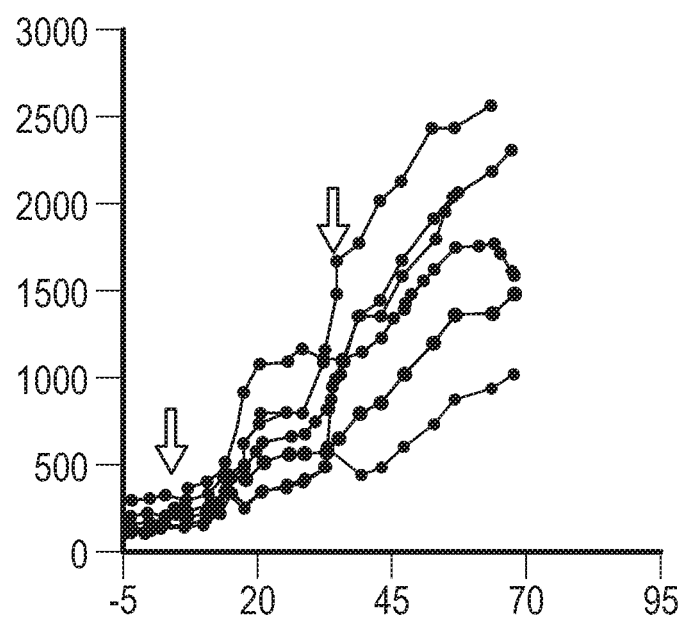
Figure 8:
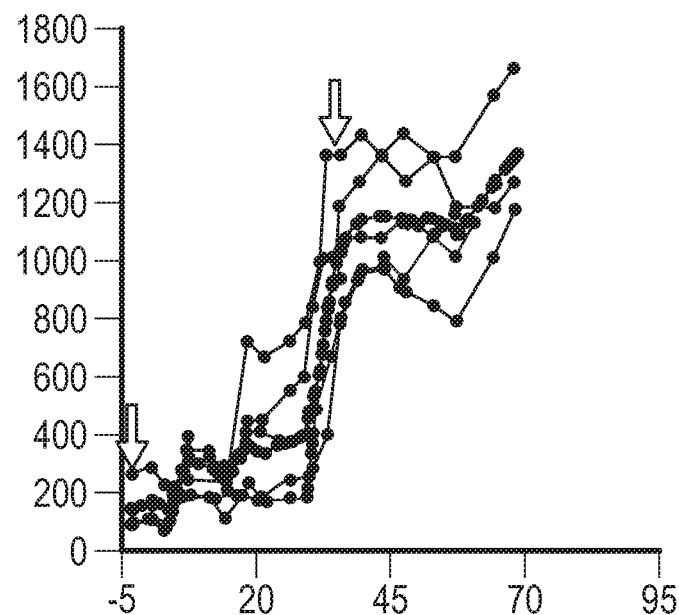
Figure 8:
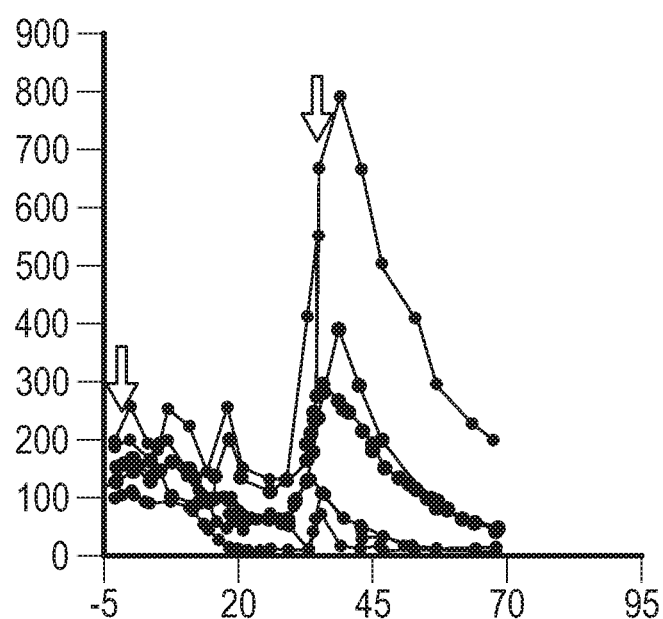
Figure 8:
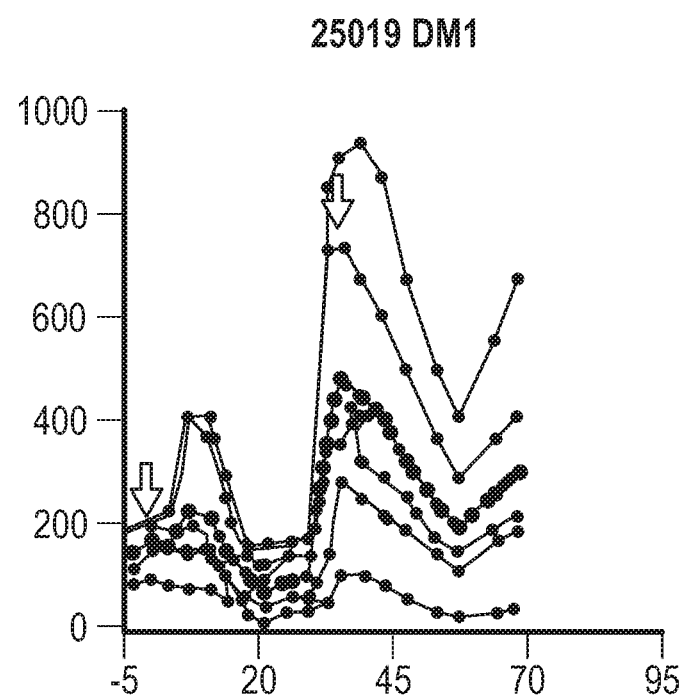
Figure 9:
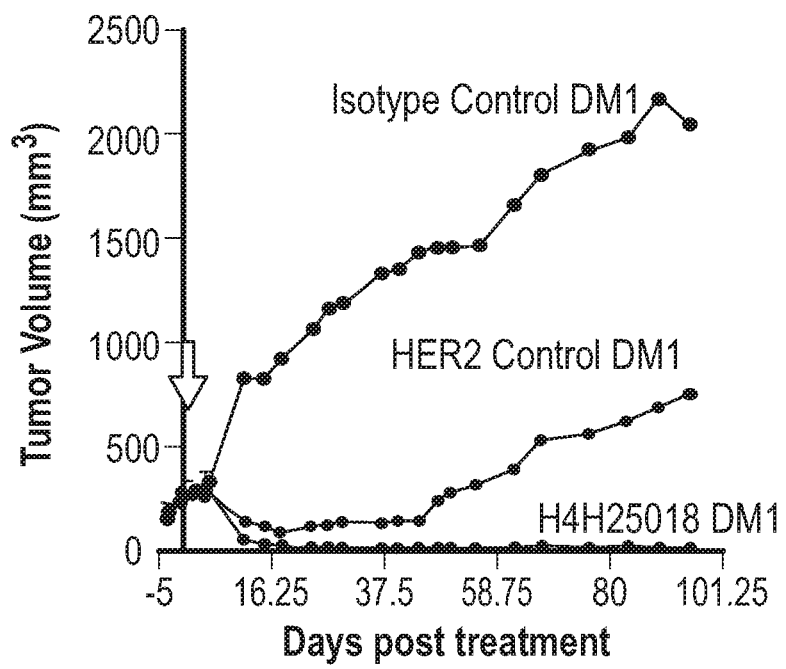
FIG. 9 provides MDA-MB-361 tumor volumes in mice treated with isotype control DM1-conjugated antibody, HER2/T control DM1-conjugated antibody, or bispecific anti-HER2×APLP2 (25018) DM1-conjugated antibody.
Figure 9:
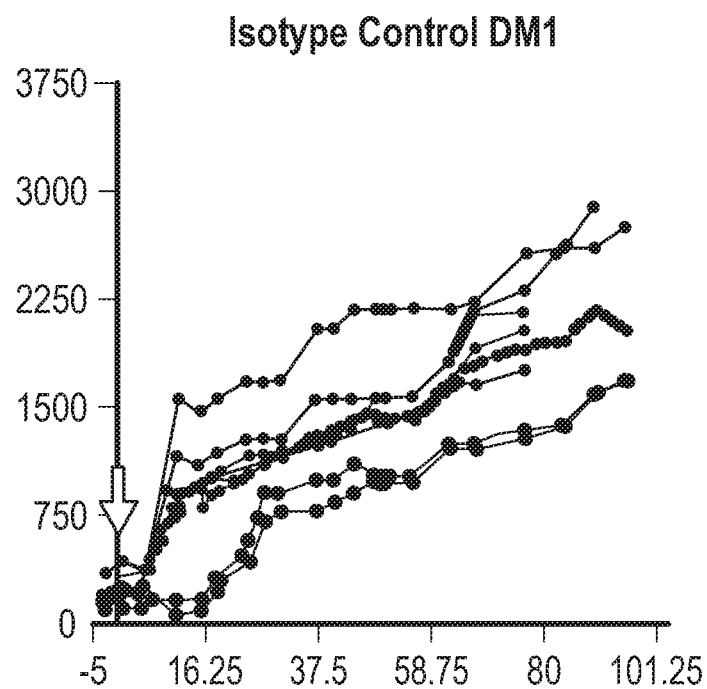
Figure 9:
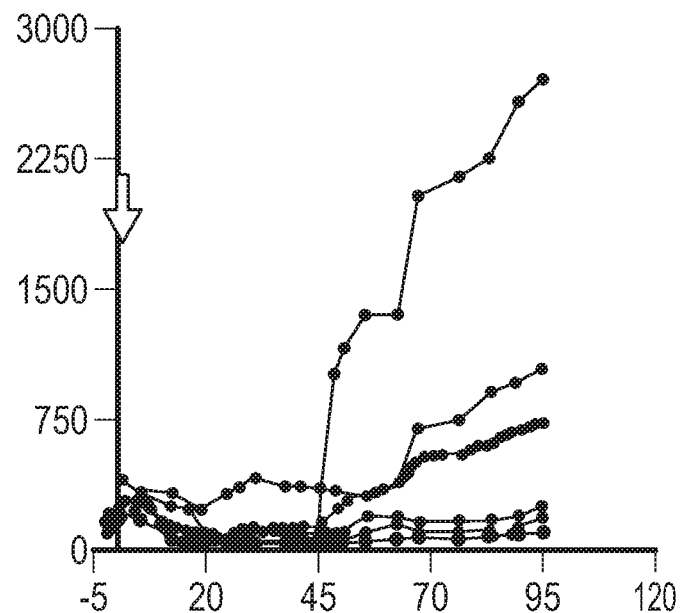
Figure 9:
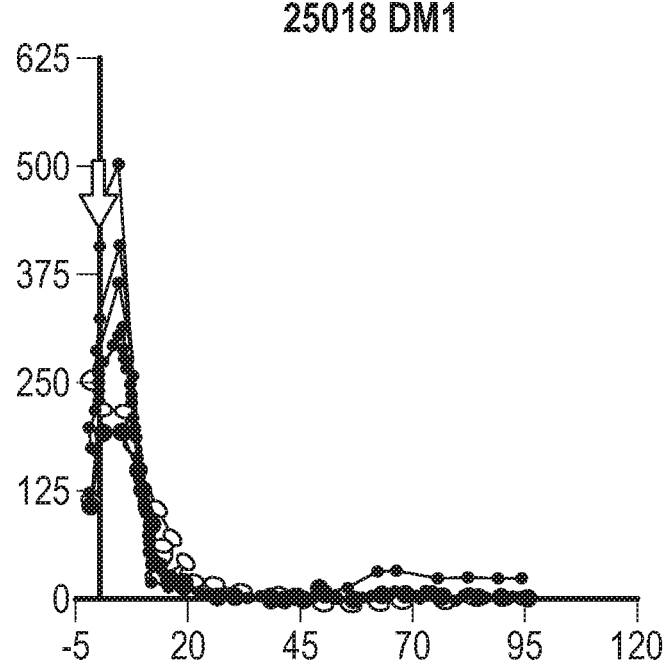

Example 12: Bispecific Anti-HER2×APLP2 ADCs Exhibit Greater Targeted Cytotoxicity in In Vivo Model of JIMT-1 Tumor Regression Compared to Monospecific Anti-HER2 Antibodies To further test the efficacy of exemplary bispecific anti-HER2×APLP2 bispecific antibody drug conjugates (ADC), an in vivo xenograft tumor study was performed. For the assay, 8 week old female SCID mice (Taconic Biosciences; n=70) were used. JIMT-1 (DSMZ, ACC589) cells were mixed with Matrigel (Corning, Cat #354234) and 150 uL of the cell and matrigel suspension containing 5×10$^6$ cells was injected to SCID mice. Three weeks later, bispecific anti-HER2×APLP2 ADCs (H4H25018D-SMCC-DM1 and H4H25019D-SMCC-DM1), HER2 control-SMCC-DM1, and Isotype control-SMCC-DM1 were administered subcutaneously at 10 mg/kg (n=6 per treatment group) to SCID mice that were randomized based on tumor size. 33 days after the first dose, a second dose was administered to all groups. The xenograft size for each mouse was measured twice a week from day 1 to day 83 post first ADC administration using a Caliper (Roboz, Cat #RS6466). The average tumor size per treatment group for each time point measured is shown in Table 17A.

to the lowest average size of 140 mm$^3$, but the xenografts later regrew in size to greater than 1600 mm$^3$. The mice that received the Isotype control-SMCC-DM1 ADC saw their JIMT-1 xenograft size increase throughout each measurement to an average size of 1933 mm$^3$. See FIG. 8.

In a similar experiment, JIMT-1 (DSMZ, ACC589) cells were mixed with Matrigel (Corning, Cat #354234) and 150 uL of the cell and matrigel suspension containing 5×10$^6$ cells was injected to SCID mice. 11 and 25 days after implantation, anti-HER2×APLP2 bispecific ADCs (H4H25014D-DM1, H4H25018D-DM1, and H4H25020D-DM1), anti-APLP2× irrelevant Ab control ADCs (H4H28695D-DM1, H4H28696D-DM1, and H4H28697D-DM1), HER2 control-DM1, and Isotype control-DM1 were administered subcutaneously at 10 mg/kg (n=6 per treatment group) to SCID mice that were randomized based on tumor size. The xenograft size for each mouse was measured on days 11, 13, 16, 19, 23, 25, 30, 33, 37, 44, 48, 53, 56, 59, 68 and 74 post implantation using a Caliper (Roboz, Cat #RS6466). The average tumor size per treatment group for each time point measured is shown in Table 17B.

Mice that received the anti-HER2×APLP2 bispecific ADC, H4H25018D-DM1, demonstrated a significant reduction in JIMT-1 xenograft size to an average size of 93 mm$^3$. Mice that received the anti-HER2×APLP2 bispecific ADCs, H4H25014D-DM1 and H4H25020D-DM1, demonstrated tumor stasis of JIMT1 xenografts that remained close to the pretreatment of 200 mm$^3$ average size for 30 days. In

TABLE 17A

JIMT-1 xenograft tumor size after treatment with anti-HER2 × APLP2-SMCC-DM1 ADCs and control-SMCC-DM1 ADCs
Average Tumor Size (mm3)

| Days post treatment | Isotype Control | | HER2/T Control | | H4H25018D | | H4H25019D | |
|---|---|---|---|---|---|---|---|---|
| | Average | St Dev | Average | St Dev | Average | St Dev | Average | St Dev |
| 1 | 167 | 31 | 169 | 27 | 167 | 24 | 170 | 17 |
| 3 | 205 | 35 | 140 | 22 | 136 | 18 | 162 | 19 |
| 7 | 237 | 36 | 316 | 29 | 160 | 31 | 232 | 57 |
| 11 | 268 | 36 | 297 | 27 | 138 | 28 | 222 | 54 |
| 14 | 362 | 48 | 226 | 26 | 92 | 18 | 156 | 38 |
| 18 | 511 | 105 | 366 | 85 | 98 | 42 | 101 | 27 |
| 21 | 628 | 119 | 341 | 82 | 60 | 25 | 77 | 25 |
| 26 | 659 | 113 | 377 | 90 | 62 | 20 | 101 | 27 |
| 29 | 677 | 119 | 412 | 100 | 62 | 23 | 105 | 28 |
| 33 | 825 | 126 | 847 | 131 | 128 | 65 | 406 | 130 |
| 35 | 1071 | 179 | 1035 | 86 | 290 | 105 | 480 | 120 |
| 39 | 1140 | 233 | 1138 | 95 | 263 | 146 | 448 | 124 |
| 43 | 1229 | 264 | 1152 | 84 | 211 | 125 | 409 | 115 |
| 47 | 1396 | 268 | 1140 | 100 | 150 | 95 | 329 | 89 |
| 53 | 1611 | 297 | 1146 | 95 | 111 | 77 | 243 | 68 |
| 57 | 1748 | 279 | 1096 | 95 | 80 | 55 | 199 | 56 |
| 64 | 1761 | 370 | 1257 | 117 | 57 | 42 | 264 | 73 |
| 68 | 1594 | 379 | 1367 | 105 | 48 | 38 | 304 | 87 |
| 72 | 1691 | 353 | 1525 | 144 | 28 | 21 | 337 | 97 |
| 76 | 1691 | 353 | 1525 | 144 | 21 | 17 | 366 | 106 |
| 83 | 1933 | 258 | 1688 | 171 | 16 | 12 | 437 | 113 |

Mice that received a bispecific anti-HER2×APLP2 H4H25018D-SMCC-DM1 ADC saw a significant and sustained reduction in JIMT-1 xenograft size on an average size of less than 16 mm$^3$. Mice that received the bispecific anti-HER2×APLP2 H4H25019D-SMCC-DM1 ADC, saw a significant reduction in JIMT-1 xenograft size to the lowest average size of 77 mm$^3$, but the xenografts later regrew in size to 437 mm$^3$. Mice that received the HER2/T control-SMCC-DM1 ADC saw a reduction in JIMT-1 xenograft size contrast, mice that received either the Isotype control-DM1 ADC or the HER2 control-DM1 ADC saw their JIMT-1 xenograft size increase throughout each measurement to an average size of over 400 mm$^3$ by day 30 and over 1000 mm$^3$ over day 53. Mice that received the anti-APLP2× irrelevant Ab control ADCs saw their JIMT-1 xenograft size increase with little tumor stasis to an average size of 283-366 mm$^3$ by day 30 and over 800 mm$^3$ over day 53.

TABLE 17B

JIMT1 xenograft tumor size afer anti-HER2 x APLP2, anti-APLP2 x Irrelevant Ab bispecific ADCs, and control ADCs treatment

| Days Post Implantation | Isotype control DM1 | | HER2 control-DM1 | | H4H25014D APLP2 x HER2-DM1 | | H4H25018D APLP2 x HER2-DM1 | | H4H25020D APLP2 x HER2-DM1 | | H4H28695D APLP2 x Irrelevant Ab-DM1 | | H4H28696D APLP2 x Irrelevant Ab-DM1 | | H4H28697D APLP2 x Irrelevant Ab-DM1 | |
|---|---|---|---|---|---|---|---|---|---|---|---|---|---|---|---|---|
| | AVE | St Error | Ave | St Error | Ave | St Error | Ave | St Error | Ave | St Error | Ave | St Error | Ave | St Error | Ave | St Error |
| 9  | 176  | 14  | 190  | 17  | 161 | 12 | 221 | 24  | 179 | 24 | 180 | 12  | 173 | 12  | 199 | 7   |
| 11 | 204  | 18  | 206  | 16  | 203 | 15 | 203 | 17  | 204 | 18 | 203 | 15  | 203 | 20  | 206 | 20  |
| 13 | 201  | 14  | 273  | 36  | 221 | 16 | 205 | 26  | 210 | 11 | 246 | 14  | 232 | 18  | 234 | 37  |
| 16 | 243  | 24  | 275  | 33  | 235 | 24 | 229 | 21  | 217 | 23 | 245 | 30  | 229 | 16  | 234 | 26  |
| 19 | 305  | 42  | 326  | 64  | 201 | 27 | 204 | 27  | 226 | 22 | 296 | 51  | 233 | 20  | 266 | 42  |
| 23 | 332  | 66  | 395  | 105 | 182 | 15 | 140 | 21  | 222 | 28 | 350 | 68  | 255 | 14  | 281 | 49  |
| 25 | 353  | 64  | 413  | 85  | 192 | 19 | 122 | 18  | 241 | 42 | 380 | 64  | 268 | 32  | 311 | 71  |
| 30 | 400  | 68  | 482  | 103 | 204 | 36 | 108 | 42  | 239 | 48 | 366 | 57  | 283 | 39  | 311 | 74  |
| 33 | 468  | 65  | 552  | 143 | 216 | 36 | 93  | 48  | 258 | 43 | 375 | 70  | 293 | 44  | 328 | 91  |
| 37 | 508  | 59  | 733  | 195 | 267 | 41 | 102 | 53  | 286 | 61 | 434 | 77  | 350 | 69  | 398 | 91  |
| 44 | 646  | 86  | 951  | 269 | 323 | 41 | 145 | 82  | 377 | 69 | 514 | 110 | 517 | 33  | 489 | 88  |
| 48 | 791  | 121 | 1233 | 333 | 377 | 51 | 179 | 101 | 443 | 69 | 707 | 171 | 634 | 120 | 649 | 152 |
| 53 | 1088 | 174 | 1405 | 369 | 419 | 69 | 208 | 118 | 447 | 61 | 866 | 229 | 842 | 94  | 886 | 222 |

Example 13: Bispecific Anti-HER2×APLP2 ADCs Exhibit Greater Targeted Cytotoxicity in In Vivo Model of MDA-MB-361 Tumor Regression Compared to Monospecific Anti-HER2 Antibodies To further test the efficacy of an exemplary bispecific anti-HER2×APLP2 antibody drug conjugate (ADC), an in vivo xenograft tumor study was performed. Briefly, 6 week old female SCID mice (Taconic Biosciences; n=60) were implanted subcutaneously with Estrogen pellets (0.72 mg/pellet; Innovative Research of America, Cat #NE-121). The following day MDA-MB-361 cells (ATCC, HTB-27) were mixed with Matrigel (Corning, Cat #354234) and 150 µL of the cell with matrigel suspension containing $5 \times 10^6$ cells were injected to SCID mice. Twelve days later, bispecific anti-HER2×APLP2 ADC (H4H25018D-SMCC-DM1), HER2/T control-SMCC-DM1, and Isotype control-DM1 were administered subcutaneously at 10 mg/kg (n=7 per treatment group) to SCID mice that were randomized based on tumor size. The xenograft size for each mouse was measured from day 1 to day 95 post ADC administration using a Caliper (Roboz, Cat #RS6466).

The average (AVG) and standard deviation (SD) of tumor size per treatment group for each time point measured is shown in Table 18.

TABLE 18

MDA-MB-361 xenograft tumor size after treatment with bispecific anti HER2 x APLP2-SMCC-DM1 ADC and control-DM1 treatments Average Tumor Size (mm3)

| Days post treatment | Isotype Control | | HER2/T Control | | H4H25018D | |
|---|---|---|---|---|---|---|
| | Average | SD | Average | SD | Average | SD |
| 1  | 262  | 111 | 275 | 89  | 273 | 76  |
| 4  | 260  | 98  | 272 | 46  | 310 | 117 |
| 11 | 814  | 531 | 137 | 109 | 53  | 34  |
| 15 | 822  | 493 | 112 | 91  | 29  | 21  |
| 18 | 918  | 471 | 83  | 71  | 17  | 11  |
| 24 | 1054 | 419 | 110 | 98  | 6   | 4   |
| 27 | 1155 | 298 | 122 | 110 | 4   | 3   |
| 30 | 1175 | 283 | 130 | 124 | 3   | 3   |
| 37 | 1317 | 404 | 131 | 103 | 2   | 2   |
| 40 | 1350 | 389 | 135 | 102 | 2   | 2   |
| 44 | 1429 | 397 | 135 | 102 | 2   | 2   |
| 48 | 1456 | 399 | 252 | 346 | 2   | 5   |
| 50 | 1456 | 399 | 272 | 399 | 2   | 5   |
| 55 | 1456 | 399 | 313 | 468 | 2   | 5   |
| 62 | 1658 | 328 | 389 | 485 | 8   | 11  |
| 67 | 1806 | 428 | 533 | 768 | 9   | 10  |
| 76 | 1923 | 471 | 556 | 816 | 7   | 8   |
| 83 | 1975 | 699 | 608 | 864 | 7   | 8   |
| 89 | 2168 | 677 | 687 | 975 | 6   | 8   |
| 95 | 2041 | 610 | 744 | 1011 | 6  | 8   |

SD = standard deviation

Mice that received the bispecific anti-HER2×APLP2 H4H25018D-SMCC-DM1 ADC saw a significant and sustained reduction in MDA-MB-361 xenograft size. Mice that received the HER2 control-SMCC-DM1 ADC saw a reduction in MDA-MB-361 xenograft size to the lowest average size of 83 mm$^3$, but the xenografts later regrew in size to greater than 744 mm$^3$. The mice that received the Isotype control-SMCC-DM1 ADC saw their MDA-MB-361 xenograft size increase throughout each measurement to an average size of 2041 mm$^3$.

Example 13: Pharmacokinetic Assessment of Anti-Her2×APLP2 Bispecific Antibodies (bsAb) in Humanized APLP2 Mice Evaluation of the pharmacokinetics of 3 anti-HER2× APLP2 bispecific antibodies (H4H25018D, H4H25014D, H4H25020D) and a hIgG4$^P$ bivalent, non-binding isotype control were conducted in mice homozygous for the expression of human APLP2 in place of mouse APLP2, (APLP2$^{hu/hu}$ mice). Cohorts of 5 mice per group received a single subcutaneous (SC) 5 mg/kg dose of each antibody. Blood samples were collected at 6 hours and 1, 2, 3, 4, 7, 10, 14, 21 and 30-days post dosing. Blood was processed into serum and frozen at 80° C. until analyzed. The serum concentrations of H4H25018D, H4H25014D, H4H25020D and isotype control antibody were measured using the GyroLab xPlore platform (Gyros).

Gyros technology uses an affinity flow-through format for automated immunoassays with laser-induced fluorescence detection. Samples are loaded onto a compact disc which contains multiple radially arranged nanoliter-scale affinity capture columns. Liquid flow is controlled by centrifugal and capillary forces.

Briefly, biotinylated mouse anti-human IgG4/IgG1-specific monoclonal antibody diluted to 100 µg/mL in a buffer comprised of 0.05% Tween-20 in phosphate-buffered saline (antibody dilution buffer) was captured on a Gyrolab Bioaffy 200 compact disc, which contained affinity columns preloaded with streptavidin-coated beads (Dynospheres™). The standards used for calibration in this assay were H4H25018D, H4H25014D, H4H25020D or isotype control antibody at concentrations ranging from 0.488 to 2000 ng/mL. Serial dilutions of standard and serum samples were prepared in a buffer comprised of 0.5% BSA in PBS containing 0.1% NMS (dilution buffer). Singlets of serum samples diluted at 1:50 and duplicates of standards were captured onto the anti-human IgG4/IgG1 specific mAbs-coated affinity columns on the compact disc at room temperature. H4H25018D, H4H25014D, H4H25020D or isotype control antibody was detected by the addition of 0.5 µg/mL of Alexa-647-conjugated mouse anti-human kappa monoclonal antibody diluted in Rexxip F buffer (Gyros, cat #P0004825) the resultant fluorescent signal was recorded in response units (RU) by the GyroLab xPlore instrument. The lowest concentration of the respective antibody standards used for calibration was in the dynamic range of the assay and was defined as the assay's lower limit of detection (LLOQ) [0.02 µg/mL]. Sample concentrations were determined by interpolation from a standard curve that was constructed using a 5-parameter logistic curve fit in Gyrolab Evaluator Software. Average concentrations from 2 replicate experiments were reported.

PK parameters were determined by non-compartmental analysis (NCA) using Phoenix®WinNonlin® software Version 6.3 (Certara, L. P., Princeton, NJ) and an extravascular dosing model. Using the respective mean concentration values for each antibody, all PK parameters including observed maximum concentration in serum ($C_{max}$), estimated half-life observed ($t_{1/2}$), and area under the concentration curve versus time up to the last measureable concentration ($AUC_{last}$) were determined using a linear trapezoidal rule with linear interpolation and uniform weighting.

Following administration of the anti-HER2×APLP2 bispecific Abs in APLP2$^{hu/hu}$ mice, H4H25018D, H4H25014D, H4H25020D all exhibited different maximum concentrations ($C_{max}$) of antibody in serum. H4H25020D had a $C_{max}$ concentration of 47 µg/mL, while H4H25014D exhibited a 1.3 lower concentration at 35 µg/mL and H4H25018D exhibited the lowest $C_{max}$ at 12 µg/mL; 4-folder lower than H4H25020D. H4H25020D, H4H25014D, and H4H25018D all exhibited lower $C_{max}$ concentrations (1.7, 2.3, 6.5-fold, respectively) than the isotype control antibody. H4H25018D, H4H25014D, H4H25020D all exhibited faster drug clearance as compared to the isotype control antibody, suggesting target-mediated clearance. The PK of H4H25018D and H4H25020D are characterized by rapid antibody clearance, with undetectable antibody concentrations at days 21 and 30, respectively. Additionally, both H4H25018D and H4H25020D have poor half-life ($T_{1/2}$), 1.6 and 1.8 days respectively, as compared to H4H25014D which had a $T_{1/2}$ of 4 days or isotype control which had a $T_{1/2}$ of around 11 days. H4H25018D, H4H25020D, and H4H25014D all exhibit lower drug exposure (AUC; 34, 212, 234 d*µg/mL, respectively) than isotype control antibody (1070 d*µg/mL). Mean terminal antibody concentrations for H4H25014D and isotype control were 0.67 µg/mL and 13.1 µg/mL, respectively.

A summary of the data for total anti-HER2×APLP2 bispecific antibody concentrations is provided in Table 19, mean PK parameters are described in Table 20 and mean total antibody concentrations versus time are shown in FIG. 10.

TABLE 19

Mean Concentrations (±SEM) of Total IgG in Serum Following a Single 5 mg/kg Sub-Cutaneous Injection of H4H25018D, H4H25014D, H4H25020D or isotype control mAb in APLP2$^{hu/hu}$ Mice Over Time

| | | Total Antibody Concentration In Mouse Serum 5 mg/kg | |
|---|---|---|---|
| Antibody | Time (d) | Mean (µg/mL) | +/−SEM |
| H4H25018D | 0.25 | 10.96 | 1.56 |
| | 1 | 9.68 | 0.69 |
| | 2 | 4.46 | 0.26 |
| | 3 | 3.73 | 0.23 |
| | 4 | 3.22 | 0.14 |
| | 7 | 1.57 | 0.42 |
| | 10 | 0.21 | 0.09 |
| | 14 | BLQ | BLQ |
| | 21 | BLQ | BLQ |
| | 30 | BLQ | BLQ |
| H4H25014D | 0.25 | 19.20 | 1.18 |
| | 1 | 34.66 | 2.53 |
| | 2 | 27.95 | 1.92 |
| | 3 | 24.55 | 1.86 |
| | 4 | 20.37 | 1.62 |
| | 7 | 14.04 | 0.92 |
| | 10 | 8.34 | 1.65 |
| | 14 | 3.33 | 1.52 |
| | 21 | 1.30 | 0.78 |
| | 30 | 0.66 | 0.40 |
| H4H25020D | 0.25 | 22.32 | 3.29 |
| | 1 | 45.91 | 1.77 |
| | 2 | 39.15 | 2.70 |
| | 3 | 27.28 | 1.68 |
| | 4 | 21.04 | 1.12 |
| | 7 | 11.15 | 1.14 |
| | 10 | 3.69 | 1.45 |
| | 14 | 1.00 | 0.88 |
| | 21 | 0.06 | 0.06 |
| | 30 | BLQ | BLQ |
| Isotype Control | 0.25 | 21.78 | 4.72 |
| | 1 | 71.58 | 5.35 |
| | 2 | 77.54 | 2.15 |
| | 3 | 69.76 | 1.46 |
| | 4 | 64.55 | 1.64 |
| | 7 | 59.54 | 2.84 |
| | 10 | 43.45 | 1.82 |
| | 14 | 32.80 | 4.56 |
| | 21 | 19.22 | 3.82 |
| | 30 | 13.09 | 2.94 |

Abbreviations:
Time = Time in days post single-dose injection;
d = Day of study;
SEM = Standard Error of the Mean;
BLQ = Below limit of quantitation.

TABLE 20

| | | 5 mg/kg | | | |
|---|---|---|---|---|---|
| Parameter | Units | H4H25018D | H4H25014D | H4H25020D | Isotype Control |
| $C_{max}$ | µg/mL | 12 ± 2.2 | 35 ± 5.7 | 47 ± 3.6 | 79 ± 3.5 |
| $T_{1/2}$ | d | 1.6 ± 0.45 | 4.1 ± 2.1 | 1.8 ± 0.63 | 11 ± 3.4 |
| $AUC_{last}$ | d*µg/mL | 34 ± 4.9 | 235 ± 69 | 212 ± 39 | 1070 ± 160 |

PK parameters were derived from mean concentration versus time profiles. $T_{1/2}$ and $AUC_{last}$ are based on concentrations out to day 30 if applicable. The mean±SEM value for each PK parameter is shown for all dose groups. Abbreviations: $AUC_{last}$=area under the curve from the time of dosing to the last measurable concentration; $t_{1/2}$=terminal half-life of elimination; $C_{max}$=peak concentration; d=days; $t_{max}$=the time at which $C_{max}$ is observed; SEM=standard error of the mean.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed:

1. A bispecific antigen-binding molecule comprising a first antigen-binding domain that binds human APLP2 and comprises a heavy chain complementarity determining region (HCDR) 1, HCDR2 and HCDR3 contained within a heavy chain variable region (HCVR) and a light chain complementarity determining region (LCDR) 1, LCDR2, and LCDR3 contained within a light chain variable region (LCVR) and a second antigen-binding domain that binds human HER2 and comprises an HCDR1, HCDR2, and HCDR3 contained within an HCVR and an LCDR1, LCDR2, and LCDR3 contained within an LCVR, wherein:
   (a) the first antigen-binding domain that binds human APLP2 comprises:
      (i) an HCDR1, HCDR2, and HCDR3 found within the HCVR amino acid sequence of SEQ ID NO: 26, an HCDR1, HCDR2, and HCDR3 found within the HCVR amino acid sequence of SEQ ID NO: 34, or an HCDR1, HCDR2, and HCDR3 found within the HCVR amino acid sequence of SEQ ID NO: 42; and
      (ii) an LCDR1, LCDR2, and LCDR3 found within the LCVR amino acid sequence of SEQ ID NO: 10; and
   (b) the second antigen-binding domain that binds human HER2 comprises:
      (i) an HCDR1, HCDR2, and HCDR3 found within the HCVR amino acid sequence of SEQ ID NO: 2, or an HCDR1, HCDR2, and HCDR3 found within the HCVR amino acid sequence of SEQ ID NO: 18; and
      (ii) an LCDR1, LCDR2, and LCDR3 found within the LCVR amino acid sequence of SEQ ID NO: 10.

2. An antibody-drug conjugate (ADC) comprising the bispecific antigen-binding molecule of claim 1 and a cytotoxic agent, optionally wherein the bispecific antigen-binding molecule and the cytotoxic agent are covalently attached via a linker, optionally wherein the cytotoxic agent is a maytansinoid, optionally wherein the maytansinoid is DM1 or DM4, optionally wherein the linker is SMCC, and optionally wherein the cytotoxic agent is DM1 and the linker is SMCC.

3. An isolated anti-APLP2 antibody or antigen-binding fragment thereof, wherein the antibody or antigen-binding fragment thereof comprises a heavy chain variable region (HCVR) and a light chain variable region (LCVR) comprising:

(a) an HCDR1, HCDR2, and HCDR3 found within HCVR amino acid sequence of SEQ ID NO: 26, an HCDR1, HCDR2, and HCDR3 found within the HCVR amino acid sequence of SEQ ID NO: 34, or an HCDR1, HCDR2, and HCDR3 found within the HCVR amino acid sequence of SEQ ID NO: 42; and (b) an LCDR1, LCDR2, and LCDR3 found within the LCVR amino acid sequence of SEQ ID NO: 10.

4. The anti-APLP2 antibody or antigen-binding fragment thereof of claim 3, wherein the anti-APLP2 antibody or antigen-binding fragment thereof binds human APLP2 with a KD of about 100 nM to about 1 µM, optionally wherein the anti-APLP2 antibody or antigen-binding fragment thereof binds human APLP2 with a KD of about 100 nM to about 200 nM, optionally wherein the anti-APLP2 antibody or antigen-binding fragment thereof binds human APLP2 with a KD of about 200 nM to about 800 nM, as measured by surface plasmon resonance, optionally wherein the anti-APLP2 antibody or antigen-binding fragment thereof binds human APLP2 with a KD of about 800 nM to about 1 µM, as measured by surface plasmon resonance.

5. The anti-APLP2 antibody or antigen-binding fragment thereof of claim 3, wherein the antibody or antigen-binding fragment comprises:
(a) an HCDR1, HCDR2, HCDR3, LCDR1, LCDR2, and LCDR3 comprising the amino acid sequences set forth in SEQ ID NOs: 28, 30, 32, 12, 14 and 16, respectively;
(b) an HCDR1, HCDR2, HCDR3, LCDR1, LCDR2, and LCDR3 comprising the amino acid sequences set forth in SEQ ID NOs: 36, 38, 40, 12, 14 and 16, respectively; or
(c) an HCDR1, HCDR2, HCDR3, LCDR1, LCDR2, and LCDR3 comprising the amino acid sequences set forth in SEQ ID NOs: 44, 46, 48, 12, 14 and 16, respectively.

6. The anti-APLP2 antibody or antigen-binding fragment thereof of claim 3, wherein the antibody or antigen-binding fragment thereof comprises an HCVR/LCVR amino acid sequence pair of: SEQ ID NOs:42/10, SEQ ID NOs: 34/10, or SEQ ID NOs:26/10.

7. An antibody-drug conjugate (ADC) comprising the anti-APLP2 antibody or antigen-binding fragment thereof of claim 3 and a cytotoxic agent, wherein the anti-APLP2 antibody or antigen-binding fragment thereof and the cytotoxic agent are covalently attached via a linker.

8. A pharmaceutical composition comprising the bispecific antigen-binding molecule of claim 1 and a pharmaceutically acceptable carrier or diluent.

9. A method for treating a cancer that expresses both HER2 and APLP2 in a subject, the method comprising administering to the subject the pharmaceutical composition of claim 8.

10. The method of claim 9, wherein the cancer is selected from the group consisting of prostate cancer, bladder cancer, cervical cancer, lung cancer, colon cancer, kidney cancer, breast cancer, pancreatic cancer, stomach cancer, uterine cancer, and ovarian cancer.

11. The method of claim 10, wherein the cancer is breast cancer, optionally an IHC2+ breast cancer.

12. The bispecific antigen-binding molecule of claim 1, wherein:
(a) the first antigen-binding domain that binds human APLP2 comprises an HCDR1, HCDR2, HCDR3, LCDR1, LCDR2, and LCDR3 comprising the amino acid sequences set forth in SEQ ID NOs: 28, 30, 32, 12, 14 and 16, respectively, and the second antigen-binding domain that binds human HER2 comprises an HCDR1, HCDR2, HCDR3, LCDR1, LCDR2, and LCDR3 comprising the amino acid sequences set forth in SEQ ID NOs: 4, 6, 8, 12, 14 and 16, respectively;
(b) the first antigen-binding domain that binds human APLP2 comprises an HCDR1, HCDR2, HCDR3, LCDR1, LCDR2, and LCDR3 comprising the amino acid sequences set forth in SEQ ID NOs: 36, 38, 40, 12, 14 and 16, respectively, and the second antigen-binding domain that binds human HER2 comprises an HCDR1, HCDR2, HCDR3, LCDR1, LCDR2, and LCDR3 comprising the amino acid sequences set forth in SEQ ID NOs: 4, 6, 8, 12, 14 and 16, respectively;
(c) the first antigen-binding domain that binds human APLP2 comprises an HCDR1, HCDR2, HCDR3, LCDR1, LCDR2, and LCDR3 comprising the amino acid sequences set forth in SEQ ID NOs: 44, 46, 48, 12, 14 and 16, respectively, and the second antigen-binding domain that binds human HER2 comprises an HCDR1, HCDR2, HCDR3, LCDR1, LCDR2, and LCDR3 comprising the amino acid sequences set forth in SEQ ID NOs: 4, 6, 8, 12, 14 and 16, respectively;
(d) the first antigen-binding domain that binds human APLP2 comprises an HCDR1, HCDR2, HCDR3, LCDR1, LCDR2, and LCDR3 comprising the amino acid sequences set forth in SEQ ID NOs: 28, 30, 32, 12, 14 and 16, respectively, and the second antigen-binding domain that binds human HER2 comprises an HCDR1, HCDR2, HCDR3, LCDR1, LCDR2, and LCDR3 comprising the amino acid sequences set forth in SEQ ID NOs: 20, 22, 24, 12, 14 and 16, respectively;
(e) the first antigen-binding domain that binds human APLP2 comprises an HCDR1, HCDR2, HCDR3, LCDR1, LCDR2, and LCDR3 comprising the amino acid sequences set forth in SEQ ID NOs: 36, 38, 40, 12, 14 and 16, respectively, and the second antigen-binding domain that binds human HER2 comprises an HCDR1, HCDR2, HCDR3, LCDR1, LCDR2, and LCDR3 comprising the amino acid sequences set forth in SEQ ID NOs: 20, 22, 24, 12, 14 and 16, respectively; or
(f) the first antigen-binding domain that binds human APLP2 comprises an HCDR1, HCDR2, HCDR3, LCDR1, LCDR2, and LCDR3 comprising the amino acid sequences set forth in SEQ ID NOs: 44, 46, 48, 12, 14 and 16, respectively, and the second antigen-binding domain that binds human HER2 comprises an HCDR1, HCDR2, HCDR3, LCDR1, LCDR2, and LCDR3 comprising the amino acid sequences set forth in SEQ ID NOs: 20, 22, 24, 12, 14 and 16, respectively.

13. The bispecific antigen-binding molecule of claim 1, wherein the second antigen-binding domain binds human cells expressing human HER2.

14. The bispecific antigen-binding molecule of claim 1, wherein each of the first antigen-binding domain and the second antigen-binding domain is fully human.

15. The bispecific antigen-binding molecule of claim 1, wherein the antigen-binding molecule binds both human APLP2 and human HER2 expressed on a cell and induces APLP2 internalization and/or degradation of HER2 in that cell.

16. The bispecific antigen-binding molecule of claim 1, wherein the antigen-binding molecule is not internalized by cells that express human APLP2 but do not express human HER2.

17. The bispecific antigen-binding molecule of claim 1, wherein the antigen-binding molecule is fully human.

18. The bispecific antigen-binding molecule of claim 1, wherein the affinity of the first antigen-binding domain that binds human APLP2 comprises a KD of about 100 nM to about 1 µM, a KD of about 100 nM to about 200 nM, a KD of about 200 nM to about 800 nM, or a KD of about 800 nM to about 1 µM, wherein KD is measured by surface plasmon resonance.

19. The bispecific antigen-binding molecule of claim 1, wherein the affinity of the second antigen-binding domain that binds human HER2 comprises a KD of less than 10 nM or with a KD of about 3 nM to about 5 nM, wherein KD is measured by surface plasmon resonance.

20. The bispecific antigen-binding molecule of claim 1, wherein the affinity of the first antigen-binding domain that binds human APLP2 comprises a KD of about 100 nM to about 1 μM, and the affinity of the second antigen-binding domain that binds human HER2 comprises a KD of less than 10 nM, wherein KD is measured by surface plasmon resonance.

21. The bispecific antigen-binding molecule of claim 1, wherein the first antigen-binding domain that binds human APLP2 comprises:
  (a) an HCVR amino acid sequence that is at least 90% identical to the amino acid sequence of SEQ ID NO:42, at least 90% identical to the amino acid sequence of SEQ ID NO:34, or at least 90% identical to the amino acid sequence of SEQ ID NO:26, and
  (b) an LCVR amino acid sequence that is at least 90% identical to the amino acid sequence of SEQ ID NO:10.

22. The bispecific antigen-binding molecule of claim 1, wherein the second antigen-binding domain that binds human HER2 comprises:
  (a) an HCVR amino acid sequence that is at least 90% identical to the amino acid sequence of SEQ ID NO:18 or at least 90% identical to the amino acid sequence of SEQ ID NO:2, and
  (b) an LCVR amino acid sequence that is at least 90% identical to the amino acid sequence of SEQ ID NO:10.

23. The bispecific antigen-binding molecule of claim 1, wherein the bispecific antigen-binding molecule inhibits tumor growth in immunocompromised mice bearing human breast cancer xenografts.

24. The bispecific antigen-binding molecule of claim 1, wherein the first antigen-binding domain that binds human APLP2 comprises an HCVR/LCVR amino acid sequence pair of: SEQ ID NOs:42/10, SEQ ID NOs: 34/10, or SEQ ID NOs:26/10.

25. The bispecific antigen-binding molecule of claim 1, wherein the second antigen-binding domain that binds human HER2 comprises an HCVR/LCVR amino acid sequence pair of: SEQ ID NOs: 18/10 or SEQ ID NOs: 2/10.

26. The bispecific antigen-binding molecule of claim 24, wherein the first antigen-binding domain that binds human APLP2 comprises an HCVR/LCVR amino acid sequence pair of SEQ ID NOs: 42/10.

27. The bispecific antigen-binding molecule of claim 25, wherein the second antigen-binding domain that binds human HER2 comprises an HCVR/LCVR amino acid sequence pair of: SEQ ID NOs: 18/10.

28. A method for preparing an antibody-drug conjugate (ADC) comprising contacting the bispecific antigen-binding molecule of claim 1 with:
  (i) a compound having the formula A1

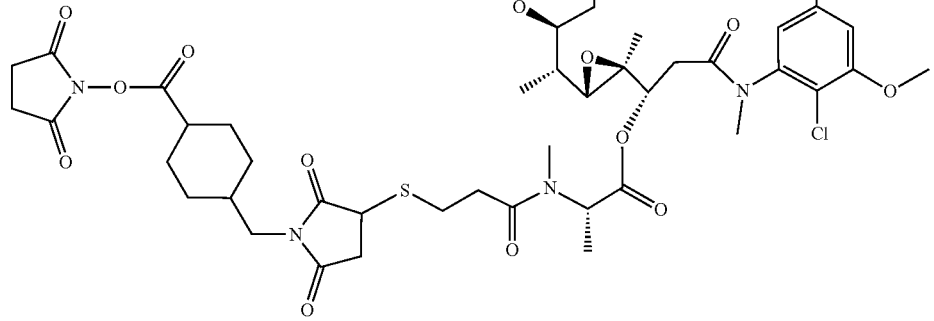

or a compound having the formula B 1

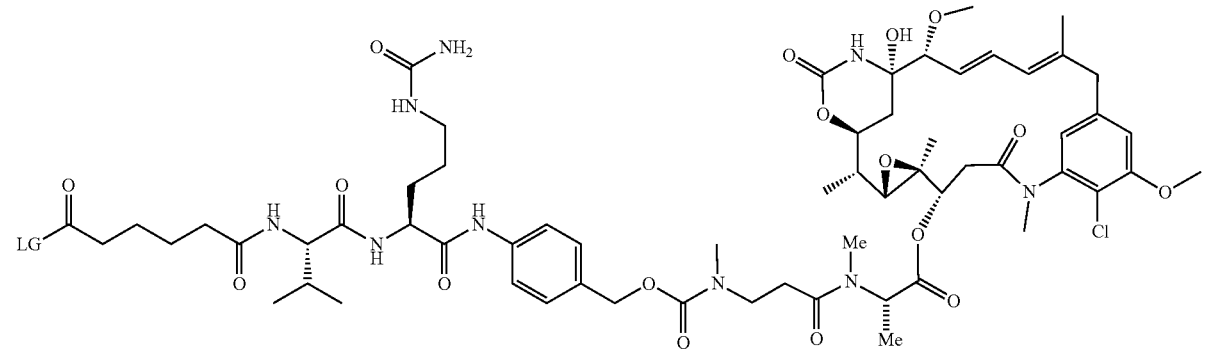

wherein LG is a leaving group, and
(ii) an aqueous diluent.

* * * * *

```
                        SEQUENCE LISTING

<160> NUMBER OF SEQ ID NOS: 78

<210> SEQ ID NO 1
<211> LENGTH: 372
<212> TYPE: DNA
<213> ORGANISM: Homo sapiens

<400> SEQUENCE: 1
caggttcagc tggtgcagtc tggacctgag gtgaagaagc ctggggcctc agtgaaggtc     60
tcctgcaagg cttctggtta cacctttccc aactttggga tcagctgggt gcgacaggcc    120
cctggacaag ggcttgagtg gatgggatgg atcgcccctt acaatgttgc cacaaactat    180
gcaccgaagc tccagggcag agtcaccatg accacagaca catccacgag cacagcctat    240
atggagctga ggagcctgag atctgacgac acggccgtgt attactgtgc gagatggggg    300
gctgggtaca tgggctacta ctactacggt atggacgtct ggggccaagg gaccacggtc    360
accgtctcct ca                                                        372

<210> SEQ ID NO 2
<211> LENGTH: 124
<212> TYPE: PRT
<213> ORGANISM: Homo sapiens

<400> SEQUENCE: 2

Gln Val Gln Leu Val Gln Ser Gly Pro Glu Val Lys Lys Pro Gly Ala
  1               5                  10                  15

Ser Val Lys Val Ser Cys Lys Ala Ser Gly Tyr Thr Phe Pro Asn Phe
             20                  25                  30

Gly Ile Ser Trp Val Arg Gln Ala Pro Gly Gln Gly Leu Glu Trp Met
         35                  40                  45

Gly Trp Ile Ala Pro Tyr Asn Val Ala Thr Asn Tyr Ala Pro Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Gly Ala Gly Tyr Met Gly Tyr Tyr Tyr Tyr Gly Met Asp
            100                 105                 110
```

Val Trp Gly Gln Gly Thr Thr Val Thr Val Ser Ser
            115                 120

<210> SEQ ID NO 3
<211> LENGTH: 24
<212> TYPE: DNA
<213> ORGANISM: Homo sapiens

<400> SEQUENCE: 3
ggttacacct ttcccaactt tggg                                          24

<210> SEQ ID NO 4
<211> LENGTH: 8
<212> TYPE: PRT
<213> ORGANISM: Homo sapiens

<400> SEQUENCE: 4

Gly Tyr Thr Phe Pro Asn Phe Gly
1               5

<210> SEQ ID NO 5
<211> LENGTH: 24
<212> TYPE: DNA
<213> ORGANISM: Homo sapiens

<400> SEQUENCE: 5
atcgcccctt acaatgttgc caca                                          24

<210> SEQ ID NO 6
<211> LENGTH: 8
<212> TYPE: PRT
<213> ORGANISM: Homo sapiens

<400> SEQUENCE: 6

Ile Ala Pro Tyr Asn Val Ala Thr
1               5

<210> SEQ ID NO 7
<211> LENGTH: 51
<212> TYPE: DNA
<213> ORGANISM: Homo sapiens

<400> SEQUENCE: 7
gcgagatggg gggctgggta catgggctac tactactacg gtatggacgt c            51

<210> SEQ ID NO 8
<211> LENGTH: 17
<212> TYPE: PRT
<213> ORGANISM: Homo sapiens

<400> SEQUENCE: 8

Ala Arg Trp Gly Ala Gly Tyr Met Gly Tyr Tyr Tyr Tyr Gly Met Asp
1               5                   10                  15

Val

<210> SEQ ID NO 9
<211> LENGTH: 324
<212> TYPE: DNA
<213> ORGANISM: Homo sapiens

<400> SEQUENCE: 9
gacatccaga tgacccagtc tccatcctcc ctgtctgcat ctgtaggaga cagagtcacc    60

```
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                            324
```

```
<210> SEQ ID NO 10
<211> LENGTH: 108
<212> TYPE: PRT
<213> ORGANISM: Homo sapiens

<400> SEQUENCE: 10
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

```
<210> SEQ ID NO 11
<211> LENGTH: 18
<212> TYPE: DNA
<213> ORGANISM: Homo sapiens

<400> SEQUENCE: 11
cagagcatta gcagctat                                                    18

<210> SEQ ID NO 12
<211> LENGTH: 6
<212> TYPE: PRT
<213> ORGANISM: Homo sapiens

<400> SEQUENCE: 12
```

Gln Ser Ile Ser Ser Tyr
1               5

```
<210> SEQ ID NO 13
<211> LENGTH: 9
<212> TYPE: DNA
<213> ORGANISM: Homo sapiens

<400> SEQUENCE: 13 gctgcatcc                                                              9

<210> SEQ ID NO 14
<211> LENGTH: 3
<212> TYPE: PRT
<213> ORGANISM: Homo sapiens

<400> SEQUENCE: 14
```

Ala Ala Ser

<210> SEQ ID NO 15
<211> LENGTH: 30
<212> TYPE: DNA
<213> ORGANISM: Homo sapiens

<400> SEQUENCE: 15
caacagagtt acagtacccc tccgatcacc                                      30

<210> SEQ ID NO 16
<211> LENGTH: 10
<212> TYPE: PRT
<213> ORGANISM: Homo sapiens

<400> SEQUENCE: 16

Gln Gln Ser Tyr Ser Thr Pro Pro Ile Thr
1               5                   10

<210> SEQ ID NO 17
<211> LENGTH: 387
<212> TYPE: DNA
<213> ORGANISM: Homo sapiens

<400> SEQUENCE: 17
caggtgcagc tgcaggagtc gggcccagga ctggtgaagc cttcacagac cctgtccctc      60
acctgcactg tctctggtgg ctccatcagc agtggtcatt acttctggag ttggatccgc     120
caacaccccg ggaagggcct ggaatggatt ggttacatct tttacagtgg gagcacccac     180
tacaacccgt ccctcaagag tcgactttcc atttcagtgg acacgtctaa gaaccagttc     240
tccctgaggc tgacctctgt gactgccgcg gacacggccg tgtattattg tgcgagagaa     300
gagggggatt acaattttg ggatgttgat tatgtccccg gccactttga ctactggggc      360
cagggaaccc tggtcaccgt ctcctca                                        387

<210> SEQ ID NO 18
<211> LENGTH: 129
<212> TYPE: PRT
<213> ORGANISM: Homo sapiens

<400> SEQUENCE: 18

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

His Tyr Phe Trp Ser Trp Ile Arg Gln His Pro Gly Lys Gly Leu Glu
            35                  40                  45

Trp Ile Gly Tyr Ile Phe Tyr Ser Gly Ser Thr His Tyr Asn Pro Ser
        50                  55                  60

Leu Lys Ser Arg Leu Ser Ile Ser Val Asp Thr Ser Lys Asn Gln Phe
65                  70                  75                  80

Ser Leu Arg Leu Thr Ser Val Thr Ala Ala Asp Thr Ala Val Tyr Tyr
                85                  90                  95

Cys Ala Arg Glu Glu Gly Asp Tyr Asn Phe Trp Asp Val Asp Tyr Val
            100                 105                 110

Pro Gly His Phe Asp Tyr Trp Gly Gln Gly Thr Leu Val Thr Val Ser
        115                 120                 125

Ser

<210> SEQ ID NO 19
<211> LENGTH: 30
<212> TYPE: DNA
<213> ORGANISM: Homo sapiens

<400> SEQUENCE: 19
ggtggctcca tcagcagtgg tcattacttc                                    30

<210> SEQ ID NO 20
<211> LENGTH: 10
<212> TYPE: PRT
<213> ORGANISM: Homo sapiens

<400> SEQUENCE: 20

Gly Gly Ser Ile Ser Ser Gly His Tyr Phe
1               5                   10

<210> SEQ ID NO 21
<211> LENGTH: 21
<212> TYPE: DNA
<213> ORGANISM: Homo sapiens

<400> SEQUENCE: 21
atcttttaca gtgggagcac c                                             21

<210> SEQ ID NO 22
<211> LENGTH: 7
<212> TYPE: PRT
<213> ORGANISM: Homo sapiens

<400> SEQUENCE: 22

Ile Phe Tyr Ser Gly Ser Thr
1               5

<210> SEQ ID NO 23
<211> LENGTH: 63
<212> TYPE: DNA
<213> ORGANISM: Homo sapiens

<400> SEQUENCE: 23
gcgagagaag aggggattac aattttttgg gatgttgatt atgtccccgg ccactttgac   60
tac                                                                 63

<210> SEQ ID NO 24
<211> LENGTH: 21
<212> TYPE: PRT
<213> ORGANISM: Homo sapiens

<400> SEQUENCE: 24

Ala Arg Glu Glu Gly Asp Tyr Asn Phe Trp Asp Val Asp Tyr Val Pro
1               5                   10                  15

Gly His Phe Asp Tyr
            20

<210> SEQ ID NO 25
<211> LENGTH: 378
<212> TYPE: DNA
<213> ORGANISM: Homo sapiens

<400> SEQUENCE: 25
gaggtgcagc tggtggagtc tgggggaggc ttggtacagc ctggggggtc cctgagactc   60
tcctgtgcag cctctggatt cacctttagc acctatgtca tgagttgggt ccgtcaggct  120

```
ccagggaagg ggccggagtg ggtctcaggt attagtggta gaactggtac cacatactac    180
gcagactccg tgaagggccg gttcaccatc tccagagaca attccaagaa cacactatat    240
ctgcaaatga acagcctgag agccgaggac acggccgtat attactgtgc gtcccgtata    300
acagcagctg gccgaggtta ctactactac tacggtatgg acgtctgggg ccagggacc     360 acggtcaccg tctcctca                                                  378
```

<210> SEQ ID NO 26
<211> LENGTH: 126
<212> TYPE: PRT
<213> ORGANISM: Homo sapiens

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Val Met Ser Trp Val Arg Gln Ala Pro Gly Lys Gly Pro Glu Trp Val
        35                  40                  45

Ser Gly Ile Ser Gly Arg Thr Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Arg Ile Thr Ala Ala Gly Arg Gly Tyr Tyr Tyr Tyr Tyr Gly
            100                 105                 110

Met Asp Val Trp Gly Arg Gly Thr Thr Val Thr Val Ser Ser
        115                 120                 125
```

<210> SEQ ID NO 27
<211> LENGTH: 24
<212> TYPE: DNA
<213> ORGANISM: Homo sapiens

<400> SEQUENCE: 27

```
ggattcacct ttagcaccta tgtc                                            24
```

<210> SEQ ID NO 28
<211> LENGTH: 8
<212> TYPE: PRT
<213> ORGANISM: Homo sapiens

<400> SEQUENCE: 28

```
Gly Phe Thr Phe Ser Thr Tyr Val
1               5
```

<210> SEQ ID NO 29
<211> LENGTH: 24
<212> TYPE: DNA
<213> ORGANISM: Homo sapiens

<400> SEQUENCE: 29

```
attagtggta gaactggtac caca                                            24
```

<210> SEQ ID NO 30
<211> LENGTH: 8
<212> TYPE: PRT
<213> ORGANISM: Homo sapiens

```
<400> SEQUENCE: 30

Ile Ser Gly Arg Thr Gly Thr Thr
1               5

<210> SEQ ID NO 31
<211> LENGTH: 57
<212> TYPE: DNA
<213> ORGANISM: Homo sapiens

<400> SEQUENCE: 31
gcgtcccgta acagcagc tggccgaggt tactactact actacggtat ggacgtc      57

<210> SEQ ID NO 32
<211> LENGTH: 19
<212> TYPE: PRT
<213> ORGANISM: Homo sapiens

<400> SEQUENCE: 32

Ala Ser Arg Ile Thr Ala Ala Gly Arg Gly Tyr Tyr Tyr Tyr Tyr Gly
1               5                   10                  15

Met Asp Val

<210> SEQ ID NO 33
<211> LENGTH: 378
<212> TYPE: DNA
<213> ORGANISM: Homo sapiens

<400> SEQUENCE: 33
gaagtgcagc tggtggagtc tgggggaggc ttggtacagc ctggcaggtc cctgagactg      60
tcctgtgtag cctctggatt cacctttgct gattatgcca tgcactgggt ccggcaagct     120
ccagggaagg gcctggagtg ggtctcaggt attagttgga atagtggaaa catagactat     180
gcggactctg tgaagggccg attcaccatc tccagagaca acgccaagaa ctccctgtat     240
ctgcaaatga acagtctgag aactgaggac acggcctat attactgtgc aaaagtccgt     300
atagttgtgg ctggttatta ctactactac tatggtatgg acgtctgggg ccaagggacc     360
acggtcaccg tctcctca                                                  378

<210> SEQ ID NO 34
<211> LENGTH: 126
<212> TYPE: PRT
<213> ORGANISM: Homo sapiens

<400> SEQUENCE: 34

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Ala Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Asn Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Val Arg Ile Val Val Ala Gly Tyr Tyr Tyr Tyr Tyr Gly
            100                 105                 110
```

Met Asp Val Trp Gly Gln Gly Thr Thr Val Thr Val Ser Ser
            115                 120                 125

<210> SEQ ID NO 35
<211> LENGTH: 24
<212> TYPE: DNA
<213> ORGANISM: Homo sapiens

<400> SEQUENCE: 35
ggattcacct ttgctgatta tgcc                                             24

<210> SEQ ID NO 36
<211> LENGTH: 8
<212> TYPE: PRT
<213> ORGANISM: Homo sapiens

<400> SEQUENCE: 36

Gly Phe Thr Phe Ala Asp Tyr Ala
1               5

<210> SEQ ID NO 37
<211> LENGTH: 24
<212> TYPE: DNA
<213> ORGANISM: Homo sapiens

<400> SEQUENCE: 37
attagttgga atagtggaaa cata                                             24

<210> SEQ ID NO 38
<211> LENGTH: 8
<212> TYPE: PRT
<213> ORGANISM: Homo sapiens

<400> SEQUENCE: 38

Ile Ser Trp Asn Ser Gly Asn Ile
1               5

<210> SEQ ID NO 39
<211> LENGTH: 57
<212> TYPE: DNA
<213> ORGANISM: Homo sapiens

<400> SEQUENCE: 39
gcaaaagtcc gtatagttgt ggctggttat tactactact actatggtat ggacgtc        57

<210> SEQ ID NO 40
<211> LENGTH: 19
<212> TYPE: PRT
<213> ORGANISM: Homo sapiens

<400> SEQUENCE: 40

Ala Lys Val Arg Ile Val Val Ala Gly Tyr Tyr Tyr Tyr Tyr Gly
1               5                   10                  15

Met Asp Val

<210> SEQ ID NO 41
<211> LENGTH: 351
<212> TYPE: DNA
<213> ORGANISM: Homo sapiens

<400> SEQUENCE: 41
caggttcagc tggtgcagtc tggagttgag gtgaagaagc ctggggcctc agtgaaggtc      60

```
tcctgcaagg cttctggtta cacctttacc gactatggta tcagctgggt gcgacaggcc    120
cctggacaag ggcttgaatg gatgggatgg atcagcgctc acaatggtaa cacaaactat    180
gcacagaaac tccagggcag agtcaccatg accacagaca catccacgaa cacagcctac    240
atggagctga ggagcctgag atctgacgac acggccgtgt attactgtgc gagacggaac    300
tggaaatact ttgactactg gggccagggc accctggtca ccgtctcctc a             351
```

<210> SEQ ID NO 42
<211> LENGTH: 117
<212> TYPE: PRT
<213> ORGANISM: Homo sapiens

<400> SEQUENCE: 42

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Gly Ile Ser Trp Val Arg Gln Ala Pro Gly Gln Gly Leu Glu Trp Met
        35                  40                  45

Gly Trp Ile Ser Ala His Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Asn Trp Lys Tyr Phe Asp Tyr Trp Gly Gln Gly Thr Leu
            100                 105                 110

Val Thr Val Ser Ser
        115

<210> SEQ ID NO 43
<211> LENGTH: 24
<212> TYPE: DNA
<213> ORGANISM: Homo sapiens

<400> SEQUENCE: 43
ggttacacct ttaccgacta tggt                                            24

<210> SEQ ID NO 44
<211> LENGTH: 8
<212> TYPE: PRT
<213> ORGANISM: Homo sapiens

<400> SEQUENCE: 44

Gly Tyr Thr Phe Thr Asp Tyr Gly
1               5

<210> SEQ ID NO 45
<211> LENGTH: 24
<212> TYPE: DNA
<213> ORGANISM: Homo sapiens

<400> SEQUENCE: 45
atcagcgctc acaatggtaa caca                                            24

<210> SEQ ID NO 46
<211> LENGTH: 8
<212> TYPE: PRT
<213> ORGANISM: Homo sapiens

<400> SEQUENCE: 46

Ile Ser Ala His Asn Gly Asn Thr
1               5

<210> SEQ ID NO 47
<211> LENGTH: 30
<212> TYPE: DNA
<213> ORGANISM: Homo sapiens

<400> SEQUENCE: 47
gcgagacgga actggaaata ctttgactac                                    30

<210> SEQ ID NO 48
<211> LENGTH: 10
<212> TYPE: PRT
<213> ORGANISM: Homo sapiens

<400> SEQUENCE: 48

Ala Arg Arg Asn Trp Lys Tyr Phe Asp Tyr
1               5                   10

<210> SEQ ID NO 49
<211> LENGTH: 1255
<212> TYPE: PRT
<213> ORGANISM: Homo sapiens

<400> SEQUENCE: 49

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

```
Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
```

```
                660             665             670
Ile Leu Ile Lys Arg Arg Gln Gln Lys Ile Arg Lys Tyr Thr Met Arg
            675             680             685

Arg Leu Leu Gln Glu Thr Glu Leu Val Glu Pro Leu Thr Pro Ser Gly
            690             695             700

Ala Met Pro Asn Gln Ala Gln Met Arg Ile Leu Lys Glu Thr Glu Leu
705             710             715             720

Arg Lys Val Lys Val Leu Gly Ser Gly Ala Phe Gly Thr Val Tyr Lys
            725             730             735

Gly Ile Trp Ile Pro Asp Gly Glu Asn Val Lys Ile Pro Val Ala Ile
            740             745             750

Lys Val Leu Arg Glu Asn Thr Ser Pro Lys Ala Asn Lys Glu Ile Leu
            755             760             765

Asp Glu Ala Tyr Val Met Ala Gly Val Gly Ser Pro Tyr Val Ser Arg
            770             775             780

Leu Leu Gly Ile Cys Leu Thr Ser Thr Val Gln Leu Val Thr Gln Leu
785             790             795             800

Met Pro Tyr Gly Cys Leu Leu Asp His Val Arg Glu Asn Arg Gly Arg
            805             810             815

Leu Gly Ser Gln Asp Leu Leu Asn Trp Cys Met Gln Ile Ala Lys Gly
            820             825             830

Met Ser Tyr Leu Glu Asp Val Arg Leu Val His Arg Asp Leu Ala Ala
            835             840             845

Arg Asn Val Leu Val Lys Ser Pro Asn His Val Lys Ile Thr Asp Phe
            850             855             860

Gly Leu Ala Arg Leu Leu Asp Ile Asp Glu Thr Glu Tyr His Ala Asp
865             870             875             880

Gly Gly Lys Val Pro Ile Lys Trp Met Ala Leu Glu Ser Ile Leu Arg
            885             890             895

Arg Arg Phe Thr His Gln Ser Asp Val Trp Ser Tyr Gly Val Thr Val
            900             905             910

Trp Glu Leu Met Thr Phe Gly Ala Lys Pro Tyr Asp Gly Ile Pro Ala
            915             920             925

Arg Glu Ile Pro Asp Leu Leu Glu Lys Gly Glu Arg Leu Pro Gln Pro
            930             935             940

Pro Ile Cys Thr Ile Asp Val Tyr Met Ile Met Val Lys Cys Trp Met
945             950             955             960

Ile Asp Ser Glu Cys Arg Pro Arg Phe Arg Glu Leu Val Ser Glu Phe
            965             970             975

Ser Arg Met Ala Arg Asp Pro Gln Arg Phe Val Val Ile Gln Asn Glu
            980             985             990

Asp Leu Gly Pro Ala Ser Pro Leu Asp Ser Thr Phe Tyr Arg Ser Leu
            995             1000            1005

Leu Glu Asp Asp Asp Met Gly Asp Leu Val Asp Ala Glu Glu Tyr
            1010            1015            1020

Leu Val Pro Gln Gln Gly Phe Phe Cys Pro Asp Pro Ala Pro Gly
            1025            1030            1035

Ala Gly Gly Met Val His His Arg His Arg Ser Ser Ser Thr Arg
            1040            1045            1050

Ser Gly Gly Gly Asp Leu Thr Leu Gly Leu Glu Pro Ser Glu Glu
            1055            1060            1065

Glu Ala Pro Arg Ser Pro Leu Ala Pro Ser Glu Gly Ala Gly Ser
            1070            1075            1080
```

```
Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 50
<211> LENGTH: 763
<212> TYPE: PRT
<213> ORGANISM: Homo sapiens

<400> SEQUENCE: 50

Met Ala Ala Thr Gly Thr Ala Ala Ala Ala Thr Gly Arg Leu Leu
1               5                   10                  15

Leu Leu Leu Leu Val Gly Leu Thr Ala Pro Ala Leu Ala Leu Ala Gly
                20                  25                  30

Tyr Ile Glu Ala Leu Ala Ala Asn Ala Gly Thr Gly Phe Ala Val Ala
                35                  40                  45

Glu Pro Gln Ile Ala Met Phe Cys Gly Lys Leu Asn Met His Val Asn
50                  55                  60

Ile Gln Thr Gly Lys Trp Glu Pro Asp Pro Thr Gly Thr Lys Ser Cys
65                  70                  75                  80

Phe Glu Thr Lys Glu Glu Val Leu Gln Tyr Cys Gln Glu Met Tyr Pro
                85                  90                  95

Glu Leu Gln Ile Thr Asn Val Met Glu Ala Asn Gln Arg Val Ser Ile
                100                 105                 110

Asp Asn Trp Cys Arg Arg Asp Lys Lys Gln Cys Lys Ser Arg Phe Val
                115                 120                 125

Thr Pro Phe Lys Cys Leu Val Gly Glu Phe Val Ser Asp Val Leu Leu
                130                 135                 140

Val Pro Glu Lys Cys Gln Phe Phe His Lys Glu Arg Met Glu Val Cys
145                 150                 155                 160

Glu Asn His Gln His Trp His Thr Val Lys Glu Ala Cys Leu Thr
                165                 170                 175

Gln Gly Met Thr Leu Tyr Ser Tyr Gly Met Leu Leu Pro Cys Gly Val
```

```
              180             185             190
Asp Gln Phe His Gly Thr Glu Tyr Val Cys Cys Pro Gln Thr Lys Ile
            195                 200                 205
Ile Gly Ser Val Ser Lys Glu Glu Glu Glu Asp Glu Glu Glu Glu Glu
            210                 215                 220
Glu Glu Glu Asp Glu Glu Glu Asp Tyr Asp Val Tyr Lys Ser Glu Phe
225                 230                 235                 240
Pro Thr Glu Ala Asp Leu Glu Asp Phe Thr Glu Ala Ala Val Asp Glu
                245                 250                 255
Asp Asp Glu Asp Glu Glu Glu Gly Glu Glu Val Val Glu Asp Arg Asp
            260                 265                 270
Tyr Tyr Tyr Asp Thr Phe Lys Gly Asp Asp Tyr Asn Glu Glu Asn Pro
            275                 280                 285
Thr Glu Pro Gly Ser Asp Gly Thr Met Ser Asp Lys Glu Ile Thr His
            290                 295                 300
Asp Val Lys Ala Val Cys Ser Gln Glu Ala Met Thr Gly Pro Cys Arg
305                 310                 315                 320
Ala Val Met Pro Arg Trp Tyr Phe Asp Leu Ser Lys Gly Lys Cys Val
                325                 330                 335
Arg Phe Ile Tyr Gly Gly Cys Gly Gly Asn Arg Asn Asn Phe Glu Ser
                340                 345                 350
Glu Asp Tyr Cys Met Ala Val Cys Lys Ala Met Ile Pro Pro Thr Pro
            355                 360                 365
Leu Pro Thr Asn Asp Val Asp Val Tyr Phe Glu Thr Ser Ala Asp Asp
            370                 375                 380
Asn Glu His Ala Arg Phe Gln Lys Ala Lys Glu Gln Leu Glu Ile Arg
385                 390                 395                 400
His Arg Asn Arg Met Asp Arg Val Lys Lys Glu Trp Glu Glu Ala Glu
                405                 410                 415
Leu Gln Ala Lys Asn Leu Pro Lys Ala Glu Arg Gln Thr Leu Ile Gln
            420                 425                 430
His Phe Gln Ala Met Val Lys Ala Leu Glu Lys Glu Ala Ala Ser Glu
            435                 440                 445
Lys Gln Gln Leu Val Glu Thr His Leu Ala Arg Val Glu Ala Met Leu
            450                 455                 460
Asn Asp Arg Arg Arg Met Ala Leu Glu Asn Tyr Leu Ala Ala Leu Gln
465                 470                 475                 480
Ser Asp Pro Pro Arg Pro His Arg Ile Leu Gln Ala Leu Arg Arg Tyr
                485                 490                 495
Val Arg Ala Glu Asn Lys Asp Arg Leu His Thr Ile Arg His Tyr Gln
                500                 505                 510
His Val Leu Ala Val Asp Pro Glu Lys Ala Ala Gln Met Lys Ser Gln
            515                 520                 525
Val Met Thr His Leu His Val Ile Glu Glu Arg Asn Gln Ser Leu
            530                 535                 540
Ser Leu Leu Tyr Lys Val Pro Tyr Val Ala Gln Glu Ile Gln Glu Glu
545                 550                 555                 560
Ile Asp Glu Leu Leu Gln Glu Gln Arg Ala Asp Met Asp Gln Phe Thr
                565                 570                 575
Ala Ser Ile Ser Glu Thr Pro Val Asp Val Arg Val Ser Ser Glu Glu
                580                 585                 590
Ser Glu Glu Ile Pro Pro Phe His Pro Phe His Pro Phe Pro Ala Leu
            595                 600                 605
```

```
Pro Glu Asn Glu Asp Thr Gln Pro Glu Leu Tyr His Pro Met Lys Lys
    610                 615                 620

Gly Ser Gly Val Gly Glu Gln Asp Gly Gly Leu Ile Gly Ala Glu Glu
625                 630                 635                 640

Lys Val Ile Asn Ser Lys Asn Lys Val Asp Glu Asn Met Val Ile Asp
                645                 650                 655

Glu Thr Leu Asp Val Lys Glu Met Ile Phe Asn Ala Glu Arg Val Gly
            660                 665                 670

Gly Leu Glu Glu Glu Arg Glu Ser Val Gly Pro Leu Arg Glu Asp Phe
        675                 680                 685

Ser Leu Ser Ser Ser Ala Leu Ile Gly Leu Leu Val Ile Ala Val Ala
    690                 695                 700

Ile Ala Thr Val Ile Val Ile Ser Leu Val Met Leu Arg Lys Arg Gln
705                 710                 715                 720

Tyr Gly Thr Ile Ser His Gly Ile Val Glu Val Asp Pro Met Leu Thr
                725                 730                 735

Pro Glu Glu Arg His Leu Asn Lys Met Gln Asn His Gly Tyr Glu Asn
            740                 745                 750

Pro Thr Tyr Lys Tyr Leu Glu Gln Met Gln Ile
        755                 760

<210> SEQ ID NO 51
<211> LENGTH: 630
<212> TYPE: PRT
<213> ORGANISM: Homo sapiens

<400> SEQUENCE: 51

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
```

```
                210                 215                 220
Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
                260                 265                 270

Cys Val Thr Ala Cys Pro Tyr Asn Tyr Leu Ser Thr Asp Val Gly Ser
                275                 280                 285

Cys Thr Leu Val Cys Pro Leu His Asn Gln Glu Val Thr Ala Glu Asp
                290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
                340                 345                 350

Ala Phe Leu Pro Glu Ser Phe Asp Gly Asp Pro Ala Ser Asn Thr Ala
                355                 360                 365

Pro Leu Gln Pro Glu Gln Leu Gln Val Phe Glu Thr Leu Glu Glu Ile
                370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
                420                 425                 430

Leu Arg Ser Leu Arg Glu Leu Gly Ser Gly Leu Ala Leu Ile His His
                435                 440                 445

Asn Thr His Leu Cys Phe Val His Thr Val Pro Trp Asp Gln Leu Phe
                450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
                500                 505                 510

Leu Arg Gly Gln Glu Cys Val Glu Glu Cys Arg Val Leu Gln Gly Leu
                515                 520                 525

Pro Arg Glu Tyr Val Asn Ala Arg His Cys Leu Pro Cys His Pro Glu
530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
                580                 585                 590

Lys Phe Pro Asp Glu Glu Gly Ala Cys Gln Pro Cys Pro Ile Asn Cys
                595                 600                 605

Thr His Ser Cys Val Asp Leu Asp Asp Lys Gly Cys Pro Ala Glu Gln
                610                 615                 620

Arg Ala Ser Pro Leu Thr
625                 630
```

<210> SEQ ID NO 52
<211> LENGTH: 661
<212> TYPE: PRT
<213> ORGANISM: Homo sapiens

<400> SEQUENCE: 52

```
Gly Tyr Ile Glu Ala Leu Ala Ala Asn Ala Gly Thr Gly Phe Ala Val
1               5                   10                  15

Ala Glu Pro Gln Ile Ala Met Phe Cys Gly Lys Leu Asn Met His Val
            20                  25                  30

Asn Ile Gln Thr Gly Lys Trp Glu Pro Asp Pro Thr Gly Thr Lys Ser
        35                  40                  45

Cys Phe Glu Thr Lys Glu Glu Val Leu Gln Tyr Cys Gln Glu Met Tyr
    50                  55                  60

Pro Glu Leu Gln Ile Thr Asn Val Met Glu Ala Asn Gln Arg Val Ser
65                  70                  75                  80

Ile Asp Asn Trp Cys Arg Arg Asp Lys Lys Gln Cys Lys Ser Arg Phe
                85                  90                  95

Val Thr Pro Phe Lys Cys Leu Val Gly Glu Phe Val Ser Asp Val Leu
            100                 105                 110

Leu Val Pro Glu Lys Cys Gln Phe Phe His Lys Glu Arg Met Glu Val
        115                 120                 125

Cys Glu Asn His Gln His Trp His Thr Val Val Lys Glu Ala Cys Leu
    130                 135                 140

Thr Gln Gly Met Thr Leu Tyr Ser Tyr Gly Met Leu Leu Pro Cys Gly
145                 150                 155                 160

Val Asp Gln Phe His Gly Thr Glu Tyr Val Cys Cys Pro Gln Thr Lys
                165                 170                 175

Ile Ile Gly Ser Val Ser Lys Glu Glu Glu Glu Asp Glu Glu Glu
            180                 185                 190

Glu Glu Glu Glu Asp Glu Glu Asp Tyr Asp Val Tyr Lys Ser Glu
        195                 200                 205

Phe Pro Thr Glu Ala Asp Leu Glu Asp Phe Thr Glu Ala Ala Val Asp
    210                 215                 220

Glu Asp Asp Glu Asp Glu Glu Gly Glu Glu Val Val Glu Asp Arg
225                 230                 235                 240

Asp Tyr Tyr Tyr Asp Thr Phe Lys Gly Asp Tyr Asn Glu Glu Asn
                245                 250                 255

Pro Thr Glu Pro Gly Ser Asp Gly Thr Met Ser Asp Lys Glu Ile Thr
            260                 265                 270

His Asp Val Lys Ala Val Cys Ser Gln Glu Ala Met Thr Gly Pro Cys
        275                 280                 285

Arg Ala Val Met Pro Arg Trp Tyr Phe Asp Leu Ser Lys Gly Lys Cys
    290                 295                 300

Val Arg Phe Ile Tyr Gly Gly Cys Gly Gly Asn Arg Asn Asn Phe Glu
305                 310                 315                 320

Ser Glu Asp Tyr Cys Met Ala Val Cys Lys Ala Met Ile Pro Pro Thr
                325                 330                 335

Pro Leu Pro Thr Asn Asp Val Asp Val Tyr Phe Glu Thr Ser Ala Asp
            340                 345                 350

Asp Asn Glu His Ala Arg Phe Gln Lys Ala Lys Glu Gln Leu Glu Ile
        355                 360                 365

Arg His Arg Asn Arg Met Asp Arg Val Lys Lys Glu Trp Glu Glu Ala
```

```
                    370                 375                 380
Glu Leu Gln Ala Lys Asn Leu Pro Lys Ala Glu Arg Gln Thr Leu Ile
385                 390                 395                 400

Gln His Phe Gln Ala Met Val Lys Ala Leu Glu Lys Glu Ala Ala Ser
                405                 410                 415

Glu Lys Gln Gln Leu Val Glu Thr His Leu Ala Arg Val Glu Ala Met
            420                 425                 430

Leu Asn Asp Arg Arg Met Ala Leu Glu Asn Tyr Leu Ala Ala Leu
            435                 440                 445

Gln Ser Asp Pro Pro Arg Pro His Arg Ile Leu Gln Ala Leu Arg Arg
        450                 455                 460

Tyr Val Arg Ala Glu Asn Lys Asp Arg Leu His Thr Ile Arg His Tyr
465                 470                 475                 480

Gln His Val Leu Ala Val Asp Pro Glu Lys Ala Ala Gln Met Lys Ser
                485                 490                 495

Gln Val Met Thr His Leu His Val Ile Glu Arg Arg Asn Gln Ser
            500                 505                 510

Leu Ser Leu Leu Tyr Lys Val Pro Tyr Val Ala Gln Glu Ile Gln Glu
            515                 520                 525

Glu Ile Asp Glu Leu Leu Gln Glu Gln Arg Ala Asp Met Asp Gln Phe
        530                 535                 540

Thr Ala Ser Ile Ser Glu Thr Pro Val Asp Val Arg Val Ser Ser Glu
545                 550                 555                 560

Glu Ser Glu Glu Ile Pro Pro Phe His Pro Phe His Pro Phe Pro Ala
                565                 570                 575

Leu Pro Glu Asn Glu Asp Thr Gln Pro Glu Leu Tyr His Pro Met Lys
            580                 585                 590

Lys Gly Ser Gly Val Gly Glu Gln Asp Gly Leu Ile Gly Ala Glu
            595                 600                 605

Glu Lys Val Ile Asn Ser Lys Asn Lys Val Asp Glu Asn Met Val Ile
        610                 615                 620

Asp Glu Thr Leu Asp Val Lys Glu Met Ile Phe Asn Ala Glu Arg Val
625                 630                 635                 640

Gly Gly Leu Glu Glu Glu Arg Glu Ser Val Gly Pro Leu Arg Glu Asp
                645                 650                 655

Phe Ser Leu Ser Ser
            660

<210> SEQ ID NO 53
<211> LENGTH: 658
<212> TYPE: PRT
<213> ORGANISM: Artificial Sequence
<220> FEATURE:
<223> OTHER INFORMATION: hHER2-MMH

<400> SEQUENCE: 53

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
```

```
                65                  70                  75                  80
Arg Gly Thr Gln Leu Phe Glu Asp Asn Tyr Ala Leu Ala Val Leu Asp
                    85                  90                  95

Asn Gly Asp Pro Leu Asn Asn Thr Thr Pro Val Thr Gly Ala Ser Pro
                100                 105                 110

Gly Gly Leu Arg Glu Leu Gln Leu Arg Ser Leu Thr Glu Ile Leu Lys
                115                 120                 125

Gly Gly Val Leu Ile Gln Arg Asn Pro Gln Leu Cys Tyr Gln Asp Thr
            130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
                180                 185                 190

Leu Thr Arg Thr Val Cys Ala Gly Gly Cys Ala Arg Cys Lys Gly Pro
            195                 200                 205

Leu Pro Thr Asp Cys Cys His Glu Gln Cys Ala Ala Gly Cys Thr Gly
210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
                260                 265                 270

Cys Val Thr Ala Cys Pro Tyr Asn Tyr Leu Ser Thr Asp Val Gly Ser
            275                 280                 285

Cys Thr Leu Val Cys Pro Leu His Asn Gln Glu Val Thr Ala Glu Asp
290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
                340                 345                 350

Ala Phe Leu Pro Glu Ser Phe Asp Gly Asp Pro Ala Ser Asn Thr Ala
            355                 360                 365

Pro Leu Gln Pro Glu Gln Leu Gln Val Phe Glu Thr Leu Glu Glu Ile
370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
                420                 425                 430

Leu Arg Ser Leu Arg Glu Leu Gly Ser Gly Leu Ala Leu Ile His His
            435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495
```

```
His Cys Trp Gly Pro Gly Pro Thr Gln Cys Val Asn Cys Ser Gln Phe
                500                 505                 510
Leu Arg Gly Gln Glu Cys Val Glu Glu Cys Arg Val Leu Gln Gly Leu
                515                 520                 525
Pro Arg Glu Tyr Val Asn Ala Arg His Cys Leu Pro Cys His Pro Glu
                530                 535                 540
Cys Gln Pro Gln Asn Gly Ser Val Thr Cys Phe Gly Pro Glu Ala Asp
545                 550                 555                 560
Gln Cys Val Ala Cys Ala His Tyr Lys Asp Pro Pro Phe Cys Val Ala
                565                 570                 575
Arg Cys Pro Ser Gly Val Lys Pro Asp Leu Ser Tyr Met Pro Ile Trp
                580                 585                 590
Lys Phe Pro Asp Glu Glu Gly Ala Cys Gln Pro Cys Pro Ile Asn Cys
                595                 600                 605
Thr His Ser Cys Val Asp Leu Asp Asp Lys Gly Cys Pro Ala Glu Gln
                610                 615                 620
Arg Ala Ser Pro Leu Thr Glu Gln Lys Leu Ile Ser Glu Glu Asp Leu
625                 630                 635                 640
Gly Gly Glu Gln Lys Leu Ile Ser Glu Glu Asp Leu His His His His
                645                 650                 655
His His

<210> SEQ ID NO 54
<211> LENGTH: 689
<212> TYPE: PRT
<213> ORGANISM: Artificial Sequence
<220> FEATURE:
<223> OTHER INFORMATION: hAPLP2-MMH

<400> SEQUENCE: 54

Gly Tyr Ile Glu Ala Leu Ala Ala Asn Ala Gly Thr Gly Phe Ala Val
1               5                   10                  15
Ala Glu Pro Gln Ile Ala Met Phe Cys Gly Lys Leu Asn Met His Val
                20                  25                  30
Asn Ile Gln Thr Gly Lys Trp Glu Pro Asp Pro Thr Gly Thr Lys Ser
                35                  40                  45
Cys Phe Glu Thr Lys Glu Glu Val Leu Gln Tyr Cys Gln Glu Met Tyr
50                  55                  60
Pro Glu Leu Gln Ile Thr Asn Val Met Glu Ala Asn Gln Arg Val Ser
65                  70                  75                  80
Ile Asp Asn Trp Cys Arg Arg Asp Lys Lys Gln Cys Lys Ser Arg Phe
                85                  90                  95
Val Thr Pro Phe Lys Cys Leu Val Gly Glu Phe Val Ser Asp Val Leu
                100                 105                 110
Leu Val Pro Glu Lys Cys Gln Phe Phe His Lys Glu Arg Met Glu Val
                115                 120                 125
Cys Glu Asn His Gln His Trp His Thr Val Val Lys Glu Ala Cys Leu
                130                 135                 140
Thr Gln Gly Met Thr Leu Tyr Ser Tyr Gly Met Leu Leu Pro Cys Gly
145                 150                 155                 160
Val Asp Gln Phe His Gly Thr Glu Tyr Val Cys Cys Pro Gln Thr Lys
                165                 170                 175
Ile Ile Gly Ser Val Ser Lys Glu Glu Glu Glu Asp Glu Glu Glu
                180                 185                 190
```

-continued

Glu Glu Glu Glu Asp Glu Glu Asp Tyr Asp Val Tyr Lys Ser Glu
            195                 200                 205

Phe Pro Thr Glu Ala Asp Leu Glu Asp Phe Thr Glu Ala Ala Val Asp
210                 215                 220

Glu Asp Asp Glu Asp Glu Glu Gly Glu Glu Val Val Glu Asp Arg
225                 230                 235                 240

Asp Tyr Tyr Tyr Asp Thr Phe Lys Gly Asp Tyr Asn Glu Glu Asn
                245                 250                 255

Pro Thr Glu Pro Gly Ser Asp Gly Thr Met Ser Asp Lys Glu Ile Thr
            260                 265                 270

His Asp Val Lys Ala Val Cys Ser Gln Glu Ala Met Thr Gly Pro Cys
            275                 280                 285

Arg Ala Val Met Pro Arg Trp Tyr Phe Asp Leu Ser Lys Gly Lys Cys
290                 295                 300

Val Arg Phe Ile Tyr Gly Gly Cys Gly Gly Asn Arg Asn Asn Phe Glu
305                 310                 315                 320

Ser Glu Asp Tyr Cys Met Ala Val Cys Lys Ala Met Ile Pro Pro Thr
                325                 330                 335

Pro Leu Pro Thr Asn Asp Val Asp Val Tyr Phe Glu Thr Ser Ala Asp
            340                 345                 350

Asp Asn Glu His Ala Arg Phe Gln Lys Ala Lys Glu Gln Leu Glu Ile
            355                 360                 365

Arg His Arg Asn Arg Met Asp Arg Val Lys Lys Glu Trp Glu Ala
            370                 375                 380

Glu Leu Gln Ala Lys Asn Leu Pro Lys Ala Glu Arg Gln Thr Leu Ile
385                 390                 395                 400

Gln His Phe Gln Ala Met Val Lys Ala Leu Glu Lys Glu Ala Ala Ser
                405                 410                 415

Glu Lys Gln Gln Leu Val Glu Thr His Leu Ala Arg Val Glu Ala Met
            420                 425                 430

Leu Asn Asp Arg Arg Arg Met Ala Leu Glu Asn Tyr Leu Ala Ala Leu
            435                 440                 445

Gln Ser Asp Pro Pro Arg Pro His Arg Ile Leu Gln Ala Leu Arg Arg
450                 455                 460

Tyr Val Arg Ala Glu Asn Lys Asp Arg Leu His Thr Ile Arg His Tyr
465                 470                 475                 480

Gln His Val Leu Ala Val Asp Pro Glu Lys Ala Ala Gln Met Lys Ser
                485                 490                 495

Gln Val Met Thr His Leu His Val Ile Glu Glu Arg Arg Asn Gln Ser
            500                 505                 510

Leu Ser Leu Leu Tyr Lys Val Pro Tyr Val Ala Gln Glu Ile Gln Glu
            515                 520                 525

Glu Ile Asp Glu Leu Leu Gln Glu Gln Arg Ala Asp Met Asp Gln Phe
530                 535                 540

Thr Ala Ser Ile Ser Glu Thr Pro Val Asp Val Arg Val Ser Ser Glu
545                 550                 555                 560

Glu Ser Glu Glu Ile Pro Pro Phe His Pro Phe His Pro Phe Pro Ala
                565                 570                 575

Leu Pro Glu Asn Glu Asp Thr Gln Pro Glu Leu Tyr His Pro Met Lys
            580                 585                 590

Lys Gly Ser Gly Val Gly Glu Gln Asp Gly Gly Leu Ile Gly Ala Glu
            595                 600                 605

Glu Lys Val Ile Asn Ser Lys Asn Lys Val Asp Glu Asn Met Val Ile

```
                  610                 615                 620
Asp Glu Thr Leu Asp Val Lys Glu Met Ile Phe Asn Ala Glu Arg Val
625                 630                 635                 640

Gly Gly Leu Glu Glu Glu Arg Glu Ser Val Gly Pro Leu Arg Glu Asp
                645                 650                 655

Phe Ser Leu Ser Ser Glu Gln Lys Leu Ile Ser Glu Glu Asp Leu Gly
                660                 665                 670

Gly Glu Gln Lys Leu Ile Ser Glu Glu Asp Leu His His His His His
            675                 680                 685

His

<210> SEQ ID NO 55
<211> LENGTH: 330
<212> TYPE: PRT
<213> ORGANISM: Artificial Sequence
<220> FEATURE:
<223> OTHER INFORMATION: synthetic

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 56
<211> LENGTH: 330
<212> TYPE: PRT
<213> ORGANISM: Artificial Sequence
<220> FEATURE:
<223> OTHER INFORMATION: synthetic

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn Arg Phe Thr
305                 310                 315                 320

```
Gln Lys Ser Leu Ser Leu Ser Pro Gly Lys
            325                 330

<210> SEQ ID NO 57
<211> LENGTH: 326
<212> TYPE: PRT
<213> ORGANISM: Artificial Sequence
<220> FEATURE:
<223> OTHER INFORMATION: synthetic

<400> SEQUENCE: 57

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 58
```

<211> LENGTH: 326
<212> TYPE: PRT
<213> ORGANISM: Artificial Sequence
<220> FEATURE:
<223> OTHER INFORMATION: synthetic

<400> SEQUENCE: 58

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Pro Gly Lys
                325

<210> SEQ ID NO 59
<211> LENGTH: 327
<212> TYPE: PRT
<213> ORGANISM: Artificial Sequence
<220> FEATURE:
<223> OTHER INFORMATION: synthetic

<400> SEQUENCE: 59

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 60
<211> LENGTH: 327
<212> TYPE: PRT
<213> ORGANISM: Artificial Sequence
<220> FEATURE:
<223> OTHER INFORMATION: synthetic

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

```
                 20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn Arg Phe Thr Gln Lys Ser
305                 310                 315                 320

Leu Ser Leu Ser Leu Gly Lys
                325

<210> SEQ ID NO 61
<211> LENGTH: 329
<212> TYPE: PRT
<213> ORGANISM: Artificial Sequence
<220> FEATURE:
<223> OTHER INFORMATION: synthetic

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
                    50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Val Ala Gly Pro Ser Val Phe Leu Phe Pro Pro Lys
                115                 120                 125

Pro Lys Asp Thr Leu Met Ile Ser Arg Thr Pro Glu Val Thr Cys Val
                130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
                195                 200                 205

Gly Leu Pro Ser Ser Ile Glu Lys Thr Ile Ser Lys Ala Lys Gly Gln
                210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
                260                 265                 270

Tyr Lys Thr Thr Pro Pro Val Leu Asp Ser Asp Gly Ser Phe Phe Leu
                275                 280                 285

Tyr Ser Lys Leu Thr Val Asp Lys Ser Arg Trp Gln Gln Gly Asn Val
                290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 62
<211> LENGTH: 329
<212> TYPE: PRT
<213> ORGANISM: Artificial Sequence
<220> FEATURE:
<223> OTHER INFORMATION: synthetic

<400> SEQUENCE: 62

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
                 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
```

```
                85                  90                  95
Lys Val Glu Pro Lys Ser Cys Asp Lys Thr His Thr Cys Pro Pro Cys
            100                 105                 110
Pro Ala Pro Pro Val Ala Gly Pro Ser Val Phe Leu Phe Pro Pro Lys
            115                 120                 125
Pro Lys Asp Thr Leu Met Ile Ser Arg Thr Pro Glu Val Thr Cys Val
        130                 135                 140
Val Val Asp Val Ser Gln Glu Asp Pro Glu Val Gln Phe Asn Trp Tyr
145                 150                 155                 160
Val Asp Gly Val Glu Val His Asn Ala Lys Thr Lys Pro Arg Glu Glu
                165                 170                 175
Gln Phe Asn Ser Thr Tyr Arg Val Val Ser Val Leu Thr Val Leu His
                180                 185                 190
Gln Asp Trp Leu Asn Gly Lys Glu Tyr Lys Cys Lys Val Ser Asn Lys
                195                 200                 205
Gly Leu Pro Ser Ser Ile Glu Lys Thr Ile Ser Lys Ala Lys Gly Gln
            210                 215                 220
Pro Arg Glu Pro Gln Val Tyr Thr Leu Pro Pro Ser Arg Asp Glu Leu
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
                260                 265                 270
Tyr Lys Thr Thr Pro Pro Val Leu Asp Ser Asp Gly Ser Phe Phe Leu
                275                 280                 285
Tyr Ser Lys Leu Thr Val Asp Lys Ser Arg Trp Gln Gln Gly Asn Val
            290                 295                 300
Phe Ser Cys Ser Val Met His Glu Ala Leu His Asn Arg Phe Thr Gln
305                 310                 315                 320
Lys Ser Leu Ser Leu Ser Pro Gly Lys
            325

<210> SEQ ID NO 63
<211> LENGTH: 327
<212> TYPE: PRT
<213> ORGANISM: Artificial Sequence
<220> FEATURE:
<223> OTHER INFORMATION: CH sequence

<400> SEQUENCE: 63

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
            50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
                100                 105                 110
Glu Phe Leu Gly Gly Pro Ser Val Phe Leu Phe Pro Pro Lys Pro Lys
```

```
            115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 64
<211> LENGTH: 326
<212> TYPE: PRT
<213> ORGANISM: Artificial Sequence
<220> FEATURE:
<223> OTHER INFORMATION: synthetic

<400> SEQUENCE: 64

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
    130                 135                 140
Val Ser Gln Glu Asp Pro Glu Val Gln Phe Asn Trp Tyr Val Asp Gly
```

```
145                 150                 155                 160
Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
        210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 65
<211> LENGTH: 326
<212> TYPE: PRT
<213> ORGANISM: Artificial Sequence
<220> FEATURE:
<223> OTHER INFORMATION: synthetic

<400> SEQUENCE: 65

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
```

```
            180                 185                 190
Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
        210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                    245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
        290                 295                 300

Ser Val Met His Glu Ala Leu His Asn Arg Phe Thr Gln Lys Ser Leu
305                 310                 315                 320

Ser Leu Ser Leu Gly Lys
                325

<210> SEQ ID NO 66
<211> LENGTH: 232
<212> TYPE: PRT
<213> ORGANISM: Artificial Sequence
<220> FEATURE:
<223> OTHER INFORMATION: synthetic

<400> SEQUENCE: 66

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
```

```
                210                 215                 220
Ser Leu Ser Leu Ser Pro Gly Lys
225                 230
```

<210> SEQ ID NO 67
<211> LENGTH: 232
<212> TYPE: PRT
<213> ORGANISM: Artificial Sequence
<220> FEATURE:
<223> OTHER INFORMATION: synthetic

<400> SEQUENCE: 67

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Arg Phe Thr Gln Lys
    210                 215                 220

Ser Leu Ser Leu Ser Pro Gly Lys
225                 230
```

<210> SEQ ID NO 68
<211> LENGTH: 228
<212> TYPE: PRT
<213> ORGANISM: Artificial Sequence
<220> FEATURE:
<223> OTHER INFORMATION: synthetic

<400> SEQUENCE: 68

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45
```

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
                115                 120                 125

Val Tyr Thr Leu Pro Pro Ser Arg Glu Glu Met Thr Lys Asn Gln Val
 130                 135                 140

Ser Leu Thr Cys Leu Val Lys Gly Phe Tyr Pro Ser Asp Ile Ser Val
145                  150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
                195                 200                 205

Met His Glu Ala Leu His Asn His Tyr Thr Gln Lys Ser Leu Ser Leu
210                  215                 220

Ser Pro Gly Lys
225

<210> SEQ ID NO 69
<211> LENGTH: 228
<212> TYPE: PRT
<213> ORGANISM: Artificial Sequence
<220> FEATURE:
<223> OTHER INFORMATION: synthetic

<400> SEQUENCE: 69

Glu Arg Lys Cys Cys Val Glu Cys Pro Pro Cys Pro Ala Pro Pro Val
1                5                  10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
                35                  40                  45

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
                115                 120                 125

Val Tyr Thr Leu Pro Pro Ser Arg Glu Glu Met Thr Lys Asn Gln Val
 130                 135                 140

Ser Leu Thr Cys Leu Val Lys Gly Phe Tyr Pro Ser Asp Ile Ser Val
145                  150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn Arg Phe Thr Gln Lys Ser Leu Ser Leu
    210                 215                 220

Ser Pro Gly Lys
225

<210> SEQ ID NO 70
<211> LENGTH: 229
<212> TYPE: PRT
<213> ORGANISM: Artificial Sequence
<220> FEATURE:
<223> OTHER INFORMATION: synthetic

<400> SEQUENCE: 70

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn Arg Phe Thr Gln Lys Ser Leu Ser
    210                 215                 220

Leu Ser Leu Gly Lys
225

<210> SEQ ID NO 71
<211> LENGTH: 229
<212> TYPE: PRT
<213> ORGANISM: Artificial Sequence
<220> FEATURE:
<223> OTHER INFORMATION: synthetic

<400> SEQUENCE: 71

Glu Ser Lys Tyr Gly Pro Pro Cys Pro Ser Cys Pro Ala Pro Glu Phe
1               5                   10                  15

```
Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
                210                 215                 220

Leu Ser Leu Gly Lys
225

<210> SEQ ID NO 72
<211> LENGTH: 228
<212> TYPE: PRT
<213> ORGANISM: Artificial Sequence
<220> FEATURE:
<223> OTHER INFORMATION: Fc sequence

<400> SEQUENCE: 72

Glu Ser Lys Tyr Gly Pro Pro Cys Pro Pro Cys Pro Ala Pro Pro Val
 1               5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

Gln Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Gln Glu Glu Met Thr Lys Asn Gln Val
130                 135                 140
```

-continued

```
Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
210                 215                 220

Ser Leu Gly Lys
225
```

<210> SEQ ID NO 73
<211> LENGTH: 231
<212> TYPE: PRT
<213> ORGANISM: Artificial Sequence
<220> FEATURE:
<223> OTHER INFORMATION: synthetic

<400> SEQUENCE: 73

```
Glu Pro Lys Ser Cys Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser Gln Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
            100                 105                 110

Pro Ser Ser Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 74
<211> LENGTH: 231
<212> TYPE: PRT
<213> ORGANISM: Artificial Sequence
<220> FEATURE:
<223> OTHER INFORMATION: synthetic

<400> SEQUENCE: 74

Glu Pro Lys Ser Cys Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser Gln Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
            100                 105                 110

Pro Ser Ser Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn Arg Phe Thr Gln Lys Ser
    210                 215                 220

Leu Ser Leu Ser Pro Gly Lys
225                 230

<210> SEQ ID NO 75
<211> LENGTH: 228
<212> TYPE: PRT
<213> ORGANISM: Artificial Sequence
<220> FEATURE:
<223> OTHER INFORMATION: Fc sequence

<400> SEQUENCE: 75

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser

```
            100                 105                 110
Ile Glu Lys Thr Ile Ser Lys Ala Lys Gly Gln Pro Arg Glu Pro Gln
            115                 120                 125

Val Tyr Thr Leu Pro Pro Ser Gln Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn Arg Phe Thr Gln Lys Ser Leu Ser Leu
    210                 215                 220

Ser Leu Gly Lys
225

<210> SEQ ID NO 76
<211> LENGTH: 229
<212> TYPE: PRT
<213> ORGANISM: Artificial Sequence
<220> FEATURE:
<223> OTHER INFORMATION: Fc sequence

<400> SEQUENCE: 76

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 77
<211> LENGTH: 229
<212> TYPE: PRT
<213> ORGANISM: Artificial Sequence
<220> FEATURE:
<223> OTHER INFORMATION: Fc sequence

<400> SEQUENCE: 77

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn Arg Phe Thr Gln Lys Ser Leu Ser
    210                 215                 220

Leu Ser Leu Gly Lys
225

<210> SEQ ID NO 78
<211> LENGTH: 327
<212> TYPE: PRT
<213> ORGANISM: Artificial Sequence
<220> FEATURE:
<223> OTHER INFORMATION: CH sequence

<400> SEQUENCE: 78

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

-continued

```
Leu Ser Ser Val Val Thr Val Pro Ser Ser Ser Leu Gly Thr Lys Thr
 65              70                  75                  80

Tyr Thr Cys Asn Val Asp His Lys Pro Ser Asn Thr Lys Val Asp Lys
             85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn Arg Phe Thr Gln Lys Ser
305                 310                 315                 320

Leu Ser Leu Ser Leu Gly Lys
                325
```